(12) United States Patent
Leuschner et al.

(10) Patent No.: US 9,492,563 B2
(45) Date of Patent: Nov. 15, 2016

(54) ANTIBODY/DRUG CONJUGATES AND METHODS OF USE

(71) Applicant: ESPERANCE PHARMACEUTICALS, INC., Baton Rouge, LA (US)

(72) Inventors: Carola Leuschner, Baton Rouge, LA (US); Hector Alila, Baton Rouge, LA (US)

(73) Assignee: ESPERANCE PHARMACEUTICALS, INC., Houston, TX (US)

( * ) Notice: Subject to any disclaimer, the term of this patent is extended or adjusted under 35 U.S.C. 154(b) by 0 days.

(21) Appl. No.: 14/067,819

(22) Filed: Oct. 30, 2013

(65) Prior Publication Data

US 2014/0127241 A1  May 8, 2014

Related U.S. Application Data

(60) Provisional application No. 61/720,257, filed on Oct. 30, 2012.

(51) Int. Cl.
*A61K 39/395* (2006.01)
*A61K 47/48* (2006.01)
*C07K 16/28* (2006.01)
*C07K 16/32* (2006.01)

(52) U.S. Cl.
CPC ... *A61K 47/48438* (2013.01); *A61K 47/48561* (2013.01); *C07K 16/2887* (2013.01); *C07K 16/32* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,459,237 A | 10/1995 | Berkowitz et al. | |
| 5,561,107 A | 10/1996 | Jaynes et al. | |
| 5,635,479 A | 6/1997 | Jacob et al. | |
| 5,712,379 A * | 1/1998 | Davidson | 536/23.4 |
| 5,717,064 A | 2/1998 | Julian et al. | |
| 5,744,445 A | 4/1998 | Jaynes et al. | |
| 5,773,413 A | 6/1998 | Janes et al. | |
| 5,789,542 A | 8/1998 | Mclaughlin et al. | |
| 5,792,831 A | 8/1998 | Maloy | |
| 5,821,337 A * | 10/1998 | Carter et al. | 530/387.3 |
| 5,861,478 A | 1/1999 | Jaynes | |
| 5,968,904 A | 10/1999 | Julian et al. | |
| 6,001,805 A | 12/1999 | Jaynes et al. | |
| 6,018,102 A | 1/2000 | Garbabino et al. | |
| 6,084,156 A | 7/2000 | Garbabino et al. | |
| 6,191,110 B1 | 2/2001 | Jaynes et al. | |
| 6,255,282 B1 | 7/2001 | Jaynes | |
| 6,303,568 B1 | 10/2001 | Jaynes et al. | |
| 6,348,445 B1 | 2/2002 | Kari et al. | |
| 6,440,935 B1 | 8/2002 | Jaynes et al. | |
| 6,448,391 B1 | 9/2002 | Garbarino et al. | |
| 6,514,692 B2 | 2/2003 | Jaynes | |
| 6,559,281 B1 | 5/2003 | Jaynes | |
| 6,566,334 B1 | 5/2003 | Mclaughlin et al. | |
| 6,635,740 B1 | 10/2003 | Enright et al. | |
| 6,656,906 B1 | 12/2003 | Barney et al. | |
| 6,680,058 B1 | 1/2004 | Enright et al. | |
| 6,875,744 B2 | 4/2005 | Owen | |
| 7,091,185 B2 | 8/2006 | Strom et al. | |
| 7,097,840 B2 * | 8/2006 | Erickson et al. | 424/178.1 |
| 7,262,163 B2 | 8/2007 | Mclaughlin et al. | |
| 7,288,622 B1 | 10/2007 | Jaynes et al. | |
| 7,566,777 B2 | 7/2009 | Enright et al. | |
| 7,803,755 B2 | 9/2010 | Jaynes | |
| 7,850,962 B2 * | 12/2010 | Teeling et al. | 424/130.1 |
| 8,258,100 B2 | 9/2012 | Enright et al. | |
| 8,318,899 B2 | 11/2012 | Leuschner et al. | |
| 8,546,535 B2 | 10/2013 | Leuschner et al. | |
| 2001/0003042 A1 | 6/2001 | Lorens | |
| 2004/0018967 A1 | 1/2004 | Enright et al. | |
| 2004/0167319 A1 * | 8/2004 | Teeling et al. | 530/388.22 |
| 2005/0187151 A1 | 8/2005 | Strom et al. | |
| 2009/0285837 A1 * | 11/2009 | Kao et al. | 424/174.1 |
| 2011/0113497 A1 * | 5/2011 | Lee | 800/13 |
| 2011/0124564 A1 | 5/2011 | Alila et al. | |
| 2011/0217702 A1 | 9/2011 | Leuschner et al. | |
| 2013/0157961 A1 | 6/2013 | Alila et al. | |
| 2014/0127241 A1 | 5/2014 | Leuschner et al. | |
| 2014/0161767 A1 | 6/2014 | Leuschner et al. | |

FOREIGN PATENT DOCUMENTS

| | | |
|---|---|---|
| AU | 2009206212 | 5/2014 |
| CA | 2283630 | 8/2011 |
| EP | 0975354 | 6/2007 |
| WO | WO91/12015 A1 | 8/1991 |
| WO | WO92/22317 A1 | 12/1992 |
| WO | WO93/11783 A1 | 6/1993 |
| WO | 93/21319 * | 10/1993 |

(Continued)

OTHER PUBLICATIONS

Russell et al Cancer Immunol Immunother (2004) 53:411.*
Paul, Fundamental Immunology, 3rd Edition, 1993, pp. 292-295.*
Rudikoff et al Proc. Natl. Acad. Sci. USA 1982 vol. 79: p. 1979.*
Pascalis et al (The Journal of Immunology (2002) 169, 3076-3084).*
Casset et al. (2003) BBRC 307, 198-205.*
Brown et al (J. Immunol. May 1996; 156(9):3285-3291).*
Vajdos et al (J. Mol. Biol. Jul. 5, 2002;320(2); 415-428).*
Almagro, Frontiers in Bioscience 2008; 13:1619-33.*
Carter, Nat Rev Immunol, 2006; 6:343-357).*
Bodek, G., et al., A Novel Approach of Targeted Ablation of Mammary Carcinoma Cells Through Luteinizing Hormone Receptors Using Hecate-CG Conjugate, Breast Cancer Research and Treatment, 2003, 79:1-10.

(Continued)

*Primary Examiner* — Sheela J Huff
(74) *Attorney, Agent, or Firm* — Pillsbury Winthrop Shaw Pittman LLP

(57) ABSTRACT

The invention relates to conjugates that bind to targets, methods of using conjugates that bind to targets and methods of treating undesirable or aberrant cell proliferation or hyperproliferative disorders, such as tumors, cancers, neoplasia and malignancies that express a target.

31 Claims, 12 Drawing Sheets

(56) References Cited

FOREIGN PATENT DOCUMENTS

| WO | WO93/24138 A1 | 12/1993 |
|---|---|---|
| WO | WO94/12206 A1 | 6/1994 |
| WO | WO94/13697 A1 | 6/1994 |
| WO | WO94/19369 A1 | 9/1994 |
| WO | WO94/25616 | 11/1994 |
| WO | WO96/03522 A1 | 2/1996 |
| WO | WO98/42364 A1 | 10/1998 |
| WO | WO99/03488 A2 | 1/1999 |
| WO | WO99/03488 A3 | 1/1999 |
| WO | WO00/53755 A2 | 9/2000 |
| WO | WO00/53755 A3 | 9/2000 |
| WO | WO01/19852 A2 | 3/2001 |
| WO | WO01/21194 A2 | 3/2001 |
| WO | WO01/68676 A2 | 9/2001 |
| WO | WO03/041741 A1 | 5/2003 |
| WO | WO03/089455 A2 | 10/2003 |
| WO | WO2004/030650 A2 | 4/2004 |
| WO | WO2004/087215 A1 | 10/2004 |
| WO | WO2004/094462 A2 | 11/2004 |
| WO | WO2005/014639 A2 | 2/2005 |
| WO | WO2005/023264 A1 | 3/2005 |
| WO | WO2005/062881 A2 | 7/2005 |
| WO | WO2006/106311 A2 | 10/2006 |
| WO | WO2007/115033 A2 | 10/2007 |
| WO | WO2009/094634 | 7/2009 |
| WO | WO2011/031477 | 7/2011 |
| WO | WO2012/050892 | 4/2012 |
| WO | WO2011/137245 | 8/2012 |
| WO | WO2014/070957 | 5/2014 |
| WO | WO2014/078533 | 5/2014 |

OTHER PUBLICATIONS

Bodek, G., et al., A Novel Targeted Therapy of Leydig and Granulosa Cell Tumors through the Luteinizing Hormone Receptor Using a Hecate-Chorionic GonadotropinConjugate in Transgenic Mice, Neoplasia, 2005, 7(5):497-508.

Bodek, G., et al., Targeted Ablation of Prostate Carcinoma Cells Through LH Receptor Using Hecate-CGConjugate: Functional Characteristic and Molecular Mechanism of Cell Death Pathway, Exp. Bioi. Med. 2005, 230:421-428.

Boman, H.G., Antibacterial Peptides: Basic Facts and Emerging Concepts, Journal of Internal Medicine, 2003, 254:197-215.

Cavicchioni, G., et al., Biological Variation Responses in fMLP-OMe Analogs, Introducing Bulky Protecting Groups on the Side-Chain of Hydrophilic Residues at Position 2, J.Peptide Res., 2002, 60:223-231.

Dharap, S.S., et al., Tumor-Specific Targeting of an Anticancer Drug Delivery System by LHRH Peptide, PNAS, 2005, 102(36):12962-12967.

Ellerby, H.M., et al., Anti-Cancer Activity of Targeted Pro-Apoptotic Peptides, Nature Medicine, 1999, 5(9):1032-1038.

Gawronska, B., et al., Effect of Lytic Peptide Conjugated toLH on Ovarian Cancer: Studies in Vivo Study, Biology of Reproduction, 2001, 64 (Supp.1):228, #311.

Gawronska, B., et al., Effects of Lytic Peptide Conjugated tohcG on Ovarian Cancer: Studies in Vitro and in Vivo, Gynecologic Oncology, 2002, 85:45-52.

Hansel, W., et al., Conjugates of Lytic Peptides and LHRH or CG Target and Cause Necrosis of Prostate Cancers and Metastases, Molecular and Cellular Endocrinology [in press], Mol. Cell. Endocrinol. (2007), doi:10.1016/j.mce.2006.06.017.

Hansel, W., et al., Destruction of Breast Cancers and Their Metastases by Lytic Peptide Conjugates in vitro and in vivo, 2007, Molecular and Cellular Endocrinology, 260-262:183-189.

Hansel, W., et al., Targeted Destruction of Prostate Cancer Cells and Xenografts by Lytic Peptide-LH Conjugates, Reproductive Biology, 2001, 1(1)20-32.

Isaacs, C.E., et al., A Lipid-Peptide Microbicide Inactivates Herpes Simplex Virus, Antimicrobial Agents and Chemotherapy, 2004, 48(8):3182-3184.

Javadpour, M.M., et al., De Novo Antimicrobial Peptides with Low Mammalian Cell Toxicity, J. Med. Chem., 1996,39:3107-3113.

Javadpour, M.M., et al., Self-Assembly of Designed Antimicrobial Peptides in Solution and Micelles, 1997, 36:9540-9549.

Johnstone, S.A., et al., In vitro Characterization of the Anticancer Activity of Membrane-Active Cationic Peptides. I. Peptide-Mediated Cytotoxicity and Peptide-Enhanced Cytotoxic Activity of Doxorubicin Against Wild-Type and p-Glycoprotein Over-Expressing Tumor Cell Lines, Anti-Cancer Drug Design, 2000, 15:151-160.

Kalia, V., et al., Rational Site-Directed Mutations of the LLP-1 and LLP-2 Lentivirus Lytic Peptide Domains in the Intracytoplasmic Tail of Human Immunodeficiency virus Type 1 gp41 Indicate Common Functions in Cell-Cell Fusion but Distinct Roles in Virion Envelop Incorporation, Journal of Virology, 2003, 77(6):3634-3646.

Lee, D.L., et al., Effects of Single 0-Amino Acid Substitutions on Disruption of f3-Sheet Structure and Hydrophobicity in Cyclic 14-Residue Antimicrobial Peptide Analogs Related to Gramicidin S, J. Pept. Res., 2004, 63(2):69-84.

Leuschner, C., et al., A Novel Approach in Prostate Cancer Therapy: Lytic Peptides Conjugated to Luteinizing Hormone Kill Prostate Cancer Cells, Biology of Reproduction, 60{Supp. 1):251, #510, (1999).

Leuschner, C., et al., Human Prostate Cancer Cells and Xenografts are Targeted and Destroyed Through Luteinizing Hormone Receptors, The Prostate, 2003, 56:239-249.

Leuschner, C., et al., LHRH-Conjugated Magnetic Iron Oxide Nanoparticles for Detection of Breast Cancer Metastases, Breast Cancer Research and Treatment, 2006, DOI 10.1007/s10549-006-9199-7.

Leuschner, C., et al., Lytic Peptide Conjugated to Gonadotropin Releasing Hormone Kills Prostate Cancer Cells, 2000, Proc. Am. Assoc. Cancer Res., 3:45, #287.

Leuschner, C., et al., Lytic Peptide Conjugated to Luteinizing Hormone (LH) Kills Prostate Cancer Cells in vivo: Increased Toxicity by Pretreatment with Folicle Stimulating Hormone (FSH) or Estradiol, Proc. Am. Assoc. Cancer Res. (Supplement), 2000, 6:4500s, #172.

Leuschner, C., et al., Lytic Peptide Conjugates Destroy Hormone-Dependent and Independent Breast Cancer Cells, Proc. Am. Assoc. Cancer Res. !(Supplement), 2001, 7:3752s, #489.

Leuschner, C., et al., Lytic Peptide-CG Conjugate Destroys Breast Cancer Metastases, Proc. Am. Assoc. Cancer Res., 2003, 44:1352, #LB-138.

Leuschner, C., et al., Membrane Disrupting Lytic Peptide Conjugates Destroy Hormone Dependent and Independent Breast Cancer Cells in vitro and in vivo, Breast Cancer Research and Treatment, 2003, 78:17-27.

Leuschner, C., et al., Membrane Disrupting Lytic Peptides for Cancer Treatments, Current Pharmaceutical Design, 2004, 10:2299-2310.

Leuschner, C., et al., Targeted Destruction of Androgen-Sensitive and- Insensitive Prostate Cancer Cells and Xenografts Through Luteinizing Hormone Receptors, The Prostate, 2006,46:116-125.

Leuschner, C., et al., Targeting Breast and Prostate Cancers Through Their Hormone Receptors, BioloQY of Reproduction, 2005, 73:860-865.

Leuschner, C., et al., Targeting Breast Cancer and Metastases with a Combination of LHRH and Lytic Peptide, Hecate, Bound to Iron Oxide Nanoparticles, Clin. Cancer Res., 2005, 11(24 Suppl.):9097s, #B262.

Leuschner, et al., A Novel Lytic Peptide CG Conjugate Destrys Breast Cancer Tumors and Metastases, Pennington Biomedical Research Center, Baton Rouge, LA, USA; Louisiana State University, Baton Rouge, LA, USA; email: Leuschc@pbrc.edu, (2003).

Lyu, P.C., et al., Side Chain Contributions to the Stability of Alpha-Helical Structure in Peptides, Science, 1990, 250:669-673.

Lyu, P.C., et al., α-Helix Stabilization by Natural and Unnatural Amino Acids With Alkyl Side Chains, Proc. Natl. Acad. Sci. USA, 1991, 88:5317-5320.

Ma, J., et al., Inhibitory Activity of Synthetic Peptide Antibodies on Feline Immunodeficiency Virus Infectivity In Vitro, Journal of Virology, 2002, 76(19):9952-9961.

(56) References Cited

OTHER PUBLICATIONS

Mader, J.S., et al., Cationic Antimicrobial Peptides as Novel Cytotoxic Agents for Cancer Treatment, Expert Opin. Investig. Drugs, 2006, 15(8):933-946.
Marks, A.J., et al., Selective Apoptotic Killing of Malignant Hemopoietic Cells by Antibody-Targeted Delivery of an Amphipathic Peptide, Cancer Res., 2005, 65(6):2373-2377.
Mclaughlin, M.L., et al., Structure-function Studies of De Novo Lytic Peptides, Peptides: Chemistry, Structure and Biology, Pravin T.P. Kaumaya and Robert S. Hodges (Eds.}, Mayflower Scientific Ltd., 1996, pp. 569-570.
Melrose, P.A., et al., Selectivity and Synergy of Lytic Peptide Conjugated Mammalian (M) and Lamprey III (L} Gonadotropin-Releasing Hormone (GnRH) on Primary Prostatic Cancer, Pituitary, and GnRH Neuronal Cell Lines,, Proc. Am. Assoc. Cancer Res., 2001,42:778, #4174.
Min Chen, H., et al., Effects of the Anti-Bacterial Peptide Cecropin B and its Analogs, Cecropins B-1 and B-2, on Liposomes, Bacteria, and Cancer Cells, Biochimica et Biophysica Acta, 1997, 1336:171-179.
Min Chen, H., et al., Structure Stability of Lytic Peptides During Their Interactions With Lipid Bilayers, Journal of Biomolecular Structure & Dynamics, 2001, 19(2):193-199.
O'Neil, K.T., et al., A Thermodynamic Scale for the Helix-Forming Tendencies of the Commonly Occurring Amino Acids, Science, 1990, 250:646-651.
Oren, Z., et al., A Repertoire of Novel Antibacterial Diastereomeric Peptides with Selective Cytolytic Activity, The Journal of Biological Chemistry, 1997, 272(23):14643-14649.
Oren, Z., et al., Structures and Mode of Membrane Interaction of a Short a Helical Lyctic Peptide and its Diastereomer Determined by NMR, FTIR, and Fluorescence Spectroscopy, Eur. J. Biochem., 2002, 269:3869-3880.
Papo, N., et al., A Novel Lytic Peptide Composed of oL-Amino Acids Selectively Kills Cancer Cells in Culture and in Mice, The Journal of Biological Chemistry, 2003, 278(23):21018-21023.
Papo,N., et al., Effect of Drastic Sequence Alteration and 0-Amino Acid Incorporation on the Membrane Binding Behavior of Lytic Peptides, Biochemistry, 2004, 43:6393-6403.
Rivett, D.E., et al., Dimerization of Truncated Melittin Analogues Results in Cytolytic Peptides, Biochem. J., 1996, 316:525-529.
Robertson, C.N., et al., Peptidyl Membrane-Interactive Molecules are Cytotoxic to Prostatic Cancer Cells in vitro, World J. Urol., 1998, 16:405-409.
Shai, Y., From Innate Immunity to de-Novo Designed Antimicrobial Peptides, Current Pharmaceutical Design, 2002, 8:715-725.
Shin, S.Y., et al., Antibacterial, Antitumor and Hemolytic Activities of a-Helical Antibiotic Peptide, P18 and Its Analogs, J. Peptide Res., 2001, 58:504-514.
Wade, D., et al., All-$_0$ Amino Acid-Containing Channel-Forming Antibiotic Peptides, Proc. Natl. Acad. Sci. USA, 1990, 87:4761-4765.
Werkmeister, J.A., et al., Sequence Requirements for the Activity of Membrane-Active Peptides, J. Peptide. Res., 2002, 60:232-238.
Yokum, T.S., et al., Antimicrobial Peptides with Activity Against an Intracellular Pathogen, Peptides, Frontiers of Peptide Science, Proceeding of the Fifteenth American Peptide Symposium, Jun. 14-19, 1997, Nashville, Tennessee, U.S.A., pp. 652-653.
Yokum, T.S., et al., Lytic Peptide-Calixarene Conjugates, Abstracts of Papers, Part 2, 211$^{th}$ACS National Meeting 0-8412-3397-7, American Chemical Soc., New Orleans, LA, Mar. 24-28, 1996, #262.
Yokum, T.S., et al., Peptides With Indirect in vivo Activity Against an Intracellular Pathogen: Selective Lysis of Infected Macrophages, J. Peptide Res., 2002, 59:9-17.
Zaleska, M., et al., Growth Repression in Diethylstilbestrol/Dimethylbenz[a]anthracene-Induced Rat Mammary Gland Tumor Using Hecate-CGI3 Conjugate, Exp. Bioi. Med., 2004, 229:335-344.
Zaleska, M., et al., Targeted Destruction of Normal and Cancer Cells Through Lutropin/Choriogonadotropin Receptors Using Hecate-!3CG Conugate, Exp. Clin. Endocrinol Diabetes, 2003, 111:146-153.
PCT International Application No. PCT/US2013/067621, International Preliminary Report on Patentability, dated May 5, 2015.
NCBI, PDB Accession No. 20SL__L (Oct. 10, 2012).
NCBI, PDB Accession No. 20SL__H (Oct. 10, 2012).
NCBI, PDB Accession No. IN8Z__A (Oct. 10, 2012).
NCBI, GenBank Accession No. BAJ17684.2 (Sep. 14, 2010).

* cited by examiner

Figures 1A and 1B
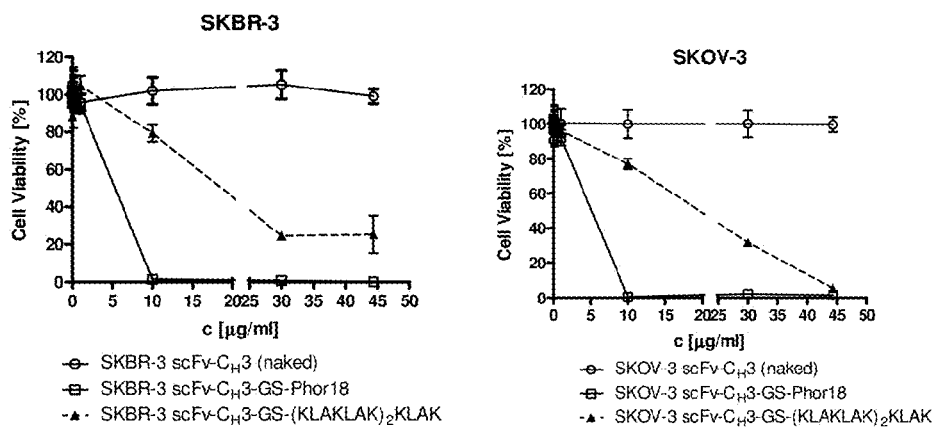
Figures 2A and 2B
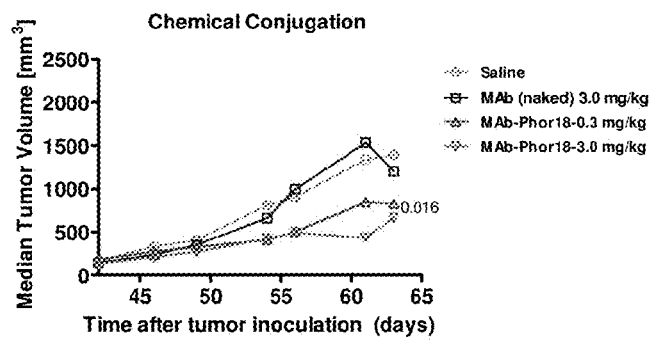
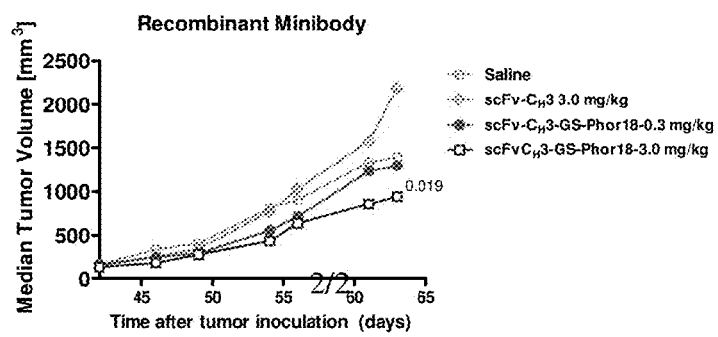

A. Anti-Phor18 probe of reduced proteins

B. Anti-kappa light chain probe of reduced proteins

Figure 10
A)
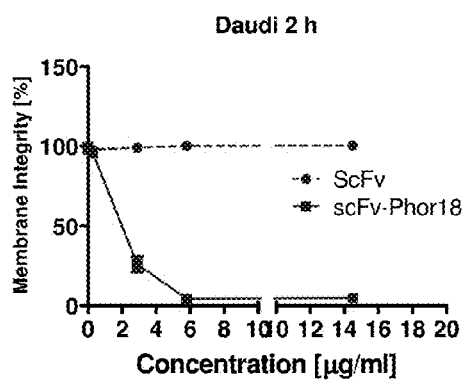
B)
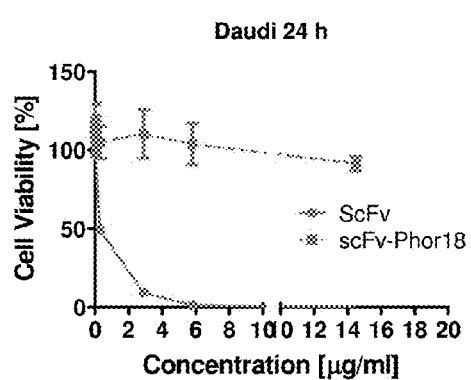

Figure 13a-D

SEQUENCE LISTING

<160> NUMBER OF SEQ ID NOS: 154

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 1

Lys Phe Ala Lys Phe Ala Lys Lys Phe Ala Lys Phe Ala Lys Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 2

Lys Phe Ala Lys Phe Ala Lys Lys Phe Ala Lys Phe Ala Lys Lys Phe
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 3

Lys Phe Ala Lys Phe Ala Lys Lys Phe Ala Lys Phe Ala Lys Lys Phe
1               5                   10                  15
Ala

<210> SEQ ID NO 4
<211> LENGTH: 18

```
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 4

Lys Phe Ala Lys Phe Ala Lys Lys Phe Ala Lys Phe Ala Lys Lys Phe
1               5                   10                  15

Ala Lys

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 5

Lys Phe Ala Lys Phe Ala Lys Lys Phe Ala Lys Phe Ala Lys Lys Phe
1               5                   10                  15

Ala Lys Phe

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 6

Lys Phe Ala Lys Phe Ala Lys Lys Phe Ala Lys Phe Ala Lys Lys Phe
1               5                   10                  15

Ala Lys Phe Ala
            20

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 7

Lys Phe Ala Lys Phe Ala Lys Lys Phe Ala Lys Phe Ala Lys Lys Phe
1               5                   10                  15

Ala Lys Phe Ala Lys Lys Phe Ala Lys Phe Ala Lys
            20                  25

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 8

Gly Ser Gly Gly Ser
1               5

<210> SEQ ID NO 9
```

```
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 9

Ala Ser Ala Ala Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 10

Gly Ser Gly Arg Ser Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 11

Arg Val Arg Arg Ser Val
1               5

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Heavy
``` chain mammalian humanized antibody

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Tyr Ala Asp Ser Val
    50                  55                  60

Lys Gly Arg Phe Thr Ile Ser Ala Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gly Asp Gly Phe Tyr Ala Met Asp Val Trp Gly Gln
            100                 105                 110

Gly Thr Leu Val Thr Val Ser Ser
            115                 120

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Val Trp Gly Gln
            100                 105                 110
```

Gly Thr Leu Val Thr Val Ser Ser
            115                 120

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
            115                 120

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

```
<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
 65                 70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105
```

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 23

```
Glu Val Gln Leu Val Glu Ser Gly Gly Leu Val Gln Pro Gly Gly
 1               5                   10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                 70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
                100                 105                 110

Gly Thr Leu Val Thr Val Ser Ser
        115                 120
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 24

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Glu Ser Gly Val Pro Ser Arg Phe Ser Gly
     50                  55                  60

Ser Arg Ser Gly Thr Asp Phe Thr Leu Thr Ile Ser Ser Leu Gln Pro
 65                 70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105
```

```
<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 27

Glu Val Gln Leu Val Glu Ser Gly Gly Gly Leu Val Gln Pro Gly Gly
```

```
                1               5                  10                 15
Ser Leu Arg Leu Ser Cys Ala Ala Ser Gly Phe Asn Ile Lys Asp Thr
                20                  25                 30

Tyr Ile His Trp Val Arg Gln Ala Pro Gly Lys Gly Leu Glu Trp Val
            35                  40                 45

Ala Arg Ile Tyr Pro Thr Asn Gly Tyr Thr Arg Tyr Ala Asp Ser Val
        50                  55                 60

Lys Gly Arg Phe Thr Ile Ser Ala Asp Thr Ser Lys Asn Thr Ala Tyr
 65                  70                  75                 80

Leu Gln Met Asn Ser Leu Arg Ala Glu Asp Thr Ala Val Tyr Tyr Cys
                85                  90                 95

Ser Arg Trp Gly Gly Asp Gly Phe Tyr Ala Met Asp Tyr Trp Gly Gln
                100                 105                110

Gly Thr Leu Val Thr Val Ser Ser
            115                 120

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 28

Asp Ile Gln Met Thr Gln Ser Pro Ser Ser Leu Ser Ala Ser Val Gly
 1               5                  10                 15

Asp Arg Val Thr Ile Thr Cys Arg Ala Ser Gln Asp Val Asn Thr Ala
                20                  25                 30

Val Ala Trp Tyr Gln Gln Lys Pro Gly Lys Ala Pro Lys Leu Leu Ile
            35                  40                 45

Tyr Ser Ala Ser Phe Leu Tyr Ser Gly Val Pro Ser Arg Phe Ser Gly
        50                  55                 60

Ser Arg Ser Gly Thr Asp Phe Thr Leu Thr Ile Ser Ser Leu Gln Pro
 65                  70                  75                 80

Glu Asp Phe Ala Thr Tyr Tyr Cys Gln Gln His Tyr Thr Thr Pro Pro
                85                  90                 95

Thr Phe Gly Gln Gly Thr Lys Val Glu Ile Lys
                100                 105

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 29

Glu Val Gln Leu Val Glu Ser Gly Gly Gly Leu Val Gln Pro Gly Gly
 1               5                  10                 15

Ser Leu Arg Leu Ser Cys Ala Ala Ser Gly Phe Asn Ile Lys Asp Thr
                20                  25                 30

Tyr Ile His Trp Val Arg Gln Ala Pro Gly Lys Gly Leu Glu Trp Val
            35                  40                 45

Ala Arg Ile Tyr Pro Thr Asn Gly Tyr Thr Arg Tyr Ala Asp Ser Val
        50                  55                 60

Lys Gly Arg Phe Thr Ile Ser Ala Asp Thr Ser Lys Asn Thr Ala Tyr
```

```
                65                  70                  75                  80
Leu Gln Met Asn Ser Leu Arg Ala Glu Asp Thr Ala Val Tyr Tyr Cys
                        85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence:  Heavy
      chain mammalian humanized antibody

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
            115                 120
```

```
<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Asp Trp Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys
            100                 105

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Trp Gly Pro Lys Leu Ala Met Asp Tyr Trp Gly
            100                 105                 110

Gln Gly Thr Leu Val Thr Val Ser Ser
        115                 120

<210> SEQ ID NO 34
<211> LENGTH: 216
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 34

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Asn Phe Tyr Pro Arg Glu
    130                 135                 140

Ala Lys Val Gln Trp Lys Val Asp Asn Ala Leu Gln Ser Gly Glu Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 35
<211> LENGTH: 448
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
145                 150                 155                 160
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 36
<211> LENGTH: 217
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 36

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
                20                  25                  30

Ser Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser Arg
    50                  55                  60
```

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 37
<211> LENGTH: 448
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

-continued

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Val Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu Asn His Tyr Thr Gln Lys Ser Leu Ser Leu Ser Pro Gly Lys
            435                 440                 445

<210> SEQ ID NO 38
<211> LENGTH: 216
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Asn Phe Tyr Pro Arg Glu
    130                 135                 140

Ala Lys Val Gln Trp Lys Val Asp Asn Ala Leu Gln Ser Gly Glu Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 39
<211> LENGTH: 448
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 40
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 40

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 41
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 41

Val Asp Asn Lys Phe Asn Lys Glu Leu Arg Gln Ala Tyr Trp Glu Ile
1               5                   10                  15

Gln Ala Leu Pro Asn Leu Asn Trp Thr Gln Ser Arg Ala Phe Ile Arg
            20                  25                  30

Ser Leu Tyr Asp Asp Pro Ser Gln Ser Ala Asn Leu Leu Ala Glu Ala
        35                  40                  45
```

Lys Lys Leu Asn Asp Ala Gln Ala Pro Lys
        50                  55

<210> SEQ ID NO 42
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 42

Val Asp Asn Lys Phe Asn Lys Glu Pro Lys Thr Ala Tyr Trp Glu Ile
1               5                   10                  15

Val Lys Leu Pro Asn Leu Asn Pro Glu Gln Arg Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 43
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 43

Val Asp Asn Lys Phe Asn Lys Glu Pro Arg Glu Ala Tyr Trp Glu Ile
1               5                   10                  15

Gln Arg Leu Pro Asn Leu Asn Asn Lys Gln Lys Ala Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 44
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 44

Val Asp Asn Lys Phe Asn Lys Glu Trp Met Thr Ala Gly Lys Glu Ile
1               5                   10                  15

Tyr Arg Leu Pro Asn Leu Asn Gly Thr Gln Val Arg Ala Phe Ile Gln
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 45
<211> LENGTH: 58
<212> TYPE: PRT
<213> ORGANISM: Artificial Sequence
<220> FEATURE:
<223> OTHER INFORMATION: Description of Artificial Sequence: Mammalian

```
humanized antibody

<400> SEQUENCE: 45

Val Asp Asn Lys Phe Asn Lys Glu Trp Val Gln Ala Gly Ser Glu Ile
1               5                   10                  15

Tyr Asn Leu Pro Asn Leu Asn Arg Ala Gln Met Arg Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 46
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 46

Val Asp Asn Lys Phe Asn Lys Glu Ile Lys Gln Ala Phe His Glu Ile
1               5                   10                  15

Val Arg Leu Pro Asn Leu Asn Ala Asp Gln Val Arg Ala Phe Ile Tyr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 47
<211> LENGTH: 57
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 47

Val Asp Asn Lys Phe Asn Lys Glu Met Val Asp Ala Gly Ala Glu Ile
1               5                   10                  15

Trp Arg Leu Pro Asn Leu Asn Ala Lys Gln Met Ala Phe Ile Asp Ser
            20                  25                  30

Leu Gly Asp Asp Pro Ser Gln Ser Ala Asn Leu Leu Ala Glu Ala Lys
        35                  40                  45

Lys Leu Asn Asp Ala Gln Ala Pro Lys
    50                  55

<210> SEQ ID NO 48
<211> LENGTH: 106
<212> TYPE: PRT
<213> ORGANISM: Artificial Sequence
<220> FEATURE:
<223> OTHER INFORMATION: Description of Artificial Sequence: Light
      chain antibody

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30
```

```
His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
 50                      55                  60

Arg Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Thr Ser Asn Pro Pro Thr
                 85                  90                  95

Phe Gly Gln Gly Thr Lys Val Glu Ile Lys
            100                 105
```

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Heavy
      chain antibody

<400> SEQUENCE: 49

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Ala Ala Ile Tyr Pro Gly Asn Gly Asp Thr Ser Tyr Asn Gln Lys Phe
 50                      55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Ser Thr Tyr Tyr Gly Gly Asp Trp Tyr Phe Asp Val Trp Gly
            100                 105                 110

Gln Gly Thr Leu Val Thr Val Ser Ser
        115                 120
```

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence:  Light
      chain antibody

<400> SEQUENCE: 50

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
 50                      55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95
```

```
Phe Gly Gly Gly Thr Lys Leu Glu Ile Lys
            100                 105
```

<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Heavy
    chain antibody

<400> SEQUENCE: 51

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser
        115                 120
```

<210> SEQ ID NO 52
<211> LENGTH: 106
<212> TYPE: PRT
<213> ORGANISM: Artificial Sequence
<220> FEATURE:
<223> OTHER INFORMATION: Description of Artificial Sequence: Light
    chain antibody

<400> SEQUENCE: 52

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys
            100                 105
```

<210> SEQ ID NO 53
<211> LENGTH: 121
<212> TYPE: PRT
<213> ORGANISM: Artificial Sequence
<220> FEATURE:
<223> OTHER INFORMATION: Description of Artificial Sequence: Heavy
    chain antibody

<400> SEQUENCE: 53

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser
        115                 120

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Light
      chain antibody

<400> SEQUENCE: 54

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys
            100                 105

<210> SEQ ID NO 55
<211> LENGTH: 121
<212> TYPE: PRT
<213> ORGANISM: Artificial Sequence
<220> FEATURE:
<223> OTHER INFORMATION: Description of Artificial Sequence: Heavy
      chain antibody

<400> SEQUENCE: 55

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe

```
                   50                  55                  60
Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Val Val Tyr Tyr Ser Asn Ser Tyr Trp Tyr Phe Asp Val Trp
                100                 105                 110

Gly Thr Gly Thr Thr Val Thr Val Ser
            115                 120

<210> SEQ ID NO 56
<211> LENGTH: 123
<212> TYPE: PRT
<213> ORGANISM: Artificial Sequence
<220> FEATURE:
<223> OTHER INFORMATION: Description of Artificial Sequence: Heavy
      chain antibody

<400> SEQUENCE: 56

Ala Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Gly Asp Tyr
             20                  25                  30

Thr Met His Trp Val Arg Gln Ala Pro Gly Leu Gly Leu Glu Trp Val
         35                  40                  45

Ser Gly Ile Ser Trp Asn Ser Gly Ser Ile Gly Tyr Ala Asp Ser Val
     50                  55                  60

Leu Gly Arg Phe Thr Ile Ser Arg Asp Asn Ala Leu Asn Ser Leu Tyr
 65                  70                  75                  80

Leu Gln Met Asn Ser Leu Arg Ala Glu Asp Thr Ala Leu Tyr Tyr Cys
                 85                  90                  95

Thr Leu Asp Asn Gln Tyr Gly Ser Gly Ser Thr Tyr Gly Leu Gly Val
                100                 105                 110

Trp Gly Gln Gly Thr Leu Val Thr Val Ser Ser
            115                 120

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Light
      chain antibody

<400> SEQUENCE: 57

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Leu
```

<210> SEQ ID NO 58
<211> LENGTH: 141
<212> TYPE: PRT
<213> ORGANISM: Artificial Sequence
<220> FEATURE:
<223> OTHER INFORMATION: Description of Artificial Sequence: Heavy
      chain antibody

<400> SEQUENCE: 58

Met Phe Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asn Asp Tyr Ala Met His Trp Val Arg Gln Ala Pro Gly Lys Gly Leu
    50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Tyr Gly Met
        115                 120                 125

Asp Val Trp Gly Gln Gly Thr Thr Val Thr Val Ser Ser
    130                 135                 140

<210> SEQ ID NO 59
<211> LENGTH: 126
<212> TYPE: PRT
<213> ORGANISM: Artificial Sequence
<220> FEATURE:
<223> OTHER INFORMATION: Description of Artificial Sequence: Light
      chain antibody

<400> SEQUENCE: 59

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Ile Thr Phe Gly Gln Gly Thr Arg Leu Glu Ile Lys
        115                 120                 125

<210> SEQ ID NO 60
<211> LENGTH: 144
<212> TYPE: PRT

```
<213> ORGANISM: Artificial Sequence
<220> FEATURE:
<223> OTHER INFORMATION: Description of Artificial Sequence: Heavy
      chain antibody

<400> SEQUENCE: 60

Met Glu Leu Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Thr Gly Ser Gly Phe Thr Phe
        35                  40                  45

Ser Tyr His Ala Met His Trp Val Arg Gln Ala Pro Gly Lys Gly Leu
    50                  55                  60

Glu Trp Val Ser Ile Ile Gly Thr Gly Gly Val Thr Tyr Tyr Ala Asp
65                  70                  75                  80

Ser Val Lys Gly Arg Phe Thr Ile Ser Arg Asp Asn Val Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Asp Tyr Tyr Gly Ala Gly Ser Phe Tyr Asp Gly Leu
        115                 120                 125

Tyr Gly Met Asp Val Trp Gly Gln Gly Thr Thr Val Thr Val Ser Ser
    130                 135                 140

<210> SEQ ID NO 61
<211> LENGTH: 127
<212> TYPE: PRT
<213> ORGANISM: Artificial Sequence
<220> FEATURE:
<223> OTHER INFORMATION: Description of Artificial Sequence: Light
      chain antibody

<400> SEQUENCE: 61

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asp Trp Pro Leu Thr Phe Gly Gly Gly Thr Lys Val Glu Ile Lys
        115                 120                 125

<210> SEQ ID NO 62
<211> LENGTH: 141
<212> TYPE: PRT
<213> ORGANISM: Artificial Sequence
<220> FEATURE:
<223> OTHER INFORMATION: Description of Artificial Sequence: Heavy
      chain antibody

<400> SEQUENCE: 62
```

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Asp Arg Ser Leu Arg Leu Ser Cys Ala Ala Ser Gly Phe Thr Phe
            35                  40                  45

His Asp Tyr Ala Met His Trp Val Arg Gln Ala Pro Gly Lys Gly Leu
    50                  55                  60

Glu Trp Val Ser Thr Ile Ser Trp Asn Ser Gly Thr Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Tyr Gly Met
        115                 120                 125

Asp Val Trp Gly Gln Gly Thr Thr Val Thr Val Ser Ser
    130                 135                 140
```

<210> SEQ ID NO 63
<211> LENGTH: 127
<212> TYPE: PRT
<213> ORGANISM: Artificial Sequence
<220> FEATURE:
<223> OTHER INFORMATION: Description of Artificial Sequence: Light
      chain antibody

<400> SEQUENCE: 63

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys
        115                 120                 125
```

<210> SEQ ID NO 64
<211> LENGTH: 443
<212> TYPE: PRT
<213> ORGANISM: Artificial Sequence
<220> FEATURE:
<223> OTHER INFORMATION: Description of Artificial Sequence: Heavy
      chain antibody

<400> SEQUENCE: 64

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30
```

-continued

```
Asn Met His Trp Val Lys Gln Thr Pro Arg Gln Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Val Asp Lys Ser Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Val Val Tyr Tyr Ser Asn Ser Tyr Trp Tyr Phe Asp Val Trp
            100                 105                 110
Gly Thr Gly Thr Thr Val Thr Val Ser Ala Pro Ser Val Tyr Pro Leu
            115                 120                 125
Ala Pro Val Cys Gly Asp Thr Thr Gly Ser Ser Val Thr Leu Gly Cys
        130                 135                 140
Leu Val Lys Gly Tyr Phe Pro Glu Pro Val Thr Leu Thr Trp Asn Ser
145                 150                 155                 160
Gly Ser Leu Ser Ser Gly Val His Thr Phe Pro Ala Val Leu Gln Ser
                165                 170                 175
Asp Leu Tyr Thr Leu Ser Ser Ser Val Thr Val Thr Ser Ser Thr Trp
            180                 185                 190
Pro Ser Gln Ser Ile Thr Cys Asn Val Ala His Pro Ala Ser Ser Thr
            195                 200                 205
Lys Val Asp Lys Lys Ile Glu Pro Arg Gly Pro Thr Ile Lys Pro Cys
        210                 215                 220
Pro Pro Cys Lys Cys Pro Ala Pro Asn Leu Leu Gly Gly Pro Ser Val
225                 230                 235                 240
Phe Ile Phe Pro Pro Lys Ile Lys Asp Val Leu Met Ile Ser Leu Ser
                245                 250                 255
Pro Ile Val Thr Cys Val Val Asp Val Ser Glu Asp Asp Pro Asp
            260                 265                 270
Val Gln Ile Ser Trp Phe Val Asn Asn Val Glu Val His Thr Ala Gln
        275                 280                 285
Thr Gln Thr His Arg Glu Asp Tyr Asn Ser Thr Leu Arg Val Val Ser
        290                 295                 300
Ala Leu Pro Ile Gln His Gln Asp Trp Met Ser Gly Lys Glu Phe Lys
305                 310                 315                 320
Cys Lys Val Asn Asn Lys Asp Leu Pro Ala Pro Ile Glu Arg Thr Ile
                325                 330                 335
Ser Lys Pro Lys Gly Ser Val Arg Ala Pro Gln Val Tyr Val Leu Pro
            340                 345                 350
Pro Pro Glu Glu Glu Met Thr Lys Lys Gln Val Thr Leu Thr Cys Met
            355                 360                 365
Val Thr Asp Phe Met Pro Glu Asp Ile Tyr Val Glu Trp Thr Asn Asn
        370                 375                 380
Gly Lys Thr Glu Leu Asn Tyr Lys Asn Thr Glu Pro Val Leu Asp Ser
385                 390                 395                 400
Asp Gly Ser Tyr Phe Met Tyr Ser Lys Leu Arg Val Glu Lys Lys Asn
                405                 410                 415
Trp Val Glu Arg Asn Ser Tyr Ser Cys Ser Val Val His Glu Gly Leu
            420                 425                 430
His Asn His His Thr Thr Lys Ser Phe Ser Arg
            435                 440
```

<210> SEQ ID NO 65
<211> LENGTH: 209
<212> TYPE: PRT
<213> ORGANISM: Artificial Sequence
<220> FEATURE:
<223> OTHER INFORMATION: Description of Artificial Sequence: Light chain antibody

<400> SEQUENCE: 65

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Ala Asp Ala Ala Pro
            100                 105                 110

Thr Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn

<210> SEQ ID NO 66
<211> LENGTH: 451
<212> TYPE: PRT
<213> ORGANISM: Artificial Sequence
<220> FEATURE:
<223> OTHER INFORMATION: Description of Artificial Sequence: Heavy chain antibody

<400> SEQUENCE: 66

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys 85                  90                  95
Ala Arg Ser Thr Tyr Tyr Gly Gly Asp Trp Tyr Phe Asn Val Trp Gly
                100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 67
<211> LENGTH: 213
<212> TYPE: PRT
<213> ORGANISM: Artificial Sequence
<220> FEATURE:
<223> OTHER INFORMATION: Description of Artificial Sequence: Light
      chain antibody

```
<400> SEQUENCE: 67

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 68
<211> LENGTH: 447
<212> TYPE: PRT
<213> ORGANISM: Artificial Sequence
<220> FEATURE:
<223> OTHER INFORMATION: Description of Artificial Sequence: Heavy
      chain antibody

<400> SEQUENCE: 68

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
        115                 120                 125
```

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 69
<211> LENGTH: 210
<212> TYPE: PRT
<213> ORGANISM: Artificial Sequence
<220> FEATURE:
<223> OTHER INFORMATION: Description of Artificial Sequence: Light
      chain antibody

<400> SEQUENCE: 69

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
```

```
                35                  40                  45
Ala Pro Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Phe Asn Pro Pro Thr
                 85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 70
<211> LENGTH: 396
<212> TYPE: DNA
<213> ORGANISM: Artificial Sequence
<220> FEATURE:
<223> OTHER INFORMATION: Description of Artificial Sequence:
      Immunoglobulin light chain

<400> SEQUENCE: 70
atggattcac aggcccaggt tcttatattg ctgctgctat gggtatctgg tacctgtggg      60
gacattgtga tgtcacagtc tccatcctcc ctggctgtgt cagcaggaga gaaggtcact     120
atgagctgca aatccagtca gagtctgctc aacagtagaa cccgaaagaa ctacttggct     180
tggtaccagc agaaaccagg gcagtctcct aaactgctga tctactgggc atccactagg     240
gaatctgggg tccctgatcg cttcacaggc agtggatctg gacagatttc actctcacc      300 atcagcagtg tgcaggctga agacctggca gtttattact gcaagcaatc ttataatctt     360
tacacgttcg gaggggggac caagctggaa ataaaa                               396

<210> SEQ ID NO 71
<211> LENGTH: 130
<212> TYPE: PRT
<213> ORGANISM: Artificial Sequence
<220> FEATURE:
<223> OTHER INFORMATION: Description of Artificial Sequence:
      Immunoglobulin light chain

<400> SEQUENCE: 71

Met Asp Ser Gln Ala Gln Val Leu Leu Leu Leu Leu Trp Val Ser Gly
 1               5                  10                  15

Thr Cys Gly Asp Ile Val Met Ser Gln Ser Pro Ser Ser Leu Ala Val
            20                  25                  30

Ser Ala Gly Glu Lys Val Thr Met Ser Cys Lys Ser Ser Gln Ser Leu
        35                  40                  45
```

Leu Asn Ser Arg Thr Arg Lys Asn Tyr Leu Ala Trp Tyr Gln Gln Lys
    50                  55                  60

Pro Gly Gln Ser Pro Lys Leu Leu Ile Tyr Trp Ala Ser Arg Glu Ser
 65              70                  75                  80

Gly Val Pro Asp Arg Phe Thr Gly Ser Gly Ser Gly Thr Asp Phe Thr
                85                  90                  95

Leu Thr Ile Ser Ser Val Gln Ala Glu Asp Leu Ala Val Tyr Tyr Cys
            100                 105                 110

Lys Gln Ser Tyr Asn Leu Tyr Thr Phe Gly Gly Gly Thr Lys Leu Glu
        115                 120                 125

Ile Lys
    130

<210> SEQ ID NO 72
<211> LENGTH: 354
<212> TYPE: DNA
<213> ORGANISM: Artificial Sequence
<220> FEATURE:
<223> OTHER INFORMATION: Description of Artificial Sequence:
      Immunoglobulin heavy chain

<400> SEQUENCE: 72
caggtgcagc tgaaggagtc aggacctggc ctggtggcac cctcacagag cctgtccatc      60
acatgcactg tctctgggtt ctcattatcc agatatagtg tacactgggt tcgccagcct    120
ccaggaaagg gcctggagtg gctgggaatg atatggggtg gtggaagcac agactataat    180
tcagctctca atccagact gagcatcagc aaggacaact ccaagagcca agttttctta    240
aaaatgaaca gtctgcaaac tgatgacaca gccatgtact actgtgccag aggcaatgat    300
ggttactact cgtttgctta ctggggccaa gggactctgg tcactgtctc ttca          354

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence:
      Immunoglobulin heavy chain

<400> SEQUENCE: 73

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
 65              70                  75                  80

Lys Met Asn Ser Leu Gln Thr Asp Asp Thr Ala Met Tyr Tyr Cys Ala
                85                  90                  95

Arg Gly Asn Asp Gly Tyr Tyr Ser Phe Ala Tyr Trp Gly Gln Gly Thr
            100                 105                 110

Leu Val Thr Val Ser Ser
        115

<210> SEQ ID NO 74

```
<211> LENGTH: 12
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 74

Lys Leu Ala Lys Leu Ala Lys Lys Leu Ala Lys
1               5                   10

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Linker

<400> SEQUENCE: 75

Asn Arg Val Arg Arg Ser
1               5

<210> SEQ ID NO 76
<211> LENGTH: 2217
<212> TYPE: DNA
<213> ORGANISM: Artificial Sequence
<220> FEATURE:
<223> OTHER INFORMATION: Description of Artificial Sequence:
      Her2/neu antibody

<400> SEQUENCE: 76
catatgcatc accaccacca ccacgacgac gacgacaaag atattcaaat gacccagtcc      60
ccgagcagcc tgagtgcctc cgttggcgac cgcgtgacca ttacgtgccg tgcgagccag     120
gatgtcaaca ccgcggtggc ctggtatcag caaaaaccgg gcaaagcgcc gaaactgctg     180
atctattcag cctcgtttct gtacagcggt gttccgtctc gtttcagcgg ctctcgcagt     240
ggtaccgatt ttaccctgac gattagctct ctgcagccgg aagactttgc gacgtattac     300
tgccagcaac attacaccac gccgccgacc ttcggccagg gtacgaaagt ggaaatcaaa     360
ggttccacct caggcggtgg cagtggtggc ggttccggcg gtggcggtag ttccgaagtt     420
cagctggtcg aaagtggcgg tggcctggtt caaccgggtg gctcactgcg tctgtcgtgt     480
gcagcaagcg gtttcaacat caaagatacc tacatccact gggttcgtca ggcgccgggc     540
aaaggtctgg aatgggtcgc ccgcatttac ccgaccaatg gctatacgcg ttacgcagat     600
agcgtgaaag gtcgctttac catctctgcg gacaccagta aaaacacggc ctatctgcag     660
atgaatagcc tgcgtgcgga agatacggcc gtttattact gctctcgctg gggtggcgat     720
ggcttctatg ctatggacta ctggggccag ggtaccctgg tgacggtttc atcgggtcag     780
ccgcgtgaac cgcaagtgta taccctgccg ccgtcacgcg atgaactgac gaaaaaccag     840
gtgtcgctga cgtgtctggt taaaggcttt tacccgagcg acatcgcggt tgaatgggaa     900
tctaatggtc aaccggaaaa caattataaa accacgccgc cggtcctgga tagtgacggc     960
tccttttttc tgtacagtaa actgaccgtg gataaatccc gttggcagca gggtaacgtc    1020
ttctcgtgta gcgtgatgca tgaagccctg cataatcact atacccagaa atctctgagt    1080
ctgtccccgg gcaaaggttc aacgtcgggt ggcggttccg gcggtggctc aggtggcggt    1140
ggcagctctg gccaaccgcg cgaaccgcag gtttacaccc tgccgccgag ccgtgacgaa    1200
ctgaccaaaa accaagtcag cctgacgtgc ctggtgaaag cttttaccc gagtgacatt    1260 gcagttgaat gggaatccaa tggtcagccg gaaaataact acaaaacgac gccgccggtt    1320
```

```
ctggattcag acggctcgtt tttcctgtac tcaaaactga ccgtcgataa atcgcgctgg    1380
caacagggta acgttttcag ctgctctgtc atgcacgaag ccctgcacaa ccattatacc    1440
cagaaaagtc tgtccctgtc accgggcaaa gaagtgcagc tggttgaatc tggtggcggt    1500
ctggtgcaac cggcggttc gctgcgtctg agctgtgcag cttctggctt taatattaaa    1560
gacacgtaca tccactgggt gcgtcaggca ccgggtaaag gcctggaatg ggttgctcgt    1620
atctatccga cgaacggtta tacgcgttac gccgatagcg tcaaaggccg ttttaccatc    1680
agtgcagaca cctccaaaaa cacggcttat ctgcagatga atagtctgcg tgcagaagat    1740
accgctgttt attactgcag ccgctggggc ggtgatggct tctatgcaat ggattattgg    1800
ggtcaaggta ccctggtcac cgtgagttcc ggttcgacca gcggcggtgg ctcaggtggc    1860
ggttcgggcg gtggcggttc atcggacatt cagatgacgc aaagcccgag ctctctgtct    1920
gcgagtgttg gcgatcgtgt caccatcacg tgtcgcgcct ctcaggacgt gaataccgca    1980
gttgcttggt accaacaaaa accgggcaaa gcaccgaaac tgctgattta ctccgcttca    2040
ttcctgtaca gcggtgtgcc gtctcgtttt tcgggcagcc gctctggtac cgatttcacc    2100
ctgacgatta gttccctgca accggaagat ttcgccacct actactgcca gcaacactat    2160
acgaccccgc cgacgtttgg tcagggcacg aaagtggaaa ttaaataatg aaagctt     2217

<210> SEQ ID NO 77
<211> LENGTH: 2277
<212> TYPE: DNA
<213> ORGANISM: Artificial Sequence
<220> FEATURE:
<223> OTHER INFORMATION: Description of Artificial Sequence:
      Her2/neu antibody

<400> SEQUENCE: 77
catatgcatc accaccacca ccacgacgac gacgacaaag atattcaaat gacccagtcc    60
ccgagcagcc tgagtgcctc cgttggcgac cgcgtgacca ttacgtgccg tgcgagccag    120
gatgtcaaca ccgcggtggc ctggtatcag caaaaaccgg gcaaagcgcc gaaactgctg    180
atctattcag cctcgtttct gtacagcggt gttccgtctc gtttcagcgg ctctcgcagt    240
ggtaccgatt ttaccctgac gattagctct ctgcagccgg aagactttgc gacgtattac    300
tgccagcaac attacaccac gccgccgacc ttcggccagg gtacgaaagt ggaaatcaaa    360
ggttccacct caggcggtgg cagtggtggc ggttccggcg gtggcggtag ttccgaagtt    420
cagctggtcg aaagtggcgg tggcctggtt caaccgggtg gctcactgcg tctgtcgtgt    480
gcagcaagcg gtttcaacat caaagatacc tacatccact gggttcgtca ggcgccgggc    540
aaaggtctgg aatgggtcgc cgcatttac ccgaccaatg gctatacgcg ttacgcagat    600
agcgtgaaag gtcgctttac catctctgcg gacaccagta aaaacacggc ctatctgcag    660
atgaatagcc tgcgtgcgga agatacggcc gtttattact gctctcgctg gggtggcgat    720
ggcttctatg ctatggacta ctggggccag ggtaccctgg tgacggtttc atcgggtcag    780
ccgcgtgaac cgcaagtgta taccctgccg ccgtcacgcg atgaactgac gaaaaaccag    840
gtgtcgctga cgtgtctggt taaaggcttt tacccgagcg acatcgcggt tgaatgggaa    900
tctaatggtc aaccggaaaa caattataaa accacgccgc cggtcctgga tagtgacggc    960
tccttttttc tgtacagtaa actgaccgtg gataaatccc gttggcagca gggtaacgtc    1020
ttctcgtgta gcgtgatgca tgaagccctg cataatcact ataccagaa atctctgagt    1080 ctgtccccgg gcaaaggttc aacgtcgggt ggcggttccg gcggtggctc aggtggcggt    1140
```

| | |
|---|---|
| ggcagctctg gccaaccgcg cgaaccgcag gtttacaccc tgccgccgag ccgtgacgaa | 1200 |
| ctgaccaaaa accaagtcag cctgacgtgc ctggtgaaag cttttaccc gagtgacatt | 1260 |
| gcagttgaat gggaatccaa tggtcagccg gaaaataact acaaaacgac gccgccggtt | 1320 |
| ctggattcag acggctcgtt tttcctgtac tcaaaactga ccgtcgataa atcgcgctgg | 1380 |
| caacagggta acgttttcag ctgctctgtc atgcacgaag ccctgcacaa ccattatacc | 1440 |
| cagaaaagtc tgtccctgtc accgggcaaa gaagtgcagc tggttgaatc tggtggcggt | 1500 |
| ctggtgcaac cgggcggttc gctgcgtctg agctgtgcag cttctggctt taatattaaa | 1560 |
| gacacgtaca tccactgggt gcgtcaggca ccgggtaaag gcctggaatg ggttgctcgt | 1620 |
| atctatccga cgaacggtta tacgcgttac gccgatagcg tcaaaggccg ttttaccatc | 1680 |
| agtgcagaca cctccaaaaa cacggcttat ctgcagatga atagtctgcg tgcagaagat | 1740 |
| accgctgttt attactgcag ccgctggggc ggtgatggct ctatgcaat ggattattgg | 1800 |
| ggtcaaggta ccctggtcac cgtgagttcc ggttcgacca gcggcggtgg ctcaggtggc | 1860 |
| ggttcgggcg gtggcggttc atcggacatt cagatgacgc aaagcccgag ctctctgtct | 1920 |
| gcgagtgttg gcgatcgtgt caccatcacg tgtcgcgcct ctcaggacgt gaataccgca | 1980 |
| gttgcttggt accaacaaaa accgggcaaa gcaccgaaac tgctgattta ctccgcttca | 2040 |
| ttcctgtaca gcggtgtgcc gtctcgtttt tcgggcagcc gctctggtac cgatttcacc | 2100 |
| ctgacgatta gttccctgca accggaagat ttcgccacct actactgcca gcaacactat | 2160 |
| acgaccccgc cgacgtttgg tcagggcacg aaagtggaaa ttaaaggcag caaatttgcg | 2220 |
| aaattcgcca aaaattcgc aaaattcgcg aaaaaattcg cgaataatg aaagctt | 2277 |

<210> SEQ ID NO 78
<211> LENGTH: 2265
<212> TYPE: DNA
<213> ORGANISM: Artificial Sequence
<220> FEATURE:
<223> OTHER INFORMATION: Description of Artificial Sequence:
    Her2/neu antibody

<400> SEQUENCE: 78

| | |
|---|---|
| catatggaaa atctgtattt ccaaggtgat attcaaatga cccagtcccc gagcagcctg | 60 |
| agtgcctccg ttggcgaccg cgtgaccatt acgtgccgtg cgagccagga tgtcaacacc | 120 |
| gcggtggcct ggtatcagca aaaaccgggc aaagcgccga actgctgat ctattcagcc | 180 |
| tcgtttctgt acagcggtgt tccgtctcgt ttcagcggct ctcgcagtgg taccgatttt | 240 |
| accctgacga ttagctctct gcagccggaa gactttgcga cgtattactg ccagcaacat | 300 |
| tacaccacgc cgccgacctt cggccagggt acgaaagtgg aaatcaaagg ttccaccta | 360 |
| ggcggtggca gtggtggcgg ttccggcggt ggcggtagtt ccgaagttca gctggtcgaa | 420 |
| agtggcggtg gcctggttca accgggtggc tcactgcgtc tgtcgtgtgc agcaagcgt | 480 |
| ttcaacatca agataccta catccactgg gttcgtcagg cgccgggcaa aggtctggaa | 540 |
| tgggtcgccc gcatttaccc gaccaatggc tatacgcgtt acgcagatag cgtgaaaggt | 600 |
| cgctttacca tctctgcgga caccagtaaa aacacggcct atctgcagat gaatagcctg | 660 |
| cgtgcggaag atacggccgt ttattactgc tctcgctggg gtggcgatgg cttctatgct | 720 |
| atggactact ggggccaggg taccctggtc acggttcat cgggtcagcc gcgtgaaccg | 780 |
| caagtgtata ccctgccgcc gtcacgcgat gaactgacga aaaaccaggt gtcgctgacg | 840 |
| tgtctggtta aaggcttta cccgagcgac atcgcggttg aatgggaatc taatggtcaa | 900 |

```
ccggaaaaca attataaaac cacgccgccg gtcctggata gtgacggctc ctttttcctg      960
tacagtaaac tgaccgtgga taaatcccgt tggcagcagg gtaacgtctt ctcgtgtagc     1020
gtgatgcatg aagccctgca taatcactat acccagaaat ctctgagtct gtccccgggc     1080
aaaggttcaa cgtcgggtgg cggttccggc ggtggctcag gtggcggtgg cagctctggc     1140
caaccgcgcg aaccgcaggt ttacaccctg ccgccgagcc gtgacgaact gaccaaaaac     1200
caagtcagcc tgacgtgcct ggtgaaaggc ttttacccga gtgacattgc agttgaatgg     1260
gaatccaatg gtcagccgga aaataactac aaaacgacgc cgccggttct ggattcagac     1320
ggctcgtttt tcctgtactc aaaactgacc gtcgataaat cgcgctggca cagggtaac      1380 gttttcagct gctctgtcat gcacgaagcc ctgcacaacc attataccca gaaaagtctg     1440
tccctgtcac cgggcaaaga agtgcagctg gttgaatctg gtggcggtct ggtgcaaccg     1500
ggcggttcgc tgcgtctgag ctgtgcagct tctggcttta atattaaaga cacgtacatc     1560
cactgggtgc gtcaggcacc gggtaaaggc ctggaatggg ttgctcgtat ctatccgacg     1620
aacggttata cgcgttacgc cgatagcgtc aaaggccgtt ttaccatcag tgcagacacc     1680
tccaaaaaca cggcttatct gcagatgaat agtctgcgtg cagaagatac cgctgtttat     1740
tactgcagcc gctggggcgg tgatggcttc tatgcaatgg attattgggg tcaaggtacc     1800
ctggtcaccg tgagttccgg ttcgaccagc ggcggtggct caggtggcgg ttcgggcggt     1860
ggcggttcat cggacattca gatgacgcaa agcccgagct ctctgtctgc gagtgttggc     1920
gatcgtgtca ccatcacgtg tcgcgcctct caggacgtga ataccgcagt tgcttggtac     1980
caacaaaaac cgggcaaagc accgaaactg ctgatttact ccgcttcatt cctgtacagc     2040
ggtgtgccgt ctcgttttc gggcagccgc tctggtaccg atttcaccct gacgattagt     2100
tccctgcaac cggaagattt cgccacctac tactgccagc aacactatac gaccccgccg     2160
acgtttggtc agggcacgaa agtggaaatt aaaggcagca actggcgaa actggccaaa     2220 aaactggcaa aactggcgaa aaaactggcg aaataatgaa agctt                     2265
```

<210> SEQ ID NO 79
<211> LENGTH: 2277
<212> TYPE: DNA
<213> ORGANISM: Artificial Sequence
<220> FEATURE:
<223> OTHER INFORMATION: Description of Artificial Sequence:
      Her2/neu antibody

<400> SEQUENCE: 79

```
catatggaaa atctgtattt ccaaggtgat attcaaatga cccagtcccc gagcagcctg       60
agtgcctccg ttggcgaccg cgtgaccatt acgtgccgtg cgagccagga tgtcaacacc      120
gcggtggcct ggtatcagca aaaaccgggc aaagcgccga aactgctgat ctattcagcc      180
tcgtttctgt acagcggtgt tccgtctcgt ttcagcggct ctcgcagtgg taccgatttt      240
accctgacga ttagctctct gcagccggaa gactttgcga cgtattactg ccagcaacat      300
tacaccacgc cgccgacctt cggccagggt acgaaagtgg aaatcaaagg ttccacctca      360
ggcggtggca gtggtggcgg ttccggcggt ggcggtagtt ccgaagttca gctggtcgaa      420
agtggcggtg gcctggttca accgggtggc tcactgcgtc tgtcgtgtgc agcaagcggt      480
ttcaacatca agataccta catccactgg gttcgtcagg cgccgggcaa aggtctggaa      540
tgggtcgccc gcatttaccc gaccaatggc tatacgcgtt acgcagatag cgtgaaaggt      600
cgctttacca tctctgcgga caccagtaaa aacacggcct atctgcagat gaatagcctg      660
```

```
cgtgcggaag atacggccgt ttattactgc tctcgctggg gtggcgatgg cttctatgct    720
atggactact ggggccaggg taccctggtg acggtttcat cgggtcagcc gcgtgaaccg    780
caagtgtata ccctgccgcc gtcacgcgat gaactgacga aaaaccaggt gtcgctgacg    840
tgtctggtta aaggctttta cccgagcgac atcgcggttg aatgggaatc taatggtcaa    900
ccggaaaaca attataaaac cacgccgccg gtcctggata tgacggctc ctttttcctg     960
tacagtaaac tgaccgtgga taaatcccgt tggcagcagg gtaacgtctt ctcgtgtagc   1020
gtgatgcatg aagccctgca taatcactat acccagaaat ctctgagtct gtccccgggc   1080
aaaggttcaa cgtcgggtgg cggttccggc ggtggctcag gtggcggtgg cagctctggc   1140
caaccgcgcg aaccgcaggt ttacaccctg ccgccgagcc gtgacgaact gaccaaaaac   1200
caagtcagcc tgacgtgcct ggtgaaaggc ttttacccga gtgacattgc agttgaatgg   1260
gaatccaatg gtcagccgga aaataactac aaaacgacgc cgccggttct ggattcagac   1320
ggctcgtttt tcctgtactc aaaactgacc gtcgataaat cgcgctggca acagggtaac   1380
gttttcagct gctctgtcat gcacgaagcc ctgcacaacc attatcccca gaaaagtctg   1440
tccctgtcac cgggcaaaga agtgcagctg gttgaatctg gtggcggtct ggtgcaaccg   1500
ggcggttcgc tgcgtctgag ctgtgcagct tctggcttta atattaaaga cacgtacatc   1560
cactgggtgc gtcaggcacc gggtaaaggc ctggaatggg ttgctcgtat ctatccgacg   1620
aacggttata cgcgttacgc cgatagcgtc aaaggccgtt ttaccatcag tgcagacacc   1680
tccaaaaaca cggcttatct gcagatgaat agtctgcgtg cagaagatac cgctgtttat   1740
tactgcagcc gctggggcgg tgatggcttc tatgcaatgg attattgggg tcaaggtacc   1800
ctggtcaccg tgagttccgg ttcgaccagc ggcggtggct caggtggcgg ttcgggcggt   1860
ggcggttcat cggacattca gatgacgcaa agcccgagct ctctgtctgc gagtgttggc   1920
gatcgtgtca ccatcacgtg tcgcgcctct caggacgtga ataccgcagt tgcttggtac   1980
caacaaaaac cgggcaaagc accgaaactg ctgatttact ccgcttcatt cctgtacagc   2040
ggtgtgccgt ctcgttttc gggcagccgc tctggtaccg atttcaccct gacgattagt   2100
tccctgcaac cggaagattt cgccacctac tactgccagc aacactatac gaccccgccg   2160
acgtttggtc agggcacgaa agtggaaatt aaaaaccgtg tgcgtcgcag caaatttgcg   2220
aaattcgcca aaaatttgc aaaattcgct aaaaaatttg cgaaataatg aaagctt       2277
```

<210> SEQ ID NO 80
<211> LENGTH: 2289
<212> TYPE: DNA
<213> ORGANISM: Artificial Sequence
<220> FEATURE:
<223> OTHER INFORMATION: Description of Artificial Sequence:
      Her2/neu antibody

<400> SEQUENCE: 80

```
catatgcatc accaccacca ccacgacgac gacgacaaag atattcaaat gacccagtcc     60
ccgagcagcc tgagtgcctc cgttggcgac cgcgtgacca ttacgtgccg tgcgagccag    120
gatgtcaaca ccgcggtggc ctggtatcag caaaaaccgg gcaaagcgcc gaaactgctg    180
atctattcag cctcgtttct gtacagcggt gttccgtctc gtttcagcgg ctctcgcagt    240
ggtaccgatt ttaccctgac gattagtctc ctgcagccgg aagactttgc gacgtattac    300
tgccagcaac attacaccac gccgccgacc ttcggccagg gtacgaaagt ggaaatcaaa    360
ggttccacct caggcggtgg cagtggtggc ggttccggcg gtggcggtag ttccgaagtt    420
```

```
cagctggtcg aaagtggcgg tggcctggtt caaccgggtg gctcactgcg tctgtcgtgt     480
gcagcaagcg gtttcaacat caaagatacc tacatccact gggttcgtca ggcgccgggc     540
aaaggtctgg aatgggtcgc ccgcatttac ccgaccaatg gctatacgcg ttacgcagat     600
agcgtgaaag gtcgctttac catctctgcg gacaccagta aaaacacggc ctatctgcag     660
atgaatagcc tgcgtgcgga agatacggcc gtttattact gctctcgctg gggtggcgat     720
ggcttctatg ctatggacta ctggggccag ggtaccctgg tgacggtttc atcgggtcag     780
ccgcgtgaac cgcaagtgta ccctgccgcc gtcacgcg atgaactgac gaaaaaccag       840
gtgtcgctga cgtgtctggt taaaggcttt tacccgagcg acatcgcggt tgaatgggaa     900
tctaatggtc aaccggaaaa caattataaa accacgccgc cggtcctgga tagtgacggc     960 tccttttttcc tgtacagtaa actgaccgtg gataaatccc gttggcagca gggtaacgtc    1020
ttctcgtgta gcgtgatgca tgaagccctg cataatcact atcccagaa atctctgagt     1080 ctgtccccgg gcaaaggttc aacgtcgggt ggcggttccg gcggtggctc aggtggcggt     1140
ggcagctctg gccaaccgcg cgaaccgcag gtttacaccc tgccgccgag ccgtgacgaa     1200
ctgaccaaaa accaagtcag cctgacgtgc ctggtgaaag cttttaccc gagtgacatt     1260 gcagttgaat gggaatccaa tggtcagccg gaaaataact acaaaacgac gccgccggtt    1320
ctggattcag acggctcgtt tttcctgtac tcaaaactga ccgtcgataa atcgcgctgg    1380
caacagggta acgttttcag ctgctctgtc atgcacgaag ccctgcacaa ccattatacc    1440
cagaaaagtc tgtccctgtc accgggcaaa gaagtgcagc tggttgaatc tggtggcggt    1500
ctggtgcaac cgggcggttc gctgcgtctg agctgtgcag cttctggctt taatattaaa    1560
gacacgtaca tccactgggt gcgtcaggca ccgggtaaag gcctggaatg ggttgctcgt    1620
atctatccga cgaacggtta tacgcgttac gccgatagcg tcaaaggccg tttttaccatc    1680 agtgcagaca cctccaaaaa cacggcttat ctgcagatga atagtctgcg tgcagaagat    1740
accgctgttt attactgcag ccgctggggc ggtgatggct tctatgcaat ggattattgg    1800
ggtcaaggta ccctggtcac cgtgagttcc ggttcgacca gcggcggtgg ctcaggtggc    1860
ggttcgggcg gtggcggttc atcggacatt cagatgacgc aaagcccgag ctctctgtct    1920
gcgagtgttg gcgatcgtgt caccatcacg tgtcgcgcct tcaggacgt gaataccgca    1980 gttgcttggt accaacaaaa accgggcaaa gcaccgaaac tgctgattta ctccgcttca    2040
ttcctgtaca gcggtgtgcc gtctcgtttt tcgggcagcc gctctggtac cgatttcacc    2100
ctgacgatta gttccctgca accggaagat ttcgccacct actactgcca gcaacactat    2160 acgacccgc cgacgtttgg tcagggcacg aaagtggaaa ttaaaaaccg tgtgcgtcgc    2220
agcaaactgg cgaaactggc caaaaaactg gcaaaactgg ctaaaaaact ggcgaaataa    2280
tgaaagctt                                                            2289
```

<210> SEQ ID NO 81
<211> LENGTH: 2313
<212> TYPE: DNA
<213> ORGANISM: Artificial Sequence
<220> FEATURE:
<223> OTHER INFORMATION: Description of Artificial Sequence:
      Her2/neu antibody

<400> SEQUENCE: 81

```
catatggaaa atctgtattt ccaaggtaaa tttgcgaaat tcgccaaaaa attcgcaaaa      60
ttcgcgaaaa aattcgcgaa agatattcaa atgacccagt ccccgagcag cctgagtgcc    120
```

```
tccgttggcg accgcgtgac cattacgtgc cgtgcgagcc aggatgtcaa caccgcggtg      180
gcctggtatc agcaaaaacc gggcaaagcg ccgaaactgc tgatctattc agcctcgttt      240
ctgtacagcg gtgttccgtc tcgtttcagc ggctctcgca gtggtaccga ttttaccctg      300
acgattagct ctctgcagcc ggaagacttt gcgacgtatt actgccagca acattacacc      360
acgccgccga ccttcggcca gggtacgaaa gtggaaatca aggttccac ctcaggcggt       420
ggcagtggtg gcggttccgg cggtggcggt agttccgaag ttcagctggt cgaaagtggc      480
ggtggcctgg ttcaaccggg tggctcactg cgtctgtcgt gtgcagcaag cggtttcaac      540
atcaaagata cctacatcca ctgggttcgt caggcgccgg gcaaaggtct ggaatgggtc      600
gcccgcattt acccgaccaa tggctatacg cgttacgcag atagcgtgaa aggtcgcttt      660
accatctctg cggacaccag taaaaacacg gcctatctgc agatgaatag cctgcgtgcg      720
gaagatacgg ccgtttatta ctgctctcgc tggggtggcg atggcttcta tgctatggac      780
tactggggcc agggtaccct ggtgacggtt tcatcgggtc agccgcgtga accgcaagtg      840
tataccctgc cgccgtcacg cgatgaactg acgaaaaacc aggtgtcgct gacgtgtctg      900
gttaaaggct tttacccgag cgacatcgcg gttgaatggg aatctaatgg tcaaccggaa      960
aacaattata aaccacgcc gccggtcctg gatagtgacg gctcctttt cctgtacagt       1020
aaactgaccg tggataaatc ccgttggcag caggtaacg tcttctcgtg tagcgtgatg       1080
catgaagccc tgcataatca ctatacccag aaatctctga gtctgtcccc gggcaaaggt      1140
tcaacgtcgg gtggcggttc cggcggtggc tcaggtggcg gtggcagctc tggccaaccg      1200
cgcgaaccgc aggtttacac cctgccgccg agccgtgacg aactgaccaa aaaccaagtc      1260
agcctgacgt gcctggtgaa aggctttttac ccgagtgaca ttgcagttga atgggaatcc      1320
aatggtcagc cggaaaataa ctacaaaacg acgccgccgg ttctggattc agacggctcg      1380
ttttcctgt actcaaaact gaccgtcgat aaatcgcgct ggcaacaggg taacgttttc       1440
agctgctctg tcatgcacga agccctgcac aaccattata cccagaaaag tctgtccctg      1500
tcaccgggca agaagtgca gctggttgaa tctggtggcg gtctggtgca accgggcggt       1560
tcgctgcgtc tgagctgtgc agcttctggc tttaatatta agacacgta catccactgg       1620
gtgcgtcagg caccgggtaa aggcctggaa tgggttgctc gtatctatcc gacgaacggt      1680
tatacgcgtt acgccgatag cgtcaaaggc cgttttacca tcagtgcaga cacctccaaa      1740
aacacggctt atctgcagat gaatagtctg cgtgcagaag ataccgctgt ttattactgc      1800
agccgctggg gcgtgatgg cttctatgca atggattatt ggggtcaagg taccctggtc       1860
accgtgagtt ccggttcgac cagcggcggt ggctcaggtg gcggttcggg cggtggcggt      1920
tcatcggaca ttcagatgac gcaaagcccg agctctctgt ctgcgagtgt tggcgatcgt      1980
gtcaccatca cgtgtcgcgc ctctcaggac gtgaataccg cagttgcttg gtaccaacaa      2040
aaaccgggca agcaccgaa actgctgatt tactccgctt cattcctgta cagcggtgtg       2100
ccgtctcgtt tttcgggcag ccgctctggt accgatttca ccctgacgat tagttccctg      2160
caaccggaag atttcgccac ctactactgc cagcaacact atacgacccc gccgacgttt      2220
ggtcagggca cgaaagtgga aattaaaaaa tttgcgaaat cgccaaaaa attcgcaaaa      2280
ttcgcgaaaa aattcgcgaa ataatgaaag ctt                                   2313
```

<210> SEQ ID NO 82
<211> LENGTH: 948
<212> TYPE: PRT

<213> ORGANISM: Artificial Sequence
<220> FEATURE:
<223> OTHER INFORMATION: Description of Artificial Sequence:
      Recombinant anti-Her2 antibody

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Ser Ser Glu Val Gln
            115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
        405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys Gly Ser Thr Ser Gly Gly Ser Gly Gly Ser Gly Gly Gly
465                 470                 475                 480

Gly Ser Ser Gly Gln Pro Arg Glu Pro Gln Val Tyr Thr Leu Pro Pro
            485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
            565                 570                 575

Asn His Tyr Thr Gln Lys Ser Leu Ser Leu Ser Pro Gly Lys Pro Cys
        580                 585                 590

Pro Ala Pro Glu Leu Leu Gly Gly Pro Ser Val Phe Leu Phe Pro Pro
        595                 600                 605

Lys Pro Lys Asp Thr Leu Met Ile Ser Arg Thr Pro Glu Val Thr Cys
610                 615                 620

Val Val Val Asp Val Ser His Glu Asp Pro Glu Val Lys Phe Asn Trp
625                 630                 635                 640

Tyr Val Asp Gly Val Glu Val His Asn Ala Lys Thr Lys Pro Arg Glu
            645                 650                 655

Glu Gln Tyr Asn Ser Thr Tyr Arg Val Val Ser Val Leu Thr Val Leu
            660                 665                 670

His Gln Asp Trp Leu Asn Gly Lys Glu Tyr Lys Cys Lys Val Ser Asn
        675                 680                 685

Lys Ala Leu Pro Ala Pro Ile Glu Lys Thr Ile Ser Lys Ala Lys Glu
        690                 695                 700

Val Gln Leu Val Glu Ser Gly Gly Leu Val Gln Pro Gly Gly Ser
705                 710                 715                 720

Leu Arg Leu Ser Cys Ala Ala Ser Gly Phe Asn Ile Lys Asp Thr Tyr
                725                 730                 735

Ile His Trp Val Arg Gln Ala Pro Gly Lys Gly Leu Glu Trp Val Ala
            740                 745                 750

Arg Ile Tyr Pro Thr Asn Gly Tyr Thr Arg Tyr Ala Asp Ser Val Lys
            755                 760                 765

Gly Arg Phe Thr Ile Ser Ala Asp Thr Ser Lys Asn Thr Ala Tyr Leu
        770                 775                 780

Gln Met Asn Ser Leu Arg Ala Glu Asp Thr Ala Val Tyr Tyr Cys Ser
785                 790                 795                 800

Arg Trp Gly Gly Asp Gly Phe Tyr Ala Met Asp Tyr Trp Gly Gln Gly
```

```
                    805                 810                 815
Thr Leu Val Thr Val Ser Ser Gly Ser Thr Gly Gly Ser Gly
                820                 825                 830

Gly Gly Ser Gly Gly Gly Ser Ser Asp Ile Gln Met Thr Gln Ser
                835                 840                 845

Pro Ser Ser Leu Ser Ala Ser Val Gly Asp Arg Val Thr Ile Thr Cys
    850                 855                 860

Arg Ala Ser Gln Asp Val Asn Thr Ala Val Ala Trp Tyr Gln Gln Lys
865                 870                 875                 880

Pro Gly Lys Ala Pro Lys Leu Leu Ile Tyr Ser Ala Ser Phe Leu Tyr
                885                 890                 895

Ser Gly Val Pro Ser Arg Phe Ser Gly Ser Arg Ser Gly Thr Asp Phe
                900                 905                 910

Thr Leu Thr Ile Ser Ser Leu Gln Pro Glu Asp Phe Ala Thr Tyr Tyr
                915                 920                 925

Cys Gln Gln His Tyr Thr Thr Pro Pro Thr Phe Gly Gln Gly Thr Lys
                930                 935                 940

Val Glu Ile Lys
945

<210> SEQ ID NO 83
<211> LENGTH: 968
<212> TYPE: PRT
<213> ORGANISM: Artificial Sequence
<220> FEATURE:
<223> OTHER INFORMATION: Description of Artificial Sequence:
      Lytic peptide conjugate

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
                100                 105                 110

Gly Gly Ser Gly Gly Gly Ser Gly Gly Gly Ser Ser Glu Val Gln
            115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205
```

-continued

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Asp Val Ser His Glu Asp
            275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Lys Gly Ser Thr Ser Gly Gly Gly Ser Gly Gly Gly Ser Gly Gly Gly
465                 470                 475                 480

Gly Ser Ser Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys Pro Cys
            580                 585                 590

Pro Ala Pro Glu Leu Leu Gly Gly Pro Ser Val Phe Leu Phe Pro Pro
        595                 600                 605

Lys Pro Lys Asp Thr Leu Met Ile Ser Arg Thr Pro Glu Val Thr Cys
610                 615                 620

Val Val Val Asp Val Ser His Glu Asp Pro Glu Val Lys Phe Asn Trp

Tyr Val Asp Gly Val Glu Val His Asn Ala Lys Thr Lys Pro Arg Glu
            625                 630                 635                 640

Glu Gln Tyr Asn Ser Thr Tyr Arg Val Val Ser Val Leu Thr Val Leu
            645                 650                 655

His Gln Asp Trp Leu Asn Gly Lys Glu Tyr Lys Cys Lys Val Ser Asn
            660                 665                 670

Lys Ala Leu Pro Ala Pro Ile Glu Lys Thr Ile Ser Lys Ala Lys Glu
            675                 680                 685

Val Gln Leu Val Glu Ser Gly Gly Leu Val Gln Pro Gly Gly Ser
705             710                 715                 720

Leu Arg Leu Ser Cys Ala Ala Ser Gly Phe Asn Ile Lys Asp Thr Tyr
                725                 730                 735

Ile His Trp Val Arg Gln Ala Pro Gly Lys Gly Leu Glu Trp Val Ala
                740                 745                 750

Arg Ile Tyr Pro Thr Asn Gly Tyr Thr Arg Tyr Ala Asp Ser Val Lys
                755                 760                 765

Gly Arg Phe Thr Ile Ser Ala Asp Thr Ser Lys Asn Thr Ala Tyr Leu
770                 775                 780

Gln Met Asn Ser Leu Arg Ala Glu Asp Thr Ala Val Tyr Tyr Cys Ser
785                 790                 795                 800

Arg Trp Gly Gly Asp Gly Phe Tyr Ala Met Asp Tyr Trp Gly Gln Gly
                805                 810                 815

Thr Leu Val Thr Val Ser Ser Gly Ser Thr Gly Gly Ser Gly
                820                 825                 830

Gly Gly Ser Gly Gly Gly Ser Ser Asp Ile Gln Met Thr Gln Ser
                835                 840                 845

Pro Ser Ser Leu Ser Ala Ser Val Gly Asp Arg Val Thr Ile Thr Cys
                850                 855                 860

Arg Ala Ser Gln Asp Val Asn Thr Ala Val Ala Trp Tyr Gln Gln Lys
865                 870                 875                 880

Pro Gly Lys Ala Pro Lys Leu Leu Ile Tyr Ser Ala Ser Phe Leu Tyr
                885                 890                 895

Ser Gly Val Pro Ser Arg Phe Ser Gly Ser Arg Ser Gly Thr Asp Phe
                900                 905                 910

Thr Leu Thr Ile Ser Ser Leu Gln Pro Glu Asp Phe Ala Thr Tyr Tyr
                915                 920                 925

Cys Gln Gln His Tyr Thr Thr Pro Pro Thr Phe Gly Gln Gly Thr Lys
                930                 935                 940

Val Glu Ile Lys Gly Ser Lys Phe Ala Lys Phe Ala Lys Lys Phe Ala
945                 950                 955                 960

Lys Phe Ala Lys Lys Phe Ala Lys
                965

<210> SEQ ID NO 84
<211> LENGTH: 214
<212> TYPE: PRT
<213> ORGANISM: Artificial Sequence
<220> FEATURE:
<223> OTHER INFORMATION: Description of Artificial Sequence:
      Anti-Her2/neu light chain antibody

<400> SEQUENCE: 84

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 451
<212> TYPE: PRT
<213> ORGANISM: Artificial Sequence
<220> FEATURE:
<223> OTHER INFORMATION: Description of Artificial Sequence:
      Her2/neu heavy chain antibody

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 86
<211> LENGTH: 234
<212> TYPE: PRT
<213> ORGANISM: Artificial Sequence
<220> FEATURE:
<223> OTHER INFORMATION: Description of Artificial Sequence:
      Light chain antibody

<400> SEQUENCE: 86

Lys Phe Ala Lys Phe Ala Lys Lys Phe Ala Lys Phe Ala Lys Lys Phe
1               5                   10                  15

Ala Lys Gly Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
```

```
                50                  55                  60
Lys Leu Leu Ile Tyr Ser Ala Ser Phe Leu Tyr Ser Gly Val Pro Ser
 65                  70                  75                  80

Arg Phe Ser Gly Ser Arg Ser Gly Thr Asp Phe Thr Leu Thr Ile Ser
                 85                  90                  95

Ser Leu Gln Pro Glu Asp Phe Ala Thr Tyr Tyr Cys Gln Gln His Tyr
                100                 105                 110

Thr Thr Pro Pro Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 87
<211> LENGTH: 235
<212> TYPE: PRT
<213> ORGANISM: Artificial Sequence
<220> FEATURE:
<223> OTHER INFORMATION: Description of Artificial Sequence:
      Light chain antibody

<400> SEQUENCE: 87

```
Asp Ile Gln Met Thr Gln Ser Pro Ser Ser Leu Ser Ala Ser Val Gly
 1                   5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ser Lys Phe Ala Lys Phe Ala Lys Lys
    210                 215                 220

Phe Ala Lys Phe Ala Lys Lys Phe Ala Lys Ala
225                 230                 235

<210> SEQ ID NO 88
<211> LENGTH: 255
<212> TYPE: PRT
<213> ORGANISM: Artificial Sequence
<220> FEATURE:
<223> OTHER INFORMATION: Description of Artificial Sequence:
      Light chain antibody

<400> SEQUENCE: 88

Lys Phe Ala Lys Phe Ala Lys Lys Phe Ala Lys Phe Ala Lys Lys Phe
1               5                   10                  15

Ala Lys Gly Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Ser Lys Phe Ala Lys
225                 230                 235                 240

Phe Ala Lys Lys Phe Ala Lys Phe Ala Lys Lys Phe Ala Lys Ala
                245                 250                 255

<210> SEQ ID NO 89
<211> LENGTH: 471
<212> TYPE: PRT
<213> ORGANISM: Artificial Sequence
<220> FEATURE:
<223> OTHER INFORMATION: Description of Artificial Sequence:
      Heavy chain antibody
```

<400> SEQUENCE: 89

Lys Phe Ala Lys Phe Ala Lys Phe Ala Lys Phe Ala Lys Lys Phe
1               5                   10                  15

Ala Lys Gly Ser Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys

```
                    405                 410                 415
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 90
<211> LENGTH: 472
<212> TYPE: PRT
<213> ORGANISM: Artificial Sequence
<220> FEATURE:
<223> OTHER INFORMATION: Description of Artificial Sequence:
      Heavy chain antibody

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Ser Lys Phe Ala Lys Phe Lys Lys Phe Ala Lys
    450                 455                 460

Phe Ala Lys Lys Phe Ala Lys Ala
465                 470

<210> SEQ ID NO 91
<211> LENGTH: 492
<212> TYPE: PRT
<213> ORGANISM: Artificial Sequence
<220> FEATURE:
<223> OTHER INFORMATION: Description of Artificial Sequence:
      Heavy chain antibody

<400> SEQUENCE: 91

Lys Phe Ala Lys Phe Ala Lys Lys Phe Ala Lys Phe Ala Lys Lys Phe
1               5                   10                  15

Ala Lys Gly Ser Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
            210                 215                 220

Val Asn His Lys Pro Ser Asn Thr Lys Val Asp Lys Val Glu Pro
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys Gly Ser Lys Phe Ala Lys Phe Ala Lys
465                 470                 475                 480

Lys Phe Ala Lys Phe Ala Lys Lys Phe Ala Lys Ala
                485                 490

<210> SEQ ID NO 92
<211> LENGTH: 249
<212> TYPE: PRT
<213> ORGANISM: Artificial Sequence
<220> FEATURE:
<223> OTHER INFORMATION: Description of Artificial Sequence:
      scFv fragment

<400> SEQUENCE: 92

His His His His His Asp Ile Gln Leu Thr Gln Ser Pro Ala Ile
1               5                   10                  15

Leu Ser Ala Ser Pro Gly Glu Lys Val Thr Met Thr Cys Arg Ala Ser
            20                  25                  30

Ser Ser Val Ser Tyr Ile His Trp Phe Gln Gln Lys Pro Gly Ser Ser
```

```
        35                  40                  45
Pro Lys Pro Trp Ile Tyr Ala Thr Ser Asn Leu Ala Ser Gly Val Pro
 50                  55                  60

Val Arg Phe Ser Gly Ser Gly Ser Gly Thr Ser Tyr Ser Leu Thr Ile
 65                  70                  75                  80

Ser Arg Val Glu Ala Glu Asp Ala Ala Thr Tyr Tyr Cys Gln Gln Trp
                 85                  90                  95

Thr Ser Asn Pro Pro Thr Phe Gly Gly Gly Thr Lys Leu Glu Ile Gly
                100                 105                 110

Ser Thr Ser Gly Gly Gly Ser Gly Gly Ser Gly Gly Gly Gly Ser
                115                 120                 125

Ser Val Gln Leu Gln Gln Pro Gly Ala Glu Leu Val Lys Pro Gly Ala
            130                 135                 140

Ser Val Lys Met Ser Cys Lys Ala Ser Gly Tyr Thr Phe Thr Ser Tyr
145                 150                 155                 160

Asn Met His Trp Val Lys Gln Thr Pro Gly Arg Gly Leu Glu Trp Ile
                165                 170                 175

Gly Ala Ile Tyr Pro Gly Asn Gly Asp Thr Ser Tyr Asn Gln Lys Phe
                180                 185                 190

Lys Gly Lys Ala Thr Leu Thr Ala Asp Lys Ser Ser Ser Thr Ala Tyr
            195                 200                 205

Met Gln Leu Ser Ser Leu Thr Ser Glu Asp Ser Ala Val Tyr Tyr Cys
        210                 215                 220

Ala Arg Ser Thr Tyr Tyr Gly Gly Asp Trp Tyr Phe Asp Val Trp Gly
225                 230                 235                 240

Gln Gly Thr Thr Val Thr Val Ser Ser
                245

<210> SEQ ID NO 93
<211> LENGTH: 269
<212> TYPE: PRT
<213> ORGANISM: Artificial Sequence
<220> FEATURE:
<223> OTHER INFORMATION: Description of Artificial Sequence:
      scFv-Phor18 conjugate

<400> SEQUENCE: 93

His His His His His His Asp Ile Gln Leu Thr Gln Ser Pro Ala Ile
  1               5                  10                  15

Leu Ser Ala Ser Pro Gly Glu Lys Val Thr Met Thr Cys Arg Ala Ser
                 20                  25                  30

Ser Ser Val Ser Tyr Ile His Trp Phe Gln Gln Lys Pro Gly Ser Ser
             35                  40                  45

Pro Lys Pro Trp Ile Tyr Ala Thr Ser Asn Leu Ala Ser Gly Val Pro
 50                  55                  60

Val Arg Phe Ser Gly Ser Gly Ser Gly Thr Ser Tyr Ser Leu Thr Ile
 65                  70                  75                  80

Ser Arg Val Glu Ala Glu Asp Ala Ala Thr Tyr Tyr Cys Gln Gln Trp
                 85                  90                  95

Thr Ser Asn Pro Pro Thr Phe Gly Gly Gly Thr Lys Leu Glu Ile Gly
                100                 105                 110

Ser Thr Ser Gly Gly Gly Ser Gly Gly Ser Gly Gly Gly Gly Ser
                115                 120                 125

Ser Val Gln Leu Gln Gln Pro Gly Ala Glu Leu Val Lys Pro Gly Ala
            130                 135                 140
```

```
Ser Val Lys Met Ser Cys Lys Ala Ser Gly Tyr Thr Phe Thr Ser Tyr
145                 150                 155                 160

Asn Met His Trp Val Lys Gln Thr Pro Gly Arg Gly Leu Glu Trp Ile
                165                 170                 175

Gly Ala Ile Tyr Pro Gly Asn Gly Asp Thr Ser Tyr Asn Gln Lys Phe
            180                 185                 190

Lys Gly Lys Ala Thr Leu Thr Ala Asp Lys Ser Ser Thr Ala Tyr
        195                 200                 205

Met Gln Leu Ser Ser Leu Thr Ser Glu Asp Ser Ala Val Tyr Tyr Cys
    210                 215                 220

Ala Arg Ser Thr Tyr Tyr Gly Gly Asp Trp Tyr Phe Asp Val Trp Gly
225                 230                 235                 240

Gln Gly Thr Thr Val Thr Val Ser Ser Gly Ser Lys Phe Ala Lys Phe
                245                 250                 255

Ala Lys Lys Phe Ala Lys Phe Ala Lys Lys Phe Ala Lys
            260                 265

<210> SEQ ID NO 94
<211> LENGTH: 717
<212> TYPE: PRT
<213> ORGANISM: Artificial Sequence
<220> FEATURE:
<223> OTHER INFORMATION: Description of Artificial Sequence:
      Anti-CD20 mimibody

<400> SEQUENCE: 94

Asp Ile Gln Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Gly Ser Thr Ser Gly Gly Gly
            100                 105                 110

Ser Gly Gly Gly Ser Gly Gly Gly Ser Ser Val Gln Leu Gln Gln
        115                 120                 125

Pro Gly Ala Glu Leu Val Lys Pro Gly Ala Ser Val Lys Met Ser Cys
130                 135                 140

Lys Ala Ser Gly Tyr Thr Phe Thr Ser Tyr Asn Met His Trp Val Lys
145                 150                 155                 160

Gln Thr Pro Gly Arg Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Ser Thr Tyr Tyr
    210                 215                 220

Gly Gly Asp Trp Tyr Phe Asp Val Trp Gly Gln Gly Thr Thr Val Thr
225                 230                 235                 240
```

```
Val Ser Ser Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys Gly Ser
            340                 345                 350

Thr Ser Gly Gly Gly Ser Gly Gly Gly Ser Gly Gly Gly Ser Ser
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Val Gln Leu Gln Gln
465                 470                 475                 480

Pro Gly Ala Glu Leu Val Lys Pro Gly Ala Ser Val Lys Met Ser Cys
                485                 490                 495

Lys Ala Ser Gly Tyr Thr Phe Thr Ser Tyr Asn Met His Trp Val Lys
            500                 505                 510

Gln Thr Pro Gly Arg Gly Leu Glu Trp Ile Gly Ala Ile Tyr Pro Gly
        515                 520                 525

Asn Gly Asp Thr Ser Tyr Asn Gln Lys Phe Lys Gly Lys Ala Thr Leu
    530                 535                 540

Thr Ala Asp Lys Ser Ser Thr Ala Tyr Met Gln Leu Ser Ser Leu
545                 550                 555                 560

Thr Ser Glu Asp Ser Ala Val Tyr Tyr Cys Ala Arg Ser Thr Tyr Tyr
                565                 570                 575

Gly Gly Asp Trp Tyr Phe Asp Val Trp Gly Gln Gly Thr Thr Val Thr
            580                 585                 590

Val Ser Gly Ser Thr Ser Gly Gly Gly Ser Gly Gly Gly Ser Gly
        595                 600                 605

Gly Gly Gly Ser Ser Asp Ile Gln Leu Thr Gln Ser Pro Ala Ile Leu
    610                 615                 620

Ser Ala Ser Pro Gly Glu Lys Val Thr Met Thr Cys Arg Ala Ser Ser
625                 630                 635                 640

Ser Val Ser Tyr Ile His Trp Phe Gln Gln Lys Pro Gly Ser Ser Pro
                645                 650                 655
```

```
Lys Pro Trp Ile Tyr Ala Thr Ser Asn Leu Ala Ser Gly Val Pro Val
            660                 665                 670

Phe Ser Gly Ser Gly Ser Gly Thr Ser Tyr Ser Leu Thr Ile Ser Arg
        675                 680                 685

Val Glu Ala Glu Asp Ala Ala Thr Tyr Tyr Cys Gln Gln Trp Thr Ser
    690                 695                 700

Asn Pro Pro Thr Phe Gly Gly Gly Thr Lys Leu Glu Ile
705                 710                 715

<210> SEQ ID NO 95
<211> LENGTH: 737
<212> TYPE: PRT
<213> ORGANISM: Artificial Sequence
<220> FEATURE:
<223> OTHER INFORMATION: Description of Artificial Sequence:
      Anti-CD20-Phor18 mimibody conjugate

<400> SEQUENCE: 95

Asp Ile Gln Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Gly Ser Thr Ser Gly Gly Gly
            100                 105                 110

Ser Gly Gly Gly Ser Gly Gly Gly Ser Ser Val Gln Leu Gln Gln
        115                 120                 125

Pro Gly Ala Glu Leu Val Lys Pro Gly Ala Ser Val Lys Met Ser Cys
130                 135                 140

Lys Ala Ser Gly Tyr Thr Phe Thr Ser Tyr Asn Met His Trp Val Lys
145                 150                 155                 160

Gln Thr Pro Gly Arg Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Ser Thr Tyr Tyr
    210                 215                 220

Gly Gly Asp Trp Tyr Phe Asp Val Trp Gly Gln Gly Thr Thr Val Thr
225                 230                 235                 240

Val Ser Ser Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300
```

```
Gly Ser Phe Phe Leu Tyr Ser Lys Leu Thr Val Asp Lys Ser Arg Trp
305                 310                 315                 320
Gln Gln Gly Asn Val Phe Ser Cys Ser Val Met His Glu Ala Leu His
            325                 330                 335
Asn His Tyr Thr Gln Lys Ser Leu Ser Leu Ser Pro Gly Lys Gly Ser
                340                 345                 350
Thr Ser Gly Gly Gly Ser Gly Gly Gly Ser Gly Gly Gly Gly Ser Ser
            355                 360                 365
Gly Gln Pro Arg Glu Pro Gln Val Tyr Thr Leu Pro Pro Ser Arg Asp
370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
                420                 425                 430
Phe Leu Tyr Ser Lys Leu Thr Val Asp Lys Ser Arg Trp Gln Gln Gly
            435                 440                 445
Asn Val Phe Ser Cys Ser Val Met His Glu Ala Leu His Asn His Tyr
450                 455                 460
Thr Gln Lys Ser Leu Ser Leu Ser Pro Gly Lys Val Gln Leu Gln Gln
465                 470                 475                 480
Pro Gly Ala Glu Leu Val Lys Pro Gly Ala Ser Val Lys Met Ser Cys
                485                 490                 495
Lys Ala Ser Gly Tyr Thr Phe Thr Ser Tyr Asn Met His Trp Val Lys
            500                 505                 510
Gln Thr Pro Gly Arg Gly Leu Glu Trp Ile Gly Ala Ile Tyr Pro Gly
            515                 520                 525
Asn Gly Asp Thr Ser Tyr Asn Gln Lys Phe Lys Gly Lys Ala Thr Leu
            530                 535                 540
Thr Ala Asp Lys Ser Ser Ser Thr Ala Tyr Met Gln Leu Ser Ser Leu
545                 550                 555                 560
Thr Ser Glu Asp Ser Ala Val Tyr Tyr Cys Ala Arg Ser Thr Tyr Tyr
                565                 570                 575
Gly Gly Asp Trp Tyr Phe Asp Val Trp Gly Gln Gly Thr Thr Val Thr
            580                 585                 590
Val Ser Ser Gly Ser Thr Ser Gly Gly Gly Ser Gly Gly Gly Ser Gly
            595                 600                 605
Gly Gly Gly Ser Ser Asp Ile Gln Leu Thr Gln Ser Pro Ala Ile Leu
            610                 615                 620
Ser Ala Ser Pro Gly Glu Lys Val Thr Met Thr Cys Arg Ala Ser Ser
625                 630                 635                 640
Ser Val Ser Tyr Ile His Trp Phe Gln Gln Lys Pro Gly Ser Ser Pro
                645                 650                 655
Lys Pro Trp Ile Tyr Ala Thr Ser Asn Leu Ala Ser Gly Val Pro Val
                660                 665                 670
Phe Ser Gly Ser Gly Ser Gly Thr Ser Tyr Ser Leu Thr Ile Ser Arg
            675                 680                 685
Val Glu Ala Glu Asp Ala Ala Thr Tyr Tyr Cys Gln Gln Trp Thr Ser
690                 695                 700
Asn Pro Pro Thr Phe Gly Gly Gly Thr Lys Leu Glu Ile Gly Ser Lys
705                 710                 715                 720
```

```
Phe Ala Lys Phe Ala Lys Lys Phe Ala Lys Phe Ala Lys Lys Phe Ala
                725                 730                 735
Lys

<210> SEQ ID NO 96
<211> LENGTH: 22
<212> TYPE: PRT
<213> ORGANISM: Artificial Sequence
<220> FEATURE:
<223> OTHER INFORMATION: Description of Artificial Sequence: Signal
      sequence

<400> SEQUENCE: 96

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 97
<211> LENGTH: 454
<212> TYPE: PRT
<213> ORGANISM: Artificial Sequence
<220> FEATURE:
<223> OTHER INFORMATION: Description of Artificial Sequence: Naked
      antibody

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gln Gly Thr Lys Val Glu Ile Lys Gly Gly Gly Gly Ser Glu
            100                 105                 110

Val Gln Leu Val Glu Ser Gly Gly Gly Leu Val Gln Pro Gly Gly Ser
        115                 120                 125

Leu Arg Leu Ser Cys Ala Ala Ser Gly Tyr Thr Phe Thr Ser Tyr Asn
    130                 135                 140

Met His Trp Val Arg Gln Ala Pro Gly Lys Gly Leu Glu Trp Val Ala
145                 150                 155                 160

Ala Ile Tyr Pro Gly Asn Gly Asp Thr Ser Tyr Asn Gln Lys Phe Lys
                165                 170                 175

Gly Arg Phe Thr Ile Ser Ala Asp Thr Ser Lys Asn Thr Ala Tyr Leu
            180                 185                 190

Gln Met Asn Ser Leu Arg Ala Glu Asp Thr Ala Val Tyr Tyr Cys Ser
        195                 200                 205

Arg Ser Thr Tyr Tyr Gly Gly Asp Trp Tyr Phe Asp Val Trp Gly Gln
    210                 215                 220

Gly Thr Leu Val Thr Val Ser Ser Val Gln Pro Cys Pro Ala Pro Glu
225                 230                 235                 240

Leu Leu Gly Gly Pro Ser Val Phe Leu Phe Pro Pro Lys Pro Lys Asp
```

```
            245         250              255
Thr Leu Met Ile Ser Arg Thr Pro Glu Val Thr Cys Val Val Asp
            260             265             270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
        450

<210> SEQ ID NO 98
<211> LENGTH: 494
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 98

Lys Phe Ala Lys Phe Ala Lys Lys Phe Ala Lys Phe Ala Lys Lys Phe
1               5                   10                  15

Ala Lys Gly Ser Asp Ile Gln Met Thr Gln Ser Pro Ser Ser Leu Ser
            20                  25                  30

Ala Ser Val Gly Asp Arg Val Thr Ile Thr Cys Arg Ala Ser Ser Ser
        35                  40                  45

Val Ser Tyr Ile His Trp Tyr Gln Gln Lys Pro Gly Lys Ala Pro Lys
    50                  55                  60

Leu Leu Ile Tyr Ala Thr Ser Asn Leu Ala Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln Trp Thr Ser
            100                 105                 110

Asn Pro Pro Thr Phe Gly Gln Gly Thr Lys Val Glu Ile Lys Gly Gly
        115                 120                 125

Gly Gly Ser Glu Val Gln Leu Val Glu Ser Gly Gly Gly Leu Val Gln
    130                 135                 140
```

```
Pro Gly Gly Ser Leu Arg Leu Ser Cys Ala Ala Ser Gly Tyr Thr Phe
145                 150                 155                 160

Thr Ser Tyr Asn Met His Trp Val Arg Gln Ala Pro Gly Lys Gly Leu
            165                 170                 175

Glu Trp Val Ala Ala Ile Tyr Pro Gly Asn Gly Asp Thr Ser Tyr Asn
        180                 185                 190

Gln Lys Phe Lys Gly Arg Phe Thr Ile Ser Ala Asp Thr Ser Lys Asn
    195                 200                 205

Thr Ala Tyr Leu Gln Met Asn Ser Leu Arg Ala Glu Asp Thr Ala Val
210                 215                 220

Tyr Tyr Cys Ser Arg Ser Thr Tyr Tyr Gly Gly Asp Trp Tyr Phe Asp
225                 230                 235                 240

Val Trp Gly Gln Gly Thr Leu Val Thr Val Ser Ser Val Gln Pro Cys
            245                 250                 255

Pro Ala Pro Glu Leu Leu Gly Gly Pro Ser Val Phe Leu Phe Pro Pro
        260                 265                 270

Lys Pro Lys Asp Thr Leu Met Ile Ser Arg Thr Pro Glu Val Thr Cys
    275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
    355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
    435                 440                 445

Val Phe Ser Cys Ser Val Met His Glu Ala Leu His Asn His Tyr Thr
450                 455                 460

Gln Lys Ser Leu Ser Leu Ser Pro Gly Lys Gly Ser Lys Phe Ala Lys
465                 470                 475                 480

Phe Ala Lys Lys Phe Ala Lys Phe Ala Lys Lys Phe Ala Lys
                485                 490

<210> SEQ ID NO 99
<211> LENGTH: 474
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 99

Lys Phe Ala Lys Phe Ala Lys Lys Phe Ala Lys Phe Ala Lys Lys Phe
1               5                   10                  15
```

```
Ala Lys Gly Ser Asp Ile Gln Met Thr Gln Ser Pro Ser Ser Leu Ser
             20                  25                  30

Ala Ser Val Gly Asp Arg Val Thr Ile Thr Cys Arg Ala Ser Ser Ser
         35                  40                  45

Val Ser Tyr Ile His Trp Tyr Gln Gln Lys Pro Gly Lys Ala Pro Lys
     50                  55                  60

Leu Leu Ile Tyr Ala Thr Ser Asn Leu Ala Ser Gly Val Pro Ser Arg
65                  70                  75                  80

Phe Ser Gly Ser Arg Ser Gly Thr Asp Phe Thr Leu Thr Ile Ser Ser
                 85                  90                  95

Leu Gln Pro Glu Asp Phe Ala Thr Tyr Tyr Cys Gln Gln Trp Thr Ser
             100                 105                 110

Asn Pro Pro Thr Phe Gly Gln Gly Thr Lys Val Glu Ile Lys Gly Gly
         115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Ala Ala Ser Gly Tyr Thr Phe
145                 150                 155                 160

Thr Ser Tyr Asn Met His Trp Val Arg Gln Ala Pro Gly Lys Gly Leu
             165                 170                 175

Glu Trp Val Ala Ala Ile Tyr Pro Gly Asn Gly Asp Thr Ser Tyr Asn
         180                 185                 190

Gln Lys Phe Lys Gly Arg Phe Thr Ile Ser Ala Asp Thr Ser Lys Asn
     195                 200                 205

Thr Ala Tyr Leu Gln Met Asn Ser Leu Arg Ala Glu Asp Thr Ala Val
210                 215                 220

Tyr Tyr Cys Ser Arg Ser Thr Tyr Tyr Gly Gly Asp Trp Tyr Phe Asp
225                 230                 235                 240

Val Trp Gly Gln Gly Thr Leu Val Thr Val Ser Ser Val Gln Pro Cys
             245                 250                 255

Pro Ala Pro Glu Leu Leu Gly Gly Pro Ser Val Phe Leu Phe Pro Pro
         260                 265                 270

Lys Pro Lys Asp Thr Leu Met Ile Ser Arg Thr Pro Glu Val Thr Cys
     275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
             325                 330                 335

His Gln Asp Trp Leu Asn Gly Lys Glu Tyr Lys Cys Lys Val Ser Asn
         340                 345                 350

Lys Ala Leu Pro Ala Pro Ile Glu Lys Thr Ile Ser Lys Ala Lys Gly
     355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
             405                 410                 415

Asn Tyr Lys Thr Thr Pro Pro Val Leu Asp Ser Asp Gly Ser Phe Phe
         420                 425                 430
```

```
Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 100
<211> LENGTH: 474
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Ile
            20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gln Gly Thr Lys Val Glu Ile Lys Gly Gly Gly Gly Ser Glu
            100                 105                 110

Val Gln Leu Val Glu Ser Gly Gly Gly Leu Val Gln Pro Gly Gly Ser
            115                 120                 125

Leu Arg Leu Ser Cys Ala Ala Ser Gly Tyr Thr Phe Thr Ser Tyr Asn
            130                 135                 140

Met His Trp Val Arg Gln Ala Pro Gly Lys Gly Leu Glu Trp Val Ala
145                 150                 155                 160

Ala Ile Tyr Pro Gly Asn Gly Asp Thr Ser Tyr Asn Gln Lys Phe Lys
                165                 170                 175

Gly Arg Phe Thr Ile Ser Ala Asp Thr Ser Lys Asn Thr Ala Tyr Leu
            180                 185                 190

Gln Met Asn Ser Leu Arg Ala Glu Asp Thr Ala Val Tyr Tyr Cys Ser
            195                 200                 205

Arg Ser Thr Tyr Tyr Gly Gly Asp Trp Tyr Phe Asp Val Trp Gly Gln
            210                 215                 220

Gly Thr Leu Val Thr Val Ser Ser Val Gln Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320
```

```
Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Ser Lys Phe Ala Lys Phe Ala Lys Lys
    450                 455                 460

Phe Ala Lys Phe Ala Lys Lys Phe Ala Lys
465                 470

<210> SEQ ID NO 101
<211> LENGTH: 467
<212> TYPE: PRT
<213> ORGANISM: Artificial Sequence
<220> FEATURE:
<223> OTHER INFORMATION: Description of Artificial Sequence: Naked
      antibody

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gln Gly Thr Lys Val Glu Ile Lys Gly Gly Gly Gly Ser Gly
            100                 105                 110

Gly Gly Gly Ser Gly Gly Gly Ser Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Tyr Thr Phe Thr Ser Tyr Asn Met His Trp Val Arg Gln
145                 150                 155                 160

Ala Pro Gly Lys Gly Leu Glu Trp Val Ala Ala Ile Tyr Pro Gly Asn
                165                 170                 175

Gly Asp Thr Ser Tyr Asn Gln Lys Phe Lys Gly Arg Phe Thr Ile Ser
            180                 185                 190

Ala Asp Thr Ser Lys Asn Thr Ala Tyr Leu Gln Met Asn Ser Leu Arg
```

-continued

```
                195                 200                 205
Ala Glu Asp Thr Ala Val Tyr Tyr Cys Ser Arg Ser Thr Tyr Tyr Gly
    210                 215                 220

Gly Asp Trp Tyr Phe Asp Val Trp Gly Gln Gly Thr Leu Val Thr Val
225                 230                 235                 240

Ser Ser Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Asp Glu Leu Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
    450                 455                 460

Pro Gly Lys
465

<210> SEQ ID NO 102
<211> LENGTH: 507
<212> TYPE: PRT
<213> ORGANISM: Artificial Sequence
<220> FEATURE:
<223> OTHER INFORMATION: Description of Artificial Sequence: Conjugated
      antibody

<400> SEQUENCE: 102

Lys Phe Ala Lys Phe Ala Lys Lys Phe Ala Lys Phe Ala Lys Lys Phe
1               5                   10                  15

Ala Lys Gly Ser Asp Ile Gln Met Thr Gln Ser Pro Ser Ser Leu Ser
                20                  25                  30

Ala Ser Val Gly Asp Arg Val Thr Ile Thr Cys Arg Ala Ser Ser Ser
            35                  40                  45

Val Ser Tyr Ile His Trp Tyr Gln Gln Lys Pro Gly Lys Ala Pro Lys
        50                  55                  60

Leu Leu Ile Tyr Ala Thr Ser Asn Leu Ala Ser Gly Val Pro Ser Arg
65                  70                  75                  80
```

```
Phe Ser Gly Ser Arg Ser Gly Thr Asp Phe Thr Leu Thr Ile Ser Ser
                85                  90                  95
Leu Gln Pro Glu Asp Phe Ala Thr Tyr Tyr Cys Gln Gln Trp Thr Ser
            100                 105                 110
Asn Pro Pro Thr Phe Gly Gln Gly Thr Lys Val Glu Ile Lys Gly Gly
        115                 120                 125
Gly Gly Ser Gly Gly Gly Gly Ser Gly Gly Gly Gly Ser Glu Val Gln
130                 135                 140
Leu Val Glu Ser Gly Gly Gly Leu Val Gln Pro Gly Gly Ser Leu Arg
145                 150                 155                 160
Leu Ser Cys Ala Ala Ser Gly Tyr Thr Phe Thr Ser Tyr Asn Met His
                165                 170                 175
Trp Val Arg Gln Ala Pro Gly Lys Gly Leu Glu Trp Val Ala Ala Ile
            180                 185                 190
Tyr Pro Gly Asn Gly Asp Thr Ser Tyr Asn Gln Lys Phe Lys Gly Arg
        195                 200                 205
Phe Thr Ile Ser Ala Asp Thr Ser Lys Asn Thr Ala Tyr Leu Gln Met
    210                 215                 220
Asn Ser Leu Arg Ala Glu Asp Thr Ala Val Tyr Tyr Cys Ser Arg Ser
225                 230                 235                 240
Thr Tyr Tyr Gly Gly Asp Trp Tyr Phe Asp Val Trp Gly Gln Gly Thr
                245                 250                 255
Leu Val Thr Val Ser Ser Thr His Thr Cys Pro Pro Cys Pro Ala Pro
            260                 265                 270
Glu Leu Leu Gly Gly Pro Ser Val Phe Leu Phe Pro Pro Lys Pro Lys
        275                 280                 285
Asp Thr Leu Met Ile Ser Arg Thr Pro Glu Val Thr Cys Val Val Val
    290                 295                 300
Asp Val Ser His Glu Asp Pro Glu Val Lys Phe Asn Trp Tyr Val Asp
305                 310                 315                 320
Gly Val Glu Val His Asn Ala Lys Thr Lys Pro Arg Glu Glu Gln Tyr
                325                 330                 335
Asn Ser Thr Tyr Arg Val Val Ser Val Leu Thr Val Leu His Gln Asp
            340                 345                 350
Trp Leu Asn Gly Lys Glu Tyr Lys Cys Lys Val Ser Asn Lys Ala Leu
        355                 360                 365
Pro Ala Pro Ile Glu Lys Thr Ile Ser Lys Ala Lys Gly Gln Pro Arg
    370                 375                 380
Glu Pro Gln Val Tyr Thr Leu Pro Pro Ser Arg Asp Glu Leu Thr Lys
385                 390                 395                 400
Asn Gln Val Ser Leu Thr Cys Leu Val Lys Gly Phe Tyr Pro Ser Asp
                405                 410                 415
Ile Ala Val Glu Trp Glu Ser Asn Gly Gln Pro Glu Asn Asn Tyr Lys
            420                 425                 430
Thr Thr Pro Pro Val Leu Asp Ser Asp Gly Ser Phe Phe Leu Tyr Ser
        435                 440                 445
Lys Leu Thr Val Asp Lys Ser Arg Trp Gln Gln Gly Asn Val Phe Ser
    450                 455                 460
Cys Ser Val Met His Glu Ala Leu His Asn His Tyr Thr Gln Lys Ser
465                 470                 475                 480
Leu Ser Leu Ser Pro Gly Lys Gly Ser Lys Ala Phe Lys Lys Ala Phe
                485                 490                 495
Lys Ala Phe Lys Lys Ala Phe Lys Ala Phe Lys
```

<210> SEQ ID NO 103
<211> LENGTH: 487
<212> TYPE: PRT
<213> ORGANISM: Artificial Sequence
<220> FEATURE:
<223> OTHER INFORMATION: Description of Artificial Sequence: Conjugated antibody

<400> SEQUENCE: 103

```
Lys Phe Ala Lys Phe Ala Lys Phe Ala Lys Phe Ala Lys Lys Phe
1               5                   10                  15

Ala Lys Gly Ser Asp Ile Gln Met Thr Gln Ser Pro Ser Ser Leu Ser
            20                  25                  30

Ala Ser Val Gly Asp Arg Val Thr Ile Thr Cys Arg Ala Ser Ser Ser
        35                  40                  45

Val Ser Tyr Ile His Trp Tyr Gln Gln Lys Pro Gly Lys Ala Pro Lys
    50                  55                  60

Leu Leu Ile Tyr Ala Thr Ser Asn Leu Ala Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln Trp Thr Ser
            100                 105                 110

Asn Pro Pro Thr Phe Gly Gln Gly Thr Lys Val Glu Ile Lys Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Tyr Thr Phe Thr Ser Tyr Asn Met His
                165                 170                 175

Trp Val Arg Gln Ala Pro Gly Lys Gly Leu Glu Trp Val Ala Ala Ile
            180                 185                 190

Tyr Pro Gly Asn Gly Asp Thr Ser Tyr Asn Gln Lys Phe Lys Gly Arg
        195                 200                 205

Phe Thr Ile Ser Ala Asp Thr Ser Lys Asn Thr Ala Tyr Leu Gln Met
    210                 215                 220

Asn Ser Leu Arg Ala Glu Asp Thr Ala Val Tyr Tyr Cys Ser Arg Ser
225                 230                 235                 240

Thr Tyr Tyr Gly Gly Asp Trp Tyr Phe Asp Val Trp Gly Gln Gly Thr
                245                 250                 255

Leu Val Thr Val Ser Ser Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350
```

```
Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 104
<211> LENGTH: 487
<212> TYPE: PRT
<213> ORGANISM: Artificial Sequence
<220> FEATURE:
<223> OTHER INFORMATION: Description of Artificial Sequence: Conjugated
      antibody

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gln Gly Thr Lys Val Glu Ile Lys Gly Gly Gly Gly Ser Gly
            100                 105                 110

Gly Gly Gly Ser Gly Gly Gly Ser Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Tyr Thr Phe Thr Ser Tyr Asn Met His Trp Val Arg Gln
145                 150                 155                 160

Ala Pro Gly Lys Gly Leu Glu Trp Val Ala Ala Ile Tyr Pro Gly Asn
                165                 170                 175

Gly Asp Thr Ser Tyr Asn Gln Lys Phe Lys Gly Arg Phe Thr Ile Ser
            180                 185                 190

Ala Asp Thr Ser Lys Asn Thr Ala Tyr Leu Gln Met Asn Ser Leu Arg
        195                 200                 205

Ala Glu Asp Thr Ala Val Tyr Tyr Cys Ser Arg Ser Thr Tyr Tyr Gly
    210                 215                 220
```

```
Gly Asp Trp Tyr Phe Asp Val Trp Gly Gln Gly Thr Leu Val Thr Val
225                 230                 235                 240

Ser Ser Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Gly Ser Lys Ala Phe Lys Ala Phe Lys Ala Phe Lys
465                 470                 475                 480

Lys Ala Phe Lys Ala Phe Lys
                485
```

<210> SEQ ID NO 105
<211> LENGTH: 108
<212> TYPE: PRT
<213> ORGANISM: Artificial Sequence
<220> FEATURE:
<223> OTHER INFORMATION: Description of Artificial Sequence: Anti-CD20
      light chain antibody

<400> SEQUENCE: 105

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Ser Val Ser Tyr
            20                  25                  30

Ile His Trp Tyr Gln Gln Lys Pro Gly Lys Ala Pro Lys Leu Leu Ile
        35                  40                  45

Tyr Ala Thr Ser Asn Leu Ala Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Thr Ser Asn Pro Pro
```

```
                85                  90                  95
Thr Phe Gly Gln Gly Thr Lys Val Glu Ile Lys Arg
            100                 105

<210> SEQ ID NO 106
<211> LENGTH: 106
<212> TYPE: PRT
<213> ORGANISM: Artificial Sequence
<220> FEATURE:
<223> OTHER INFORMATION: Description of Artificial Sequence: Anti-CD20
      light chain antibody

<400> SEQUENCE: 106

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 107
<211> LENGTH: 122
<212> TYPE: PRT
<213> ORGANISM: Artificial Sequence
<220> FEATURE:
<223> OTHER INFORMATION: Description of Artificial Sequence: Anti-CD20
      heavy chain antibody

<400> SEQUENCE: 107

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr Ser
            20                  25                  30

Tyr Asn Met His Trp Val Arg Gln Ala Pro Gly Lys Gly Leu Glu Trp
        35                  40                  45

Val Ala Ala Ile Tyr Pro Gly Asn Gly Asp Thr Ser Tyr Asn Gln Lys
    50                  55                  60

Phe Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Ser Thr Tyr Tyr Gly Gly Asp Trp Tyr Phe Asp Val Trp
            100                 105                 110

Gly Gln Gly Thr Leu Val Thr Val Ser Ser
        115                 120

<210> SEQ ID NO 108
<211> LENGTH: 110
<212> TYPE: PRT
<213> ORGANISM: Artificial Sequence
<220> FEATURE:
<223> OTHER INFORMATION: Description of Artificial Sequence: Anti-CD20
``` hinge antibody

<400> SEQUENCE: 108

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

<210> SEQ ID NO 109
<211> LENGTH: 216
<212> TYPE: PRT
<213> ORGANISM: Artificial Sequence
<220> FEATURE:
<223> OTHER INFORMATION: Description of Artificial Sequence: Anti-CD20
      heavy chain antibody

<400> SEQUENCE: 109

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
210                 215

```
<210> SEQ ID NO 110
<211> LENGTH: 765
<212> TYPE: DNA
<213> ORGANISM: Artificial Sequence
<220> FEATURE:
<223> OTHER INFORMATION: Description of Artificial Sequence: ADC light
      chain target

<400> SEQUENCE: 110
atgaagttcg caaagttcgc caaaaagttc gcaaagttcg caaaaaagtt cgccaaaggg        60
tcagatattc agatgactca gagccccagc tccctgtccg catctgtggg cgaccgagtc       120
actatcacct gccgagcctc tagttcagtg agctacattc actggtatca gcagaagcct       180
gggaaagccc caaagctgct catctacgcc acaagcaacc tggcttccgg tgtgccttct       240
aggttcagtg gtcaagaag cggtacagac tttacactga ctattagctc cctccagcca       300
gaggatttcg ccacttacta ttgccagcag tggacttcca atcccctac ctttggccag        360 ggaacaaaag tggaaatcaa ggggcagccc aaagctaacc ctaccgtcac actgttccca       420
ccctctagtg aggaactcca ggcaaataag gccactctgg tgtgtctcat tccgactttt       480
taccccggag ctgtgaccgt cgcttggaag gcagatggct ctccagtgaa gcaggagtc       540 gagaccacaa acccagtaa gcagtcaaac aataagtacg ccgcttcaag ctatctgagt       600 ctcaccctg aacagtggaa aagccatagg tcctattctt gccaggtcac tcacgaaggt       660
agcactgtgg aaaagactgt cgcaccaacc gaatgtagcg gctccaaggc tttcaagaag       720
gccttcaagg ccttcaagaa agcattcaag gcctttaaat gataa                       765

<210> SEQ ID NO 111
<211> LENGTH: 1470
<212> TYPE: DNA
<213> ORGANISM: Artificial Sequence
<220> FEATURE:
<223> OTHER INFORMATION: Description of Artificial Sequence: ADC heavy
      chain target

<400> SEQUENCE: 111
atgaagttcg ccaaatttgc taagaaattc gcaaagtttg ccaagaaatt cgctaaaggc        60
tccgaagtgc agctcgtcga aagcggggg ggactcgtgc agccaggggg aagcctcaga       120
ctctcatgcg ccgcctcagg ttatactttc acaagctaca acatgcactg ggtcagacag       180
gcacctggga agggtctgga gtgggtggcc gctatctacc caggcaacgg agacacatct       240
tataatcaga gttcaaagg ccggtttact attagcgcag atacatccaa gaacactgcc        300
tacctgcaga tgaatagcct ccgggctgaa gacactgcag tgtactattg cagtcgctca       360
acctactatg gcggagactg gtatttcgat gtgtggggc agggtactct ggtcaccgtg       420
agctccgcct ctaccaaggg cccagtgtg tttccactgg ctccctgcag ccggtccacc       480
tctgagagta cagcagccct gggttgtctc gtgaaagatt acttccctga accagtcacc       540
gtgtcctgga ctctggcgc tctgaccagc ggagtccaca catttcctgc agtgctccag       600
tctagtgggc tgtactccct ctcaagcgtg gtcacagtcc catcctctaa tttcggtact       660
cagacctata catgcaacgt ggaccataag ccctccaata ctaaggtcga taaaaccgtg       720
gagcgcaaat gctgtgtgga atgcccacct tgtccagcac caccagtcgc tgggcctagc       780
gtgttcctgt tcctccaaa gccaaaagac actctcatga tctctcgaac tcccgaggtc       840
acctgtgtgg tcgtggacgt cagtcacgag gatcctgaag tccagtttaa ctggtacgtg       900
gatggagtcg aagtgcataa tgcaaagacc aaaccaaggg aggaacagtt caactcaacc       960
```

-continued

```
tttagagtcg tgagcgtgct gacagtcgtg catcaggact ggctcaacgg gaaggagtat    1020
aagtgcaaag tgtctaataa gggtctgccc gctcctatcg agaaaacaat tagcaagact    1080
aaaggacagc ctcgagaacc acaggtgtac acactgcccc ctagcaggga ggaaatgaca    1140 agaaccagg  tctccctgac ttgtctcgtg aaaggcttct atcccagtga cattgccgtg    1200
gagtgggaat caaatggaca gcctgagaac aattacaaga ccacaccacc catgctggac    1260
agtgatggct cattctttct gtattccaag ctcaccgtgg ataaatctag gtggcagcag    1320
ggaaatgtct tttcatgtag cgtgatgcac gaggctctcc ataaccatta cacccagaag    1380
tccctgtcac tctcccccgg caaaggctcc aaggctttca gaaggcctt  caaggccttc    1440 aagaaagcat tcaaggcctt taaatgataa                                     1470
```

<210> SEQ ID NO 112
<211> LENGTH: 33
<212> TYPE: DNA
<213> ORGANISM: Artificial Sequence
<220> FEATURE:
<223> OTHER INFORMATION: Description of Artificial Sequence: ADC light
      chain primer

<400> SEQUENCE: 112
gggggcgcgc cgatattcag atgactcaga gcc                                   33

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence: ADC light
      chain primer

<400> SEQUENCE: 113
gggggcgcgc caagttcgca aagttcgcca a                                     31

<210> SEQ ID NO 114
<211> LENGTH: 31
<212> TYPE: DNA
<213> ORGANISM: Artificial Sequence
<220> FEATURE:
<223> OTHER INFORMATION: Description of Artificial Sequence: ADC light
      chain primer

<400> SEQUENCE: 114
ggggaattct tatcagctac attcggttgg t                                     31

<210> SEQ ID NO 115
<211> LENGTH: 34
<212> TYPE: DNA
<213> ORGANISM: Artificial Sequence
<220> FEATURE:
<223> OTHER INFORMATION: Description of Artificial Sequence: ADC light
      chain primer

<400> SEQUENCE: 115
ggggaattct tatcatttaa aggccttgaa tgct                                  34

<210> SEQ ID NO 116
<211> LENGTH: 31
<212> TYPE: DNA
<213> ORGANISM: Artificial Sequence
<220> FEATURE:
<223> OTHER INFORMATION: Description of Artificial Sequence: ADC heavy
      chain primer -continued

<400> SEQUENCE: 116
gggggcgcgc cgaagtgcag ctcgtcgaaa g                                31

<210> SEQ ID NO 117
<211> LENGTH: 33
<212> TYPE: DNA
<213> ORGANISM: Artificial Sequence
<220> FEATURE:
<223> OTHER INFORMATION: Description of Artificial Sequence: ADC heavy
      chain primer

<400> SEQUENCE: 117
gggggcgcgc caagttcgcc aaatttgcta aga                              33

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: ADC heavy
      chain primer

<400> SEQUENCE: 118
ggggaattct tatcatttgc cggggga                                     27

<210> SEQ ID NO 119
<211> LENGTH: 212
<212> TYPE: PRT
<213> ORGANISM: Artificial Sequence
<220> FEATURE:
<223> OTHER INFORMATION: Description of Artificial Sequence: Light chain
      naked antibody

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gln Gly Thr Lys Val Glu Ile Lys Gly Gln Pro Lys Ala Asn
            100                 105                 110

Pro Thr Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Gly Ser Pro Val Lys Ala Gly Val Glu
145                 150                 155                 160

Thr Thr Lys Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 120
<211> LENGTH: 447
<212> TYPE: PRT
<213> ORGANISM: Artificial Sequence
<220> FEATURE:
<223> OTHER INFORMATION: Description of Artificial Sequence: Heavy chain
      naked antibody

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Ala Ala Ile Tyr Pro Gly Asn Gly Asp Thr Ser Tyr Asn Gln Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Ser Thr Tyr Tyr Gly Gly Asp Trp Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro

```
                340             345             350
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 121
<211> LENGTH: 233
<212> TYPE: PRT
<213> ORGANISM: Artificial Sequence
<220> FEATURE:
<223> OTHER INFORMATION: Description of Artificial Sequence: Light chain
      naked antibody

<400> SEQUENCE: 121

Met Lys Phe Ala Lys Phe Ala Lys Lys Phe Ala Lys Phe Ala Lys Lys
1               5                   10                  15

Phe Ala Lys Gly Ser Asp Ile Gln Met Thr Gln Ser Pro Ser Ser Leu
            20                  25                  30

Ser Ala Ser Val Gly Asp Arg Val Thr Ile Thr Cys Arg Ala Ser Ser
        35                  40                  45

Ser Val Ser Tyr Ile His Trp Tyr Gln Gln Lys Pro Gly Lys Ala Pro
    50                  55                  60

Lys Leu Leu Ile Tyr Ala Thr Ser Asn Leu Ala Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Trp Thr
            100                 105                 110

Ser Asn Pro Pro Thr Phe Gly Gln Gly Thr Lys Val Glu Ile Lys Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 122
<211> LENGTH: 447
```

<212> TYPE: PRT
<213> ORGANISM: Artificial Sequence
<220> FEATURE:
<223> OTHER INFORMATION: Description of Artificial Sequence: Heavy chain
      naked antibody

<400> SEQUENCE: 122

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Ala Ala Ile Tyr Pro Gly Asn Gly Asp Thr Ser Tyr Asn Gln Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Ser Thr Tyr Tyr Gly Gly Asp Trp Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 123
<211> LENGTH: 212
<212> TYPE: PRT
<213> ORGANISM: Artificial Sequence
<220> FEATURE:
<223> OTHER INFORMATION: Description of Artificial Sequence: Light chain
      naked antibody

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Arg Ser Gly Thr Asp Phe Thr Leu Thr Ile Ser Ser Leu Gln Pro Glu
65              70                  75                  80

Asp Phe Ala Thr Tyr Tyr Cys Gln Gln Trp Thr Ser Asn Pro Pro Thr
            85                  90                  95

Phe Gly Gln Gly Thr Lys Val Glu Ile Lys Gly Gln Pro Lys Ala Asn
            100                 105                 110

Pro Thr Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Gly Ser Pro Val Lys Ala Gly Val Glu
145                 150                 155                 160

Thr Thr Lys Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 124
<211> LENGTH: 468
<212> TYPE: PRT
<213> ORGANISM: Artificial Sequence
<220> FEATURE:
<223> OTHER INFORMATION: Description of Artificial Sequence: Heavy chain
      naked antibody

<400> SEQUENCE: 124

Met Lys Phe Ala Lys Phe Ala Lys Lys Phe Ala Lys Phe Ala Lys Lys
1               5                   10                  15

Phe Ala Lys Gly Ser Glu Val Gln Leu Val Glu Ser Gly Gly Leu
            20                  25                  30

Val Gln Pro Gly Gly Ser Leu Arg Leu Ser Cys Ala Ala Ser Gly Tyr
            35                  40                  45

Thr Phe Thr Ser Tyr Asn Met His Trp Val Arg Gln Ala Pro Gly Lys
    50                      55                  60

Gly Leu Glu Trp Val Ala Ala Ile Tyr Pro Gly Asn Gly Asp Thr Ser
65                  70                  75                  80

Tyr Asn Gln Lys Phe Lys Gly Arg Phe Thr Ile Ser Ala Asp Thr Ser
                85                  90                  95

Lys Asn Thr Ala Tyr Leu Gln Met Asn Ser Leu Arg Ala Glu Asp Thr
                100                 105                 110

Ala Val Tyr Tyr Cys Ser Arg Ser Thr Tyr Tyr Gly Gly Asp Trp Tyr
            115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
    195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
    275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
    355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

-continued

```
Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 125
<211> LENGTH: 233
<212> TYPE: PRT
<213> ORGANISM: Artificial Sequence
<220> FEATURE:
<223> OTHER INFORMATION: Description of Artificial Sequence: Light chain
      naked antibody

<400> SEQUENCE: 125

Met Lys Phe Ala Lys Phe Ala Lys Lys Phe Ala Lys Phe Ala Lys Lys
1               5                   10                  15

Phe Ala Lys Gly Ser Asp Ile Gln Met Thr Gln Ser Pro Ser Ser Leu
            20                  25                  30

Ser Ala Ser Val Gly Asp Arg Val Thr Ile Thr Cys Arg Ala Ser Ser
        35                  40                  45

Ser Val Ser Tyr Ile His Trp Tyr Gln Gln Lys Pro Gly Lys Ala Pro
    50                  55                  60

Lys Leu Leu Ile Tyr Ala Thr Ser Asn Leu Ala Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Trp Thr
            100                 105                 110

Ser Asn Pro Pro Thr Phe Gly Gln Gly Thr Lys Val Glu Ile Lys Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 126
<211> LENGTH: 468
<212> TYPE: PRT
<213> ORGANISM: Artificial Sequence
<220> FEATURE:
<223> OTHER INFORMATION: Description of Artificial Sequence: Heavy chain
      naked antibody

<400> SEQUENCE: 126

Met Lys Phe Ala Lys Phe Ala Lys Lys Phe Ala Lys Phe Ala Lys Lys
1               5                   10                  15
```

-continued

```
Phe Ala Lys Gly Ser Glu Val Gln Leu Val Glu Ser Gly Gly Gly Leu
            20                  25                  30
Val Gln Pro Gly Gly Ser Leu Arg Leu Ser Cys Ala Ala Ser Gly Tyr
        35                  40                  45
Thr Phe Thr Ser Tyr Asn Met His Trp Val Arg Gln Ala Pro Gly Lys
    50                  55                  60
Gly Leu Glu Trp Val Ala Ala Ile Tyr Pro Gly Asn Gly Asp Thr Ser
65                  70                  75                  80
Tyr Asn Gln Lys Phe Lys Gly Arg Phe Thr Ile Ser Ala Asp Thr Ser
                85                  90                  95
Lys Asn Thr Ala Tyr Leu Gln Met Asn Ser Leu Arg Ala Glu Asp Thr
            100                 105                 110
Ala Val Tyr Tyr Cys Ser Arg Ser Thr Tyr Tyr Gly Gly Asp Trp Tyr
        115                 120                 125
Phe Asp Val Trp Gly Gln Gly Thr Leu Val Thr Val Ser Ser Ala Ser
    130                 135                 140
Thr Lys Gly Pro Ser Val Phe Pro Leu Ala Pro Cys Ser Arg Ser Thr
145                 150                 155                 160
Ser Glu Ser Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Asn Phe Gly Thr Gln Thr Tyr Thr
    210                 215                 220
Cys Asn Val Asp His Lys Pro Ser Asn Thr Lys Val Asp Lys Thr Val
225                 230                 235                 240
Glu Arg Lys Cys Cys Val Glu Cys Pro Pro Cys Pro Ala Pro Pro Val
                245                 250                 255
Ala Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Gln Phe Asn Trp Tyr Val Asp Gly Val Glu
    290                 295                 300
Val His Asn Ala Lys Thr Lys Pro Arg Glu Glu Gln Phe Asn Ser Thr
305                 310                 315                 320
Phe Arg Val Val Ser Val Leu Thr Val Val His Gln Asp Trp Leu Asn
                325                 330                 335
Gly Lys Glu Tyr Lys Cys Lys Val Ser Asn Lys Gly Leu Pro Ala Pro
            340                 345                 350
Ile Glu Lys Thr Ile Ser Lys Thr Lys Gly Gln Pro Arg Glu Pro Gln
        355                 360                 365
Val Tyr Thr Leu Pro Pro Ser Arg Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Met Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
```

```
                435                 440                 445
Met His Glu Ala Leu His Asn His Tyr Thr Gln Lys Ser Leu Ser Leu
        450                 455                 460

Ser Pro Gly Lys
465

<210> SEQ ID NO 127
<211> LENGTH: 253
<212> TYPE: PRT
<213> ORGANISM: Artificial Sequence
<220> FEATURE:
<223> OTHER INFORMATION: Description of Artificial Sequence: Light chain
      naked antibody

<400> SEQUENCE: 127

Met Lys Phe Ala Lys Phe Ala Lys Lys Phe Ala Lys Phe Ala Lys Lys
1               5                   10                  15

Phe Ala Lys Gly Ser Asp Ile Gln Met Thr Gln Ser Pro Ser Ser Leu
            20                  25                  30

Ser Ala Ser Val Gly Asp Arg Val Thr Ile Thr Cys Arg Ala Ser Ser
        35                  40                  45

Ser Val Ser Tyr Ile His Trp Tyr Gln Gln Lys Pro Gly Lys Ala Pro
    50                  55                  60

Lys Leu Leu Ile Tyr Ala Thr Ser Asn Leu Ala Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Trp Thr
            100                 105                 110

Ser Asn Pro Pro Thr Phe Gly Gln Gly Thr Lys Val Glu Ile Lys Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser Gly Ser Lys Ala Phe Lys Lys
225                 230                 235                 240

Ala Phe Lys Ala Phe Lys Lys Ala Phe Lys Ala Phe Lys
                245                 250

<210> SEQ ID NO 128
<211> LENGTH: 468
<212> TYPE: PRT
<213> ORGANISM: Artificial Sequence
<220> FEATURE:
<223> OTHER INFORMATION: Description of Artificial Sequence: Heavy chain
      naked antibody

<400> SEQUENCE: 128

Met Lys Phe Ala Lys Phe Ala Lys Lys Phe Ala Lys Phe Ala Lys Lys
```

```
1               5                   10                  15
Phe Ala Lys Gly Ser Glu Val Gln Leu Val Glu Ser Gly Gly Leu
                20                  25                  30
Val Gln Pro Gly Gly Ser Leu Arg Leu Ser Cys Ala Ala Ser Gly Tyr
                35                  40                  45
Thr Phe Thr Ser Tyr Asn Met His Trp Val Arg Gln Ala Pro Gly Lys
                50                  55                  60
Gly Leu Glu Trp Val Ala Ala Ile Tyr Pro Gly Asn Gly Asp Thr Ser
65                  70                  75                  80
Tyr Asn Gln Lys Phe Lys Gly Arg Phe Thr Ile Ser Ala Asp Thr Ser
                85                  90                  95
Lys Asn Thr Ala Tyr Leu Gln Met Asn Ser Leu Arg Ala Glu Asp Thr
                100                 105                 110
Ala Val Tyr Tyr Cys Ser Arg Ser Thr Tyr Tyr Gly Gly Asp Trp Tyr
                115                 120                 125
Phe Asp Val Trp Gly Gln Gly Thr Leu Val Thr Val Ser Ser Ala Ser
                130                 135                 140
Thr Lys Gly Pro Ser Val Phe Pro Leu Ala Pro Cys Ser Arg Ser Thr
145                 150                 155                 160
Ser Glu Ser Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
                195                 200                 205
Ser Val Val Thr Val Pro Ser Ser Asn Phe Gly Thr Gln Thr Tyr Thr
                210                 215                 220
Cys Asn Val Asp His Lys Pro Ser Asn Thr Lys Val Asp Lys Thr Val
225                 230                 235                 240
Glu Arg Lys Cys Cys Val Glu Cys Pro Pro Cys Pro Ala Pro Pro Val
                245                 250                 255
Ala Gly Pro Ser Val Phe Leu Phe Pro Pro Lys Pro Lys Asp Thr Leu
                260                 265                 270
Met Ile Ser Arg Thr Pro Glu Val Thr Cys Val Val Val Asp Val Ser
                275                 280                 285
His Glu Asp Pro Glu Val Gln Phe Asn Trp Tyr Val Asp Gly Val Glu
                290                 295                 300
Val His Asn Ala Lys Thr Lys Pro Arg Glu Glu Gln Phe Asn Ser Thr
305                 310                 315                 320
Phe Arg Val Val Ser Val Leu Thr Val Val His Gln Asp Trp Leu Asn
                325                 330                 335
Gly Lys Glu Tyr Lys Cys Lys Val Ser Asn Lys Gly Leu Pro Ala Pro
                340                 345                 350
Ile Glu Lys Thr Ile Ser Lys Thr Lys Gly Gln Pro Arg Glu Pro Gln
                355                 360                 365
Val Tyr Thr Leu Pro Pro Ser Arg Glu Glu Met Thr Lys Asn Gln Val
                370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Met Leu Asp Ser Asp Gly Ser Phe Phe Leu Tyr Ser Lys Leu Thr
                420                 425                 430
```

```
Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 129
<211> LENGTH: 253
<212> TYPE: PRT
<213> ORGANISM: Artificial Sequence
<220> FEATURE:
<223> OTHER INFORMATION: Description of Artificial Sequence: Light chain
      naked antibody

<400> SEQUENCE: 129

Met Lys Phe Ala Lys Phe Ala Lys Lys Phe Ala Lys Phe Ala Lys Lys
1               5                   10                  15

Phe Ala Lys Gly Ser Asp Ile Gln Met Thr Gln Ser Pro Ser Ser Leu
            20                  25                  30

Ser Ala Ser Val Gly Asp Arg Val Thr Ile Thr Cys Arg Ala Ser Ser
        35                  40                  45

Ser Val Ser Tyr Ile His Trp Tyr Gln Gln Lys Pro Gly Lys Ala Pro
    50                  55                  60

Lys Leu Leu Ile Tyr Ala Thr Ser Asn Leu Ala Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln Trp Thr
            100                 105                 110

Ser Asn Pro Pro Thr Phe Gly Gln Gly Thr Lys Val Glu Ile Lys Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser Gly Ser Lys Ala Phe Lys Lys
225                 230                 235                 240

Ala Phe Lys Ala Phe Lys Lys Ala Phe Lys Ala Phe Lys
                245                 250

<210> SEQ ID NO 130
<211> LENGTH: 488
<212> TYPE: PRT
<213> ORGANISM: Artificial Sequence
<220> FEATURE:
<223> OTHER INFORMATION: Description of Artificial Sequence: Heavy chain
      naked antibody

<400> SEQUENCE: 130
```

```
Met Lys Phe Ala Lys Phe Ala Lys Phe Ala Lys Phe Ala Lys Lys
1               5                   10                  15

Phe Ala Lys Gly Ser Glu Val Gln Leu Val Glu Ser Gly Gly Leu
            20                  25                  30

Val Gln Pro Gly Gly Ser Leu Arg Leu Ser Cys Ala Ala Ser Gly Tyr
            35                  40                  45

Thr Phe Thr Ser Tyr Asn Met His Trp Val Arg Gln Ala Pro Gly Lys
            50                  55                  60

Gly Leu Glu Trp Val Ala Ala Ile Tyr Pro Gly Asn Gly Asp Thr Ser
65                  70                  75                  80

Tyr Asn Gln Lys Phe Lys Gly Arg Phe Thr Ile Ser Ala Asp Thr Ser
                85                  90                  95

Lys Asn Thr Ala Tyr Leu Gln Met Asn Ser Leu Arg Ala Glu Asp Thr
            100                 105                 110

Ala Val Tyr Tyr Cys Ser Arg Ser Thr Tyr Tyr Gly Gly Asp Trp Tyr
            115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
            355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415
```

```
Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Cys Ser Val
            435                 440                 445

Met His Glu Ala Leu His Asn His Tyr Thr Gln Lys Ser Leu Ser Leu
450                 455                 460

Ser Pro Gly Lys Gly Ser Lys Ala Phe Lys Ala Phe Lys Ala Phe
465                 470                 475                 480

Lys Lys Ala Phe Lys Ala Phe Lys
                485
```

<210> SEQ ID NO 131
<211> LENGTH: 1255
<212> TYPE: PRT
<213> ORGANISM: Artificial Sequence
<220> FEATURE:
<223> OTHER INFORMATION: Description of Artificial Sequence: Target sequence

<400> SEQUENCE: 131

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285
```

```
Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700
```

```
Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
```

```
            1115                1120                1125

Ala Pro Leu Thr Cys Ser Pro Gln Pro Glu Tyr Val Asn Gln Pro
            1130                1135                1140

Asp Val Arg Pro Gln Pro Pro Ser Pro Arg Glu Gly Pro Leu Pro
            1145                1150                1155

Ala Ala Arg Pro Ala Gly Ala Thr Leu Glu Arg Pro Lys Thr Leu
            1160                1165                1170

Ser Pro Gly Lys Asn Gly Val Val Lys Asp Val Phe Ala Phe Gly
            1175                1180                1185

Gly Ala Val Glu Asn Pro Glu Tyr Leu Thr Pro Gln Gly Gly Ala
            1190                1195                1200

Ala Pro Gln Pro His Pro Pro Ala Phe Ser Pro Ala Phe Asp
            1205                1210                1215

Asn Leu Tyr Tyr Trp Asp Gln Asp Pro Pro Glu Arg Gly Ala Pro
            1220                1225                1230

Pro Ser Thr Phe Lys Gly Thr Pro Thr Ala Glu Asn Pro Glu Tyr
            1235                1240                1245

Leu Gly Leu Asp Val Pro Val
            1250                1255

<210> SEQ ID NO 132
<211> LENGTH: 557
<212> TYPE: PRT
<213> ORGANISM: Artificial Sequence
<220> FEATURE:
<223> OTHER INFORMATION: Description of Artificial Sequence: Target
      sequence

<400> SEQUENCE: 132

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205
```

```
Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
                260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
                355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
            450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
                485                 490                 495

Gly Ser Gln Ser Tyr Glu Asp Met Arg Gly Ile Leu Tyr Ala Ala Pro
                500                 505                 510

Gln Leu Arg Ser Ile Arg Gly Gln Pro Gly Pro Asn His Glu Glu Asp
            515                 520                 525

Ala Asp Ser Tyr Glu Asn Met Asp Asn Pro Asp Gly Pro Asp Pro Ala
530                 535                 540

Trp Gly Gly Gly Gly Arg Met Gly Thr Trp Ser Thr Arg
545                 550                 555

<210> SEQ ID NO 133
<211> LENGTH: 297
<212> TYPE: PRT
<213> ORGANISM: Artificial Sequence
<220> FEATURE:
<223> OTHER INFORMATION: Description of Artificial Sequence: Target
      sequence

<400> SEQUENCE: 133

Met Thr Thr Pro Arg Asn Ser Val Asn Gly Thr Phe Pro Ala Glu Pro
1               5                   10                  15
```

```
Met Lys Gly Pro Ile Ala Met Gln Ser Gly Pro Lys Pro Leu Phe Arg
             20                  25                  30

Arg Met Ser Ser Leu Val Gly Pro Thr Gln Ser Phe Phe Met Arg Glu
         35                  40                  45

Ser Lys Thr Leu Gly Ala Val Gln Ile Met Asn Gly Leu Phe His Ile
 50                  55                  60

Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Ile Met Tyr Ile Ile
             85                  90                  95

Ser Gly Ser Leu Leu Ala Ala Thr Glu Lys Asn Ser Arg Lys Cys Leu
             100                 105                 110

Val Lys Gly Lys Met Ile Met Asn Ser Leu Ser Leu Phe Ala Ala Ile
             115                 120                 125

Ser Gly Met Ile Leu Ser Ile Met Asp Ile Leu Asn Ile Lys Ile Ser
 130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
             165                 170                 175

Ser Pro Ser Thr Gln Tyr Cys Tyr Ser Ile Gln Ser Leu Phe Leu Gly
             180                 185                 190

Ile Leu Ser Val Met Leu Ile Phe Ala Phe Phe Gln Glu Leu Val Ile
             195                 200                 205

Ala Gly Ile Val Glu Asn Glu Trp Lys Arg Thr Cys Ser Arg Pro Lys
             210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
             245                 250                 255

Lys Asn Glu Glu Asp Ile Glu Ile Ile Pro Ile Gln Glu Glu Glu Glu
             260                 265                 270

Glu Glu Thr Glu Thr Asn Phe Pro Glu Pro Pro Gln Asp Gln Glu Ser
             275                 280                 285

Ser Pro Ile Glu Asn Asp Ser Ser Pro
             290                 295

<210> SEQ ID NO 134
<211> LENGTH: 759
<212> TYPE: PRT
<213> ORGANISM: Artificial Sequence
<220> FEATURE:
<223> OTHER INFORMATION: Description of Artificial Sequence: Target
      sequence

<400> SEQUENCE: 134

Met His Leu Leu Gly Pro Trp Leu Leu Leu Leu Val Leu Glu Tyr Leu
  1               5                  10                  15

Ala Phe Ser Asp Ser Ser Lys Trp Val Phe Glu His Pro Glu Thr Leu
             20                  25                  30

Tyr Ala Trp Glu Gly Ala Cys Val Trp Ile Pro Cys Thr Tyr Arg Ala
             35                  40                  45

Leu Asp Gly Asp Leu Glu Ser Phe Ile Leu Phe His Asn Pro Glu Tyr
 50                  55                  60

Asn Lys Asn Thr Ser Lys Phe Asp Gly Thr Arg Leu Tyr Glu Ser Thr
```

```
                65                  70                  75                  80
            Lys Asp Gly Lys Val Pro Ser Glu Gln Lys Arg Val Gln Phe Leu Gly
                            85                  90                  95

Asp Lys Asn Lys Asn Cys Thr Leu Ser Ile His Pro Val His Leu Asn
                        100                 105                 110

Asp Ser Gly Gln Leu Gly Leu Arg Met Glu Ser Lys Thr Glu Lys Trp
                    115                 120                 125

Met Glu Arg Ile His Leu Asn Val Ser Glu Arg Pro Phe Pro Pro His
                130                 135                 140

Ile Gln Leu Pro Pro Glu Ile Gln Glu Ser Gln Glu Val Thr Leu Thr
            145                 150                 155                 160

Cys Leu Leu Asn Phe Ser Cys Tyr Gly Tyr Pro Ile Gln Leu Gln Trp
                            165                 170                 175

Leu Leu Glu Gly Val Pro Met Arg Gln Ala Ala Val Thr Ser Thr Ser
                        180                 185                 190

Leu Thr Ile Lys Ser Val Phe Thr Arg Ser Glu Leu Lys Phe Ser Pro
                    195                 200                 205

Gln Trp Ser His His Gly Lys Ile Val Thr Cys Gln Leu Gln Asp Ala
                210                 215                 220

Asp Gly Lys Phe Leu Ser Asn Asp Thr Val Gln Leu Asn Val Lys His
            225                 230                 235                 240

Thr Pro Lys Leu Glu Ile Lys Val Thr Pro Ser Asp Ala Ile Val Arg
                            245                 250                 255

Glu Gly Asp Ser Val Thr Met Thr Cys Glu Val Ser Ser Asn Pro
                        260                 265                 270

Glu Tyr Thr Thr Val Ser Trp Leu Lys Asp Gly Thr Ser Leu Lys Lys
                    275                 280                 285

Gln Asn Thr Phe Thr Leu Asn Leu Arg Glu Val Thr Lys Asp Gln Ser
                290                 295                 300

Gly Lys Tyr Cys Cys Gln Val Ser Asn Asp Val Gly Pro Gly Arg Ser
            305                 310                 315                 320

Glu Glu Val Phe Leu Gln Val Gln Tyr Pro Pro Lys Lys Val Thr Thr
                            325                 330                 335

Val Ile Gln Asn Pro Met Pro Ile Arg Glu Gly Asp Thr Val Thr Leu
                        340                 345                 350

Ser Cys Asn Tyr Asn Ser Ser Asn Pro Ser Val Thr Arg Tyr Glu Trp
                    355                 360                 365

Lys Pro His Gly Ala Trp Glu Glu Pro Ser Leu Gly Val Leu Lys Ile
                370                 375                 380

Gln Asn Val Gly Trp Asp Asn Thr Thr Ile Ala Cys Ala Ala Cys Asn
            385                 390                 395                 400

Ser Trp Cys Ser Trp Ala Ser Pro Val Ala Leu Asn Val Gln Tyr Ala
                            405                 410                 415

Pro Arg Asp Val Arg Val Arg Lys Ile Lys Pro Leu Ser Glu Ile His
                        420                 425                 430

Ser Gly Asn Ser Val Ser Leu Gln Cys Asp Phe Ser Ser Ser His Pro
                    435                 440                 445

Lys Glu Val Gln Phe Phe Trp Glu Lys Asn Gly Arg Leu Leu Gly Lys
                450                 455                 460

Glu Ser Gln Leu Asn Phe Asp Ser Ile Ser Pro Glu Asp Ala Gly Ser
            465                 470                 475                 480

Tyr Ser Cys Trp Val Asn Asn Ser Ile Gly Gln Thr Ala Ser Lys Ala
                            485                 490                 495
```

```
Trp Thr Leu Glu Val Leu Tyr Ala Pro Arg Leu Arg Val Ser Met
            500                 505                 510

Ser Pro Gly Asp Gln Val Met Glu Gly Lys Ser Ala Thr Leu Thr Cys
            515                 520                 525

Glu Ser Asp Ala Asn Pro Pro Val Ser His Tyr Thr Trp Phe Asp Trp
530                 535                 540

Asn Asn Gln Ser Leu Pro Tyr His Ser Gln Lys Leu Arg Leu Glu Pro
545                 550                 555                 560

Val Lys Val Gln His Ser Gly Ala Tyr Trp Cys Gln Gly Thr Asn Ser
                565                 570                 575

Val Gly Lys Gly Arg Ser Pro Leu Ser Thr Leu Thr Val Tyr Tyr Ser
            580                 585                 590

Pro Glu Thr Ile Gly Arg Arg Val Ala Val Gly Leu Gly Ser Cys Leu
            595                 600                 605

Ala Ile Leu Ile Leu Ala Ile Cys Gly Leu Lys Leu Gln Arg Arg Trp
610                 615                 620

Lys Arg Thr Gln Ser Gln Gln Gly Leu Gln Glu Asn Ser Ser Gly Gln
625                 630                 635                 640

Ser Phe Phe Val Arg Asn Lys Lys Val Arg Arg Ala Pro Leu Ser Glu
                645                 650                 655

Gly Pro His Ser Leu Gly Cys Tyr Asn Pro Met Met Glu Asp Gly Ile
            660                 665                 670

Ser Tyr Thr Thr Leu Arg Phe Pro Glu Met Asn Ile Pro Arg Thr Gly
            675                 680                 685

Asp Ala Glu Ser Ser Glu Met Gln Arg Pro Pro Asp Cys Asp Asp
690                 695                 700

Thr Val Thr Tyr Ser Ala Leu His Lys Arg Gln Val Gly Asp Tyr Glu
705                 710                 715                 720

Asn Val Ile Pro Asp Phe Pro Glu Asp Glu Gly Ile His Tyr Ser Glu
                725                 730                 735

Leu Ile Gln Phe Gly Val Gly Glu Arg Pro Gln Ala Gln Glu Asn Val
            740                 745                 750

Asp Tyr Val Ile Leu Lys His
            755

<210> SEQ ID NO 135
<211> LENGTH: 320
<212> TYPE: PRT
<213> ORGANISM: Artificial Sequence
<220> FEATURE:
<223> OTHER INFORMATION: Description of Artificial Sequence: Target
      sequence

<400> SEQUENCE: 135

Met Asn Pro Pro Ser Gln Glu Ile Glu Glu Leu Pro Arg Arg Arg Cys
1               5                   10                  15

Cys Arg Arg Gly Thr Gln Ile Val Leu Leu Gly Leu Val Thr Ala Ala
            20                  25                  30

Leu Trp Ala Gly Leu Leu Thr Leu Leu Leu Trp His Trp Asp Thr
            35                  40                  45

Thr Gln Ser Leu Lys Gln Leu Glu Glu Arg Ala Ala Arg Asn Val Ser
        50                  55                  60

Gln Val Ser Lys Asn Leu Glu Ser His His Gly Asp Gln Met Ala Gln
65                  70                  75                  80

Lys Ser Gln Ser Thr Gln Ile Ser Gln Glu Leu Glu Glu Leu Arg Ala
```

```
                85                  90                  95
Glu Gln Gln Arg Leu Lys Ser Gln Asp Leu Glu Leu Ser Trp Asn Leu
            100                 105                 110

Asn Gly Leu Gln Ala Asp Leu Ser Ser Phe Lys Ser Gln Glu Leu Asn
            115                 120                 125

Glu Arg Asn Glu Ala Ser Asp Leu Leu Glu Arg Leu Arg Glu Glu Val
            130                 135                 140

Thr Lys Leu Arg Met Glu Leu Gln Val Ser Ser Gly Phe Val Cys Asn
145                 150                 155                 160

Thr Cys Pro Glu Lys Trp Ile Asn Phe Gln Arg Lys Cys Tyr Tyr Phe
                165                 170                 175

Gly Lys Gly Thr Lys Gln Trp Val His Ala Arg Tyr Ala Cys Asp Asp
                180                 185                 190

Met Glu Gly Gln Leu Val Ser Ile His Ser Pro Glu Glu Gln Asp Phe
                195                 200                 205

Leu Thr Lys His Ala Ser His Thr Gly Ser Trp Ile Gly Leu Arg Asn
            210                 215                 220

Leu Asp Leu Lys Gly Glu Phe Ile Trp Val Asp Gly Ser His Val Asp
225                 230                 235                 240

Tyr Ser Asn Trp Ala Pro Gly Glu Pro Thr Ser Arg Ser Gln Gly Glu
                245                 250                 255

Asp Cys Val Met Met Arg Gly Ser Gly Arg Trp Asn Asp Ala Phe Cys
            260                 265                 270

Asp Arg Lys Leu Gly Ala Trp Val Cys Asp Arg Leu Ala Thr Cys Thr
            275                 280                 285

Pro Pro Ala Ser Glu Gly Ser Ala Glu Ser Met Gly Pro Asp Ser Arg
            290                 295                 300

Pro Asp Pro Asp Gly Arg Leu Pro Thr Pro Ser Ala Pro Leu His Ser
305                 310                 315                 320

<210> SEQ ID NO 136
<211> LENGTH: 260
<212> TYPE: PRT
<213> ORGANISM: Artificial Sequence
<220> FEATURE:
<223> OTHER INFORMATION: Description of Artificial Sequence: Target
      sequence

<400> SEQUENCE: 136

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
            115                 120                 125
```

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
                195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 137
<211> LENGTH: 220
<212> TYPE: PRT
<213> ORGANISM: Artificial Sequence
<220> FEATURE:
<223> OTHER INFORMATION: Description of Artificial Sequence: Target
      sequence

<400> SEQUENCE: 137

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 138
<211> LENGTH: 595
<212> TYPE: PRT
<213> ORGANISM: Artificial Sequence
<220> FEATURE:
<223> OTHER INFORMATION: Description of Artificial Sequence: Target sequence

<400> SEQUENCE: 138

```
Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
```

```
                    355                 360                 365
Ser Ala Pro Val Ala Leu Ser Ser Thr Gly Lys Pro Val Leu Asp Ala
370                 375                 380

Gly Pro Val Leu Phe Trp Val Ile Leu Val Leu Val Val Val Val Gly
385                 390                 395                 400

Ser Ser Ala Phe Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
    595

<210> SEQ ID NO 139
<211> LENGTH: 132
<212> TYPE: PRT
<213> ORGANISM: Artificial Sequence
<220> FEATURE:
<223> OTHER INFORMATION: Description of Artificial Sequence: Target
      sequence

<400> SEQUENCE: 139

Met Ser Gln Pro Leu Met Glu Thr Cys His Ser Val Gly Ala Ala Tyr
1               5                   10                  15

Leu Glu Ser Leu Pro Leu Gln Asp Ala Ser Pro Ala Gly Gly Pro Ser
            20                  25                  30

Ser Pro Arg Asp Leu Pro Glu Pro Arg Val Ser Thr Glu His Thr Asn
        35                  40                  45

Asn Lys Ile Glu Lys Ile Tyr Ile Met Lys Ala Asp Thr Val Ile Val
    50                  55                  60

Gly Thr Val Lys Ala Glu Leu Pro Glu Gly Arg Gly Leu Ala Gly Pro
65                  70                  75                  80

Ala Glu Pro Glu Leu Glu Glu Leu Glu Ala Asp His Thr Pro His
                85                  90                  95

Tyr Pro Glu Gln Glu Thr Glu Pro Pro Leu Gly Ser Cys Ser Asp Val
            100                 105                 110
```

```
Met Leu Ser Val Glu Glu Glu Gly Lys Glu Asp Pro Leu Pro Thr Ala
            115                 120                 125
Ala Ser Gly Lys
        130

<210> SEQ ID NO 140
<211> LENGTH: 738
<212> TYPE: PRT
<213> ORGANISM: Artificial Sequence
<220> FEATURE:
<223> OTHER INFORMATION: Description of Artificial Sequence: Target
      sequence

<400> SEQUENCE: 140

Met Gln Pro Arg Trp Ala Gln Gly Ala Thr Met Trp Leu Gly Val Leu
1               5                   10                  15
Leu Thr Leu Leu Leu Cys Ser Ser Leu Glu Gly Gln Glu Asn Ser Phe
            20                  25                  30
Thr Ile Asn Ser Val Asp Met Lys Ser Leu Pro Asp Trp Thr Val Gln
        35                  40                  45
Asn Gly Lys Asn Leu Thr Leu Gln Cys Phe Ala Asp Val Ser Thr Thr
    50                  55                  60
Ser His Val Lys Pro Gln His Gln Met Leu Phe Tyr Lys Asp Asp Val
65                  70                  75                  80
Leu Phe Tyr Asn Ile Ser Ser Met Lys Ser Thr Glu Ser Tyr Phe Ile
                85                  90                  95
Pro Glu Val Arg Ile Tyr Asp Ser Gly Thr Tyr Lys Cys Thr Val Ile
            100                 105                 110
Val Asn Asn Lys Glu Lys Thr Thr Ala Glu Tyr Gln Leu Leu Val Glu
        115                 120                 125
Gly Val Pro Ser Pro Arg Val Thr Leu Asp Lys Lys Glu Ala Ile Gln
    130                 135                 140
Gly Gly Ile Val Arg Val Asn Cys Ser Val Pro Glu Glu Lys Ala Pro
145                 150                 155                 160
Ile His Phe Thr Ile Glu Lys Leu Glu Leu Asn Glu Lys Met Val Lys
                165                 170                 175
Leu Lys Arg Glu Lys Asn Ser Arg Asp Gln Asn Phe Val Ile Leu Glu
            180                 185                 190
Phe Pro Val Glu Glu Gln Asp Arg Val Leu Ser Phe Arg Cys Gln Ala
        195                 200                 205
Arg Ile Ile Ser Gly Ile His Met Gln Thr Ser Glu Ser Thr Lys Ser
    210                 215                 220
Glu Leu Val Thr Val Thr Glu Ser Phe Ser Thr Pro Lys Phe His Ile
225                 230                 235                 240
Ser Pro Thr Gly Met Ile Met Glu Gly Ala Gln Leu His Ile Lys Cys
                245                 250                 255
Thr Ile Gln Val Thr His Leu Ala Gln Glu Phe Pro Glu Ile Ile Ile
            260                 265                 270
Gln Lys Asp Lys Ala Ile Val Ala His Asn Arg His Gly Asn Lys Ala
        275                 280                 285
Val Tyr Ser Val Met Ala Met Val Glu His Ser Gly Asn Tyr Thr Cys
    290                 295                 300
Lys Val Glu Ser Ser Arg Ile Ser Lys Val Ser Ser Ile Val Val Asn
305                 310                 315                 320
Ile Thr Glu Leu Phe Ser Lys Pro Glu Leu Glu Ser Ser Phe Thr His
                325                 330                 335
```

```
Leu Asp Gln Gly Glu Arg Leu Asn Leu Ser Cys Ser Ile Pro Gly Ala
            340                 345                 350

Pro Pro Ala Asn Phe Thr Ile Gln Lys Glu Asp Thr Ile Val Ser Gln
            355                 360                 365

Thr Gln Asp Phe Thr Lys Ile Ala Ser Lys Ser Asp Ser Gly Thr Tyr
    370                 375                 380

Ile Cys Thr Ala Gly Ile Asp Lys Val Val Lys Ser Asn Thr Val
385                 390                 395                 400

Gln Ile Val Val Cys Glu Met Leu Ser Gln Pro Arg Ile Ser Tyr Asp
                405                 410                 415

Ala Gln Phe Glu Val Ile Lys Gly Gln Thr Ile Glu Val Arg Cys Glu
            420                 425                 430

Ser Ile Ser Gly Thr Leu Pro Ile Ser Tyr Gln Leu Leu Lys Thr Ser
            435                 440                 445

Lys Val Leu Glu Asn Ser Thr Lys Asn Ser Asn Asp Pro Ala Val Phe
    450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
                485                 490                 495

Ile Ala Pro Val Asp Glu Val Gln Ile Ser Ile Leu Ser Ser Lys Val
            500                 505                 510

Val Glu Ser Gly Glu Asp Ile Val Leu Gln Cys Ala Val Asn Glu Gly
            515                 520                 525

Ser Gly Pro Ile Thr Tyr Lys Phe Tyr Arg Glu Lys Glu Gly Lys Pro
            530                 535                 540

Phe Tyr Gln Met Thr Ser Asn Ala Thr Gln Ala Phe Trp Thr Lys Gln
545                 550                 555                 560

Lys Ala Ser Lys Glu Gln Glu Gly Glu Tyr Tyr Cys Thr Ala Phe Asn
                565                 570                 575

Arg Ala Asn His Ala Ser Ser Val Pro Arg Ser Lys Ile Leu Thr Val
            580                 585                 590

Arg Val Ile Leu Ala Pro Trp Lys Lys Gly Leu Ile Ala Val Val Ile
            595                 600                 605

Ile Gly Val Ile Ile Ala Leu Leu Ile Ile Ala Ala Lys Cys Tyr Phe
            610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
                645                 650                 655

Met Glu Ala Asn Ser His Tyr Gly His Asn Asp Asp Val Arg Asn His
            660                 665                 670

Ala Met Lys Pro Ile Asn Asp Asn Lys Glu Pro Leu Asn Ser Asp Val
            675                 680                 685

Gln Tyr Thr Glu Val Gln Val Ser Ser Ala Glu Ser His Lys Asp Leu
            690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
                725                 730                 735

Gly Thr
```

```
<210> SEQ ID NO 141
<211> LENGTH: 364
<212> TYPE: PRT
<213> ORGANISM: Artificial Sequence
<220> FEATURE:
<223> OTHER INFORMATION: Description of Artificial Sequence: Target
      sequence

<400> SEQUENCE: 141
```

| | | | | | | | | | | | | | | |
|---|---|---|---|---|---|---|---|---|---|---|---|---|---|---|
|Met|Pro|Leu|Leu|Leu|Leu|Pro|Leu|Leu|Trp|Ala|Gly|Ala|Leu|Ala|
|1| | |5| | | | |10| | | | |15| |

Met Asp Pro Asn Phe Trp Leu Gln Val Gln Glu Ser Val Thr Val Gln
             20                  25                  30

Glu Gly Leu Cys Val Leu Val Pro Cys Thr Phe Phe His Pro Ile Pro
         35                  40                  45

Tyr Tyr Asp Lys Asn Ser Pro Val His Gly Tyr Trp Phe Arg Glu Gly
     50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                 85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 142
<211> LENGTH: 385
<212> TYPE: PRT
<213> ORGANISM: Artificial Sequence
<220> FEATURE:
<223> OTHER INFORMATION: Description of Artificial Sequence: Target sequence

<400> SEQUENCE: 142

```
Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110

Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
        195                 200                 205

Gly Leu Ala Arg Val Leu Cys Gly Glu Glu Gln Ala Asp Ala Asp Ala
    210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
        275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
305                 310                 315                 320

Gly Glu Arg Leu Gly Glu Asp Pro Tyr Tyr Thr Glu Asn Gly Gly Gly
                325                 330                 335

Gln Gly Tyr Ser Ser Gly Pro Gly Thr Ser Pro Glu Ala Gln Gly Lys
            340                 345                 350

Ala Ser Val Asn Arg Gly Ala Gln Glu Asn Gly Thr Gly Gln Ala Thr
        355                 360                 365
```

```
Ser Arg Asn Gly His Ser Ala Arg Gln His Val Val Ala Asp Thr Glu
    370             375                 380

Leu
385

<210> SEQ ID NO 143
<211> LENGTH: 277
<212> TYPE: PRT
<213> ORGANISM: Artificial Sequence
<220> FEATURE:
<223> OTHER INFORMATION: Description of Artificial Sequence: Target
      sequence

<400> SEQUENCE: 143

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 144
<211> LENGTH: 61
<212> TYPE: PRT
<213> ORGANISM: Artificial Sequence
<220> FEATURE:
<223> OTHER INFORMATION: Description of Artificial Sequence: Target
```

-continued sequence

<400> SEQUENCE: 144

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45

Phe Val Ala Asn Ala Ile Ile His Leu Phe Cys Phe Ser
    50                  55                  60

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: Target
      sequence

<400> SEQUENCE: 145

Met Lys Arg Phe Leu Phe Leu Leu Leu Thr Ile Ser Leu Leu Val Met
1               5                   10                  15

Val Gln

<210> SEQ ID NO 146
<211> LENGTH: 858
<212> TYPE: PRT
<213> ORGANISM: Artificial Sequence
<220> FEATURE:
<223> OTHER INFORMATION: Description of Artificial Sequence: Target
      sequence

<400> SEQUENCE: 146

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

```
Ile Leu Ala Arg Gly Glu Ile Asn Phe Lys Asp Ile Gln Val Ile Val
            195                 200                 205

Asn Val Pro Pro Thr Ile Gln Ala Arg Gln Asn Ile Val Asn Ala Thr
210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
            245                 250                 255

Glu Glu Asp Asp Glu Lys Tyr Ile Phe Ser Asp Ser Ser Gln Leu
            260                 265                 270

Thr Ile Lys Lys Val Asp Lys Asn Asp Glu Ala Glu Tyr Ile Cys Ile
            275                 280                 285

Ala Glu Asn Lys Ala Gly Glu Gln Asp Ala Thr Ile His Leu Lys Val
            290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
            325                 330                 335

Pro Ser Ile Thr Trp Arg Thr Ser Thr Arg Asn Ile Ser Ser Glu Glu
            340                 345                 350

Lys Ala Ser Trp Thr Arg Pro Glu Lys Gln Glu Thr Leu Asp Gly His
            355                 360                 365

Met Val Val Arg Ser His Ala Arg Val Ser Ser Leu Thr Leu Lys Ser
            370                 375                 380

Ile Gln Tyr Thr Asp Ala Gly Glu Tyr Ile Cys Thr Ala Ser Asn Thr
385                 390                 395                 400

Ile Gly Gln Asp Ser Gln Ser Met Tyr Leu Glu Val Gln Tyr Ala Pro
            405                 410                 415

Lys Leu Gln Gly Pro Val Ala Val Tyr Thr Trp Glu Gly Asn Gln Val
            420                 425                 430

Asn Ile Thr Cys Glu Val Phe Ala Tyr Pro Ser Ala Thr Ile Ser Trp
            435                 440                 445

Phe Arg Asp Gly Gln Leu Leu Pro Ser Ser Asn Tyr Ser Asn Ile Lys
450                 455                 460

Ile Tyr Asn Thr Pro Ser Ala Ser Tyr Leu Glu Val Thr Pro Asp Ser
465                 470                 475                 480

Glu Asn Asp Phe Gly Asn Tyr Asn Cys Thr Ala Val Asn Arg Ile Gly
            485                 490                 495

Gln Glu Ser Leu Glu Phe Ile Leu Val Gln Ala Asp Thr Pro Ser Ser
            500                 505                 510

Pro Ser Ile Asp Gln Val Glu Pro Tyr Ser Ser Thr Ala Gln Val Gln
            515                 520                 525

Phe Asp Glu Pro Glu Ala Thr Gly Gly Val Pro Ile Leu Lys Tyr Lys
            530                 535                 540

Ala Glu Trp Arg Ala Val Gly Glu Glu Val Trp His Ser Lys Trp Tyr
545                 550                 555                 560

Asp Ala Lys Glu Ala Ser Met Glu Gly Ile Val Thr Ile Val Gly Leu
            565                 570                 575

Lys Pro Glu Thr Thr Tyr Ala Val Arg Leu Ala Ala Leu Asn Gly Lys
            580                 585                 590

Gly Leu Gly Glu Ile Ser Ala Ala Ser Glu Phe Lys Thr Gln Pro Val
            595                 600                 605

Gln Gly Glu Pro Ser Ala Pro Lys Leu Glu Gly Gln Met Gly Glu Asp
```

-continued

```
                610                 615                 620
Gly Asn Ser Ile Lys Val Asn Leu Ile Lys Gln Asp Gly Gly Ser
625                 630                 635                 640

Pro Ile Arg His Tyr Leu Val Arg Tyr Arg Ala Leu Ser Ser Glu Trp
                645                 650                 655

Lys Pro Glu Ile Arg Leu Pro Ser Gly Ser Asp His Val Met Leu Lys
                660                 665                 670

Ser Leu Asp Trp Asn Ala Glu Tyr Glu Val Tyr Val Val Ala Glu Asn
            675                 680                 685

Gln Gln Gly Lys Ser Lys Ala Ala His Phe Val Phe Arg Thr Ser Ala
        690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
                725                 730                 735

Val Val Val Asp Ile Thr Cys Tyr Phe Leu Asn Lys Cys Gly Leu Phe
                740                 745                 750

Met Cys Ile Ala Val Asn Leu Cys Gly Lys Ala Gly Pro Gly Ala Lys
            755                 760                 765

Gly Lys Asp Met Glu Glu Gly Lys Ala Ala Phe Ser Lys Asp Glu Ser
        770                 775                 780

Lys Glu Pro Ile Val Glu Val Arg Thr Glu Glu Arg Thr Pro Asn
785                 790                 795                 800

His Asp Gly Gly Lys His Thr Glu Pro Asn Glu Thr Thr Pro Leu Thr
                805                 810                 815

Glu Pro Glu Lys Gly Pro Val Glu Ala Lys Pro Glu Cys Gln Glu Thr
            820                 825                 830

Glu Thr Lys Pro Ala Pro Ala Glu Val Lys Thr Val Pro Asn Asp Ala
        835                 840                 845

Thr Gln Thr Lys Glu Asn Glu Ser Lys Ala
    850                 855

<210> SEQ ID NO 147
<211> LENGTH: 193
<212> TYPE: PRT
<213> ORGANISM: Artificial Sequence
<220> FEATURE:
<223> OTHER INFORMATION: Description of Artificial Sequence: Target
      sequence

<400> SEQUENCE: 147

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Gln Leu Asn His
        50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
                100                 105                 110
```

```
Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
        130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 148
<211> LENGTH: 378
<212> TYPE: PRT
<213> ORGANISM: Artificial Sequence
<220> FEATURE:
<223> OTHER INFORMATION: Description of Artificial Sequence: Target
      sequence

<400> SEQUENCE: 148

Met Val Leu Leu Trp Leu Thr Leu Leu Leu Ile Ala Leu Pro Cys Leu
1               5                   10                  15

Leu Gln Thr Lys Glu Asp Pro Asn Pro Ile Thr Asn Leu Arg Met
            20                  25                  30

Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
    50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
    130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
    210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270
```

```
Arg Ala Arg Glu Arg Val Tyr Glu Phe Leu Ser Ala Trp Ser Thr Pro
            275                 280                 285

Gln Arg Phe Glu Cys Asp Gln Glu Gly Ala Asn Thr Arg Ala Trp
    290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
                340                 345                 350

Lys Leu Val Val Trp Glu Ala Gly Lys Ala Gly Leu Glu Glu Cys Leu
            355                 360                 365

Val Thr Glu Val Gln Val Val Gln Lys Thr
            370                 375

<210> SEQ ID NO 149
<211> LENGTH: 240
<212> TYPE: PRT
<213> ORGANISM: Artificial Sequence
<220> FEATURE:
<223> OTHER INFORMATION: Description of Artificial Sequence: Target
      sequence

<400> SEQUENCE: 149

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Val Leu Gln Trp Ala Glu Lys Gly Tyr Tyr Thr Met Ser
        115                 120                 125

Asn Asn Leu Val Thr Leu Glu Asn Gly Lys Gln Leu Thr Val Lys Arg
    130                 135                 140

Gln Gly Leu Tyr Tyr Ile Tyr Ala Gln Val Thr Phe Cys Ser Asn Arg
145                 150                 155                 160

Glu Ala Ser Ser Gln Ala Pro Phe Ile Ala Ser Leu Cys Leu Lys Ser
                165                 170                 175

Pro Gly Arg Phe Glu Arg Ile Leu Leu Arg Ala Ala Asn Thr His Ser
            180                 185                 190

Ser Ala Lys Pro Cys Gly Gln Gln Ser Ile His Leu Gly Gly Val Phe
        195                 200                 205

Glu Leu Gln Pro Gly Ala Ser Val Phe Val Asn Val Thr Asp Pro Ser
    210                 215                 220

Gln Val Ser His Gly Thr Gly Phe Thr Ser Phe Gly Leu Leu Lys Leu
225                 230                 235                 240

<210> SEQ ID NO 150
```

<211> LENGTH: 320
<212> TYPE: PRT
<213> ORGANISM: Artificial Sequence
<220> FEATURE:
<223> OTHER INFORMATION: Description of Artificial Sequence: Target sequence

<400> SEQUENCE: 150

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala Lys Pro Thr Lys Gln Glu Glu Phe Tyr Ala
305                 310                 315                 320

<210> SEQ ID NO 151
<211> LENGTH: 420
<212> TYPE: PRT
<213> ORGANISM: Artificial Sequence
<220> FEATURE:
<223> OTHER INFORMATION: Description of Artificial Sequence: Target sequence

<400> SEQUENCE: 151

-continued

```
Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
            165                 170                 175

Glu Leu Ile Leu Asn His Ile Val Pro Pro Glu Asp Glu Arg Gln Asn
        180                 185                 190

Arg Ser Phe Glu Gly Met Val Val Ala Leu Leu Ala Gly Arg Ala
    195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
            245                 250                 255

Leu Thr His Leu Glu Ser Leu His Leu Glu Asp Asn Ala Leu Lys Val
        260                 265                 270

Leu His Asn Gly Thr Leu Ala Glu Leu Gln Gly Leu Pro His Ile Arg
    275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
            325                 330                 335

Leu Asn Ser Ala Asp Leu Asp Cys Asp Pro Ile Leu Pro Pro Ser Leu
        340                 345                 350

Gln Thr Ser Tyr Val Phe Leu Gly Ile Val Leu Ala Leu Ile Gly Ala
    355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
            405                 410                 415
```

```
Asn Ser Asp Val
            420

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Signal
      peptide

<400> SEQUENCE: 152

Asp Ala Ala Gln Pro Ala
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Motif

<400> SEQUENCE: 153

Pro Asn Asn Pro Asn Asn Pro
1               5

<210> SEQ ID NO 154
<211> LENGTH: 21
<212> TYPE: PRT
<213> ORGANISM: Homo sapiens

<400> SEQUENCE: 154

Met Gln Thr Asp Thr Leu Leu Leu Trp Val Leu Leu Leu Trp Val Pro
1               5                   10                  15

Gly Ser Thr Gly Ala
            20
```

ANTIBODY/DRUG CONJUGATES AND METHODS OF USE

RELATED APPLICATIONS

This application claims priority to application Ser. No. 61/720,257, filed Oct. 30, 2012, which application is expressly incorporated herein by reference in its entirety.

TECHNICAL FIELD

The invention relates to antibodies, and Heavy (H) chains and/or Light (L) chains of antibodies, and antibody fragments fused or conjugated to drugs, such as lytic peptide conjugates, methods of using conjugates, for example, in methods of treating undesirable or aberrant cell proliferation or hyperproliferative disorders, such as non-metastatic and metastatic neoplasias, cancers, tumors and malignancies that express targets that bind to such antibodies, and Heavy (H) chains and/or Light (L) chains of antibodies.

INTRODUCTION

The need to develop new therapeutics for treatment of primary tumors and metastases is clearly evident when the five year survival rate of cancer patients is considered: Only 10-40% for patients with lung, colorectal, breast and prostate cancer survive if diagnosed with distant metastatic disease.

SUMMARY

The invention is based, at least in part on lytic domains fused to an antibody, lytic domains fused or conjugated to Heavy (H) chains and/or Light (L) chains of antibodies, and lytic domains fused or conjugated to antibody fragments, that bind to a target (e.g., Her2/neu, Human Epidermal growth factor Receptor 2, also known as ErbB-2, CD20). Such fusions can also be referred to herein as antibody or polypeptide conjugates or fusion constructs. Contact of a cell with a lytic domain is believed to cause disruption of the cell membrane which results in cell death. The antibody, or Heavy (H) chain and/or Light (L) chain of an antibody that binds to the target allows the lytic domain to target expressing cells for destruction, including undesirable or aberrant proliferating cells or hyperproliferating cells, such as non-metastatic and metastatic neoplasias, cancers, tumors and malignancies, that express the target to which the antibody or Heavy (H) chain and/or Light (L) chain binds. A number of non-metastatic and metastatic neoplastic, cancer, tumor and malignant cells overexpress targets, such as receptors or ligands. For example, many non-metastatic and metastatic neoplasias, cancers, tumors and malignancies, express a receptor target (e.g., Her2/neu or CD20) that can be used as a target of the antibody or polypeptide conjugate or fusion construct.

Conjugates can be designed to bind to any cell or cell population that expresses a target of interest. An antibody, fragment thereof, or Heavy (H) chain and/or Light (L) chain of an antibody or fragment thereof, selected based upon the target to which it binds, can be linked to a lytic domain. The resulting antibody or polypeptide conjugate or fusion construct can in turn reduce or inhibit proliferation of cells that express or target, thereby reducing or inhibiting proliferation or growth of the target expressing cells.

Conjugates do not require cells to divide in order to kill the target cells. Accordingly, conjugates are useful against dividing and non-dividing cells.

In accordance with the invention, there are provided antibody and polypeptide conjugates that include a lytic domain. In one embodiment, an antibody conjugate includes or consists of an antibody (or fragment thereof) that binds to a target, linked to a lytic domain that includes or consists of an L- or D-amino acid sequence that includes a peptide sequence selected from for example, KFAKFAKKFAK-FAKK, KFAKFAKKFAKFAKKF, KFAKFAKKFAKFAK-KFA, KFAKFAKKFAKFAKKFAK, KFAKFAKKFAK-FAKKFAKF, KFAKFAKKFAKFAKKFAKFA and KFAKFAKKFAKFAKKFAKFAKKFAKFAK (SEQ ID NOs.:1-7), or an L- or D-amino acid sequence that includes a peptide selected from KFAKFAKKFAKFAKK, KFAK-FAKKFAKFAKKF, KFAKFAKKFAKFAKKFA, KFAK-FAKKFAKFAKKFAK, KFAKFAKKFAKFAKKFAKF and KFAKFAKKFAKFAKKFAKFA (SEQ ID NOs.:1-6) having one or more of the K residues substituted with any of an F or L residue, one or more of the F residues substituted with any of a K, A or L residue, or one or more of the A residues substituted with any of a K, F or L residue. In another embodiment, a polypeptide conjugate includes or consists of a Heavy (H) chain and/or Light (L) chain of an antibody or fragment thereof that binds to a target, linked to a lytic domain that includes or consists of an L- or D-amino acid sequence selected from for example, KFAKFAKKFAK-FAKK, KFAKFAKKFAKFAKKF, KFAKFAKKFAKFAK-KFA, KFAKFAKKFAKFAKKFAK, KFAKFAKKFAK-FAKKFAKF, KFAKFAKKFAKFAKKFAKFA and KFAKFAKKFAKFAKKFAKFAKKFAKFAK (SEQ ID NOs.:1-7), or a sequence that includes a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF and KFAKFAKKFAKFAK-KFAKFA (SEQ ID NOs.:1-6) having one or more of the K residues substituted with any of an F or L residue, one or more of the F residues substituted with any of a K, A or L residue, or one or more of the A residues substituted with any of a K, F or L residue.

In a more particular embodiment, an antibody or polypeptide conjugate includes an antibody (or fragment thereof) or Heavy (H) chain and/or Light (L) chain of an antibody (e.g., trastuzumab or pertuzumab) or fragment thereof (trastuzumab or pertuzumab fragment) that binds to Her2/neu, linked to a lytic domain that includes or consists of an L- or D-amino acid sequence selected from, KFAKFAKKFAK-FAKK, KFAKFAKKFAKFAKKF, KFAKFAKKFAKFAK-KFA, KFAKFAKKFAKFAKKFAK, KFAKFAKKFAK-FAKKFAKF, KFAKFAKKFAKFAKKFAKFA and KFAKFAKKFAKFAKKFAKFAKKFAKFAK (SEQ ID NOs.:1-7), or a sequence that includes a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF and KFAKFAKKFAKFAK-KFAKFA (SEQ ID NOs.:1-6) having one or more of the K residues substituted with any of an F or L residue, one or more of the F residues substituted with any of a K, A or L residue, or one or more of the A residues substituted with any of a K, F or L residue.

In accordance with the invention, there are also provided isolated and purified conjugates that include or consist of an antibody (or fragment thereof) or a Heavy (H) chain and/or Light (L) chain of an antibody or fragment thereof that binds to a target, and a second domain. In various embodiments, a second domain includes or consists of a lytic domain:

KFAKFAKKFAKFAKK, KFAKFAKKFAKFAKKF, KFAKFAKKFAKFAKKFA, KFAKFAKKFAKFAKKFAK, KFAKFAKKFAKFAKKFAKF or KFAKFAKKFAKFAKKFAKFA (SEQ ID NOs.:1-7). In additional embodiments, a second domain includes or consists of: KFAKFAKKFAKFAKK, KFAKFAKKFAKFAKKF, KFAKFAKKFAKFAKKFA, KFAKFAKKFAKFAKKFAK, KFAKFAKKFAKFAKKFAKF or KFAKFAKKFAKFAKKFAKFA (SEQ ID NOs.:1-6) having one or more of the K residues substituted with any of an F or L residue, one or more of the F residues substituted with any of a K, A or L residue, or one or more of the A residues substituted with any of a K, F or L residue.

In accordance with the invention, there are further provided polypeptides that include one or more lytic domains. In various embodiments, a polypeptide includes or consists of: 1) lytic domain linked to the amino(NH$_2$)-terminus of an antibody Heavy (H) chain; 2) a lytic domain linked to the amino(NH$_2$)-terminus of an antibody Light (L) chain; 3) a lytic domain linked to a carboxy(C)-terminus of the antibody Heavy (H) chain; or 4) a lytic domain linked to a carboxy(C)-terminus of the antibody Light (L) chain. In additional various embodiments, a polypeptide includes or consists of: 1) lytic domain linked to an amino(NH$_2$)-terminus and a lytic domain linked to a carboxy(C)-terminus of an antibody Heavy (H) chain; or 2) a lytic domain linked to the amino(NH$_2$)-terminus and a lytic domain linked to a carboxy(C)-terminus of an antibody Light (L) chain.

Specific non-limiting examples of targets include amino acid sequences (e.g., polypeptides, peptides, proteins), polysaccharides, oligosaccharides, carbohydrates, and lipids. Specific non-limiting classes of targets include receptors and antigens.

Targets include receptors that bind to antigens, receptors or ligands, including hormones, growth factors, cluster of differentiation (collectively known as CD molecules or CD markers), hormone and growth factor analogues, and fragments of hormones, hormone analogs, growth factors, growth factor analogues, and fragments of growth factors and analogues. Particular non-limiting examples of receptor targets include Her2/neu (Human Epidermal growth factor Receptor 2, also known as ErbB-2), luteinizing hormone releasing hormone receptor (LHRH-R), epidermal growth factor (EGF) receptor, folate, and growth hormone (GH) receptor. Particular non-limiting examples of CD domains include CD19, CD20, CD22, CD23, CD27, CD28, CD30, CD31, CD33, CD34, CD40, CD52, CD56, CD70, CD123, CD138, or CD154, and others.

Antigen targets include viral, bacterial, fungal and parasite antigens. Antigen targets also include tumor associated antigens (TAAs).

An antibody includes 2 Heavy (H) chains and 2 Light (L) chains as well as antibody fragments. A polypeptide that includes or consists of a Heavy (H) chain and/or Light (L) chain of an antibody or fragment of a Heavy (H) chain or Light (L) chain can include a single H or L chain or a single H or L chain fragment, or a plurality (2, 3, 4 or more) of Heavy (H) chains and/or Light (L) chains, or a plurality of fragments of Heavy (H) chains and/or Light (L) chains A polypeptide that includes a Heavy (H) chain and/or Light (L) chain of an antibody or fragment can but is not required to include 2 Heavy (H) chains and 2 Light (L) chains and therefore polypeptide conjugates as set forth herein can exclude native antibodies that comprise 2 Heavy (H) chains and 2 Light (L) chains.

An antibody or fragment thereof may be an oligomeric (higher order or valent) forms, such as a trimer, tetramer, pentamer, hexamer, heptamer, and so forth, with other antibodies, fragments thereof, Heavy (H) chain, Light (L) chain, or polypeptides sequence distinct from an antibody Heavy (H) or Light (L) chain Antibodies include monoclonals and fragments of monoclonal antibodies. Antibodies include mammalian, human, humanized, primatized and chimeric sequences.

Amino acid sequences (e.g., polypeptides, peptides, proteins, antibodies, Heavy (H) chains, Light (L) chains, lytic domains, etc.) include or consist of natural (L-) or non-natural (e.g., D-) amino acids. In particular aspects, an amino acid sequence has about 2 to 10, 10 to 14, 15 to 20, (i.e., 15, 16, 17, 18, 19 or 20 amino acids), 10 to 20, 20 to 30, 30 to 40, 40 to 50, 60 to 70, 70 to 80, 80 to 90, 90 to 100, 100 to 125, 125 to 150, 150 to 175, 175 to 200, 200 to 250, 250 to 300, or more amino acid residues. Full-length antibody Heavy (H) chains, Light (L) chains, are typically 90 to 130 amino acids in length, but may be shorter, for example, comprise a variable Heavy (H) chain, or Light (L) chain sequence, comprising one, two, or three complemetarity determining regions (CDRs) with or without framework regions. Lytic domains are typically 10 to 14, 15 to 20, (i.e., 15, 16, 17, 18, 19 or 20 amino acids), 10 to 20, 20 to 30, 30 to 40, or 40 to 50, but may optionally be longer (50 or more) or shorter (less than 10). An amino acid sequence can include or consist of a linear or cyclic structure.

Conjugates that include lytic domains can have the lytic domain at any location of the antibody (or fragment thereof) or Heavy (H) chain or Light (L) chain of an antibody. Thus, a lytic domain can be positioned at any amino acid position (amino acid residue) of the antibody (or fragment thereof) or Heavy (H) chain or Light (L) chain of an antibody. In addition, a conjugate can include multiple lytic domains. Accordingly, one or more (e.g., two, three, four, five, six, seven, eight or more) lytic domains linked to the Heavy (H) chain or Light (L) chain.) lytic domains can be included in a conjugate of the invention.

Lytic domains can also be positioned at the C-terminus, the NH$_2$-terminus, or both the C-terminus and the NH$_2$-terminus of a polypeptide sequence. In particular embodiments, a conjugate has a lytic domain positioned at either (or both) the NH$_2$-terminus or the C-terminus of the antibody (or fragment thereof) Heavy (H) chain or Light (L) chain, or Heavy (H) chain or Light (L) chain. In particular aspects, a lytic domain is linked to the amino(NH$_2$)-terminus of the Heavy (H) chain or linked to the carboxy(C)-terminus of the Heavy (H) chain; a lytic domain is linked to the amino (NH$_2$)-terminus of the Light (L) chain or linked to the carboxy(C)-terminus of the Light (L) chain. In a conjugate with a plurality of lytic domains, such domains can be linked to the Heavy (H) chain or Light (L) chain, to the amino (NH$_2$)-terminus of the Heavy (H) chain, to the carboxy(C)-terminus of the Heavy (H) chain, to the amino(NH$_2$)-terminus of the Light (L) chain, or to the carboxy(C)-terminus of the Light (L) chain. In more particular aspects, at least one of a plurality of lytic domains is linked to the amino(NH$_2$)-terminus of the Heavy (H) chain, and at least one is linked to the amino(NH$_2$)-terminus of the Light (L) chain; at least one of the lytic domains is linked to the amino(NH$_2$)-terminus of the Heavy (H) chain, at least one of the lytic domains is linked to the amino(NH$_2$)-terminus of the Light (L) chain, and at least one of the lytic domains is linked to the carboxy(C)-terminus of the Heavy (H) chain or is linked to the carboxy(C)-terminus of the Light (L) chain; and at least one of a plurality of lytic domains is linked to the amino(NH$_2$)-terminus of the Heavy (H) chain, at least one of the lytic domains is linked to the amino(NH$_2$)-terminus of the Light (L) chain, at least one of the lytic domains is linked to the carboxy(C)-terminus of the Heavy (H) chain and at least one of the lytic domains is linked to the carboxy(C)-terminus of the Light (L) chain.

In embodiments in which conjugates include a plurality of lytic domains, the lytic domains have an identical amino acid sequence, or have a different amino acid sequence. Accordingly a conjugate can include two, a third, fourth, fifth, sixth, seventh lytic domain, etc., any or all of which may be identical or different from each other.

In particular embodiments, a lytic domain is joined to a Heavy (H) chain or Light (L) chain immediately after the last amino acid at the amino($NH_2$)-terminus or the carboxy (C)-terminus of the Heavy (H) chain or the Light (L) chain, for example, by a covalent (e.g., peptide or nonpeptide) bond thereby forming a continuous amino acid sequence between the lytic domain and the Heavy (H) chain or Light (L) chain. In additional embodiments, antibodies, Heavy (H) chains and Light (L) chains and lytic domains can be joined by a peptide or a non-peptide linker or spacer. In particular aspects, antibodies, Heavy (H) chains and Light (L) chains and lytic domains and lytic domains are joined by a peptide sequence having from about 1 to 25 amino acid residues, or are joined by a linear carbon chain, such as $C_N$ (where N=1-100 carbon atoms, e.g., C, CC, CCC, CCCC, CCCCC, CCCCCC, CCCCCCC, CCCCCCCC, etc.). In more particular aspects, antibodies, Heavy (H) chains and Light (L) chains and lytic domains and lytic domains are joined by a peptide sequence that includes or consist of one or more A, S or G amino acid residues (e.g., a peptide sequence including or consisting of GSGGS (SEQ ID No.:8), ASAAS (SEQ ID No.:9), GS, AF, FK, VK, FFK, FA, GSGRSA (SEQ ID NO.:10), RVRRSV (SEQ ID NO.:11), SS, Cit-V (Cit=Citrulline ($H_2NC(O)NH(CH_2)_3CH(NH_2)CO_2H$); Val=Valine), F-Cit (F=Phenylalanine, Cit=Citrulline).

Conjugates further include or consist of additional (e.g., non-lytic) domains Thus, in various aspects, a conjugate includes a second, third, fourth, fifth, sixth, seventh domain, etc., which may be distinct from one or more (or all) lytic domains included in the conjugate.

Conjugates include or consist of isolated and/or purified forms. Conjugates also include or consist of a formulation or a mixture. Such formulations and mixtures include compositions, such as a mixture of conjugate and a pharmaceutically acceptable carrier or excipient appropriate for use, administration to or in vivo contact with a subject, or a mixture of conjugate and an anti-cell proliferative or immune stimulating agent.

Conjugates include or consist of a unit dosage form, such as a dosage form for use or administration to a subject. In one embodiment, a conjugate is a unit dosage to administer or in an amount effective to or treat a subject having undesirable cell proliferation or a hyperproliferative disorder. In another embodiment, a conjugate is a unit dosage to administer or in an amount effective to treat a subject having a neoplasia, tumor or cancer. In an additional embodiment, a conjugate is a unit dosage to administer or in an amount effective to reduce fertility of a subject.

Conjugates can be included within kits, optionally with instructions for practicing a method or use of the invention. In one embodiment, a kit includes a conjugate and instructions for reducing or inhibiting proliferation of a cell, reducing or inhibiting proliferation of a hyperproliferating cell, reducing or inhibiting proliferation of a neoplastic, tumor or cancer cell, treating a subject having a hyperproliferative disorder, treating a subject having a neoplasia, tumor or cancer, or reducing fertility of an animal.

There are also provided nucleic acids that encode conjugates. In various embodiments, a nucleic acid sequence encodes a: 1) lytic domain linked to the amino($NH_2$)-terminus of the antibody Heavy (H) chain; 2) a lytic domain linked to the amino($NH_2$)-terminus of the antibody Light (L) chain; 3) a lytic domain linked to the carboxy(C)-terminus of the antibody Heavy (H) chain; or 4) a lytic domain linked to the carboxy(C)-terminus of the antibody Light (L) chain, of an antibody or polypeptide conjugate. In another embodiment, a nucleic acid sequence encodes a: 1) lytic domain linked to the amino($NH_2$)-terminus and a lytic domain linked to the carboxy(C)-terminus of the antibody Heavy (H) chain; 2) a lytic domain linked to the amino($NH_2$)-terminus and a lytic domain linked to the carboxy(C)-terminus of the antibody Light (L) chain, of the antibody or polypeptide conjugate.

Nucleic acids can be included in a vector, such as an expression vector that when expressed in a cell encodes a conjugate. Host cells can be transformed with a nucleic acid (e.g., encoding all or a portion of a conjugate, e.g., a Heavy (H) chain and/or Light (L) chain sequence linked to a lytic domain) in a vector, such that the cell expresses a conjugate encoded by the nucleic acid.

As disclosed herein, targets can be expressed in or on a cell. Cells that express a target to which a conjugate binds can be targeted for binding by the conjugates of the invention. Accordingly, such cells can be selectively targeted by selecting a conjugate that binds to a target expressed by the cells.

Non-limiting target expressing cells include, for example, hyperproliferative cells. Additional cells that express targets include, for example, breast, ovarian, uterine, cervical, stomach, lung, gastric, colon, bladder, glial, dermal (e.g., melanocytes), hematologic and endometrial cells.

Conjugates are useful for, among other things, reducing or inhibiting proliferation of a cell, reducing or inhibiting cell proliferation, reducing or inhibiting proliferation of a hyperproliferating cell, reducing or inhibiting proliferation of a neoplastic, tumor, cancer or malignant cell and treating undesirable or aberrant cell proliferation, such as hyperproliferating cells or hyperproliferative disorders. Non-limiting examples of hyperproliferative disorders include benign hyperplasia, non-metastatic and metastatic neoplasias, cancers tumors and malignancies.

In accordance with the invention, there are further provided methods of reducing or inhibiting proliferation of a cell; methods of reducing or inhibiting cell proliferation; methods of reducing or inhibiting proliferation of a hyperproliferating cell; and methods of reducing or inhibiting proliferation of a neoplastic, tumor, cancer or malignant cell. In various embodiments, a method includes contacting a cell with a conjugate in an amount sufficient to reduce or inhibit proliferation of the cell; contacting a cell with a conjugate in an amount sufficient to reduce or inhibit cell proliferation; contacting a cell with a conjugate in an amount sufficient to reduce or inhibit proliferation of the hyperproliferating cell; and contacting a cell with a conjugate in an amount sufficient to reduce or inhibit proliferation of the neoplastic, tumor, cancer or malignant cell.

In accordance with the invention, there are moreover provided methods of selectively reducing or inhibiting proliferation of a cell that expresses a target to which a conjugate binds; selectively reducing or inhibiting proliferation of a hyperproliferating cell that express a target to which a conjugated binds; and selectively reducing or inhibiting proliferation of a neoplastic, tumor, cancer or malignant cell that expresses a target to which a conjugated binds. In various embodiments, a method includes contacting a target expressing cell with a conjugate in an amount sufficient to reduce or inhibit proliferation of the cell; contacting a target expressing cell with the conjugate in an amount sufficient to reduce or inhibit proliferation of the hyperproliferating cell; and contacting a target expressing cell with a conjugate in an amount sufficient to reduce or inhibit proliferation of the neoplastic, tumor, cancer or malignant cell, wherein the conjugate binds to a target expressed by the cell.

Exemplary cells to be targeted in accordance with the invention uses and methods include cells that express any desired target. Such non-limiting cells therefore include, for example, breast, ovarian, uterine, cervical, stomach, lung, gastric, colon, bladder, glial, dermal (e.g., melanocytes), hematologic and endometrial cells. More particular non-limiting cells express a receptor, such as Her2/neu, an antigen (e.g., a tumor associated antigen) or a cluster of differentiation domain (CD).

Methods performed include, among others, administering to or contacting a subject in need of inhibiting, reducing or preventing proliferation, survival, differentiation, death, or activity of a cell, such as a hyperproliferative cell or an undesirably proliferating cell. Exemplary subjects include a subject having or at risk of having undesirable or aberrant cell proliferation; a subject having or at risk of having a benign hyperplasia; or a non-metastatic or metastatic neoplasia, cancer, tumor or malignancy (e.g., a solid or liquid tumor, in any of breast, ovarian, uterine, cervical, stomach, lung, gastric, colon, bladder, glial, dermal (e.g., melanocytes), hematologic or endometrial cells).

In accordance with the invention, there are additionally provided uses and methods of treating a subject having a hyperproliferative disorder and uses and methods of treating a subject having a neoplasia, tumor, cancer or malignancy (metastatic, non-metastatic or benign). In various embodiments, a use or method includes, administering to a subject an amount of the conjugate sufficient to treat the hyperproliferative disorder; and administering to a subject an amount of the conjugate sufficient to reduce or inhibit proliferation of the neoplasia, tumor, cancer or malignancy.

Methods and uses include treating a subject having or at risk of having a metastasis. For example, an amount of a conjugate effective to reduce or inhibit spread or dissemination of a tumor, cancer or neoplasia to other sites, locations or regions within the subject. In various embodiments, a method or use reduces or inhibits metastasis of a primary tumor or cancer to one or more other sites, formation or establishment of a metastasis at one or more other sites, locations or regions thereby reducing or inhibiting tumor or cancer relapse or tumor or cancer progression. In further embodiments, a method or use reduces or inhibits growth, proliferation, mobility or invasiveness of tumor or cancer cells that potentially or do develop metastases (e.g., disseminated tumor cells); reduces or inhibits formation or establishment of metastases arising from a primary tumor or cancer to one or more other sites, locations or regions distinct from the primary tumor or cancer; reduces or inhibits growth or proliferation of a metastasis at one or more other sites, locations or regions distinct from the primary tumor or cancer after the metastasis has formed or has been established; or reduces or inhibits formation or establishment of additional metastasis after the metastasis has been formed or established. In yet another embodiment, a method or use reduces or inhibits relapse or progression of the neoplasia, tumor, cancer or malignancy.

In accordance with the invention, there are still further provided methods and uses of reducing or inhibiting metastasis of a neoplasia, tumor, cancer or malignancy to other sites, or formation or establishment of metastatic neoplasia, tumor, cancer or malignancy at other sites distal from a primary neoplasia, tumor, cancer or malignancy. In various embodiments, a method includes administering to a subject an amount of the conjugate sufficient to reduce or inhibit metastasis of the neoplasia, tumor, cancer or malignancy to other sites, or formation or establishment of metastatic neoplasia, tumor, cancer or malignancy at other sites distal from the primary neoplasia, tumor, cancer or malignancy.

Neoplasia, tumor, cancer and malignancy treatable in accordance with the invention therefore include metastatic, and non-metastatic or benign forms. Non-limiting examples include a solid cellular mass, hematopoietic cells, or a carcinoma, sarcoma (e.g. lymphosarcoma, liposarcoma, osteosarcoma, chondrosarcoma, leiomyosarcoma, rhabdomyosarcoma or fibrosarcoma), lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic or haematopoietic (e.g., myeloma, lymphoma or leukemia) neoplasia, tumor, cancer or malignancy.

Neoplasia, tumor, cancer and malignancy treatable in accordance with the invention can be present in or affect a lung (small cell lung or non-small cell lung cancer), thyroid, head or neck, nasopharynx, throat, nose or sinuses, brain, spine, adrenal gland, pituitary gland, breast, ovarian, uterine, cervical, gastrointestinal (mouth, esophagus, stomach, duodenum, ileum, jejunum (small intestine), colon, rectum), lung, genito-urinary tract (uterus, ovary, cervix, endometrial, bladder, testicle, penis, prostate), glial, hematologic, endometrial, lymph, blood, muscle, dermal (e.g., melanocytes) or skin cell, kidney, pancreas, liver, bone, bone marrow, Wilm's tumors, biliary tract, B-ALL (B-cell lymphoblastic leukemia), stem cell, or hematologic neoplasia, tumor, cancer, or malignancy.

Methods and uses may be practiced alone, for example, in subjects that are not candidates for other therapies (e.g., surgical resection, chemotherapy, immunotherapy, radiotherapy, thermal therapy, vaccination, etc.). Methods and uses may also be practiced with other treatments or therapies (e.g., surgical resection, radiotherapy, ionizing or chemical radiation therapy, chemotherapy, immunotherapy, local or regional thermal (hyperthermia) therapy, or vaccination). Such treatments or therapies can be administered prior to, substantially contemporaneously with (separately or in a mixture), or following administration of a conjugate. In one embodiment, a method or use includes administering an anti-cell proliferative, anti-neoplastic, anti-tumor, anti-cancer or immune-enhancing treatment or therapy. In further embodiments, a method or use includes administering an alkylating agent, anti-metabolite, plant extract, plant alkaloid, nitrosourea, hormone, nucleoside or nucleotide analog; cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, 5-azacytidine (5-AZC) and 5-azacytidine related compounds, bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, a taxane (e.g., taxol or paclitaxel), vinblastine, vincristine, doxorubicin or dibromomannitol, topoisomerase inhibitors, (irinotecan, topotecan, etoposide, teniposide), gemcitabine, pemetrexed etc.

Cell or immunotherapies include lymphocytes, plasma cells, macrophages, dendritic cells, T-cells, NK cells or B-cells; an antibody, a cell growth factor, a cell survival factor, a cell differentiative factor, a cytokine or a chemokine. Additional agents that are applicable with conjugates in compostions, methods or uses of the invention include targeted drugs or biologicals, such as antibodies (monoclonal) or small molecules.

Methods of the invention include providing a subject with a benefit. In particular embodiments, a method of treatment results in partial or complete destruction of the neoplastic, tumor, cancer or malignant cell mass, volume, size or numbers of cells, stimulating, inducing or increasing neoplastic, tumor, cancer or malignant cell necrosis, lysis or apoptosis, reducing neoplasia, tumor, cancer or malignancy volume size, cell mass, inhibiting or preventing progression or an increase in neoplasia, tumor, cancer or malignancy volume, mass, size or cell numbers, or prolonging lifespan; results in reducing or decreasing severity, duration or frequency of an adverse symptom or complication associated with or caused by the neoplasia, tumor, cancer or malignancy; results in reducing or decreasing pain, discomfort, nausea, weakness or lethargy; or results in increased energy, appetite, improved mobility or psychological well being.

Subjects treatable in accordance with the methods include mammals. In particular embodiments, a subject is a human.

DESCRIPTION OF DRAWINGS

FIGS. 1A and 1B show cytotoxicity of recombinant 1 scFv-CH3 (naked antibody), scFv-$C_H$3-GS-Phor18 and scFv-$C_H$3-GS-(KLAKLAK)$_2$KLAK (SEQ ID NO.:74) to Her2-neu receptor positive A) breast (SKBR-3); and B) ovarian (SKOV-3) cancer cell lines determined after 48 hours.

FIGS. 2A and 2B show median tumor volumes from mice treated with naked monoclonal antibody (MAb), A) MAb-Phor18 and B) recombinant scFv-$C_H$3 naked antibody and scFv-$C_H$3-Phor18 conjugates during the study period of 64 days in SKOV-3 xenografted mice in comparison with saline injected mice.

FIGS. 10A and 10B show in vitro activity of recombinantly produced scFv-Phor18 compared to naked scFv in CD20 expressing Daudi cells. A) Cell membrane integrity was determined after 2 h, and B) cell viability was determined after 24 h of incubation with each naked and conjugated AB. Naked scFv did not disintegrate cell membranes or killed the target cells, whereas scFv-Phor18 conjugates showed membrane disintegration and cell killing.

DETAILED DESCRIPTION

Figure 3:
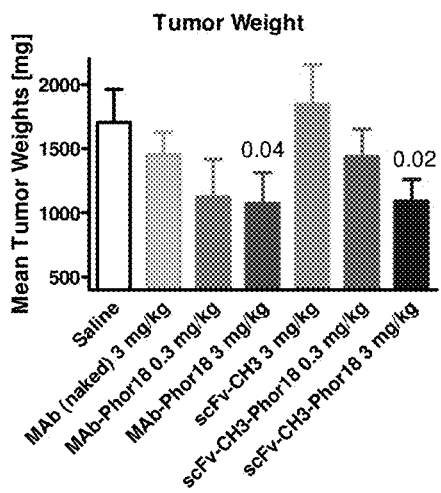
FIG. 3 shows mean tumor weights from mice treated with MAb (naked), MAb-Phor18 and recombinantly scFv-$C_H$3 naked antibody and scFv-$C_H$3-Phor18 conjugates on day 64 in SKOV-3 xenografted mice in comparison with saline injected mice.

The invention is based at least in part on a conjugate that includes a portion that binds to a target joined or fused to a second lytic domain. In a typical configuration, a conjugate includes a first target binding domain (e.g., an antibody, or a Heavy (H) chain and/or Light (L) chain of an antibody) and a second domain that includes a lytic portion, which is/are directly or indirectly toxic to a cell, which can thereby reduce cell proliferation or survival, or stimulate, induce, increase or enhance cell death, killing or apoptosis.

In accordance with the invention, there are provided conjugates that include or consist of an antibody, or a Heavy (H) chain and/or Light (L) chain of an antibody, that bind to a target, and a second lytic or toxic domain. In one embodiment, a conjugate includes an antibody or fragment thereof and a lytic domain comprising or consisting of a 10-100 residue L- or D-amino acid sequence that includes a peptide sequence (selected from amino acids such as Lysine=K, Phenylalanine=F and Alanine=A), for example, KFAKFAK-KFAKFAKK, KFAKFAKKFAKFAKKF, KFAKFAK-KFAKFAKKFA, KFAKFAKKFAKFAKKFAK, KFAK-FAKKFAKFAKKFAKF, KFAKFAKKFAKFAKKFAKFA and KFAKFAKKFAKFAKKFAKFAKKFAKFAK (SEQ ID NO.:1-7). In another embodiment, a conjugate includes a Heavy (H) chain and/or Light (L) chain of an antibody and a lytic domain comprising or consisting of a 10-100 residue L- or D-amino acid sequence selected from KFAKFAK-KFAKFAKK, KFAKFAKKFAKFAKKF, KFAKFAK-KFAKFAKKFA, KFAKFAKKFAKFAKKFAK, KFAK-FAKKFAKFAKKFAKF, KFAKFAKKFAKFAKKFAKFA and KFAKFAKKFAKFAKKFAKFAKKFAKFAK (SEQ ID NOs.:1-7).

As used herein, the term "conjugate" or "fusion construct" and grammatical variations thereof, means that the construct contains portions or sections that are derived from, obtained or isolated from, or are based upon or modeled after two different molecular entities that are distinct from each other and do not typically exist together in nature. That is, for example, a first portion of the conjugate includes or consists of an antibody or antibody fragment, or a Heavy (H) chain and/or Light (L) chain of an antibody, and a second portion of the conjugate includes or consists of a lytic portion or domain, each of the first and second portions/ domains structurally distinct. A conjugate can also be referred to as a "fusion construct," wherein the conjugate includes or consists of a of an antibody or antibody fragment, or a Heavy (H) chain and/or Light (L) chain of an antibody, that bind to a target, and a second lytic domain or portion.

First domains and or second (lytic) domains of conjugates include or consist of amino acid sequences (peptides, polypeptides, proteins, lectins), nucleic acids (DNA, RNA) and carbohydrates (saccharides, sialic acid, galactose, mannose, fucose, acetylneuraminic acid, etc.). The terms "amino acid sequence," "protein," "polypeptide" and "peptide" are used interchangeably herein to refer to two or more amino acids, or "residues," covalently linked by an amide bond or equivalent Amino acid sequences can be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, NY).

First and second (lytic) domains of a conjugate or fusion construct include L-amino acid sequences, D-amino acid sequences and amino acid sequences with mixtures of L-amino acids and D-amino acids. Conjugates of amino acid sequences of first and second domains can be a linear or a cyclic structure, and can be further conjugated to another distinct moiety (e.g., third, fourth, fifth, sixth, seventh, etc. domains), form ultra or intermolecular disulfide bonds, and also form higher order multimers or oligomers (trimers, tetramers, pentamers, hexamers, heptamers, etc.) with other conjugates having the same or different antibody, Heavy (H) chain, Light (L) chain or lytic sequence, or with other entirely distinct molecules.

Exemplary lengths of conjugates are from about 10 to 15, 15 to 20, 20 to 25, 25 to 50, 50 to 100, 100 to 150, 150 to 200, or 200 to 300 or more amino acid residues in length. In particular embodiments, a first or second domain includes or consists of an amino acid sequence of about 1 to 10, 10 to 20, 15 to 20, 20 to 30, 30 to 40, 40 to 50, 60 to 70, 70 to 80, 80 to 90, 90 to 100 or more residues. In more particular embodiments, a lytic domain includes or consists of a 10, 11, 12, 13, 14, 15, 16, 17, 18, 19, 20, 21, 22, 23, 24, 25, 26, 27, 28, or more residue amino acid sequence, or a 10, 11, 12, 13, 15, 16, 17, 18, 19, 20, 22, 23, 24, 25, 26, 27, 28, or more residue amino acid sequence.

Conjugate that includes or consists of a first portion antibody or antibody fragment, or a Heavy (H) chain and/or Light (L) chain of an antibody, where the first portion binds to a target (e.g., receptor), and a second portion that includes or consists of a lytic domain, the lytic domain can form an amphipathic alpha-helix. An amphipathic alpha-helix contains mostly hydrophilic amino acids on one side of the alpha-helix and the other side contains mostly hydrophobic amino acids. Since the alpha helix makes a complete turn for every 3.6 residues, the amino acid sequence of an amphipathic alpha helix alternates between hydrophilic and hydrophobic residues every 3 to 4 residues. A PNNPNNP repeat pattern or motif is predicted to form an amphipathic alpha-helix where P represents a positively charged amino acid residue and N a neutral amino acid residue. A PNNPNNP repeat pattern provides a cationic binding site for the lytic peptide to interact with a negatively charged cell membrane and a hydrophobic site for membrane interaction/penetration. Conjugates therefore include that with lytic domains having one or more uninterrupted PNNPNNP repeat patterns or motifs, or one or more interrupted PNNPNNP repeat patterns or motifs, which can form an amphipathic alpha-helix. For example, a 15 or 18 residue amino acid sequence, such as KFAKFAKKFAKFAKK (SEQ ID NO.:1) and KFAKFAKKFAKFAKKFAK (SEQ ID NO.:4), has uninterrupted and interrupted PNNPNNP repeat motifs.

As disclosed herein, conjugates include antibodies and antibody fragments that bind to a target. An "antibody" refers to any monoclonal or polyclonal immunoglobulin molecule, such as IgM, IgG, IgA, IgE, IgD, and any subclass thereof. Exemplary subclasses for IgG are $IgG_1$, $IgG_2$, $IgG_3$ and $IgG_4$ including engineered antibody subclasses and recombinant antibodies with various glycosylation patterns.

Conjugates also include a Heavy (H) chain or a Light (L) chain of an antibody, or a fragment of a Heavy (H) chain or a Light (L) chain of an antibody, that bind to a target. Such conjugates can have a plurality of Heavy (H) chains and/or Light (L) chains of an antibody, or a fragment of Heavy (H) chains and/or Light (L) chains of an antibody, that bind to a target.

Antibody fragments, and fragments of Heavy (H) chains and/or Light (L) chains of an antibody, include the hypervariable (target binding) region, or any or all of the complementarity determining regions (CDRs) or framework regions (FRs) within a Heavy (H) chain and/or Light (L) chain of an antibody, sufficient to confer target binding. Specific non-limiting examples of antibody fragments include Fab, Fab', $F(ab')_2$, Fv, Fd, single-chain Fv (scFv), disulfide-linked Fvs (sdFv), $V_L$, $V_H$, Camel Ig, V-NAR, VHH, trispecific ($Fab_3$), bispecific ($Fab_2$), diabody (($V_L$-$V_H)_2$ or ($V_H$-$V_L)_2$), triabody (trivalent), tetrabody (tetravalent), minibody (($scF_V$-$C_H3)_2$), bispecific single-chain Fv (Bis-scFv), IgGdeltaCH2, scFv-Fc, $(scFv)_2$-Fc, affibody (e.g., ZHer2-neu:2, ZHer2-neu:4 ZHer2-neu:7 ZHer2-neu: 8), aptamer, avimer or nanobody.

Antibodies, Heavy (H) chains and Light (L) chains of an antibody, and fragments thereof, include those produced by or expressed on cells, such as B cells, or synthesized or engineered to be produced by other cells, e.g., CHO cells. Such antibodies, Heavy (H) chains and Light (L) chains of an antibody, and fragments thereof, include those with improved characteristics, such as increased serum stability and/or half life in vivo, PK, etc. (e.g., as described in Antibody Engineering Vol 1, Konterman R and Duebel S, eds., 2010, Springer, WO 2006/130834 and Horton et al., *Cancer Res* 68:8049 (2008)). Non-limiting mutations in the Fc include, for example, I253A, H310A, H435R, H435Q, G236R, L328R, S239D, I332E. Non-limiting mutations in IgG1 can be at residues 238, 252, 253, 254, 255, 256, 265, 272, 289, 288, 303, 305, 307, 309, 311, 312, 317, 340, 356, 360, 362, 376, 378, 380, 382, 386, 388, 400, 413, 415, 424, 433, 434, 435, 439 and/or 477 of the Fc region.

Antibodies, Heavy (H) chains and Light (L) chains of an antibody, and fragments thereof bind to a target. Specific non-limiting examples of targets include amino acid sequences (e.g., polypeptides, peptides, proteins), polysaccharides, oligosaccharides, carbohydrates, and lipids. Specific non-limiting classes of targets include receptors and antigens. Such targets can be expressed by or on a cell (e.g., on the cell membrane).

Targets include receptors that bind to hormones, growth factors, hormone and growth factor analogues, and fragments of hormones, hormone analogs, growth factors, growth factor analogues, and fragments of growth factors and analogues. Particular non-limiting examples of receptor targets include Her2/neu (Human Epidermal growth factor Receptor 2, also known as ErbB-2), luteinizing hormone releasing hormone receptor (LHRH-R), epidermal growth factor receptor (EGF-R), folate-, and growth hormone (GH) receptor. Further particular non-limiting examples of receptor targets include a tumor necrosis factor (TNF) family member receptor (e.g., TNF-alpha, TNF-beta (lymphtoxin, LT), TRAIL, Fas, LIGHT, or 4-1BB) or oncofetoprotein (5T4). Additional particular non-limiting examples of receptor targets include an immunoglobulin-like receptor (e.g., CD19, CD20, CD22, CD23, CD27, CD28, CD30, CD31, CD33, CD34, CD40, CD52, CD56, CD70, CD123, CD138, CD123, CD138, or CD154), or other receptors, (e.g., hormone receptor, a cytokine receptor, a growth factor receptor, or a chemokine receptor).

Antigen targets include viral, bacterial, fungal and parasite antigens. Antigen targets also include tumor associated antigens (TAAs). Particular non-limiting examples of TAA targets include carcinoembryonic antigen (CEA), alpha-fetoprotein (AFP), prostate specific antigen (PSA), prostate specific membrane antigen (PSMA), CA-125 (epithelial ovarian cancer), soluble Interleukin-2 (IL-2) receptor, RAGE-1, tyrosinase, MAGE-1, MAGE-2, NY-ESO-1, Melan-A/MART-1, glycoprotein (gp) 75, gp100, beta-catenin, PRAME, MUM-1, ZFP161, Ubiquilin-1, HOX-B6, YB-1, Osteonectin, ILF3, IGF-1, oncofetoprotein, luteinizing hormone releasing hormone receptor (LHRH-R), growth hormone receptor, phosphatidylserine, follicle stimulating hormone receptors, VGEF receptor, folate receptor, CD19, CD20, CD22, CD23, CD27, CD28, CD30, CD31, CD33, CD34, CD40, CD52, CD56, CD70, CD123, CD138, or CD154.

As disclosed herein, receptors, such as Her2/neu or CD20 are typically expressed by or present on (e.g., a membrane receptor) or within a cell. Receptors, such as Her2/neu, may associate with the cell membrane surface or traverse the cell membrane. CD20 is typically not internalized and is expressed on the surface of B cells and B-cell malignancies. Receptors therefore include full length intact native receptors containing an extracellular, transmembrane or cytoplasmic portion, as well as truncated forms or fragments thereof (e.g., an extracellular, transmembrane or cytoplasmic portion or subsequence of a receptor, such as Her2/neu alone, or in combination). For example, a soluble receptor such as Her2/neu typically lacks a transmembrane region and can optionally also lack all or a part of the native extracellular or cytoplasmic region (if present in native receptor, e.g., Her2/neu). Such truncated forms and fragments can retain at least partial binding to a conjugate.

Exemplary antibodies, Heavy (H) chains, Light (L) chains, and fragments thereof include those that bind to epitopes present on receptors. Exemplary Her2/neu epitopes to which antibodies, Heavy (H) chains or Light (L) chains of an antibody, or fragments thereof bind, include HER-2 (p5-13) A2, HER-2 (p8-16) A24, HER-2 (p48-56) A2, HER-2 (p63-71) A24, HER-2 (p106-114) A2, HER-2 (p369-377) A2, A3, A26, HER-2 (p435-443) A2, HER-2 (p654-662) A2, HER-2 (p665-673) A2, HER-2 (p689-697) A2, HER-2 (p754-762) A3, A11, A33, HER-2 (p773-782) A2, HER-2 (p780-788) A24, HER-2 (p785-794) A2, HER-2 (p789-797) A2, HER-2 (p799-807) A2, HER-2 (p952-961) A2 and HER-2 (p1023-1032) A2 (the amino acid position numbers of Her2/neu epitope is referred to by a "p" followed by arabic numbers).

Exemplary antibodies that bind to Her2/neu include humanized anti-ErbB2 antibodies huMAb4D1-1, huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN™) as described in U.S. Pat. No. 5,821,337; humanized 520C9 (WO 93/21319) and humanized 2C4 (pertuzumab) as described in U.S. Pat. No. 7,097,840 and pertuzumab variants as described in US2009/0285837A1. Non-limiting representative antibodies, Heavy (H) chains, Light (L) chains, and fragments thereof that bind to Her2/neu are set forth in Table A.

TABLE A (SEQ ID NOs.: 12-39)

huMAb4D5-1:
$V_L$ (Light chain):
```
1         10        20        30        40
DIQMTQSPSSLSASVGDRVTITCRASQDVNTAVAWYQQKPG
          50        60        70        80
KAPKLLIYSASFLESGVPSRFSGSGSGTDFTLTISSLQPEDF
          90        100
ATYYCQQHYTTPPTFGQGTKVEIK
```

$V_H$ (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISRDDSKNTLYLQ
          90        100       110       120
MNSLRAEDTAVYYCARWGGDGFYAMDVWGQGTLVTVSS
``` huMAb4D5-2:
$V_L$ (Light chain):
```
1         10        20        30        40
DIQMTQSPSSLSASVGDRVTITCRASQDVNTAVAWYQQKPG
          50        60        70        80
KAPKLLIYSASFLESGVPSRFSGSGSGTDFTLTISSLQPEDF
          90        100
ATYYCQQHYTTPPTFGQGTKVEIK
```

$V_H$ (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADDSKNTLYLQ
          90        100       110       120
MNSLRAEDTAVYYCARWGGDGFYAMDVWGQGTLVTVSS
``` huMAb4D5-3:
$V_L$ (Light chain):
```
1         10        20        30        40
DIQMTQSPSSLSASVGDRVTITCRASQDVNTAVAWYQQKPG
          50        60        70        80
KAPKLLIYSASFLESGVPSRFSGSGSGTDFTLTISSLQPEDF
          90        100
ATYYCQQHYTTPPTFGQGTKVEIK
```

$V_H$ (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGDGFYAMDVWGQGTLVTVSS
``` huMAb4D5-4:
$V_L$ (Light chain):
```
1         10        20        30        40
DIQMTQSPSSLSASVGDRVTITCRASQDVNTAVAWYQQKPG
          50        60        70        80
KAPKLLIYSASFLESGVPSRFSGSRSGTDFTLTISSLQPEDF
          90        100
ATYYCQQHYTTPPTFGQGTKVEIK
```

$V_H$ (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTLYLQ
          90        100       110       120
MNSLRAEDTAVYYCSRWGGDGFYAMDVWGQGTLVTVSS
```

TABLE A-continued

(SEQ ID NOs.: 12-39)

huMAb4D5-5:
V_L (Light chain):
```
1         10        20        30        40
DIQMTQSPSSLSASVGDRVTITCRASQDVNTAVAWYQQKPG
          50        60        70        80
KAPKLLIYSASFLESGVPSRFSGSRSGTDFTLTISSLQPEDF
          90        100
ATYYCQQHYTTPPTFGQGTKVEIK
```

V_H (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGDGFYAMDVWGQGTLVTVSS
``` huMAb4D5-6:
V_L (Light chain):
```
1         10        20        30        40
DIQMTQSPSSLSASVGDRVTITCRASQDVNTAVAWYQQKPG
          50        60        70        80
KAPKLLIYSASFLYSGVPSRFSGSRSGTDFTLTISSLQPEDF
          90        100
ATYYCQQHYTTPPTFGQGTKVEIK
```

V_H (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGDGFYAMDVWGQGTLVTVSS
``` huMAb4D5-7:
V_L (Light chain)
```
1         10        20        30        40
DIQMTQSPSSLSASVGDRVTITCRASQDVNTAVAWYQQKPG
          50        60        70        80
KAPKLLIYSASFLESGVPSRFSGSRSGTDFTLTISSLQPEDF
          90        100
ATYYCQQHYTTPPTFGQGTKVEIK
```

V_H (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGDGFYAMDVWGQGTLVTVSS
``` huMAb4D5-8:
V_L (Light chain):
```
1         10        20        30        40
DIQMTQSPSSLSASVGDRVTITCRASQDVNTAVAWYQQKPG
          50        60        70        80
KAPKLLIYSASFLYSGVPSRFSGSRSGTDFTLTISSLQPEDF
          90        100
ATYYCQQHYTTPPTFGQGTKVEIK
```

V_H (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGDGFYAMDVWGQGTLVTVSS
``` huMAb4D5:
V_L (Light chain):
```
1         10        20        30        40
DIQMTQSPSSLSASVGDRVTITCRASQDVNTAVAWYQQKPG
          50        60        70        80
KAPKLLIYSASFLYSGVPSRFSGSRSGTDFTLTISSLQPEDF
          90        100
ATYYCQQHYTTPPTFGQGTKVEIK
```

V_H (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGDGFYAMDVWGQGTLVTVSS
```

Antibody sequence permutations (U.S. Pat. No. 7,435,797 SQ 1 and 2))
huMAb4D5:
V_L (Light chain):
```
1         10        20        30        40
DIQMTQSPSSLSASVGDRVTITCRASQDVNTAVAWYQQKPG
          50        60        70        80
KAPKLLIYSASFLYSGVPSRFSGSRSGTDFTLTISSLQPEDF
          90        100
ATYYCQQHYTTPPTFGQGTKVEIK
```

V_H (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGDGFYAMDVWGQGTLVTVSS
``` huMAb4D5-8
(for VL: Q27, D28, N30, T31, A32, Y49, F53, Y55, R66 H91, Y92, T94; for VH: W95, D98, F100, Y100, Y102):
V_L (Light chain): Claim 1 mutation
```
1         10        20        30        40
DIQMTQSPSSLSASVGDRVTITCRASQDVSSAVAWYQQKPG
          50        60        70        80
KAPKLLID/WSASFLYSGVPSRFSGSRSGTDFTLTISSLQPEDF
          90        100
ATYYCQQHYTTPPTFGQGTKVEIK
```

V_H (heavy chain):
```
1         10        20        30        40
EVQLVESGGGLVQPGGSLRLSCAASGFNIKDTYIHWVRQAP
          50        60        70        80
GKGLEWVARIYPTNGYTRYADSVKGRFTISADTSKNTAYLQ
          90        100       110       120
MNSLRAEDTAVYYCSRWGGWGPK/LAMDYWGQGTLVTVSS
```

Pertuzumab Sequences (US 2010/0015157A1)
V_L (Light chain):
```
1         10        20        30        40
DIQMTQSPSSLSASVGDRVTITCKASQDVSIGVAWYQQKPG
          50        60        70        80
KAPKLLIYSASYRYTGVPSRFS GSGSGTDFTLTISS LQPED
          90        100       110       120
FATYYCQQYYIYPYTFGQGTKVEIKRTVAAPSVFIFPPSDEQ
          130       140       150       160
LKSGTASVVCLLNNNFYPREAKVQWKVDNALQSGENSQES
          170       180       190       200
VTEQDSKDSTYSLSSTLTLSKADYEKHKVYACEVTHQGLSS
          210
PVTKSFNRGEC
```

V_H (heavy chain):
```
1         10        20        30        40
EVQLVESGGGLVQPGGSLRLSCAASGFTFTDYTMDWVRQA
          50        60        70        80
PGKGLEWVADVNPNSGGSIYNQRFKGRFTLSVDRSKNTLYL
          90        100       110       120
QMNSLRAEDTAVYYCARNLGPSFYPDYWGQGTLVTVSSAST
          130       140       150       160
KGPSVFPLAPSSKSTSGGTAALGCLVKDYFPEPVTVSWNSG
          170       180       190       200
ALTSGVHTFPAVLQSSGLYSLSSVVTVPSSSLGTQTYICNVN
          210       220       230       240
HKPSNTKVDKKVEPKSCDKTHTCPPCPAPELLGGPSVFLFP
          250       260       270       280
PKPKDTLMISRTPEVTCVVVDVSHEDPEVKFNWYVDGVEVH
          290       300       310       320
```

TABLE A-continued (SEQ ID NOs.: 12-39)

```
                330       340       350       360
NAKTKPREEQYNSTYRVVSVLTVLHQDWLNGKEYKCKVSN
                370       380       390       400       410
KALPAPIEKTISKAKGQPREPQVYTLPPSREEMTKNQVSLTC
                420       430       440
LVKGFYPSDIAVEWESNGQPENNYKTTPPVLDSDGSFFLYS
KLTVDKSRWQQGNVFSCSVMHEALHNHYTQKSLSLSPG

Pertuzumab variants (US2009/0285837 A1)
V_L (Light chain):
1          10        20        30        40
VHSDIQMTQSPSSLSASVGDRVTITCKASQDVSIGVAWYQQ
                50        60        70        80
KPGKAPKLLIYSASYRYTGVPSRFSGSGSGTDFTLTISSLQP
                90        100       110       120
EDFATYYCQQYYIYPYTFGQGTKVEIKRTVAAPSVFIFPPSD
                130       140       150       160
EQLKSGTASVVCLLNNFYPREAKVQWKVDNALQSGNSQES
                170       180       190       200
VTEQDSKDSTYSLSSTLTLSKADYEKHKVYACEVTHQGLSS
                210
PVTKSFNRGEC V_H (Heavy chain):
1          10        20        30        40
EVQLVESGGGLVQPGGSLRLSCAASGFTFTDYTMDWVRQA
                50        60        70        80
PGKGLEWVADVNPNSGGSIYNQRFKGRFTLSVDRSKNTLYL
                90        100       110       120
QMNSLRAEDTAVYYCARNLGPSFYFDYWGQGTLVTVSSAS
                130       140       150       160
TKGPSVFPLAPSSKSTSGGTAALGCLVKDYFPEPVTVSWNS
                170       180       190       200
GALTSGVHTFPAVLQSSGLYSLSSVVTVPSSSLGTQTYICNV
                210       220       230       240
NHKPSNTKVDKKVEPKSCDKTHTCPPCPAPELLGGPSVFLV
                250       260       270       280
PPKPKDTLMISRTPEVTCVVVDVSHEDPEVKFNWYVDGVEV
                290       300       310       320
HNAKTKPREEQYNSTYRVVSVLTVLHQDWLNGKEYKCKVS
                330       340       350       360
NKALPAPIEKTISKAKGQPREPQVYTLPPSREEMTKNQVSLT
                370       380       390       400
CLVKGFYPSDIAVEWESNGQPENNYKTTPPVLDSDGSFFLY
                410       420       430       440
SKLTVDKSRWQQGNVFSCSVMHEALNHYTQKSLSLSPGK Pertuzumab Sequences: humanized 2C4, 7C2, 7F3,
7D3, 3E8, 4D5, 2H11, 3H4 (U.S. Pat. No. 7,097,840)
V_L (Light chain):
1          10        20        30        40
DIQMTQSPSSLSASVGDRVTITCKASQDVSIGVAWYQQKPG
                50        60        70        80
KAPKLLIYSASYRYTGVPSRFSGSGSGTDFTLTISSLQPED
                90        100       110       120
FATYYCQQYYIYPYTFGQGTKVEIKRTVAAPSVFIFPPSDEQ
                130       140       150       160
LKSGTASVVCLLNNNFYPREAKVQWKVDNALQSGENSQES
                170       180       190       200
```

TABLE A-continued (SEQ ID NOs.: 12-39)

```
VTEQDSKDSTYSLSSTLTLSKADYEKHKVYACEVTHQGLSS
                210
PVTKSFNRGEC

V_H (Heavy chain): 410
1          10        20        30        40
EVQLVESGGGLVQPGGSLRLSCAASGFTFTDYTMDWVRQA
                50        60        70        80
PGKGLEWVADVNPNSGGSIYNQRFKGRFTLSVDRSKNTLYL
                90        100       110       120
QMNSLRAEDTAVYYCARNLGPSFYFDYWGQGTLVTVSSAST
                130       140       150       160
KGPSVFPLAPSSKSTSGGTAALGCLVKDYFPEPVTVSWNSG
                170       180       190       200
ALTSGVHTFPAVLQSSGLYSLSSVVTVPSSSLGTQTYICNVN
                210       220       230       240
HKPSNTKVDKKVEPKSCDKTHTCPPCPAPELLGGPSVFLFP
                250       260       270       280
PKPKDTLMISRTPEVTCVVVDVSHEDPEVKFNWYVDGVEVH
                290       300       310       320
NAKTKPREEQYNSTYRVVSVLTVLHQDWLNGKEYKCKVSN
                330       340       350       360
KALPAPIEKTISKAKGQPREPQVYTLPPSREEMTKNQVSLTC
                370       380       390       400       410
LVKGFYPSDIAVEWESNGQPENNYKTTPPVLDSGSFFLYS
                420       430       440
KLTVDKSRWQQGNVFSCSVMHEALHNHYTQKSLSLSPG
```

Additional anti-ErbB2 antibodies with various properties have been described in Tagliabue et al. *Int. J. Cancer* 47:933-937 (1991); McKenzie et al. *Oncogene* 4:543 (1989); Maier et al. *Cancer Res.* 51:5361 (1991); Bacus et al. *Molecular Carcinogenesis* 3:350 (1990); Stancovski et al. *PNAS* (USA) 88:8691 (1991); Bacus et al. *Cancer Research* 52:2580 (1992); Xu et al. *Int. J Cancer* 53:401-408 (1993); WO 94/00136; Kasprzyk et al. *Cancer Research* 52:2771 (1992); Hancock et al. *Cancer Res.* 51:4575 (1991); Shawver et al. *Cancer Res.* 54:1367 (1994); Arteaga et al. *Cancer Res.* 54:3758 (1994); Harwerth et al. *J Biol Chem.* 267:15160 (1992); U.S. Pat. No. 5,783,186; and Mapper et al. *Oncogene* 14:2099 (1997). Conjugates based on such antibodies, Heavy (H) chains and/or Light (L) chains of an antibody, and fragments thereof, are included in the invention.

As disclosed herein, other scaffold like structures that bind to targets (e.g., receptors) can be included in an invention conjugate. Such structures include affibodies, aptamers, avimers and nanobodies. Conjugates that include such affibodies, aptamers, avimers and nanobodies are also included in the invention.

Exemplary Her2/neu binding affibodies, include ZHer2-neu:2, ZHer2-neu:4 ZHer2-neu:7 ZHer2-neu:8 and Fab63, which affibody sequences are in Table B.

TABLE B (SEQ ID NOs.: 40-47)

| | | | | | | |
|---|---|---|---|---|---|---|
| $Z_{wt}$ | VDNKFNK | EQQNAFYEILH | LPNLNE | EQRNAFIQSLKD | DPSQ | SANLLAEAKKLNDA | QAPK |
| $Z_{her2:4}$ | VDNKFNK | ELRQAYWEIQA | LPNLNW | TQSRAFIRSLYD | DPSQ | SANLLAEAKKLNDA | QAPK |
| $Z_{her2:7}$ | VDNKFNK | EPKTAYWEIVK | LPNLNP | EQRRAFIRSLYD | DPSQ | SANLLAEAKKLNDA | QAPK |
| $Z_{her2:24}$ | VDNKFNK | EPREAYWEIQR | LPNLNN | KQKAAFIRSLYD | DPSQ | SANLLAEAKKLNDA | QAPK |
| $Z_{her2:79}$ | VDNKFNK | EWMTAGKEIYR | LPNLNG | TQVRAFIQSLSD | DPSQ | SANLLAEAKKLNDA | QAPK |
| $Z_{her2:2}$ | VDNKFNK | EWVQAGSEIYN | LPNLNR | AQMRAFIRSLSD | DPSQ | SANLLAEAKKLNDA | QAPK |

TABLE B-continued (SEQ ID NOs.: 40-47)

```
Z_her2:8    VDNKFNK EIKQAFHEIVR LPNLNA DQVRAFIYSLGD DPSQ SANLLAEAKKLNDA QAPK Z_her2:25   VDNKFNK EMVDAGAEIWR LPNLNA KQM*AFIDSLGD DPSQ SANLLAEAKKLNDA QAPK
```

CD20 targeting antibodies include Rituximab, Ofatumumab (Arzerra®), Tositumumab (GSK), Ibritumomab (IDEC) (reference Ivanov 2008), 2F2 (HuMax-CD20), 7D8, IgM2C6, IgG1 2C6, 11B8, B1, 2H7, LT20, 1F5 and AT80, as described in Teeling et al. (US 2004/0167319) Exemplary anti-CD20 $V_L$ and $V_H$ chains and whole antibodies are set forth below in Table C (Bold fonts indicate respective complimentary determining regions, CDRs, for each chain, CDR1, CDR2 and CDR3):

TABLE C (SEQ ID NOs.:48-69)

$V_L$ (Light chain):
DIQMTQSPSSLSASVGDRVTITCRASSSVSYIHWYQQKPGKAPKLLIYATSNLASGVPSRFSGS

RSGTDFTLTISSLQPEDFATYYCQQWTSNPPTFGQGTKVEIK $V_H$ (heavy) chain:
EVQLVESGGGLVQPGGSLRLSCAASGYTFTSYNMHWVRQAPGKGLEWVAAIYPGNGDTSY

NQKFKGRFTISADTSKNTAYLQMNSLRAEDTAVYYCSRSTYYGGDWYFDVWGQGTLVTVS

S

Rituxan ® $V_L$ and $V_H$ chains:
$V_L$ (Light chain):
QIVLSQSPAILSASPGEKVTMTCRASSSVSYIHWFQQKPGSSPKPWIYATSNLASGVPVRFSGS

GSGTSYSLTISRVEAEDAATYYCQQWTSNPPTFGGGTKLEIK $V_H$ (heavy) chain:
QVQLQQPGAELVKPGASVKMSCKASGYTFTSYNMHWVKQTPGRGLEWIGAIYPGNGDTSY

NQKFKGKATLTADKSSSTAYMQLSSLTSEDSAVYYCARSTYYGGDWYFNVWGAGTTVTVS

Ibritumomab (IDEC)
$V_L$ (Light chain):
QIVLSQSPAILSASPGEKVTMTCRASSSVSYMHWYQQKPGSSPKPWIYAPSNLASGVPARFSG

SGSGTSYSLTISRVEAEDAATYYCQQWSFNPPTFGAGTKLELK $V_H$(heavy chain):
QAYLQQSGAELVRPGASVKMSCKASGYTFTSYNMHWVKQTPRQGLEWIGAIYPGNGDTSY

NQKFKGKATLTVDKSSSTAYMQLSSLTSEDSAVYFCARVYYSNSYWYFDVWGTGTTVTVS

Tositumomab: >Mouse-Human chimeric Anti-CD20 (same V domains as
ibritumomab-they differ in constant regions only)
$V_L$ (Light chain):
QIVLSQSPAILSASPGEKVTMTCRASSSVSYMHWYQQKPGSSPKPWIYAPSNLASGVPARFSG

SGSGTSYSLTISRVEAEDAATYYCQQWSFNPPTFGAGTKLELK $V_H$ (heavy) chain:
QAYLQQSGAELVRPGASVKMSCKASGYTFTSYNMHWVKQTPRQGLEWIGAIYPGNGDTSY

NQKFKGKATLTVDKSSSTAYMQLSSLTSEDSAVYFCARVYYSNSYWYFDVWGTGTTVTVS

2C6 US7850962 B2 (Teeling et al)
$V_H$ (heavy chain):
AVQLVESGGGLVQPGRSLRLSCAASGFTFGDYTMHWVRQAPGLGLEWVSGISWNSGSIGYAD

SVLGRFTISRDNALNSLYLQMNSLRAEDTALYYCTLDNQYGSGSTYGLGVWGQGTLVTVSS

TABLE C-continued

V<sub>L</sub> (Light chain):
EIVLTQSPATLSLSPGERATLSCRASQSVSSYLAWYQQKPGQAPRLLIYDASNRATGIPARFSGS

GSGTDFTLTISSLEPEDFAVYYCQQRSNWPLTFGGGTKVEIL

2F2 US2004/0167319A1 (Teeling et al)
V<sub>H</sub> (heavy chain):
MFLGLSWIFLLAILKGVQCEVQLVESGGGLVQPGRSLRLSCAASGFTFNDYAMHWVRQAPGK

GLEWVSTISWNSGSIGYADSVKGRFTISRDNAKKSLYLQMNSLRAEDTALYYCAKDIQYGN

YYYGMDVWGQGTTVTVSS

V<sub>L</sub> (Light chain):
MEAPAQLLFLLLLWLPDTTGEIVLTQSPATLSLSPGERATLSCRASQSVSSYLAWYQQKPGQA

PRLLIYDASNRATGIPARFSGSGSTDFTLTISSLEPEDFAVYYCQQRSNWPITFGQGTRLEIK

11B8 US2004/0167319A1 (Teeling, et al.)
V<sub>H</sub> (heavy chain):
MELGLSWVFLVAILKGVQCEVQLVQSGGGLVHPGGSLRLSCTGSGFTFSYHAMHWVRQAP

GKGLEWVSIIGTGGVTYYADSVKGRFTISRDNVKNSLYLQMNSLRAEDMAVYYCARDYYG

AGSFYDGLYGMDVWGQGTTVTVSS

V<sub>L</sub> (Light chain):
MEAPAQLLFLLLLWLPDTTGEIVLTQSPATLSLSPGERATLSCRASQSVSSYLAWYQQKPGQA

PRLLIYDASNRATGIPARFSGSGSGTDFTLTISSLEPEDFAVYYCQQRSDWPLTFGGGTKVEIK

7D8 US2004/0167319A1 (Teeling et al)
V<sub>H</sub> (heavy chain):
MELGLSWIFLLAILKGVQCEVQLVESGGGLVQPDRSLRLSCAASGFTFHDYAMHWVRQAPGK

GLEWVSTISWNSGTIGYADSVKGRFTISRDNAKNSLYLQMNSLRAEDTALYYCAKDIQYGNY

YYGMDVWGQGTTVTVSS

V<sub>L</sub> (Light chain):
MEAPAQLLFLLLLWLPDTTGEIVLTQSPATLSLSPGERATLSCRASQSVSSYLAWYQQKPGQAP

RLLIYDASNRATGIPARFSGSGSTDFTLTISSLEPEDFAVYYCQQRSNWPITFGQGTRLEIK

Whole antibody drug sequences:

Ibritumomab (IDEC) (reference Ivanov 2008)
Mouse Anti-CD20 Heavy chain 1:
QAYLQQSGAELVRPGASVKMSCKASGYTFTSYNMHWVKQTPRQGLEWIGAIYPGNGDTSYN

QKFKGKATLTVDKSSSTAYMQLSSLTSEDSAVYFCARVVYYSNSYWYFDVWGTGTTVTVSA

PSVYPLAPVCGDTTGSSVTLGCLVKGYFPEPVTLTWNSGSLSSGVHTFPAVLQSDLYTLSSSVT

VTSSTWPSQSITCNVAHPASSTKVDKKIEPRGPTIKPCPPCKCPAPNLLGGPSVFIFPPKIKDVLM

ISLSPIVTCVVVDVSEDDPDVQISWFVNNVEVHTAQTQTHREDYNSTLRVVSALPIQHQDWMS

GKEFKCKVNNKDLPAPIERTISKPKGSVRAPQVYVLPPPEEEMTKKQVTLTCMVTDFMPEDIY

VEWTNNGKTELNYKNTEPVLDSDGSYFMYSKLRVEKKNWVERNSYSCSVVHEGLHNHHTTK

SFSR

Mouse Anti-CD20 Light chain 1:
QIVLSQSPAILSASPGEKVTMTCRASSSVSYMHWYQQKPGSSPKPWIYAPSNLASGVPARFSGS

GSGTSYSLTISRVEAEDAATYYCQQWSFNPPTFGAGTKLELKRADAAPTVFIFPPSDEQLKSGT

ASVVCLLNNFYPREAKVQWKVDNALQSGNSQESVTEQDSKDSTYSLSSTLTLSKADYEKHKV

YACEVTHQGLSSPVTKSFN

Rituximab

Heavy chain chimeric:
QVQLQQPGAELVKPGASVKMSCKASGYTFTSYNMHWVKQTPGRGLEWIGAIYPGNGDTSYN

QKFKGKATLTADKSSSTAYMQLSSLTSEDSAVYYCARSTYYGGDWYFNVWGAGTTVTVSAA

TABLE C-continued

STKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHN

HYTQKSLSLSPGK

Light chain chimeric:
QIVLSQSPAILSASPGEKVTMTCRASSSVSYIHWFQQKPGSSPKPWIYATSNLASGVPVRFSGSG

SGTSYSLTISRVEAEDAATYYCQQWTSNPPTFGGGTKLEIKRTVAAPSVFIFPPSDEQLKSGTAS

VVCLLNNFYPREAKVQWKVDNALQSGNSQESVTEQDSKDSTYSLSSTLTLSKADYEKHKVYA

CEVTHQGLSSPVTKSFNRGEC

Tositumomab

Mouse-Human chimeric Anti-CD20 Heavy Chain 1:
QAYLQQSGAELVRPGASVKMSCKASGYMSYNMHWVKQTPRQGLEWIGAIYPGNGDTSYN

QKFKGKATLTVDKSSSTAYMQLSSLTSEDSAVYFCARVVYYSNSYWYFDVWGTGTTVTSG

PSVFPLAPSSKSTSGGTAALGCLVKDYFPEPVTVSWNSGALTSGVHTFPAVLQSSGLYSLSSVV

TVPSSSLGTQTYICNVNHKPSNTKVDKKAEPKSCDKTHTCPPCPAPELLGGPSVFLFPPKPKDTL

MISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSCSVMHEALHNHYT

QKSLSLSPGK

Mouse-Human chimeric Anti-CD20 Light Chain 1:
QIVLSQSPAILSASPGEKVTMTCRASSSVSYMHWYQQKPGSSPKPWIYAPSNLASGVPARFSGS

GSGTSYSLTISRVEAEDAATYYCQQWSFNPPTFGAGTKLELKRTVAAPSVFIFPPSDEQLKSGT

ASVVCLLNNFYPREAKVQWKVDNALQSGNSQESVTEQDSKDSTYSLSSTLTLSKADYEKHKV

YACEVTHQGLSSPVTKSFNR

Non-limiting exemplary anti-luteinizing hormone releasing hormone receptor (LHRH-R) Antibody Light ($V_L$) and Heavy ($V_H$) chain sequences are set for in Table D:

TABLE D (SEQ ID NOs.: 70-73)

(A) Immunoglobulin light chains (κ) of GHR-106

```
            LEADER
ATGGATTCACAGGCCCAGGTTCTTATATTGCTGCTGCTATGGGTATCTGGTACCTGTGGG
  M   D   S   Q   A   Q   V   L   I   L   L   L   W   V   S   G   T   C   G
                              FR1
GACATTGTGATGTCACAGTCTCCATCCTCCCTGGCTGTGTCAGCAGGAGAGAAGGTCACT
  D   I   V   M   S   Q   S   P   S   S   L   A   V   S   A   G   E   K   V   T
                              CDR1
ATGAGCTGCAAATCCAGTCAGAGTCTGCTCAACAGTAGAACCCGAAAGAACTACTTGGCT
  M   S   C   K   S   S   Q   S   L   L   N   S   R   T   K   N   Y   L   A
              FR2                        CDR2
TGGTACCAGCAGAAACCAGGGCAGTCTCCTAAACTGCTGATCTACTGGGCATCCACTAGG
  W   Y   Q   Q   K   P   G   Q   S   P   K   L   L   I   Y   W   A   S   T   R
                                    FR3
GAATCTGGGGTCCCTGATCGCTTCACAGGCAGTGGATCTGGGACAGATTTCACTCTCACC
  E   S   G   V   P   D   R   F   T   G   S   G   S   G   T   D   F   T   L   T
                                        CDR3
```

TABLE D-continued

(SEQ ID NOs.: 70-73)

```
ATCAGCAGTGTGCAGGCTGAAGACCTGGCAGTTTATTACTGCAAGCAATCTTATAATCTT
 I  S  S  V  Q  A  E  D  L  A  V  Y  Y  C  K  Q  S  Y  N  L
                                                        FR4
TACACGTTCGGAGGGGGGACCAAGCTGGAAATAAAA
 Y  T  F  G  G  G  T  K  L  E  I  K
```

(B) Immunoglobulin heavy chains of GHR-106

```
                            FR1
CAGGTGCAGCTGAAGGAGTCAGGACCTGGCCTGGTGGCACCCTCACAGAGCCTGTCCATC
 Q  V  Q  L  K  E  S  G  P  G  L  V  A  P  S  Q  S  L  S  I
                                   CDR1
ACATGCACTGTCTCTGGGTTCTCATTATCCAGATATAGTGTACACTGGGTTCGCCAGCCT
 I  C  T  V  S  G  F  S  L  S  R  Y  S  V  H  W  V  R  Q  P
       FR2                            CDR2
CCAGGAAAGGGCCTGGAGTGGCTGGGAATCATATGGGGTGGTGGAAGCACAGACTATAAT
 P  G  K  G  L  E  W  L  G  M  I  W  G  G  G  S  T  D  Y  N
                                              FR3
TCAGCTCTCAAATCCAGACTGAGCATCAGCAAGGACAACTCCAAGAGCCAAGTTTTCTTA
 S  A  L  K  S  R  L  S  I  S  K  D  N  S  K  S  Q  V  F  L
AAAATGAACAGTCTGCAAACTGATGACACAGCCATGTACTACTGTGCCAGAGGCAATGAT
 K  M  N  S  L  Q  T  D  D  T  A  M  Y  Y  C  A  R  G  N  D
       CDR3                 FR4
GGTTACTACTCGTTTGCTTACTGGGGCCAAGGGACTCTGGTCACTGTCTCTTCA
 G  Y  Y  S  F  A  Y  W  G  Q  G  T  L  V  T  V  S  S
```

The invention includes modifications or variations, such as amino acid modifications (e.g., conservative or non-conservative substitutions, additions or deletions) of a conjugate, in an antibody, Heavy (H) chain, Light (L) chain, or fragment thereof portion, a lytic domain, or any other domain of a conjugate. Thus, a conjugate that includes a modification of one or more residues of an antibody, an antibody Heavy (H) chain, an antibody Light (L) chain, a fragment thereof, or a lytic domain can incorporate any number of modifications or variations, as long as such modifications or variations do not destroy target binding and/or lytic activity. Thus, for example, a modified antibody, Heavy (H) chain, Light (L) chain, or fragment thereof, that binds to a target, such as a receptor (e.g., Her2/neu or CD20) can retain at least partial target (receptor) binding, or a modified lytic domain can retain at least partial lytic activity, such as cell killing or apoptosis.

A "conservative substitution" is a replacement of one amino acid by a biologically, chemically or structurally similar residue. Biologically similar means that the substitution is compatible with a biological activity, e.g., lytic activity. Structurally similar means that the amino acids have side chains with similar length, such as alanine, glycine and serine, or having similar size, or the structure of a first, second or additional domain is maintained, such as an amphipathic alpha helix. Chemical similarity means that the residues have the same charge or are both hydrophilic and hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc. Routine assays can be used to determine whether a conjugate variant has activity, e.g., target binding activity or lytic activity.

Modifications and variations therefore include of the various sequences set forth herein, such as of antibodies, Heavy (H) chains and Light (L) chains of an antibody, and fragments thereof, as well as lytic domains (or additional domains, if present). Non-limiting modifications of lytic domains are of KFAKFAKKFAKFAKK, KFAKFAKKFAK-FAKKF, KFAKFAKKFAKFAKKFA, KFAKFAKKFAK-FAKKFAK, KFAKFAKKFAKFAKKFAKF, KFAKFAK-KFAKFAKKFAKFA and KFAKFAKKFAKFAKKFAKFAKKFAKFAK (SEQ ID NOs.:1-7), or a sequence that includes or consists of such lytic domains.

In particular embodiments, a subsequence of an antibody, Heavy (H) chain, Light (L) chain, fragments thereof, or a lytic domain has at least 1 to 5, 5 to 10, 10 to 15, 15 to 20, 20 to 25, 25 to 30, 30 to 35, 35 to 40, 40 to 50, 50 to 60, 60 to 70, 70 to 80, 80 to 90, 90 to 100, or more amino acid residues identical to the reference sequence. In additional particular embodiments, a substitution or deletion of one or more amino acids (e.g., 1-3, 3-5, 5-10, 10-20, 20-30, or more) residues of an antibody, Heavy (H) chain, Light (L) chain, fragment thereof, and/or lytic domain can have a sequence with 50%, 60%, 70%, 75%, 80%, 85%, 90%, 95%, 96%, 97%, 98%, or more identity to a reference sequence (e.g., antibody, Heavy (H) chain, Light (L) chain, fragment thereof, or lytic domain, such as KFAKFAKKFAKFAKK, KFAKFAKKFAKFAKKF, KFAKFAKKFAKFAKKFA, KFAKFAKKFAKFAKKFAK, KFAKFAKKFAKFAK-KFAKF, KFAKFAKKFAKFAKKFAKFA or KFAKFAK-KFAKFAKKFAKFAKKFAKFAK (SEQ ID NOs.:1-7)).

In a particular embodiment, a conjugate includes an antibody, Heavy (H) chain, Light (L) chain, or fragment thereof, that binds to a target (e.g., receptor, such as Her2/neu or CD20) and a second lytic domain that includes or consists of an L- or D-amino acid sequence set forth as: KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAK-KFAKFA or KFAKFAKKFAKFAKKFAKFAKKFAKFAK (SEQ ID NOs.:1-7) having one or more of the K residues substituted with an F or L residue, one or more of the F residues substituted with a K, A or L residue, or one or more of the A residues substituted with a K, F or L residue. In another particular embodiment, a conjugate includes an antibody, Heavy (H) chain, Light (L) chain, or fragment thereof, that binds to a target (e.g., receptor, such as Her2/neu or CD20) and a second domain consisting of an L- or D-amino acid sequence selected from KFAKFAKKFAK-FAKK, KFAKFAKKFAKFAKKF, KFAKFAKKFAKFAK-KFA, KFAKFAKKFAKFAKKFAK, KFAKFAKKFAK-FAKKFAKF, KFAKFAKKFAKFAKKFAKFA and KFAKFAKKFAKFAKKFAKFAKKFAKFAK (SEQ ID NOs.:1-7) having one or more of the K residues substituted with an F or L residue, one or more of the F residues substituted with a K, A or L residue, or one or more of the A residues substituted with a K, F or L residue (e.g., 12, 13, 14, 15, 16, 17, 18, 19, 20, 21, 22, 23, 24, 25, 26, 27 or 28 residues in length).

The term "identity" and "homology" and grammatical variations thereof mean that two or more referenced entities are the same. Thus, where two amino acid sequences are identical, they have the same amino acid sequence. "Areas, regions or domains of identity" mean that a portion of two or more referenced entities are the same. Thus, where two amino acid sequences are identical or homologous over one or more sequence regions, they share identity in these regions. The term "complementary," when used in reference to a nucleic acid sequence means the referenced regions are 100% complementary, i.e., exhibit 100% base pairing with no mismatches.

Due to variation in the amount of sequence conservation between structurally and functionally related proteins, the amount of sequence identity required to retain a function or activity (e.g., target binding or lytic) depends upon the protein, the region and the function or activity of that region. For example, for a lytic peptide sequence multiple PNNPNNP (SEQ. ID. NO. 153) sequence repeat patterns or motifs can be present, but one or more interrupted or non-interrupted PNNPNNP (SEQ. ID. NO. 153) sequence repeat patterns or motifs need not be present.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Conjugate amino acid residues can be joined by a covalent or a non-covalent bond. Non-limiting examples of covalent bonds are amide bonds, non-natural and non-amide chemical bonds, which include, for example, glutaraldehyde, N-hydroxysuccinimide esters, bifunctional maleimides, N,N'-dicyclohexylcarbodiimide (DCC) or N,N'-diisopropylcarbodiimide (DIC) Linking groups alternative to amide bonds include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, NY).

Lytic domains (and additional domains, when present) may be positioned anywhere on the antibody, antibody fragment, Heavy (H) chain, Light (L) chain, or fragment of a Heavy (H) chain or a Light (L) chain of an antibody, provided that the lytic domain (or any additional domain) does not destroy binding to a target. Non-limiting positions include a lytic domain positioned at the amino-terminus, or at the carboxyl-terminus, of an antibody Heavy (H) chain or a Light (L) chain. Where additional domains are present (e.g., third, fourth, fifth, sixth, seventh, etc. domains), the additional domain(s) can also be positioned anywhere.

First portion antibodies, Heavy (H) chains, Light (L) chains, and fragments thereof, and second (lytic) domains (and additional domains, when present), can be fused or joined to each other by a covalent or a non-covalent bond. First portion antibodies, Heavy (H) chains, Light (L) chains, and fragments thereof, and second (lytic) domains (and additional domains, when present), can be immediately adjacent to each other or separated by an intervening region, such as a hinge, spacer or linker positioned between the two domains.

Examples of linkers or spacers include a non-peptide linker or spacer, such as a continuous carbon atom (C) chain (e.g., CCCCC). Multi-carbon chains include carboxylic acids (e.g., dicarboxylic acids) such as glutaric acid, succinic acid and adipic acid. A particular non-limiting example is a 6 carbon linker such as α-amino-caproic acid.

Additional examples of linkers or spacers include one or more amino acid residues, such as a peptide spacer or linker positioned between the antibody, Heavy (H) chain, Light (L) chainy, or fragment thereof, and the second (lytic) domains (or additional domains, when present). Peptide spacer or linker sequences can be any length, but typically range from about 1-10, 10-20, 20-30, 30-40, or 40-50 amino acid residues. In particular embodiments, a peptide spacer or linker positioned between two (or more) domains is from 1 to 5, 1 to 10, 1 to 20, 1 to 25 L- or D-amino acid residues, or 1 to 4, 1 to 6 or 1 to 8L- or D-amino acid residues. Particular amino acid residues that are included in sequences positioned between the first and second domains include one or more of or A, S or G amino acid residues. Specific non-limiting examples of peptides positioned between the first and second domains include a sequence within or set forth as: GSGGS(SEQ ID NO.:9), ASAAS(SEQ ID NO.:8) or multiples of the particular linker sequence (GSGGS(SEQ ID NO.:9))n or (ASAAS(SEQ ID NO.:8))n, where n=1-5, 5-10, 10-20, etc. Derivatives of amino acids and peptides can be positioned between the two (or more) domains A specific non-limiting example of an amino acid derivative is a lysine derivative.

Conjugates with or without a spacer or linker, or a third, fourth, fifth, sixth, seventh, etc. domain can be entirely composed of natural amino acids or synthetic, non-natural amino acids or amino acid analogues, or can include derivatized forms. In various embodiments, a conjugate includes in a antibody, Heavy (H) chain, Light (L) chainy, or fragment thereof, and/or a second (lytic) domain (and additional domains, when present), one or more D-amino acids, mixtures of D-amino acids and L-amino acids, or a sequence composed entirely of D-amino acid residues.

Conjugates can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., an alpha helix conformation. Conjugates can include cyclic structures such as an end-to-end amide bond between the amino and carboxy-terminus of the molecule or intra- or inter-molecular disulfide bond(s). Conjugates may be modified in vitro or in vivo, e.g., post-translationally modified to include, for example, sugar or carbohydrate residues, phosphate groups, fatty acids, lipids, etc.

Specific examples of an addition include a third, fourth, fifth, sixth or seventh domain. Conjugates with two domains can therefore include one or more additional domains (third, fourth, fifth, sixth, seventh, etc.) covalently linked thereto to impart a distinct or complementary function or activity. Exemplary additional domains include domains facilitating isolation, which include, for example, metal chelating peptides such as polyhistidine tracts and histidine-tryptophan modules that allow purification on immobilized metals; protein A binding domains that allow purification on immobilized immunoglobulin; and domain utilized in the FLAGS extension/affinity purification system (Immunex Corp, Seattle Wash.). Optional inclusion of a cleavable sequence such as Factor Xa or enterokinase between a purification domain and the conjugate can be used to facilitate purification. For example, an expression vector can include a conjugate-encoding nucleic acid sequence linked to six histidine residues followed by a thioredoxin and an enterokinase cleavage site. The histidine residues facilitate detection and purification of the conjugate while the enterokinase cleavage site provides a means for purifying the construct from the remainder of the protein (see e.g., Kroll, *DNA Cell. Biol.* 12:441 (1993)).

Conjugate activity can be affected by various factors and therefore conjugates can be designed or optimized by taking into consideration one or more of these factors. Such factors include, for example, length, which can affect toxicity to cells. Cell killing activity of alpha helix forming lytic peptide domains can also depend on the stability of the helix Linkers and spacers can affect membrane interaction of a lytic domain and the helical structure of a lytic domain. The charge of lytic peptide domains, which is determined in part by the particular amino acid residues present in the domain, also affects cell killing potency. The positioning of antibody, Heavy (H) chain, Light (L) chain, and second (lytic) domains (and additional domains, when present), relative to lytic domain (particular amino acid residue, or N- or C-terminus) also can affect cell killing activity of conjugates.

Conjugate in vivo half-life can be increased by constructing lytic peptide domains with one or more non-naturally occurring amino acids or derivatives. For example, conjugates with D-amino acids (e.g., up to 30%, 40%, 50%, 60%, or more of all residues are D-enantiomers) are resistant to serum proteolysis and therefore can be active for longer times thereby increasing in vivo potency. Furthermore, constructing lytic peptide domains with one or more non-naturally occurring amino acids or derivatives can reduce hemolytic activity. Such conjugates with D-enantiomers also have a greater tendency to be monomeric in solution—they do not significantly aggregate.

Peptides and peptidomimetics can be produced and isolated using methods known in the art. Peptides can be synthesized, whole or in part, using chemical methods known in the art (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge *Science* 269:202 (1995); Merrifield, *Methods Enzymol.* 289:3(1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994).

The invention further provides nucleic acids encoding the conjugates of the invention (and portions of antibodies, Heavy (H) chains, Light (L) chains, and fragments thereof, and second (lytic) domains, and additional domains, when present), and vectors that include nucleic acid encoding conjugates. Nucleic acid, which can also be referred to herein as a gene, polynucleotide, nucleotide sequence, primer, oligonucleotide or probe refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA, cDNA, and antisense. RNA nucleic acid can be spliced or unspliced mRNA, rRNA, tRNA or antisense. Nucleic acids include naturally occurring, synthetic, as well as nucleotide analogues and derivatives.

As a result of the degeneracy of the genetic code, nucleic acids include sequences degenerate with respect to sequences encoding conjugates of the invention. Thus, degenerate nucleic acid sequences encoding conjugates are provided.

Nucleic acid can be produced using any of a variety of known standard cloning and chemical synthesis methods, and can be altered intentionally by site-directed mutagenesis or other recombinant techniques known to one skilled in the art. Purity of polynucleotides can be determined through sequencing, gel electrophoresis, UV spectrometry.

Nucleic acids may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner Typically expression control elements are juxtaposed at the 5' or the 3' ends of the genes but can also be intronic.

Expression control elements include elements that activate transcription constitutively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

Nucleic acids may be inserted into a plasmid for propagation into a host cell and for subsequent genetic manipulation if desired. A plasmid is a nucleic acid that can be stably propagated in a host cell; plasmids may optionally contain expression control elements in order to drive expression of the nucleic acid. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of conjugate encoding nucleic acids, producing conjugates or antisense nucleic acid, and expressing conjugates in host cells and organisms, for example.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a conjugate in appropriate host cells.

Expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054) and CMV vectors (U.S. Pat. No. 5,561,063).

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. *Methods in Enzymology*, 153:516 (1987), eds. Wu & Grossman; Bitter *Methods in Enzymology*, 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is cotransfected into a host cell with a first vector containing a nucleic acid encoding a conjugate.

Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes which can be employed in tk-, hgprt- or aprt-cells, respectively. Additionally, antimetabolite resistance can be used as the basis of selection for dhfr, which confers resistance to methotrexate (O'Hare et al., *Proc. Natl. Acad. Sci. USA* 78:1527 (1981)); the gpt gene, which confers resistance to mycophenolic acid (Mulligan et al., *Proc. Natl. Acad. Sci. USA* 78:2072 (1981)); neomycin gene, which confers resistance to aminoglycoside G-418 (Colberre-Garapin et al., *J. Mol. Biol.* 150:1(1981)); puromycin; and hygromycin gene, which confers resistance to hygromycin (Santerre et al., *Gene* 30:147 (1984)). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: Current Communications in Molecular Biology, Cold Spring Harbor Laboratory).

Host cells that express conjugates, and host cells transformed with nucleic acids encoding conjugates (e.g., antibodies, Heavy (H) chains, Light (L) chains, and fragments thereof, and second (lytic) domains, and additional domains, when present), and vectors including a nucleic acid that encodes the conjugates are also provided. In one embodiment, a host cell is a prokaryotic cell. In another embodiment, a host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded conjugate expressed. The term also includes any progeny or subclones of the host cell. Host cells include cells that express conjugates.

Host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for transient or stable propagation or expression.

Antibody and polypeptide conjugates, nucleic acids encoding conjugates, and vectors and host cells expressing conjugates or transformed with nucleic acids encoding conjugates include isolated and purified forms. The term "isolated," when used as a modifier of an invention conjugate or composition, means that the composition is made by the hand of man or is separated, substantially completely or at least in part, from the naturally occurring in vivo environment. Generally, an isolated composition is substantially free of one or more materials with which it normally associates with in nature, for example, one or more protein, nucleic acid, lipid, carbohydrate, cell membrane. The term "isolated" does not exclude alternative physical forms of the composition, such as multimers/oligomers, variants, modifications or derivatized forms, or forms expressed in host cells produced by the hand of man. The term "isolated" also does not exclude forms (e.g., pharmaceutical formulations and combination compositions) in which there are combinations therein, any one of which is produced by the hand of man.

An "isolated" composition can also be "purified" when free of some, a substantial number of, most or all of the materials with which it typically associates with in nature. Thus, an isolated conjugate that also is substantially pure does not include polypeptides or polynucleotides present among millions of other sequences, such as proteins of a protein library or nucleic acids in a genomic or cDNA library, for example. A "purified" composition can be combined with one or more other molecules.

In accordance with the invention, there are provided mixtures of conjugates and combination compositions. In one embodiment, a mixture includes one or more conjugates and a pharmaceutically acceptable carrier or excipient. In another embodiment, a mixture includes one or more conjugates and an anti-cell proliferative, anti-tumor, anti-cancer, or anti-neoplastic treatment or agent. In a further embodiment, a mixture includes one or more conjugates and an immune enhancing agent. Combinations, such as one or more conjugates in a pharmaceutically acceptable carrier or excipient, with one or more of an anti-cell proliferative, anti-tumor, anti-cancer, or anti-neoplastic treatment or agent, and an immune enhancing treatment or agent, are also provided.

Conjugates of the invention, such as antibodies, Heavy (H) chains, Light (L) chains, and fragments thereof that bind to a target (e.g., a receptor), and second (lytic) domains, can be used to target cells for lysis, cell death or apoptosis. Such cells can be selectively targeted. For example a cell that expresses receptor such as Her2/neu or CD20 can be targeted by a conjugate and thereby be preferentially killed compared to cells that express little if any receptor.

In accordance with the invention, there are provided methods and uses of reducing or inhibiting proliferation of a cell that expresses a target (e.g., a receptor) and methods of reducing or inhibiting cell proliferation. In one embodiment, a method or use includes contacting a target expressing cell with a conjugate in an amount sufficient to reduce or inhibit proliferation of the cell. In another embodiment, a method includes contacting a target expressing cell with a conjugate in an amount sufficient to reduce or inhibit cell proliferation.

Also provided are methods and uses of reducing or inhibiting proliferation of a hyperproliferative cell that expresses a target (e.g., a receptor), and methods and uses of reducing or inhibiting proliferation of hyperproliferating cells that express a target (e.g., a receptor). In one embodiment, a method or use includes contacting a hyperproliferative target expressing cell or hyperproliferating target expressing cells with a conjugate in an amount sufficient to reduce or inhibit proliferation.

Further provided are methods and uses of reducing or inhibiting proliferation of a non-metastatic or metastatic neoplastic, cancer, tumor and malignant cells that express a target (e.g., a receptor). In one embodiment, a method or use includes contacting a neoplastic, cancer, tumor or malignant target expressing cell with a conjugate in an amount sufficient to reduce or inhibit proliferation of the target expressing cell.

Still further provided are methods and uses of reducing or inhibiting proliferation of a dormant or non-dividing non-metastatic or metastatic neoplastic, cancer, tumor and malignant cells that express a target (e.g., a receptor). In one embodiment, a method or use includes contacting a dormant or non-dividing neoplastic, cancer, tumor or malignant target expressing cell with a conjugate in an amount sufficient to reduce or inhibit proliferation of the dormant or non-dividing cell.

Additionally provided are methods and uses of selectively reducing or inhibiting proliferation of a cell (e.g., a hyperproliferating cell) that expresses a target (e.g., a receptor). In one embodiment, a method or use includes contacting the target expressing cell with a conjugate in an amount sufficient to reduce or inhibit proliferation of the cell (e.g., hyperproliferating cell), wherein the conjugate binds to a target (e.g., a receptor) expressed by the cell.

Yet additionally provided are methods and uses of selectively reducing or inhibiting proliferation of a neoplastic, tumor, cancer or malignant cell that expresses that expresses a target (e.g., a receptor). In one embodiment, a method or a use includes contacting the cell with a conjugate in an amount sufficient to reduce or inhibit proliferation of the neoplastic, tumor, cancer or malignant cell, wherein the conjugate binds to the target (e.g., a receptor) expressed by the cell.

The term "contacting" means direct or indirect binding or interaction between two or more entities (e.g., between a conjugate and a target and/or cell). Contacting as used herein includes in solution, in solid phase, in vitro, ex vivo, in a cell and in vivo. Contacting in vivo can be referred to as administering, or administration or delivery.

Cells to target for reducing or inhibiting proliferation, non-selectively or selectively, include cells that express a target (e.g., a receptor). Non-limiting exemplary cells include breast, ovarian, uterine, cervical, stomach, lung, gastric, colon, bladder, glial, dermal (e.g., melanocytes), hematologic and endometrial cells.

Conjugates and methods and uses of the invention are also applicable to treating undesirable or aberrant cell proliferation and hyperproliferative disorders, which include cells expressing a target (e.g., a receptor). Thus, in accordance with the invention, methods and uses of treating undesirable or aberrant cell proliferation and hyperproliferative disorders are provided. In one embodiment, a method or a use includes administering to a subject (in need of treatment) an amount of a conjugate sufficient to treat the undesirable or aberrant cell proliferation or the hyperproliferative disorder.

The term "hyperproliferative disorder" refers to any undesirable or aberrant cell survival (e.g., failure to undergo programmed cell death or apoptosis), growth or proliferation. Such disorders include benign hyperplasias, non-metastatic and metastatic neoplasias, cancers, tumors and malignancies. Undesirable or aberrant cell proliferation and hyperproliferative disorders can affect any cell, tissue, organ in a subject. Undesirable or aberrant cell proliferation and hyperproliferative disorders can be present in a subject, locally, regionally or systemically. A hyperproliferative disorder can arise from a multitude of tissues and organs, including but not limited to breast, lung (e.g., small cell or non-small cell), thyroid, head and neck, brain, nasopharynx, throat, nose or sinuses, lymphoid, adrenal gland, pituitary gland, thyroid, lymph, gastrointestinal (mouth, esophagus, stomach, duodenum, ileum, jejunum (small intestine), colon, rectum), genito-urinary tract (uterus, ovary, vagina, cervix, endometrium, fallopian tube, bladder, testicle, penis, prostate), kidney, pancreas, liver, bone, bone marrow, lymph, blood (hematologic), brain (glial), muscle, skin, dermal (e.g., melanocytes), and stem cells, which may or may not metastasize to other secondary sites, regions or locations.

Conjugates and methods and uses of the invention are also applicable to metastatic or non-metastatic tumor, cancer, malignancy or neoplasia of any cell, organ or tissue origin. Such disorders can affect virtually any cell or tissue type, e.g., carcinoma, sarcoma, melanoma, neural, and reticuloendothelial or hematopoietic neoplastic disorders (e.g., myeloma, lymphoma or leukemia).

As used herein, the terms "neoplasia" and "tumor" refer to a cell or population of cells whose growth, proliferation or survival is greater than growth, proliferation or survival of a normal counterpart cell, e.g. a cell proliferative or differentiative disorder. A tumor is a neoplasia that has formed a distinct mass or growth. A "cancer" or "malignancy" refers to a neoplasia or tumor that can invade adjacent spaces, tissues or organs. A "metastasis" refers to a neoplasia, tumor, cancer or malignancy that has disseminated or spread from its primary site to one or more secondary sites, locations or regions within the subject, in which the sites, locations or regions are distinct from the primary tumor or cancer. All or a portion of such cells can express a target (e.g., a receptor) can therefore be targeted with conjugates in accordance with the invention.

Neoplastic, tumor, cancer and malignant cells (metastatic or non-metastatic) include dormant or residual neoplastic, tumor, cancer and malignant cells, all or a portion of which express a target (e.g., a receptor). Such cells typically consist of remnant tumor cells that are not dividing (G0-G1 arrest). These cells can persist in a primary site or as disseminated neoplastic, tumor, cancer or malignant cells as a minimal residual disease. These dormant neoplastic, tumor, cancer or malignant cells remain asymptomatic, but can develop severe symptoms and death once these dormant cells proliferate. Invention methods can be used to reduce or inhibit proliferation of dormant neoplastic, tumor, cancer or malignant cells, which can in turn inhibit or reduce tumor or cancer relapse, or tumor or cancer metastasis or progression.

In accordance with the invention, methods of treating a subject having a metastatic or non-metastatic tumor, cancer, malignancy or neoplasia are provided. In one embodiment, a method includes administering to a subject (in need of treatment) an amount of a conjugate of sufficient to treat (e.g., reduce or inhibit proliferation) the metastatic or non-metastatic tumor, cancer, malignancy or neoplasia.

The metastatic or non-metastatic tumor, cancer, malignancy or neoplasia may be in any stage, e.g., early or advanced, such as a stage I, II, III, IV or V tumor. The metastatic or non-metastatic tumor, cancer, malignancy or neoplasia may have been subject to a prior treatment or be stabilized (non-progressing) or in remission.

In terms of metastasis, invention methods can be used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression. Thus, methods of the invention include, among other things, 1) reducing or inhibiting growth, proliferation, mobility or invasiveness of tumor or cancer cells that potentially or do develop metastases (e.g., disseminated tumor cells, DTC); 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established; and 4) reducing or inhibiting formation or establishment of additional metastasis after the metastasis has been formed or established.

Cells of a metastatic or non-metastatic tumor, cancer, malignancy or neoplasia (all or a portion of which express a target (e.g., a receptor)) may be aggregated in a "solid" cell mass or be dispersed or diffused. A "solid" tumor refers to cancer, neoplasia or metastasis that typically aggregates together and forms a mass. Specific non-limiting examples include breast, ovarian, uterine, cervical, stomach, lung, gastric, colon, bladder, glial, dermal (e.g., melanocytes) and endometrial tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterus, cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma and oligodendrocytoma.

A "liquid tumor," which refers to neoplasia that is dispersed or is diffuse in nature, as they do not typically form a solid mass. Particular examples include neoplasia of the reticuloendothelial or hematopoietic system, such as lymphomas, myelomas and leukemias. Non-limiting examples of leukemias include acute and chronic lymphoblastic, myeloblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL (B-ALL) and T-lineage ALL (T-ALL), chronic lymphocytic leukemia (CLL), prolymphocytic leukemia (PLL), hairy cell leukemia (HLL) and Waldenstroem's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As disclosed herein, undesirable or aberrant cell proliferation or hyperproliferative disorders can occur in uterus, breast, vagina, cervix, endometrium and fallopian tube. Thus, in accordance with the invention, there are provided methods and uses of treating uterus, breast, vagina, cervix, endometrium and fallopian tube hyperproliferative disorders. In one embodiment, a method or use includes administering to a subject an amount of a conjugate sufficient to treat a uterus, breast, vagina, cervix, endometrium or fallopian tube hyperproliferative disorder.

Any composition, treatment, protocol, therapy or regimen having an anti-cell proliferative activity or effect can be combined with a conjugate or used in combination in a method or use of the invention. Conjugates and methods and uses of the invention therefore include anti-proliferative, anti-tumor, anti-cancer, anti-neoplastic and anti-metastatic treatments, protocols and therapies, which include any other composition, treatment, protocol or therapeutic regimen that inhibits, decreases, retards, slows, reduces or prevents a hyperproliferative disorder, such as tumor, cancer, malignant or neoplastic growth, progression, metastasis, proliferation or survival, or worsening in vitro or in vivo. Particular non-limiting examples of an anti-proliferative (e.g., tumor) therapy include chemotherapy, immunotherapy, radiotherapy (ionizing or chemical), local thermal (hyperthermia) therapy, surgical resection and vaccination. A conjugate can be administered prior to, substantially contemporaneously with or following administration or use of the anti-cell proliferative, anti-neoplastic, anti-tumor, anti-cancer, anti-metastatic or immune-enhancing treatment or therapy. A conjugate can be administered or used as a combination composition with the anti-cell proliferative, anti-neoplastic, anti-tumor, anti-cancer, anti-metastatic or immune-enhancing treatment or therapy, metastatic or non-metastatic tumor, cancer, malignancy or neoplasia.

Anti-proliferative, anti-neoplastic, anti-tumor, anti-cancer and anti-metastatic compositions, therapies, protocols or treatments include those that prevent, disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative, anti-neoplastic, anti-tumor, anti-cancer and anti-metastatic activities include alkylating agents, antimetabolites, plant extracts, plant alkaloids, nitrosoureas, hormones, nucleoside and nucleotide analogues. Specific examples of drugs having anti-cell proliferative, anti-neoplastic, anti-tumor, anti-cancer and anti-metastatic activities include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds such as decitabine (5-aza-2'deoxycytidine), cytarabine, 1-beta-D-arabinofuranosyl-5-azacytosine and dihydro-5-azacytidine, bleomycin, actinomycin D, mithramycin, mitomycin C, carmustine, lomustine, semustine, streptozotocin, hydroxyurea, cisplatin, mitotane, procarbazine, dacarbazine, a taxane (e.g., taxol or paclitaxel), vinblastine, vincristine, doxorubicin and dibromomannitol etc.

Additional agents that are applicable with conjugates and methods and uses are known to the skilled artisan and can be employed. For example, biologicals such as antibodies that are different from the antibodies used for conjugation, cell growth factors, cell survival factors, cell differentiative factors, cytokines and chemokines can be administered or used. Non-limiting examples of monoclonal antibodies include rituximab (Rituxan®), trastuzumab (Herceptin®), pertuzumab (Perjeta®)), bevacizumab (Avastin®), ranibizumab (Lucentis®), cetuximab (Erbitux®), alemtuzumab (Campath®), panitumumab (Vectibix®), ibritumomab tiuxetan (Zevalin®), tositumomab (Bexxar®), ipilimumab, zalutumumab, dalotuzumab, figitumumab, ramucirumab, galiximab, farletuzumab, ocrelizumab, ofatumumab (Arzerra®), tositumumab, ibritumomab, 2F2 (HuMax-CD20), 7D8, IgM2C6, IgG1 2C6, 11B8, B1, 2H7, LT20, 1F5 or AT80 daclizumab (Zenapax®), anti-LHRH receptor antibodies such as clone A9E4, F1G4, AT2G7, GNRH03, GNRHR2, etc. which can be used in combination with, inter alia, a conjugate in accordance with the invention.

Other targeted drugs that are applicable for use with the conjugates are kinase inhibitors e.g., imatinib (Gleevec®), gefitinib (Iressa®), bortzomib (Velcade®), lapatinib (Tykerb®), sunitinib (Sutent®), sorafenib (Nevaxar®), nilotinib (Tasigna®) etc. Non-limiting examples of cell growth factors, cell survival factors, cell differentiative factors, cytokines and chemokines include IL-2, IL-1α, IL-1β, IL-3, IL-6, IL-7, granulocyte-macrophage-colony stimulating factor (GMCSF), IFN-γ, IL-12, TNF-α, TNFβ, MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAPIII-TG/NAP-2, Mig, PBSF/SDF-1 and lymphotactin.

Additional non-limiting examples include immune-enhancing treatments and therapies, which include cell based therapies. In particular, immune-enhancing treatments and therapies include administering lymphocytes, plasma cells, macrophages, dendritic cells, NK cells and B-cells.

Methods and uses of treating a metastatic or non-metastatic tumor, cancer, malignancy or neoplasia, methods and uses of treating a subject in need of treatment due to having or at risk of having a metastatic or non-metastatic tumor, cancer, malignancy or neoplasia, and methods and uses of increasing effectiveness or improving an anti-proliferative, anti-tumor, anti-cancer, anti-neoplasia or anti-malignancy, therapy are provided. In respective embodiments, a method or use includes administering to a subject with or at risk of a metastatic or non-metastatic tumor, cancer, malignancy or neoplasia, an amount of a conjugate sufficient to treat the metastatic or non-metastatic tumor, cancer, malignancy or neoplasia; administering to the subject an amount of a conjugate sufficient to treat the subject; and administering to a subject that is undergoing or has undergone metastatic or non-metastatic tumor, cancer, malignancy or neoplasia therapy, an amount of a conjugate sufficient to increase effectiveness of the anti-proliferative, anti-tumor, anti-cancer, anti-neoplasia or anti-malignancy therapy.

Methods and uses of the invention may be practiced prior to (i.e. prophylaxis), concurrently with or after evidence of the presence of undesirable or aberrant cell proliferation or a hyperproliferative disorder, disease or condition begins (e.g., one or more symptoms). Administering or using a conjugate prior to, concurrently with or immediately following development of a symptom of undesirable or aberrant cell proliferation or a hyperproliferative disorder may decrease the occurrence, frequency, severity, progression, or duration of one or more symptoms of the undesirable or aberrant cell proliferation or a hyperproliferative disorder, disease or condition in the subject. In addition, administering or using a conjugate prior to, concurrently with or immediately following development of one or more symptoms of the undesirable or aberrant cell proliferation or a hyperproliferative disorder, disease or condition may inhibit, decrease or prevent the spread or dissemination of hyperproliferating cells (e.g., metastasis) to other sites, regions, tissues or organs in a subject, or establishment of hyperproliferating cells (e.g., metastasis) at other sites, regions, tissues or organs in a subject.

Conjugates and the methods and uses of the invention, such as treatment methods and uses, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject.

Therapeutic benefits and improvements include, but are not limited to, reducing or decreasing occurrence, frequency, severity, progression, or duration of one or more symptoms or complications associated with a disorder, disease or condition, or an underlying cause or consequential effect of the disorder, disease or condition. Conjugates and methods and uses of the invention therefore include providing a therapeutic benefit or improvement to a subject.

In a method or use of the invention in which a therapeutic benefit or improvement is a desired outcome, a conjugate can be administered in a sufficient or effective amount to a subject in need thereof. An "amount sufficient" or "amount effective" refers to an amount that is anticipated to provide, in single or multiple doses, alone or in combination with one or more other compositions (therapeutic agents such as a chemotheraputic or immune stimulating drug), treatments, protocols, or therapeutic regimens agents, a detectable response of any duration of time (long or short term), a desired outcome in or a benefit to a subject of any measurable or detectable degree or for any duration of time (e.g., for hours, days, months, years, or cured). The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is considered a satisfactory outcome.

The term "ameliorate" means a detectable objective or subjective improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatments or uses can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods and uses affecting one or more underlying causes of the condition, disorder, disease or symptom are therefore considered to be beneficial. Stabilizing or inhibiting progression or worsening of a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is a stabilization or an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

In particular embodiments, a method or use of treatment results in partial or complete destruction of a metastatic or non-metastatic tumor, cancer, malignant or neoplastic cell mass, volume, size or numbers of cells; results in stimulating, inducing or increasing metastatic or non-metastatic tumor, cancer, malignant or neoplastic cell necrosis, lysis or apoptosis; results in reducing metastatic or non-metastatic tumor, cancer, malignant or neoplastic volume, size, cell mass; results in inhibiting or preventing progression or an increase in metastatic or non-metastatic tumor, cancer, malignant or neoplastic volume, mass, size or cell numbers; results in inhibiting or decreasing the spread or dissemination of hyperproliferating cells (e.g., metastasis) to other (secondary) sites, regions, tissues or organs in a subject, or establishment of hyperproliferating cells (e.g., metastasis) at other (secondary) sites, regions, tissues or organs in a subject; or results in prolonging lifespan of the subject. In additional particular embodiments, a method or use of treatment results in reducing or decreasing severity, duration or frequency of an adverse symptom or complication associated with or caused by the metastatic or non-metastatic tumor, cancer, malignancy or neoplasia.

An amount sufficient or an amount effective can but need not be provided in a single administration or dose and, can but need not be, administered alone or in combination with another composition (e.g., chemotherapeutic or immune enhancing or stimulating agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., chemotherapeutic or immune stimulating agent), treatment, protocol or therapeutic regimen, since additional doses, amounts or duration above and beyond such doses, or additional compositions (e.g., chemotherapeutic or immune stimulating agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, or a majority of treated subjects in a given group or population. As is typical for treatment or therapeutic methods, some subjects will exhibit greater or less response to a given treatment, therapeutic regimen or protocol. An amount sufficient or an amount effective refers to sufficiency or effectiveness in a particular subject, not a group or the general population. Such amounts will depend in part upon the condition treated, such as the type or stage of undesirable or aberrant cell proliferation or hyperproliferative disorder (e.g., a metastatic or non-metastatic tumor, cancer, malignancy or neoplasia), the therapeutic effect desired, as well as the individual subject (e.g., the bioavailability within the subject, gender, age, etc.).

Particular non-limiting examples of therapeutic benefit or improvement for undesirable or aberrant cell proliferation, such as a hyperproliferative disorder (e.g., a metastatic or non-metastatic tumor, cancer, malignancy or neoplasia) include a reduction in cell size, mass or volume, inhibiting an increase in cell size, mass or volume, a slowing or inhibition of worsening or progression, stimulating cell necrosis, lysis or apoptosis, reducing or inhibiting neoplastic or tumor malignancy or metastasis, reducing mortality, and prolonging lifespan of a subject. Thus, inhibiting or delaying an increase in cell size, mass, volume or metastasis (stabilization) can increase lifespan (reduce mortality) even if only for a few days, weeks or months, even though complete ablation of the metastatic or non-metastatic tumor, cancer, malignancy or neoplasia has not occurred. Adverse symptoms and complications associated with a hyperproliferative disorder (e.g., a metastatic or non-metastatic tumor, cancer, malignancy or neoplasia) that can be reduced or decreased include, for example, pain, nausea, discomfort, lack of appetite, lethargy and weakness. A reduction in the occurrence, frequency, severity, progression, or duration of a symptom of undesirable or aberrant cell proliferation, such as a hyperproliferative disorder (e.g., a metastatic or non-metastatic tumor, cancer, malignancy or neoplasia), such as an improvement in subjective feeling (e.g., increased energy, appetite, reduced nausea, improved mobility or psychological well being, etc.), are therefore all examples of therapeutic benefit or improvement.

For example, a sufficient or effective amount of a conjugate is considered as having a therapeutic effect if administration results in less chemotherapeutic drug, radiation or immunotherapy being required for treatment of undesirable or aberrant cell proliferation, such as a hyperproliferative disorder (e.g., a metastatic or non-metastatic tumor, cancer, malignancy or neoplasia).

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of undesirable or aberrant cell proliferation, such as a hyperproliferative disorder (e.g., a metastatic or non-metastatic tumor, cancer, malignancy or neoplasia) for analysis of conjugates in vivo.

Subjects appropriate for treatment include those having or at risk of having a metastatic or non-metastatic tumor, cancer, malignant or neoplastic cell, those undergoing as well as those who are undergoing or have undergone antiproliferative (e.g., metastatic or non-metastatic tumor, cancer, malignancy or neoplasia) therapy, including subjects where the tumor is in remission. "At risk" subjects typically have risk factors associated with undesirable or aberrant cell proliferation, development of hyperplasia (e.g., a tumor).

Particular examples of at risk or candidate subjects include those with cells that express a target (e.g., a receptor) to which a conjugate can bind, particularly where cells targeted for necrosis, lysis, killing or destruction express greater numbers or amounts of a target (e.g., a receptor) than non-target cells. Such cells can be selectively or preferentially targeted for necrosis, lysis or killing.

At risk subjects also include those that are candidates for and those that have undergone surgical resection, chemotherapy, immunotherapy, ionizing or chemical radiotherapy, local or regional thermal (hyperthermia) therapy, or vaccination. The invention is therefore applicable to treating a subject who is at risk of a metastatic or non-metastatic tumor, cancer, malignancy or neoplasia or a complication associated with a metastatic or non-metastatic tumor, cancer, malignancy or neoplasia, for example, due to metastatic or non-metastatic tumor, cancer, malignancy or neoplasia reappearance or regrowth following a period of stability or remission.

Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing cancer can therefore be identified by lifestyle, occupation, environmental factors, family history, and genetic screens for tumor associated genes, gene deletions or gene mutations. Subjects at risk for developing breast cancer lack Brca1, for example. Subjects at risk for developing colon cancer have early age or high frequency polyp formation, or deleted or mutated tumor suppressor genes, such as adenomatous polyposis coli (APC), for example.

Subjects also include those precluded from other treatments. For example, certain subjects may not be good candidates for surgical resection, chemotherapy, immunotherapy, ionizing or chemical radiotherapy, local or regional thermal (hyperthermia) therapy, or vaccination. Thus, candidate subjects for treatment in accordance with the invention include those that are not a candidate for surgical resection, chemotherapy, immunotherapy, ionizing or chemical radiotherapy, local or regional thermal (hyperthermia) therapy, or vaccination.

Conjugates may be formulated in a unit dose or unit dosage form. In a particular embodiment, a conjugate is in an amount anticipated to be effective to treat a subject having undesirable or aberrant cell proliferation or a hyperproliferative disorder. In an additional particular embodiment, a conjugate is in an amount anticipated to be effective to treat a subject having a metastatic or non-metastatic tumor, cancer, malignancy or neoplasia. Exemplary unit doses range from about 1-25, 25-250, 250-500, 500-1000, 1000-2500, 2500-5000, 5000-25,000, 5000-50,000 µg; and from about 1-25, 25-250, 250-500, 500-1000, 1000-2500 or 2500-5000, 5000-25,000, 5000-50,000 or 50,000-100,000 mg.

Conjugates and methods and uses of the invention may be contacted or provided in vitro, ex vivo or in vivo. Conjugates can be administered to provide the intended effect as a single or multiple dosages, for example, in an effective or sufficient amount. Exemplary doses range from about 1-25, 25-250, 250-500, 500-1000, 1000-2500 or 2500-5000, 5000-25,000, 5000-50,000, or 50,000-100,000 µg/kg, on consecutive days, or alternating days or intermittently. Single or multiple doses can be administered on consecutive days, alternating days or intermittently.

Conjugates can be administered and methods may be practiced via systemic, regional or local administration, by any route. For example, a conjugate can be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods and uses of the invention including pharmaceutical formulations can be administered via a (micro)encapsulated delivery system or packaged into an implant for administration.

The invention further provides conjugates and methods and uses in which the conjugates are included in pharmaceutical compositions. A pharmaceutical composition refers to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration or use. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions. Polysorbate 20 and polysorbate 80 can be added into the formulation mixture, for example, up to 1%. Other non-limiting additives include histidine HCl, $\alpha,\alpha$-treahlose dehydrate.

Additional pharmaceutical formulations and delivery systems are known to the skilled artisan and are applicable in the methods of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

The invention provides kits including conjugates of the invention, combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for reducing or inhibiting proliferation of a cell, reducing or inhibiting proliferation of undesirable or aberrant cells, such as a hyperproliferating cell, reducing or inhibiting proliferation of a metastatic or non-metastatic tumor, cancer, malignant or neoplastic cell, treating a subject having a hyperproliferative disorder, treating a subject having a metastatic or non-metastatic tumor, cancer, malignancy or neoplasia, or reducing fertility of an animal.

A kit can contain a collection of such components, e.g., two or more conjugates alone, or in combination with another therapeutically useful composition (e.g., an anti-proliferative or immune-enhancing drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include, instructions for treating an undesirable or aberrant cell proliferation, hyperproliferating cells and disorders (e.g., metastatic or non-metastatic tumor, cancer, malignancy or neoplasia). Kits of the invention therefore can additionally include labels or instructions for practicing any of the methods and uses of the invention described herein.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain host cells expressing conjugates of the invention, or that contain nucleic acids encoding conjugates. The cells in the kit can be maintained under appropriate storage conditions until the cells are ready to be used. For example, a kit including one or more cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a conjugate" or "a target (e.g., a receptor)," or a "lytic domain" includes a plurality of such conjugates, targets, or lytic domains, and so forth.

As used herein, numerical values are often presented in a range format throughout this document. The use of a range format is merely for convenience and brevity and should not be construed as an inflexible limitation on the scope of the invention unless the context clearly indicates otherwise. Accordingly, a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and any numerical range within such a ranges, such as 1-2, 5-10, 10-50, 50-100, 100-500, 100-1000, 500-1000, 1000-2000, 1000-5000, etc. In a further example, reference to a range of KD $10^{-5}$ M to about KD $10^{-13}$ M includes any numerical value or range within or encompassing such values.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, and 150-171, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-171, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

To determine, in in vitro studies, cytotoxicity of recombinantly produced antibody (as a antibody) scFv-$C_H$3 to Her-2 receptor conjugated to the lytic peptide, Phor18 (KFAKFAK KFAKFAKKFAK) (SEQ ID NO.:4) or (KLAKLAK)$_2$KLAK (SEQ ID NO.:74). Various linkers (GS and NRVRRS (SEQ ID NO.:75)) and 1 or 2 molecules of lytic peptides per antibody molecule were studied.

Peptides studied were: Phor18-scFv-$C_H$3-Phor18 (2 molecules of Phor-18 joined at N- and C-terminal ends of the antibody, scFv-$C_H$3-GS-Phor18 (one molecule of Phor18 joined to the antibody at the C-terminus by GS linker, scFv-$C_H$3-GS-(KLAKLAK)$_2$KLAK (SEQ ID NO.:74) (one molecule of (KLAKLAK)$_2$KLAK (SEQ ID NO.:74) linked to the antibody at the C-terminus by GS linker, scFv-$C_H$3-NRVRRS (SEQ ID NO.:75)-Phor18 (one molecule of Phor18 to the antibody at the C-terminus by NRVRRS linker, and scFv-$C_H$3-NRVRRS-(KLAKLAK)$_2$KLAK (SEQ ID NO.:74) (one molecule of (KLAKLAK)$_2$KLAK (SEQ ID NO.:74) to the antibody at the C-terminus by NRVRRS linker) Cytotoxicity was compared to a naked antibody (antibody without a lytic peptide) in Her-2 receptor positive cells (SKBR-3 and SKOV-3, human breast and ovarian cancer cells, respectively) and Her-2 receptor negative breast cancer cells (MDA-MB-231).

Example 2

This example describes various materials and methods used in the studies described herein.

Materials:

Recombinant DNA technique was used to synthesize anti-Her2/neu antibody as a recombinant antibody in *Escherichia coli*. The scFv-$C_H$3 antibody (Olafsen T. et al Protein Engineering, Design & Selection 17, 315-323, 2004) was conjugated via a peptide linker or without a linker as described in Table 1 to either Phor18 or an amphipathic, alpha-helical lytic peptide, (KLAKLAK)$_2$KLAK (SEQ ID NO.:74) and analyzed for cytotoxicity in vitro. The plasmid was acquired through gene codon optimization. The gene was synthesized with a N-His tag sequence and the plasmid was subcloned into an *E. coli* bacteria expression vector pUC57. After expression optimization and evaluation the His-tag product was selected and 1 L of the bacteria expression product was purified in a one-step affinity purification. The sequences of the plasmid gene insertion for each construct is described in Table 1.

TABLE 1

Nucleotide sequence of the plasmid insertion for the production of each recombinant Her2/neu antibody and antibody conjugate.

1. Her2/neu scFv-C$_H$3:

(SEQ ID NO.: 76)

```
   1  CATATGCATC ACCACCACCA CCACGACGAC GACGACAAAG ATATTCAAAT GACCCAGTCC
  61  CCGAGCAGCC TGAGTGCCTC CGTTGGCGAC CGCGTGACCA TTACGTGCCG TGCCAGCCAG
 121  GATGTCAACA CCGCGGTGGC CTGGTATCAG CAAAAACCGG GCAAAGCGCC GAAACTGCTG
 181  ATCTATTCAG CCTCGTTTCT GTACAGCGGT GTTCCGTCTC GTTTCAGCGG CTCTCGCAGT
 241  GGTACCGATT TTACCCTGAC GATTAGCTCT CTGCAGCCGG AAGACTTTGC GACGTATTAC
 301  TGCCAGCAAC ATTACACCAC GCCGCCGACC TTCGGCCAGG GTACGAAAGT GGAAATCAAA
 361  GGTTCCACCT CAGGCGGTGG CAGTGGTGGC GGTTCCGGCG GTGGCGGTAG TTCCGAAGTT
 421  CAGCTGGTCG AAAGTGGCGG TGGCCTGGTT CAACCGGGTG GCTCACTGCG TCTGTCGTGT
 481  GCAGCAAGCG GTTTCAACAT CAAAGATACC TACATCCACT GGGTTCGTCA GGCGCCGGGC
 541  AAAGGTCTGG AATGGGTCGC CGCATTTAC CCGACCAATG GCTATACGCG TTACGCAGAT
 601  AGCGTGAAAG GTCGCTTTAC CATCTCTGCG GACACCAGTA AAAACACGGC CTATCTGCAG
 661  ATGAATAGCC TGCGTGCGGA AGATACGGCC GTTTATTACT GCTCTCGCTG GGGTGGCGAT
 721  GGCTTCTATG CTATGGACTA CTGGGGCCAG GGTACCCTGG TGACGGTTTC ATCGGGTCAG
 781  CCGCGTGAAC CGCAAGTGTA TACCCTGCCG CCGTCACGCG ATGAACTGAC GAAAAACCAG
 841  GTGTCGCTGA CGTGTCTGGT TAAAGGCTTT TACCCGAGCG ACATCGCGGT TGAATGGGAA
 901  TCTAATGGTC AACCGGAAAA CAATTATAAA ACCACGCCGC CGGTCCTGGA TAGTGACGGC
 961  TCCTTTTTCC TGTACAGTAA ACTGACCGTG GATAAATCCC GTTGGCAGCA GGGTAACGTC
1021  TTCTCGTGTA GCGTGATGCA TGAAGCCCTG CATAATCACT ATACCCAGAA ATCTCTGAGT
1081  CTGTCCCCGG GCAAAGGTTC AACGTCGGGT GGCGGTTCCG GCGGTGGCTC AGGTGGCGGT
1141  GGCAGCTCTG GCCAACCGCG CGAACCGCAG GTTTACACCC TGCCGCCGAG CCGTGACGAA
1201  CTGACCAAAA ACCAAGTCAG CCTGACGTGC CTGGTGAAAG GCTTTTACCC GAGTGACATT
1261  GCAGTTGAAT GGGAATCCAA TGGTCAGCCG GAAAATAACT ACAAAACGAC GCCGCCGGTT
1321  CTGGATTCAG ACGGCTCGTT TTTCCTGTAC TCAAAACTGA CCGTCGATAA ATCGCGCTGG
1381  CAACAGGGTA ACGTTTTCAG CTGCTCTGTC ATGCACGAAG CCCTGCACAA CCATTATACC
1441  CAGAAAAGTC TGTCCCTGTC ACCGGGCAAA GAAGTGCAGC TGGTTGAATC TGGTGGCGGT
1501  CTGGTGCAAC CGGGCGGTTC GCTGCGTCTG AGCTGTGCAG CTTCTGGCTT TAATATTAAA
1561  GACACGTACA TCCACTGGGT GCGTCAGGCA CCGGGTAAAG GCCTGGAATG GGTTGCTCGT
1621  ATCTATCCGA CGAACGGTTA TACGCGTTAC GCCGATAGCG TCAAAGGCCG TTTTACCATC
1681  AGTGCAGACA CCTCCAAAAA CACGGCTTAT CTGCAGATGA ATAGTCTGCG TGCAGAAGAT
1741  ACCGCTGTTT ATTACTGCAG CCGCTGGGGC GGTGATGGCT TCTATGCAAT GGATTATTGG
1801  GGTCAAGGTA CCCTGGTCAC CGTGAGTTCC GGTTCGACCA GCGGCGGTGG CTCAGGTGGC
1861  GGTTCGGGCG GTGGCGGTTC ATCGGACATT CAGATGACGC AAAGCCCGAG CTCTCTGTCT
1921  GCGAGTGTTG GCGATCGTGT CACCATCACG TGTCGCGCCT CTCAGGACGT GAATACCGCA
1981  GTTGCTTGGT ACCAACAAAA ACCGGGCAAA GCACCGAAAC TGCTGATTTA CTCCGCTTCA
2041  TTCCTGTACA GCGGTGTGCC GTCTCGTTTT TCGGGCAGCC GCTCTGGTAC CGATTTCACC
```

TABLE 1-continued

Nucleotide sequence of the plasmid insertion for the production of each recombinant Her2/neu antibody and antibody conjugate.

```
2101 CTGACGATTA GTTCCCTGCA ACCGGAAGAT TTCGCCACCT ACTACTGCCA GCAACACTAT
2161 ACGACCCCGC CGACGTTTGG TCAGGGCACG AAAGTGGAAA TTAAATAATG AAAGCTT
```

2. scFv-$C_H$3-GS-Phor18:

(SEQ ID NO.: 77)

```
   1 CATATGCATC ACCACCACCA CCACGACGAC GACGACAAAG ATATTCAAAT GACCCAGTCC
  61 CCGAGCAGCC TGAGTGCCTC CGTTGGCGAC CGCGTGACCA TTACGTGCCG TGCGAGCCAG
 121 GATGTCAACA CCGCGGTGGC CTGGTATCAG CAAAAACCGG GCAAAGCGCC GAAACTGCTG
 181 ATCTATTCAG CCTCGTTTCT GTACAGCGGT GTTCCGTCTC GTTTCAGCGG CTCTCGCAGT
 241 GGTACCGATT TTACCCTGAC GATTAGCTCT CTGCAGCCGG AAGACTTTGC GACGTATTAC
 301 TGCCAGCAAC ATTACACCAC GCCGCCGACC TTCGGCCAGG GTACGAAAGT GGAAATCAAA
 361 GGTTCCACCT CAGGCGGTGG CAGTGGTGGC GGTTCCGGCG GTGGCGGTAG TTCCGAAGTT
 421 CAGCTGGTCG AAAGTGGCGG TGGCCTGGTT CAACCGGGTG GCTCACTGCG TCTGTCGTGT
 481 GCAGCAAGCG GTTTCAACAT CAAAGATACC TACATCCACT GGGTTCGTCA GGCGCCGGGC
 541 AAAGGTCTGG AATGGGTCGC CCGCATTTAC CCGACCAATG GCTATACGCG TTACGCAGAT
 601 AGCGTGAAAG GTCGCTTTAC CATCTCTGCG GACACCAGTA AAAACACGGC CTATCTGCAG
 661 ATGAATAGCC TGCGTGCGGA AGATACGGCC GTTTATTACT GCTCTCGCTG GGGTGGCGAT
 721 GGCTTCTATG CTATGGACTA CTGGGGCCAG GGTACCCTGG TGACGGTTTC ATCGGGTCAG
 781 CCGCGTGAAC CGCAAGTGTA TACCCTGCCG CCGTCACGCG ATGAACTGAC GAAAAACCAG
 841 GTGTCGCTGA CGTGTCTGGT TAAAGGCTTT TACCCGAGCG ACATCGCGGT TGAATGGGAA
 901 TCTAATGGTC AACCGGAAAA CAATTATAAA ACCACGCCGC CGGTCCTGGA TAGTGACGGC
 961 TCCTTTTTCC TGTACAGTAA ACTGACCGTG GATAAATCCC GTTGGCAGCA GGGTAACGTC
1021 TTCTCGTGTA GCGTGATGCA TGAAGCCCTG CATAATCACT ATACCCAGAA ATCTCTGAGT
1081 CTGTCCCCGG GCAAAGGTTC AACGTCGGGT GGCGGTTCCG GCGGTGGCTC AGGTGGCGGT
1141 GGCAGCTCTG GCCAACCGCG CGAACCGCAG GTTTACACCC TGCCGCCGAG CCGTGACGAA
1201 CTGACCAAAA ACCAAGTCAG CCTGACGTGC CTGGTGAAAG GCTTTTACCC GAGTGACATT
1261 GCAGTTGAAT GGGAATCCAA TGGTCAGCCG GAAAATAACT ACAAAACGAC GCCGCCGGTT
1321 CTGGATTCAG ACGGCTCGTT TTTCCTGTAC TCAAAACTGA CCGTCGATAA ATCGCGCTGG
1381 CAACAGGGTA ACGTTTTCAG CTGCTCTGTC ATGCACGAAG CCCTGCACAA CCATTATACC
1441 CAGAAAAGTC TGTCCCTGTC ACCGGGCAAA GAAGTGCAGC TGGTTGAATC TGGTGGCGGT
1501 CTGGTGCAAC CGGGCGGTTC GCTGCGTCTG AGCTGTGCAG CTTCTGGCTT TAATATTAAA
1561 GACACGTACA TCCACTGGGT GCGTCAGGCA CCGGGTAAAG GCCTGGAATG GGTTGCTCGT
1621 ATCTATCCGA CGAACGGTTA TACGCGTTAC GCCGATAGCG TCAAAGGCCG TTTTACCATC
1681 AGTGCAGACA CCTCCAAAAA CACGGCTTAT CTGCAGATGA ATAGTCTGCG TGCAGAAGAT
1741 ACCGCTGTTT ATTACTGCAG CCGCTGGGGC GGTGATGGCT TCTATGCAAT GGATTATTGG
1801 GGTCAAGGTA CCCTGGTCAC CGTGAGTTCC GGTTCGACCA GCGGCGGTGG CTCAGGTGGC
1861 GGTTCGGGCG GTGGCGGTTC ATCGGACATT CAGATGACGC AAAGCCCGAG CTCTCTGTCT
1921 GCGAGTGTTG GCGATCGTGT CACCATCACG TGTCGCGCCT CTCAGGACGT GAATACCGCA
1981 GTTGCTTGGT ACCAACAAAA ACCGGGCAAA GCACCGAAAC TGCTGATTTA CTCCGCTTCA
2041 TTCCTGTACA GCGGTGTGCC GTCTCGTTTT TCGGGCAGCC GCTCTGGTAC CGATTTCACC
```

TABLE 1-continued

Nucleotide sequence of the plasmid insertion for the production of each recombinant Her2/neu antibody and antibody conjugate.

```
2101 CTGACGATTA GTTCCCTGCA ACCGGAAGAT TTCGCCACCT ACTACTGCCA GCAACACTAT
2161 ACGACCCCGC CGACGTTTGG TCAGGGCACG AAAGTGGAAA TTAAAGGCAG CAAATTTGCG
2221 AAATTCGCCA AAAAATTCGC AAAATTCGCG AAAAAATTCG CGAAATAATG AAAGCTT
```

3. scFv-$C_H3$-GS-(KLAKLAK)$_2$KLAK:

(SEQ ID NO.: 78)
```
   1 CATATGGAAA ATCTGTATTT CCAAGGTGAT ATTCAAATGA CCCAGTCCCC GAGCAGCCTG
  61 AGTGCCTCCG TTGGCGACCG CGTGACCATT ACGTGCCGTG CGAGCCAGGA TGTCAACACC
 121 GCGGTGGCCT GGTATCAGCA AAACCGGGC AAAGCGCCGA AACTGCTGAT CTATTCAGCC
 181 TCGTTTCTGT ACAGCGGTGT TCCGTCTCGT TTCAGCGGCT CTCGCAGTGG TACCGATTTT
 241 ACCCTGACGA TTAGCTCTCT GCAGCCGGAA GACTTTGCGA CGTATTACTG CCAGCAACAT
 301 TACACCACGC CGCCGACCTT CGGCCAGGGT ACGAAAGTGG AAATCAAAGG TTCCACCTCA
 361 GGCGGTGGCA GTGGTGGCGG TTCCGGCGGT GGCGGTAGTT CCGAAGTTCA GCTGGTCGAA
 421 AGTGGCGGTG GCCTGGTTCA ACCGGGTGGC TCACTGCGTC TGTCGTGTGC AGCAAGCGGT
 481 TTCAACATCA AAGATACCTA CATCCACTGG GTTCGTCAGG CGCCGGGCAA AGGTCTGGAA
 541 TGGGTCGCCC GCATTTACCC GACCAATGGC TATACGCGTT ACGCAGATAG CGTGAAAGGT
 601 CGCTTTACCA TCTCTGCGGA CACCAGTAAA AACACGGCCT ATCTGCAGAT GAATAGCCTG
 661 CGTGCGGAAG ATACGGCCGT TTATTACTGC TCTCGCTGGG GTGGCGATGG CTTCTATGCT
 721 ATGGACTACT GGGGCCAGGG TACCCTGGTG ACGGTTTCAT CGGGTCAGCC GCGTGAACCG
 781 CAAGTGTATA CCCTGCCGCC GTCACGCGAT GAACTGACGA AAAACCAGGT GTCGCTGACG
 841 TGTCTGGTTA AAGGCTTTTA CCCGAGCGAC ATCGCGGTTG AATGGGAATC TAATGGTCAA
 901 CCGGAAAACA ATTATAAAAC CACGCCGCCG TCCTGGATA GTGACGGCTC CTTTTTCCTG
 961 TACAGTAAAC TGACCGTGGA TAAATCCCGT TGGCAGCAGG GTAACGTCTT CTCGTGTAGC
1021 GTGATGCATG AAGCCCTGCA TAATCACTAT ACCCAGAAAT CTCTGAGTCT GTCCCCGGGC
1081 AAAGGTTCAA CGTCGGGTGG CGGTTCCGGC GGTGGCTCAG GTGGCGGTGG CAGCTCTGGC
1141 CAACCGCGCG AACCGCAGGT TTACACCCTG CCGCCGAGCC GTGACGAACT GACCAAAAAC
1201 CAAGTCAGCC TGACGTGCCT GGTGAAAGGC TTTTACCCGA GTGACATTGC AGTTGAATGG
1261 GAATCCAATG GTCAGCCGGA AAATAACTAC AAAACGACGC CGCCGGTTCT GGATTCAGAC
1321 GGCTCGTTTT TCCTGTACTC AAAACTGACC GTCGATAAAT CGCGCTGGCA ACAGGGTAAC
1381 GTTTTCAGCT GCTCTGTCAT GCACGAAGCC CTGCACAACC ATTATACCCA GAAAAGTCTG
1441 TCCCTGTCAC CGGGCAAAGA AGTGCAGCTG GTTGAATCTG GTGGCGGTCT GGTGCAACCG
1501 GGCGGTTCGC TGCGTCTGAG CTGTGCAGCT TCTGGCTTTA ATATTAAAGA CACGTACATC
1561 CACTGGGTGC GTCAGGCACC GGGTAAAGGC CTGGAATGGG TTGCTCGTAT CTATCCGACG
1621 AACGGTTATA CGCGTTACGC CGATAGCGTC AAAGGCCGTT TTACCATCAG TGCAGACACC
1681 TCCAAAAACA CGGCTTATCT GCAGATGAAT AGTCTGCGTG CAGAAGATAC CGCTGTTTAT
1741 TACTGCAGCC GCTGGGGCGG TGATGGCTTC TATGCAATGG ATTATTGGGG TCAAGGTACC
1801 CTGGTCACCG TGAGTTCCGG TTCGACCAGC GGCGGTGGCT CAGGTGGCGG TTCGGGCGGT
1861 GGCGGTTCAT CGGACATTCA GATGACGCAA AGCCCGAGCT CTCTGTCTGC GAGTGTTGGC
1921 GATCGTGTCA CCATCACGTG TCGCGCCTCT CAGGACGTGA ATACCGCAGT TGCTTGGTAC
1981 CAACAAAAAC CGGGCAAAGC ACCGAAACTG CTGATTTACT CCGCTTCATT CCTGTACAGC
2041 GGTGTGCCGT CTCGTTTTTC GGGCAGCCGC TCTGGTACCG ATTTCACCCT GACGATTAGT
```

TABLE 1-continued

Nucleotide sequence of the plasmid insertion for the production of each recombinant Her2/neu antibody and antibody conjugate.

```
2101 TCCCTGCAAC CGGAAGATTT CGCCACCTAC TACTGCCAGC AACACTATAC GACCCCGCCG

2161 ACGTTTGGTC AGGGCACGAA AGTGGAAATT AAAGGCAGCA AACTGGCGAA ACTGGCCAAA

2221  AAACTGGCAA AACTGGCGAA AAAACTGGCG AAATAATGAA AGCTT
```

4. scFv-C$_H$3-NRVRRS-Phor18:

(SEQ ID NO.: 79)

```
   1 CATATGGAAA ATCTGTATTT CCAAGGTGAT ATTCAAATGA CCCAGTCCCC GAGCAGCCTG

61 AGTGCCTCCG TTGGCGACCG CGTGACCATT ACGTGCCGTG CGAGCCAGGA TGTCAACACC

121 GCGGTGGCCT GGTATCAGCA AAAACCGGGC AAAGCGCCGA AACTGCTGAT CTATTCAGCC

181 TCGTTTCTGT ACAGCGGTGT TCCGTCTCGT TTCAGCGGCT CTCGCAGTGG TACCGATTTT

241 ACCCTGACGA TTAGCTCTCT GCAGCCGGAA GACTTTGCGA CGTATTACTG CCAGCAACAT

301 TACACCACGC CGCCGACCTT CGGCCAGGGT ACGAAAGTGG AAATCAAAGG TTCCACCTCA

361 GGCGGTGGCA GTGGTGGCGG TTCCGGCGGT GGCGGTAGTT CCGAAGTTCA GCTGGTCGAA

421 AGTGGCGGTG GCCTGGTTCA ACCGGGTGGC TCACTGCGTC TGTCGTGTGC AGCAAGCGGT

481 TTCAACATCA AAGATACCTA CATCCACTGG GTTCGTCAGG CGCCGGGCAA AGGTCTGGAA

541 TGGGTCGCCC GCATTTACCC GACCAATGGC TATACGCGTT ACGCAGATAG CGTGAAAGGT

601 CGCTTTACCA TCTCTGCGGA CACCAGTAAA AACACGGCCT ATCTGCAGAT GAATAGCCTG

661 CGTGCGGAAG ATACGGCCGT TTATTACTGC TCTCGCTGGG GTGGCGATGG CTTCTATGCT

721 ATGGACTACT GGGGCCAGGG TACCCTGGTG ACGGTTTCAT CGGGTCAGCC GCGTGAACCG

781 CAAGTGTATA CCCTGCCGCC GTCACGCGAT GAACTGACGA AAAACCAGGT GTCGCTGACG

841 TGTCTGGTTA AAGGCTTTTA CCCGAGCGAC ATCGCGGTTG AATGGGAATC TAATGGTCAA

901 CCGGAAAACA ATTATAAAAC CACGCCGCCG GTCCTGGATA GTGACGGCTC CTTTTTCCTG

961 TACAGTAAAC TGACCGTGGA TAAATCCCGT TGGCAGCAGG GTAACGTCTT CTCGTGTAGC

1021 GTGATGCATG AAGCCCTGCA TAATCACTAT ACCCAGAAAT CTCTGAGTCT GTCCCCGGGC

1081 AAAGGTTCAA CGTCGGGTGG CGGTTCCGGC GGTGGCTCAG GTGGCGGTGG CAGCTCTGGC

1141 CAACCGCGCG AACCGCAGGT TTACACCCTG CCGCCGAGCC GTGACGAACT GACCAAAAAC

1201 CAAGTCAGCC TGACGTGCCT GGTGAAAGGC TTTTACCCGA GTGACATTGC AGTTGAATGG

1261 GAATCCAATG GTCAGCCGGA AAATAACTAC AAAACGACGC CGCCGGTTCT GGATTCAGAC

1321 GGCTCGTTTT TCCTGTACTC AAAACTGACC GTCGATAAAT CGCGCTGGCA ACAGGGTAAC

1381 GTTTTCAGCT GCTCTGTCAT GCACGAAGCC CTGCACAACC ATTATACCCA GAAAAGTCTG

1441 TCCCTGTCAC CGGGCAAAGA AGTGCAGCTG GTTGAATCTG GTGGCGGTCT GGTGCAACCG

1501 GGCGGTTCGC TGCGTCTGAG CTGTGCAGCT TCTGGCTTTA ATATTAAAGA CACGTACATC

1561 CACTGGGTGC GTCAGGCACC GGGTAAAGGC CTGGAATGGG TTGCTCGTAT CTATCCGACG

1621 AACGGTTATA CGCGTTACGC CGATAGCGTC AAAGGCCGTT TTACCATCAG TGCAGACACC

1681 TCCAAAAACA CGGCTTATCT GCAGATGAAT AGTCTGCGTG CAGAAGATAC CGCTGTTTAT

1741 TACTGCAGCC GCTGGGGCGG TGATGGCTTC TATGCAATGG ATTATTGGGG TCAAGGTACC

1801 CTGGTCACCG TGAGTTCCGG TTCGACCAGC GGCGGTGGCT CAGGTGGCGG TTCGGGCGGT

1861 GGCGGTTCAT CGGACATTCA GATGACGCAA AGCCCGAGCT CTCTGTCTGC GAGTGTTGGC

1921 GATCGTGTCA CCATCACGTG TCGCGCCTCT CAGGACGTGA ATACCGCAGT TGCTTGGTAC

1981 CAACAAAAAC CGGGCAAAGC ACCGAAACTG CTGATTTACT CCGCTTCATT CCTGTACAGC
```

TABLE 1-continued

Nucleotide sequence of the plasmid insertion for the production of each recombinant Her2/neu antibody and antibody conjugate.

```
2041 GGTGTGCCGT CTCGTTTTTC GGGCAGCCGC TCTGGTACCG ATTTCACCCT GACGATTAGT

2101 TCCCTGCAAC CGGAAGATTT CGCCACCTAC TACTGCCAGC AACACTATAC GACCCCGCCG

2161 ACGTTTGGTC AGGGCACGAA AGTGGAAATT AAAAACCGTG TGCGTCGCAG CAAATTTGCG

2221 AAATTCGCCA AAAATTTGC AAAATTCGCT AAAAAATTTG CGAATAATG AAAGCTT
```

5. scFv-C$_H$3-NRVRRS-(KLAKLAK)$_2$KLAK:

(SEQ ID NO.: 80)
```
   1 CATATGCATC ACCACCACCA CCACGACGAC GACGACAAAG ATATTCAAAT GACCCAGTCC

61 CCGAGCAGCC TGAGTGCCTC CGTTGGCGAC CGCGTGACCA TTACGTGCCG TGCGAGCCAG

121 GATGTCAACA CCGCGGTGGC CTGGTATCAG CAAAAACCGG GCAAAGCGCC GAAACTGCTG

181 ATCTATTCAG CCTCGTTTCT GTACAGCGGT GTTCCGTCTC GTTTCAGCGG CTCTCGCAGT

241 GGTACCGATT TTACCCTGAC GATTAGCTCT CTGCAGCCGG AAGACTTTGC GACGTATTAC

301 TGCCAGCAAC ATTACACCAC GCCGCCGACC TTCGGCCAGG GTACGAAAGT GGAAATCAAA

361 GGTTCCACCT CAGGCGGTGG CAGTGGTGGC GGTTCCGGCG GTGGCGGTAG TTCCGAAGTT

421 CAGCTGGTCG AAAGTGGCGG TGGCCTGGTT CAACCGGGTG GCTCACTGCG TCTGTCGTGT

481 GCAGCAAGCG GTTTCAACAT CAAAGATACC TACATCCACT GGGTTCGTCA GGCGCCGGGC

541 AAAGGTCTGG AATGGGTCGC CGCATTTAC CCGACCAATG GCTATACGCG TTACGCAGAT

601 AGCGTGAAAG GTCGCTTTAC CATCTCTGCG GACACCAGTA AAAACACGGC CTATCTGCAG

661 ATGAATAGCC TGCGTGCGGA AGATACGGCC GTTTATTACT GCTCTCGCTG GGGTGGCGAT

721 GGCTTCTATG CTATGGACTA CTGGGGCCAG GGTACCCTGG TGACGGTTTC ATCGGGTCAG

781 CCGCGTGAAC CGCAAGTGTA TACCCTGCCG CCGTCACGCG ATGAACTGAC GAAAAACCAG

841 GTGTCGCTGA CGTGTCTGGT TAAAGGCTTT TACCCGAGCG ACATCGCGGT TGAATGGGAA

901 TCTAATGGTC AACCGGAAAA CAATTATAAA ACCACGCCGC CGGTCCTGGA TAGTGACGGC

961 TCCTTTTTCC TGTACAGTAA ACTGACCGTG GATAAATCCC GTTGGCAGCA GGGTAACGTC

1021 TTCTCGTGTA GCGTGATGCA TGAAGCCCTG CATAATCACT ATACCCAGAA ATCTCTGAGT

1081 CTGTCCCCGG GCAAAGGTTC AACGTCGGGT GGCGGTTCCG GCGGTGGCTC AGGTGGCGGT

1141 GGCAGCTCTG GCCAACCGCG CGAACCGCAG GTTTACACCC TGCCGCCGAG CCGTGACGAA

1201 CTGACCAAAA ACCAAGTCAG CCTGACGTGC CTGGTGAAAG GCTTTTACCC GAGTGACATT

1261 GCAGTTGAAT GGGAATCCAA TGGTCAGCCG GAAAATAACT ACAAAACGAC GCCGCCGGTT

1321 CTGGATTCAG ACGGCTCGTT TTTCCTGTAC TCAAAACTGA CCGTCGATAA ATCGCGCTGG

1381 CAACAGGGTA ACGTTTTCAG CTGCTCTGTC ATGCACGAAG CCCTGCACAA CCATTATACC

1441 CAGAAAAGTC TGTCCCTGTC ACCGGGCAAA GAAGTGCAGC TGGTTGAATC TGGTGGCGGT

1501 CTGGTGCAAC CGGGCGGTTC GCTGCGTCTG AGCTGTGCAG CTTCTGGCTT TAATATTAAA

1561 GACACGTACA TCCACTGGGT GCGTCAGGCA CCGGGTAAAG GCCTGGAATG GGTTGCTCGT

1621 ATCTATCCGA CGAACGGTTA TACGCGTTAC GCCGATAGCG TCAAAGGCCG TTTTACCATC

1681 AGTGCAGACA CCTCCAAAAA CACGGCTTAT CTGCAGATGA ATAGTCTGCG TGCAGAAGAT

1741 ACCGCTGTTT ATTACTGCAG CCGCTGGGGC GGTGATGGCT TCTATGCAAT GGATTATTGG

1801 GGTCAAGGTA CCCTGGTCAC CGTGAGTTCC GGTTCGACCA GCGGCGGTGG CTCAGGTGGC

1861 GGTTCGGGCG GTGGCGGTTC ATCGGACATT CAGATGACGC AAAGCCCGAG CTCTCTGTCT

1921 GCGAGTGTTG GCGATCGTGT CACCATCACG TGTCGCGCCT CTCAGGACGT GAATACCGCA

1981 GTTGCTTGGT ACCAACAAAA ACCGGGCAAA GCACCGAAAC TGCTGATTTA CTCCGCTTCA
```

TABLE 1-continued

Nucleotide sequence of the plasmid insertion for the production of each recombinant Her2/neu antibody and antibody conjugate.

```
2041 TTCCTGTACA GCGGTGTGCC GTCTCGTTTT TCGGGCAGCC GCTCTGGTAC CGATTTCACC

2101 CTGACGATTA GTTCCCTGCA ACCGGAAGAT TTCGCCACCT ACTACTGCCA GCAACACTAT

2161 ACGACCCCGC CGACGTTTGG TCAGGGCACG AAAGTGGAAA TTAAAAACCG TGTGCGTCGC

2221 AGCAAACTGG CGAAACTGGC CAAAAAACTG GCAAACTGG CTAAAAAACT GGCGAAATAA

2281 TGAAAGCTT
```

6. Phor18-scFv-C$_H$3-Phor18:

(SEQ ID NO.: 81)

```
   1 CATATGGAAA ATCTGTATTT CCAAGGTAAA TTTGCGAAAT CGCCAAAAA ATTCGCAAA

61 TTCGCGAAAA AATTCGCGAA AGATATTCAA ATGACCCAGT CCCCGAGCAG CCTGAGTGCC

121 TCCGTTGGCG ACCGCGTGAC CATTACGTGC CGTGCGAGCC AGGATGTCAA CACCGCGGTG

181 GCCTGGTATC AGCAAAAACC GGGCAAAGCG CCGAAACTGC TGATCTATTC AGCCTCGTTT

241 CTGTACAGCG GTGTTCCGTC TCGTTTCAGC GGCTCTCGCA GTGGTACCGA TTTTACCCTG

301 ACGATTAGCT CTCTGCAGCC GGAAGACTTT GCGACGTATT ACTGCCAGCA ACATTACACC

361 ACGCCGCCGA CCTTCGGCCA GGGTACGAAA GTGGAAATCA AAGGTTCCAC CTCAGGCGGT

421 GGCAGTGGTG GCGGTTCCGG CGGTGGCGGT AGTTCCGAAG TTCAGCTGGT CGAAAGTGGC

481 GGTGGCCTGG TTCAACCGGG TGGCTCACTG CGTCTGTCGT GTGCAGCAAG CGGTTTCAAC

541 ATCAAAGATA CCTACATCCA CTGGGTTCGT CAGGCGCCGG GCAAAGGTCT GGAATGGGTC

601 GCCCGCATTT ACCCGACCAA TGGCTATACG CGTTACGCAG ATAGCGTGAA AGGTCGCTTT

661 ACCATCTCTG CGGACACCAG TAAAAACACG GCCTATCTGC AGATGAATAG CCTGCGTGCG

721 GAAGATACGG CCGTTTATTA CTGCTCTCGC TGGGGTGGCG ATGGCTTCTA TGCTATGGAC

781 TACTGGGGCC AGGGTACCCT GGTGACGGTT TCATCGGGTC AGCCGCGTGA ACCGCAAGTG

841 TATACCCTGC CGCCGTCACG CGATGAACTG ACGAAAAACC AGGTGTCGCT GACGTGTCTG

901 GTTAAAGGCT TTTACCCGAG CGACATCGCG GTTGAATGGG AATCTAATGG TCAACCGGAA

961 AACCATTATA AACCACGCC GCCGGTCCTG GATAGTGACG GCTCCTTTTT CCTGTACAGT

1021 AAACTGACCG TGGATAAATC CCGTTGGCAG CAGGGTAACG TCTTCTCGTG TAGCGTGATG

1081 CATGAAGCCC TGCATAATCA CTATACCCAG AAATCTCTGA GTCTGTCCCC GGGCAAAGGT

1141 TCAACGTCGG GTGGCGGTTC CGGCGGTGGC TCAGGTGGCG GTGGCAGCTC TGGCCAACCG

1201 CGCGAACCGC AGGTTTACAC CCTGCCGCCG AGCCGTGACG AACTGACCAA AAACCAAGTC

1261 AGCCTGACGT GCCTGGTGAA AGGCTTTTAC CCGAGTGACA TTGCAGTTGA ATGGGAATCC

1321 AATGGTCAGC CGGAAAATAA CTACAAAACG ACGCCGCCGG TTCTGGATTC AGACGGCTCG

1381 TTTTTCCTGT ACTCAAAACT GACCGTCGAT AAATCGCGCT GGCAACAGGG TAACGTTTTC

1441 AGCTGCTCTG TCATGCACGA AGCCCTGCAC AACCATTATA CCCAGAAAAG TCTGTCCCTG

1501 TCACCGGGCA AGAAGTGCA GCTGGTTGAA TCTGGTGGCG GTCTGGTGCA ACCGGGCGGT

1561 TCGCTGCGTC TGAGCTGTGC AGCTTCTGGC TTTAATATTA AAGACACGTA CATCCACTGG

1621 GTGCGTCAGG CACCGGGTAA AGGCCTGGAA TGGGTTGCTC GTATCTATCC GACGAACGGT

1681 TATACGCGTT ACGCCGATAG CGTCAAAGGC CGTTTTACCA TCAGTGCAGA CACCTCCAAA

1741 AACACGGCTT ATCTGCAGAT GAATAGTCTG CGTGCAGAAG ATACCGCTGT TTATTACTGC

1801 AGCCGCTGGG GCGGTGATGG CTTCTATGCA ATGGATTATT GGGGTCAAGG TACCCTGGTC

1861 ACCGTGAGTT CCGGTTCGAC CAGCGGCGGT GGCTCAGGTG GCGGTTCGGG CGGTGGCGGT
```

TABLE 1-continued

Nucleotide sequence of the plasmid insertion for the production of
each recombinant Her2/neu antibody and antibody conjugate.

```
1921 TCATCGGACA TTCAGATGAC GCAAAGCCCG AGCTCTCTGT CTGCGAGTGT TGGCGATCGT

1981 GTCACCATCA CGTGTCGCGC CTCTCAGGAC GTGAATACCG CAGTTGCTTG GTACCAACAA

2041 AAACCGGGCA AAGCACCGAA ACTGCTGATT TACTCCGCTT CATTCCTGTA CAGCGGTGTG

2101 CCGTCTCGTT TTTCGGGCAG CCGCTCTGGT ACCGATTTCA CCCTGACGAT TAGTTCCCTG

2161 CAACCGGAAG ATTTCGCCAC CTACTACTGC CAGCAACACT ATACGACCCC GCCGACGTTT

2221 GGTCAGGGCA CGAAAGTGGA AATTAAAAAA TTTGCGAAAT TCGCCAAAAA ATTCGCAAAA

2281 TTCGCGAAAA AATTCGCGAA ATAATGAAAG CTT
```

Chemical Conjugation of Phor18 to a Monoclonal Anti-Her2/Neu Antibody IgG1 (MAb)

Purified antibody in phosphate buffered saline (PBS) is concentrated to a concentration of approximately 2 mg/mL. A 20 mM solution of N-succinidyl-3-(2-pyridylothio)propionate (SPDP) is freshly prepared in dimethylsulfoxide (DMSO), and added to the antibody solution in 20-fold excess. The mixture is incubated at room temperature for about 30 minutes to produce the antibody-linker intermediate. Excess unreacted SPDP is removed by size exclusion. The cytotoxic molecule containing cysteine is thoroughly reduced by reaction with a 10-fold excess of reductacryl reagent before mixing in 10-fold excess with the antibody-linker construct. The reaction is allowed to incubate at room temperature for 18 hours, then desalted to remove unreacted cytotoxin molecule. The solution is filter-sterilized before storage.

In Vitro:

In vitro cytotoxicity studies were performed to determine the cytotoxicity of the recombinant antibody preparations (conjugated and unconjugated) and lytic peptide, Phor18, was used in control incubations. Cells were prepared in 96 well plates using 2,000 cells/well and were allowed to attach for 48 hours. Phor18 in lyophilized form was freshly dissolved in saline and added into the multi-well plates at increasing concentrations of 0, 0.00001, 0.0001, 0.001, 0.01, 0.1, 1, 10, 25, and 100 µM. The Her2/neu-antibody-Phor18 conjugates (Phor18-scFv-$C_H$3-Phor18, scFv-$C_H$3-GS-Phor18, scFv-$C_H$3-NRVRRS (SEQ ID NO.:75)-Phor18, the Her2/neu-antibody-(KLAKLAK)$_2$KLAK (SEQ ID NO.:74) (scFv-$C_H$3-GS-(KLAKLAK)$_2$KLAK (SEQ ID NO.:74), and scFv-$C_H$3-NRVRRS (SEQ ID NO.:75)-(KLAKLAK)$_2$KLAK (SEQ ID NO.:74), or scFv-$C_H$3-receptor antibody (naked) in Tris/HCL-buffer were diluted with saline and added to cells at increasing concentrations of 0, 0.0012, 0.012, 0.12, 1.2, 6.0, 12.0, 120, 360 and 720 nM. Incubations were conducted for 48 h at 37° C. Cell viability was determined using formazan conversion assays (MTT assays). Controls contained USP saline or 0.1% TritonX-100™ as reference for 0 and 100% cell death, respectively. All data were processed and analyzed using Graph Pad Prizm 4™ software (Graph Pad Prizm, Inc).

Example 3

This example describes studies indicating that anti-Her2-Phor18 antibody conjugate killed Her2 expressing breast cancer cells.

As shown in Table 2, the anti-Her2-Phor18 antibody conjugates (Phor18-scFv-$C_H$3-Phor18, scFv-$C_H$3-GS-Phor18, scFv-$C_H$3-NRVRRS (SEQ ID NO.:75)-Phor18) killed Her2/neu positive human breast cancer SKBR-3 and ovarian cancer SKOV-3 cell lines by 48 hours, whereas the Her2/neu negative human breast cancer MDA-MB-231cell line was not killed. Evidence of cytotoxicity was observed microscopically at as early as 24 hours of incubation. As expected, unconjugated Phor18 showed only modest cytotoxicity.

The HER2/neu antibody conjugated to the Phor18 was significantly more cytotoxic than antibody conjugated to the lytic peptide (KLAKLAK)$_2$KLAK (SEQ ID NO.:74). (FIG. 1, Table 2). The Her2/neu negative MDA-MB-231 cells were not killed by any of the recombinant antibody-lytic peptide conjugates indicating that the cytotoxicity of the antibodies was mediated via Her2/neu receptors. The "naked" (unconjugated) antibody (scFv-$C_H$3) was not cytotoxic in all 3 cell lines indicating that the cell-killing properties of the antibody-lytic peptide conjugates were due to the presence of lytic peptide payload and sequence of the lytic peptide. Again, as expected, unconjugated Phor18 showed very minimal non-specific cytotoxicity in all cell lines (Table 2).

TABLE 2

In vitro cytotoxicity of anti-Her2-Phor18 antibody conjugates (scFv-$C_H$3-Phor18 and-scFv-$C_H$3-(KLAKLAK)$_2$KLAK (SEQ ID NO.: 74) conjugates, Her2/neu scFv-$C_H$3 and unconjugated Phor18 in Her2/neu receptor positive SKOV-3, SKBR-3 and Her2/neu receptor negative MDA-MB-231 cancer cells. Values are IC$_{50}$ expressed in nM.

| Recombinant Antibody Conjugate | IC$_{50}$ [nM] SKOV-3 | IC$_{50}$ [nM] SKBR-3 | IC$_{50}$ [nM] MDA-MB-231 |
| --- | --- | --- | --- |
| Phor18-scFv-$C_H$3-Phor18 | 44.33 ± 9.2 | 51.56 ± 6.1 | >1000 |
| scFv-$C_H$3-GS-Phor18 | 27 ± 2.5 | 30 ± 1.9 | >1000 |
| scFv-$C_H$3-GS-(KLAKLAK)$_2$KLAK | 235 ± 6.5 | 246 ± 41 | >1000 |
| scFv-$C_H$3-NRVRRS-Phor18 | 29.3 ± 3.5 | 76.3 ± 16 | >1000 |
| scFv-$C_H$3-NRVRRS-(KLAKLAK)$_2$KLAK | 247 ± 40.5 | 338 ± 8.7 | >1000 |
| Her2/neu scFv-$C_H$3 | >1000 | >1000 | >1000 |
| Phor18 | 18,180 | 11,455 | 9,258 |

The results indicate that recombinantly produced Her2 antibody scFv-$C_H$3-Phor18 and Her2 antibody scFv-$C_H$3-(KLAKLAK)$_2$KLAK (SEQ ID NO.:74) conjugates are active in the nanomolar range against Her2/neu receptor expressing cell lines. The unconjugated antibody or free lytic peptide (Phor18) were without effect indicating that conjugation of lytic peptides to ligands (e.g., antibodies) that bind to Her2/neu receptor to enhances cell cytotoxic potency.

Example 4

This example includes a description of in vitro cytotoxicity studies of recombinantly produced antibody to Her-2 receptor conjugated to lytic peptide, Phor18 (KFAKFAK KFAKFAK KFAK (SEQ ID NO.:4)) (scFv-$C_H$3-GS-Phor18), and a chemically conjugated MAb-Phor18 conjugate against Her2 positive ovarian cancer cell line SKOV-3.

Cells were prepared in 96 well plates using 5,000 cells/well and were allowed to attach for 48 hours. MAb-Phor18, scFv-$C_H$3-GS-Phor18, scFv-$C_H$3 were diluted in saline and added at increasing concentrations of 0, 0.0012, 0.012, 0.12, 1.2, 6.0, 12, 120, 360 and 720 nM, N=8 data points per concentration. Incubations were conducted for 24 h at 37° C. Cell viability was determined using formazan conversion assays (MTT assays). Controls contained USP saline or 0.1% TritonX-100™ as reference for 0 and 100% cell death, respectively.

Data were processed and analyzed using Graph Pad Prizm 4™ software (Graph Pad Prizm, Inc). Statistical analysis for significance was determined by a two-tailed Student's T-test. The whole MAb-Phor18 resulted in $IC_{50}$ values of 60.53±3.8 nM and scFv-$C_H$3-GS-Phor18 was 59.8±3.8 nM. The "naked" (unconjugated) antibodies (MAb and scFv-$C_H$3) were not cytotoxic. In vitro chemically linked HER2 antibody (MAb-Phor18) and recombinant Phor18 conjugate (scFv-$C_H$3-GS-Phor18) showed similar toxicity to SKOV-3 cells, whereas the naked recombinant antibody (scFv-$C_H$3) was not toxic.

Example 5

This example describes an in vivo study in a mouse xenograft model of human ovarian cancer with various doses of anti-Her2-Phor18 antibody conjugates (scFv-$C_H$3-GS-Phor18, MAb-Phor18), naked whole antibody (MAb) and naked recombinant antibody (scFv-$C_H$3) treatments.

Female Nu/Nu mice were injected subcutaneously with a SKOV-3/Matrigel suspension (4×10⁶ cells). Tumor weights from mice that were killed on day 42 served as baseline. In brief, treatment started on day 43 after tumor cell injection on tumors of median tumor volume of 130.3±10.25 mm³ and continued on days 47, 50, 54, 57 and 60 as a single bolus injection into the lateral tail vein.

During the entire study tumor volumes were measured twice per week and body weights were determined Final necropsy was conducted on day 64 after tumor cell injection where tumors were excised, weighed and fixed in formalin for histological evaluation.

Treatments were: saline control, whole naked monoclonal anti-Her2-antibody, MAb, (3 mg/kg), recombinant naked-Her2-antibody (scFv-$C_H$3) (3 mg/kg), scFv-$C_H$3-GS-Phor18 (0.3 and 3 mg/kg), MAb-Phor18 (0.3 and 3 mg/kg). Tumors from mice sacrificed at treatment start underwent immunohistochemistry evaluation of Her2/neu receptors. Each group consisted of 8-9 mice.

All groups of mice tolerated the injections well. No mice died as a consequence of injection.

Figure 4:
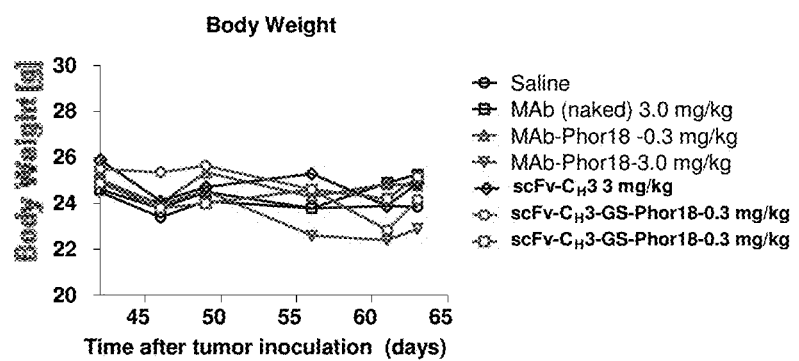
FIG. 4 shows mean body weights from mice treated with MAb (naked), MAb-Phor18 and recombinantly scFv-$C_H$3 naked antibody and scFv-$C_H$3-Phor18 conjugates during the study period of 64 days in SKOV-3 xenografted mice in comparison with saline injected mice.

The effect of antibody conjugated Phor18 injections and naked antibodies on the primary tumors (volume and tumor weights, FIGS. 2A, 2B, and 3) and body weight is illustrated in FIG. 4. FIGS. 2A and 2B show median tumor volumes during the course of the study and mean tumor weights on day 64 for each individual treatment group for saline controls, and mice treated with MAb (naked) (3 mg/kg), scFv-$C_H$3 (3 mg/kg), scFv-$C_H$3-GS-Phor18 (0.3 and 3 mg/kg), MAb-Phor18 (0.3 and 3 mg/kg).

Tumor volumes and weights decreased significantly in all animals treated with 3 mg/kg MAb-Phor18 chemically linked (p<0.04) or recombinantly produced scFv-$CH_3$-Phor18 conjugates (p<0.02). Naked MAb or scFv-$C_H$3 were not decreasing tumor volumes or tumor weights compared to saline controls at doses of 3 mg/kg (FIGS. 2A, 2B, and 3). Statistical analysis was conducted in Graphpad prizm 4 using the Wilcoxon signed rank test. Body weights were stable in all treatment groups and control animals (FIG. 4).

Example 6

This example describes in vitro cytotoxicity studies of recombinantly produced antibody to Her-2 receptor conjugated to lytic peptide, Phor18 (KFAKFAK KFAKFAK KFAK (SEQ ID NO.:4)) against ovarian cancer cells.

scFv-$C_H$2-$C_H$3-GS-Phor18 (one molecule of Phor18 joined to the antibody at the C-terminus by GS linker, consisting of $V_L$-G linker-$V_H$—$C_H$2-$C_H$3-G linker-$C_H$3-$C_H$2-$V_H$-G linker-$V_L$-GS-(Phor18). Cytotoxicity was compared to a naked antibody (scFv-$C_H$2-$C_H$3; antibody without a lytic peptide) in Her-2 receptor positive cells (SKOV-3, human ovarian cancer cells).

Materials: Recombinant DNA technique was used to synthesize anti-Her2 antibody as an scFv-$C_H$2-$C_H$3 antibody in *Escherichia coli*. The antibody (Olafsen T. et al Protein Engineering, Design & Selection 17, 315-323, 2004) was conjugated via a peptide linker to either Phor18 and analyzed for cytotoxicity in vitro. The plasmid was acquired through gene codon optimization. The gene was synthesized with a N-His tag sequence and the plasmid was subcloned into an *E. coli* bacteria expression vector pUC57. After expression optimization and evaluation the His-tag product was selected and 1 L of the bacteria expression product was purified in a one-step affinity purification. The amino acid sequence of for each construct is described in Table 3.

TABLE 3

Amino Acid sequence for the production of each recombinant antibody, (A) scFv-CH2-CH3; and antibody conjugate (B) scFv-CH2-CH3-GS-Phor18.

(SEQ ID NO.: 82)
A) scFv-CH2-CH3; and antibody conjugate:

| 10 | 20 | 30 | 40 | 50 | 60 |
|---|---|---|---|---|---|
| DIQMTQSPSS | LSASVGDRVT | ITCRASQDVN | TAVAWYQQKP | GKAPKLLIYS | ASFLYSGVPS |
| 70 | 80 | 90 | 100 | 110 | 120 |
| RFSGSRSGTD | FTLTISSLQP | EDFATYYCQQ | HYTTPPTFGQ | GTKVEIKGST | SGGGSGGGSG |
| 130 | 140 | 150 | 160 | 170 | 180 |
| GGGSSEVQLV | ESGGGLVQPG | GSLRLSCAAS | GFNIKDTYIH | WVRQAPGKGL | EWVARIYPTN |

TABLE 3-continued

Amino Acid sequence for the production of each recombinant antibody,
(A) scFv-CH2-CH3; and antibody conjugate (B) scFv-CH2-CH3-GS-Phor18.

```
         190        200        210        220        230        240
  GYTRYADSVK GRFTISADTS KNTAYLQMNS LRAEDTAVYY CSRWGGDGFY AMDYWGQGTL
         250        260        270        280        290        300
  VTVSSPCPAP ELLGGPSVFL FPPKPKDTLM ISRTPEVTCV VVDVSHEDPE VKFNWYVDGV
         310        320        330        340        350        360
  EVHNAKTKPR EEQYNSTYRV VSVLTVLHQD WLNGKEYKCK VSNKALPAPI EKTISKAKGQ
         370        380        390        400        410        420
  PREPQVYTLP PSRDELTKNQ VSLTCLVKGF YPSDIAVEWE SNGQPENNYK TTPPVLDSDG
         430        440        450        460        470        480
  SFFLYSKLTV DKSRWQQGNV FSCSVMHEAL HNHYTQKSLS LSPGKGSTSG GGSGGGSGGG
         490        500        510        520        530        540
  GSSGQPREPQ VYTLPPSRDE LTKNQVSLTC LVKGFYPSDI AVEWESNGQP ENNYKTTPPV
         550        560        570        580        590        600
  LDSDGSFFLY SKLTVDKSRW QQGNVFSCSV MHEALHNHYT QKSLSLSPGK PCPAPELLGG
         610        620        630        640        650        660
  PSVFLFPPKP KDTLMISRTP EVTCVVVDVS HEDPEVKFNW YVDGVEVHNA KTKPREEQYN
         670        680        690        700        710        720
  STYRVVSVLT VLHQDWLNGK EYKCKVSNKA LPAPIEKTIS KAKEVQLVES GGGLVQPGGS
         730        740        750        760        770        780
  LRLSCAASGF NIKDTYIHWV RQAPGKGLEW VARIYPTNGY TRYADSVKGR FTISADTSKN
         790        800        810        820        830        840
  TAYLQMNSLR AEDTAVYYCS RWGGDGFYAM DYWGQGTLVT VSSGSTSGGG SGGGSGGGGS
         850        860        870        880        890        900
  SDIQMTQSPS SLSASVGDRV TITCRASQDV NTAVAWYQQK PGKAPKLLIY SASFLYSGVP
         910        920        930        940
  SRFSGSRSGT DFTLTISSLQ PEDFATYYCQ QHYTTPPTFG QGTKVEIK
```

(SEQ ID NO.: 83)
B) scFv-CH2-CH3-GS-Phor18:

```
          10         20         30         40         50         60
  DIQMTQSPSS LSASVGDRVT ITCRASQDVN TAVAWYQQKP GKAPKLLIYS ASFLYSGVPS
          70         80         90        100        110        120
  RFSGSRSGTD FTLTISSLQP EDFATYYCQQ HYTTPPTFGQ GTKVEIKGST SGGGSGGGSG
         130        140        150        160        170        180
  GGGSSEVQLV ESGGGLVQPG GSLRLSCAAS GFNIKDTYIH WVRQAPGKGL EWVARIYPTN
         190        200        210        220        230        240
  GYTRYADSVK GRFTISADTS KNTAYLQMNS LRAEDTAVYY CSRWGGDGFY AMDYWGQGTL
         250        260        270        280        290        300
  VTVSSPCPAP ELLGGPSVFL FPPKPKDTLM ISRTPEVTCV VVDVSHEDPE VKFNWYVDGV
         310        320        330        340        350        360
  EVHNAKTKPR EEQYNSTYRV VSVLTVLHQD WLNGKEYKCK VSNKALPAPI EKTISKAKGQ
         370        380        390        400        410        420
  PREPQVYTLP PSRDELTKNQ VSLTCLVKGF YPSDIAVEWE SNGQPENNYK TTPPVLDSDG
         430        440        450        460        470        480
  SFFLYSKLTV DKSRWQQGNV FSCSVMHEAL HNHYTQKSLS LSPGKGSTSG GGSGGGSGGG
         490        500        510        520        530        540
  GSSGQPREPQ VYTLPPSRDE LTKNQVSLTC LVKGFYPSDI AVEWESNGQP ENNYKTTPPV
         550        560        570        580        590        600
  LDSDGSFFLY SKLTVDKSRW QQGNVFSCSV MHEALHNHYT QKSLSLSPGK PCPAPELLGG
         610        620        630        640        650        660
  PSVFLFPPKP KDTLMISRTP EVTCVVVDVS HEDPEVKFNW YVDGVEVHNA KTKPREEQYN
         670        680        690        700        710        720
  STYRVVSVLT VLHQDWLNGK EYKCKVSNKA LPAPIEKTIS KAKEVQLVES GGGLVQPGGS
         730        740        750        760        770        780
  LRLSCAASGF NIKDTYIHWV RQAPGKGLEW VARIYPTNGY TRYADSVKGR FTISADTSKN
         790        800        810        820        830        840
  TAYLQMNSLR AEDTAVYYCS RWGGDGFYAM DYWGQGTLVT VSSGSTSGGG SGGGSGGGS
         850        860        870        880        890        900
  SDIQMTQSPS SLSASVGDRV TITCRASQDV NTAVAWYQQK PGKAPKLLIY SASFLYSGVP
         910        920        930        940        950        960
  SRFSGSRSGT DFTLTISSLQ PEDFATYYCQ QHYTTPPTFG QGTKVEIKGS KFAKFAKKFA
  KFAKKFAK
```

In vitro cytotoxicity studies were performed to determine cytotoxicity of the recombinant antibody preparations (scFv-$C_H$2-$C_H$3, scFv-$C_H$3, and scFv-$C_H$2-$C_H$3-GS-Phor18, scFv-$C_H$3-GS-Phor18). Her-2 receptor positive SKOV-3 cells were prepared in 96 well plates using 2,000 cells/well and were allowed to attach for 48 hours. The Her2-antibody-Phor18 conjugates (scFv-$C_H$2-$C_H$3-GS-Phor18, scFv-$C_H$3 GS-Phor18) or the naked antibodies (scFv-$C_H$2-$C_H$3, scFv-$C_H$3) in Tris/HCL-buffer were diluted with saline and added to cells at increasing concentrations of 0, 0.0012, 0.012, 0.12, 1.2, 6.0, 12.0, 120, 360 and 720 nM. Incubations were conducted for 48 h at 37° C. Cell viability was determined using Cell Titer Glo luminescent cell viability assay (Promega). Controls contained USP saline or 0.1% TritonX-100™ as reference for 0 and 100% cell death, respectively. All data were processed and analyzed using Graph Pad Prizm 4™ software (Graph Pad Prizm, Inc).

The Her2 antibody (scFv-$C_H$2-$C_H$3, scFv-$C_H$3) conjugated to the Phor18 resulted in $IC_{50}$ values of 53.7±0.63 nM for scFv-$C_H$3-Phor18 and 56.7±0.92 nM for scFv-CH$_2$-

CH₃-Fv-Phor18. The "naked" (unconjugated) antibodies, scFv-C$_H$2-C$_H$3, scFv-C$_H$3, were not cytotoxic. In vitro recombinantly Phor18 conjugates show similar toxicity to SKOV-3 cells.

Example 7

This example includes a description of the construction and expression of whole anti-Her2-IgG1-Phor18 antibody conjugates with defined location lytic domain (Phor18), and specified numbers of 2, 4 and 6 Phor18 lytic domains per antibody in a mammalian expression system. These conjugates are also referred to as antibody-drug conjugates (ADC).

Recombinant expression of whole IgG1 antibody-Phor18 (KFAKFAKKFAKFAKKFAK (SEQ ID NO.:4)) conjugates in a mammalian system (CHO cells) was conducted using two different secretion signal sequences: a proprietary secretion signal sequence for antibody heavy and light chains, and human IgG kappa-light chain secretion signal. The expressed anti-Her2 IgG1 antibody (humanized variable light and heavy domains regions to Her-2 receptor) and the various antibody-Phor18 conjugates with stoichiometric ratios of Phor18: AB of 2, 4 and 6 were characterized using SDS PAGE, Western blot analyses, and surface Plasmon resonance (selected ADCs).

Yield, purity and cytotoxicity of recombinantly produced antibodies (as a full IgG1 antibody) with Heavy (H) or Light (L) chain C-terminal- or N-terminal-Phor18 conjugation was analyzed. Two, 4 and 6 molecules of lytic domains (Phor18) conjugated to whole antibody molecule were expressed. The amino acid sequences of the "unconjugated" anti-Her2 antibody, anti-Her2 antibody heavy (H) and light (L) chains are shown in Table 4.

TABLE 4

Anti-Her2/neu antibody amino acid sequence from Drugbank.ca DB00072.
There was one additional amino acid in the C$_H$1 domain of the Anti-Her2
antibody in comparison to human IgG1 (underlined).

(SEQ ID NO.: 84)
Anti-HER2/neu Light chain (naked L1):

```
        10         20         30         40         50         60
DIQMTQSPSS LSASVGDRVT ITCRASQDVN TAVAWYQQKP GKAPKLLIYS ASFLYSGVPS
        70         80         90        100        110        120
RFSGSRSGTD FTLTISSLQP EDFATYYCQQ HYTTPPTFGQ GTKVEIKRTV AAPSVFIFPP
       130        140        150        160        170        180
SDEQLKSGTA SVVCLLNNFY PREAKVQWKV DNALQSGNSQ ESVTEQDSKD STYSLSSTLT
       190        200        210
LSKADYEKHK VYACEVTHQG LSSPVTKSFN RGEC
```

(SEQ ID NO.: 85)
Anti-HER2/neu Heavy chain 2 (naked H1):

```
        10         20         30         40         50         60
EVQLVESGGG LVQPGGSLRL SCAASGFNIK DTYIHWVRQA PGKGLEWVAR IYPTNGYTRY
        70         80         90        100        110        120
ADSVKGRFTI SADTSKNTAY LQMNSLRAED TAVYYCSRWG GDGFYAMDYW GQGTLVTVSS
       130        140        150        160        170        180
ASTKGPSVFP LAPSSKSTSG GTAALGCLVK DYFPEPVTVS WNSGALTSGV HTFPAVLQSS
       190        200        210        220        230        240
GLYSLSSVVT VPSSSLGTQT YICNVNHKPS NTKVDKKVEP PKSCDKTHTC PPCPAPELLG
       250        260        270        280        290        300
GPSVFLFPPK PKDTLMISRT PEVTCVVVDV SHEDPEVKFN WYVDGVEVHN AKTKPREEQY
       310        320        330        340        350        360
NSTYRVVSVL TVLHQDWLNG KEYKCKVSNK ALPAPIEKTI SKAKGQPREP QVYTLPPSRD
       370        380        390        400        410        420
ELTKNQVSLT CLVKGFYPSD IAVEWESNGQ PENNYKTTPP VLDSDGSFFL YSKLTVDKSR
       430        440        450
WQQGNVFSCS VMHEALHNHY TQKSLSLSPG K
```

The amino acid sequences of antibody-lytic peptide conjugate heavy (H) and light (L) chains are shown in Table 5. Gene synthesis was conducted at Genewiz, Inc (South Plainfield, N.J.) using preferred codon usage for Chinese Hamster Ovary cells. The transcripts were ligated into the pUC57 bacterial plasmid.

TABLE 5

Amino acid sequences of lytic-peptide (Phor18, KFAKFAKKFAKFAKKFAK
(SEQ ID NO.: 4))-antibody heavy and light chain conjugates
Phor18-V$_L$ Light Chain (L2): (SEQ ID NO.: 86)

```
        10         20         30         40         50         60
KFAKFAKKFA KFAKKFAKGS DIQMTQSPSS LSASVGDRVT ITCRASQDVN TAVAWYQQKP
        70         80         90        100        110        120
GKAPKLLIYS ASFLYSGVPS RFSGSRSGTD FTLTISSLQP EDFATYYCQQ HYTTPPTFGQ
```

TABLE 5-continued

C_L-Phor18 Light Chain (L3): (SEQ ID NO.: 87)

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRTV AAPSVFIFPP 130        140        150        160        170        180
SDEQLKSGTA SVVCLLNNFY PREAKVQWKV DNALQSGNSQ ESVTEQDSKD STYSLSSTLT 190        200        210        220        230
LSKADYEKHK VYACEVTHQG LSSPVTKSFN RGECGSKFAK FAKKFAKFAK KFAKA
```

Phor18-V_L-C_L-Phor18 Light Chain (L4): (SEQ ID NO.: 88)

```
         10         20         30         40         50         60
KFAKFAKKFA KFAKKFAKGS DIQMTQSPSS LSASVGDRVT ITCRASQDVN TAVAWYQQKP 70         80         90        100        110        120
GKAPKLLIYS ASFLYSGVPS RFSGSRSGTD FTLTISSLQP EDFATYYCQQ HYTTPPTFGQ 130        140        150        160        170        180
GTKVEIKRTV AAPSVFIFPP SDEQLKSGTA SVVCLLNNFY PREAKVQWKV DNALQSGNSQ 190        200        210        220        230        240
ESVTEQDSKD STYSLSSTLT LSKADYEKHK VYACEVTHQG LSSPVTKSFN RGECGSKFAK

250
FAKKFAKFAK KFAKA
```

Phor18-V_H Heavy Chain (H2): (SEQ ID NO.: 89)

```
         10         20         30         40         50         60
KFAKFAKKFA KFAKKFAKGS EVQLVESGGG LVQPGGSLRL SCAASGFNIK DTYIHWVRQA 70         80         90        100        110        120
PGKGLEWVAR IYPTNGYTRY ADSVKGRFTI SADTSKNTAY LQMNSLRAED TAVYYCSRWG 130        140        150        160        170        180
GDGFYAMDYW GQGTLVTVSS ASTKGPSVFP LAPSSKSTSG GTAALGCLVK DYFPEPVTVS 190        200        210        220        230        240
WNSGALTSGV HTFPAVLQSS GLYSLSSVVT VPSSSLGTQT YICNVNHKPS NTKVDKKVEP 250        260        270        280        290        300
PKSCDKTHTC PPCPAPELLG GPSVFLFPPK PKDTLMISRT PEVTCVVVDV SHEDPEVKFN 310        320        330        340        350        360
WYVDGVEVHN AKTKPREEQY NSTYRVVSVL TVLHQDWLNG KEYKCKVSNK ALPAPIEKTI 370        380        390        400        410        420
SKAKGQPREP QVYTLPPSRD ELTKNQVSLT CLVKGFYPSD IAVEWESNGQ PENNYKTTPP 430        440        450        460        470
VLDSDGSFFL YSKLTVDKSR WQQGNVFSCS VMHEALHNHY TQKSLSLSPG K
```

C_H3-Phor18 Heavy Chain (H3): (SEQ ID NO.: 90)

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKKVEP PKSCDKTHTC PPCPAPELLG 250        260        270        280        290        300
GPSVFLFPPK PKDTLMISRT PEVTCVVVDV SHEDPEVKFN WYVDGVEVHN AKTKPREEQY 310        320        330        340        350        360
NSTYRVVSVL TVLHQDWLNG KEYKCKVSNK ALPAPIEKTI SKAKGQPREP QVYTLPPSRD
```

TABLE 5-continued

```
       370        380        390        400        410        420
ELTKNQVSLT CLVKGFYPSD IAVEWESNGQ PENNYKTTPP VLDSDGSFFL YSKLTVDKSR 430        440        450        460        470
WQQGNVFSCS VMHEALHNHY TQKSLSLSPG KGSKFAKFAK KFAKFAKKFA KA

Phor18-V_H-C_H3-Phor18 Heavy Chain (H4): (SEQ ID NO.: 91)
        10         20         30         40         50         60
KFAKFAKKFA KFAKKFAKGS EVQLVESGGG LVQPGGSLRL SCAASGFNIK DTYIHWVRQA 70         80         90        100        110        120
PGKGLEWVAR IYPTNGYTRY ADSVKGRFTI SADTSKNTAY LQMNSLRAED TAVYYCSRWG 130        140        150        160        170        180
GDGFYAMDYW GQGTLVTVSS ASTKGPSVFP LAPSSKSTSG GTAALGCLVK DYFPEPVTVS 190        200        210        220        230        240
WNSGALTSGV HTFPAVLQSS GLYSLSSVVT VPSSSLGTQT YICNVNHKPS NTKVDKKVEP 250        260        270        280        290        300
PKSCDKTHTC PPCPAPELLG GPSVFLFPPK PKDTLMISRT PEVTCVVVDV SHEDPEVKFN 310        320        330        340        350        360
WYVDGVEVHN AKTKPREEQY NSTYRVVSVL TVLHQDWLNG KEYKCKVSNK ALPAPIEKTI 370        380        390        400        410        420
SKAKGQPREP QVYTLPPSRD ELTKNQVSLT CLVKGFYPSD IAVEWESNGQ PENNYKTTPP 430        440        450        460        470        480
VLDSDGSFFL YSKLTVDKSR WQQGNVFSCS VMHEALHNHY TQKSLSLSPG KGSKFAKFAK

490
KFAKFAKKFA KA
```

Figure 5:
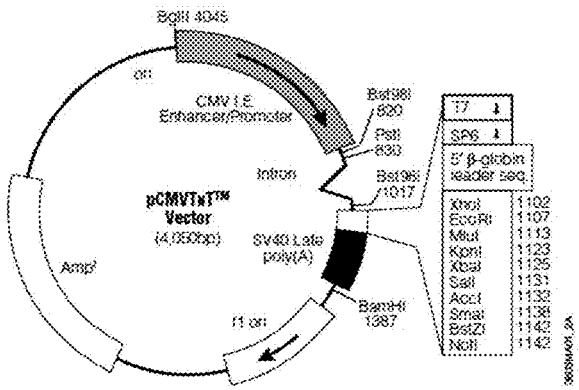
FIG. 5 shows the pCMVTnT expression vector (Promega) used for ADC heavy (H) and light (L) chain expression.

Heavy (H) and light (L) chain transcripts were synthesized out of Genewiz pUC57 plasmids using PCR with primers containing 5' EcoR1 and 3' Xba1 restriction sites for directional ligation into the multiple cloning site of the pCMVTnT mammalian expression plasmid (FIG. 5, Promega, Madison, Wis., L5620, lot 14524919). Each transcript included a Kozak consensus sequence and a secretion signal at the 5' end.

Anti-Her2/neu antibody was produced by Lonza Inc. (Cambridge, UK). A Chinese Hamster Ovary (CHO) cell mammalian expression system was used to produce naked (i.e., no lytic domain) anti-Her2/neu IgG1, and ADCs having a lytic domain (Phor18) at defined locations (N- or C-terminal) and in ratios of 2, 4 and 6 lytic domains per whole antibody.

In brief, Free-style CHO Suspension Cell Expression System (Invitrogen Life Sciences, Carlsbad, Calif., cat #K9000-20) was used to grow FS-CHO cells (according to manufacturer's directions) in FreeStyle CHO expression medium supplemented with 8 mM glutamax and 5 ml/L penicillin/streptomycin. Cells were thawed into growth medium without penicillin/streptomycin that was pre-warmed to 37° C. and equilibrated in an 8% $CO_2$ atmosphere and grown in 30 ml in shaker flasks at 125-135 rpm. Cell density was kept at or below $1 \times 10^6$ cells/ml to avoid clumping.

FS-CHO cells were transfected according to the Invitrogen protocol. FS CHO cells were expanded for 7 or more days after thawing. Cells were doubling every 24 h. The day before transfection, clumps were removed and cells were pelleted and resuspended in P/S-free medium at $5 \times 10^5$/ml. On the day of transfection, cells were adjusted to $9 \times 10^5$/ml if necessary and viability was close to 99%. Each 500 ml spinner flask (VWR, cat #PBV125) of 180 ml cells was transfected with 180 µg of total plasmid DNA mixed with 180 µl of FSMax transfection reagent (Invitrogen, cat #16447-100). Cells were swirled rapidly while adding DNA mixture slowly. Ratios of H:L chains analyzed were 3:2, 1:1, and 2:3.

ADC secreted into the cell medium, harvested on day 4 to day 6 after transfection, was purified using protein A columns Approximately 0.25 ml of protein A resin (Genscript L00210, capacity >20 mg IgG per ml resin) was used to isolate secreted ADCs from the FS CHO medium using the Genscript product protocol and buffer descriptions provided. ADC was eluted once with 0.5 ml low pH elution buffer of 0.1 M glycine pH 2.5 and eluate was reapplied to the column and collected a second time. pH was adjusted to 6.5 with 1M Tris pH 8.

To confirm the presence of protein, SDS-PAGE (4-15% TGX gels, Bio-Rad Labs, Hercules, Calif., cat #456-1084) analyses was used. ADCs separated on gels were silver-stained (Sigma-Aldrich, St Louis, Mo., Prot Sil1 kit). The anti-Phor18 rabbit polyclonal was from Covance (Denver, Pa., cat #338983), and for detection an anti-rabbit-HRP was used (cat #111-035-046, Jackson ImmunoResearch, Philadelphia, Pa.). Detection of ADCs was conducted with an anti-human IgG from Jackson ImmunoResearch (cat #109-035-088). The presence of the (L) light chain was confirmed on reduced ADCs with HRP-mouse anti-human kappa (Invitrogen, cat #053920).

To formulate the ADCs, DPBS salts in a 20× solution and polysorbate 20 (PS20) were added to the protein A elution buffer (Tris-glycine, 50 mM-100 mM) at the following final concentrations to stabilize for storage at 4° C. and during freeze-thaw cycles: $CaCl_2$ 100 mg/L, $MgCl_2$ (.6H2O) 100 mg/L, KCl 200 mg/L, NaCl 8 g/L, and 0.09 mg/ml PS20. To determine protein concentration, for some batches, the OD280 for each sample was determined on a spectrophotometer. ADC concentration [mg/ml] was calculated by using an extinction coefficient of 1.4 (based on amino acid sequence). For greater accuracy, ADC concentration was determined by anti-human IgG Elisa assay (Genway, 40-374-130037).

The first Anti-Her2/neu antibody-based ADCs were produced under the regulation of signal sequences and expression analysis was conducted. ADCs produced were: H1L1 (naked), H2L2 (Phor18-$V_L$-Phor18-$V_H$-IgG1), H2L1 (Phor18-$V_H$-IgG1), H1L2 (Phor18-$V_L$-IgG1), H1L3 ($C_L$-Phor18-IgG1) H3L1 ($C_H$3-Phor18-IgG1), H3L3 ($C_L$-Phor18-$C_H$3-Phor18-IgG1), H3L4 (Phor18-$V_L$-$C_L$-Phor18-$C_H$3-Phor18-IgG1), and H4L3 (Phor18-$V_H$-$C_L$-Phor18-$C_H$3-Phor18-IgG1). Based on spectrophotometric ($OD_{280}$) analysis, average yields for ADCs were H2L2=0.12 mg/L and H1L3=0.8 mg/L.

Table 6 shows the individual ADC descriptions, abbreviations, and the number and locations of lytic domains (Phor18).

chiometries of lytic domain (Phor18):AB of 2, 4 and 6, and lytic domain (Phor18) in pre-determined locations.

Example 8

This example includes a description of the potency and specificity of the eight ADCs.

ADCs with anti-Her-2 receptor (IgG1) conjugated to 2, 4 or 6 Phor18 molecules at the N- or C-terminus were analyzed in vitro using a Her2/neu positive ovarian cancer cell line (SKOV-3 human ovarian cancer cells) and compared to "naked" antibody. Her-2 receptor negative, ER negative, PR negative human breast cancer cells (MDA-MB-231) served as control.

In brief, the SKOV-3 (Her2/neu positive, passage number pU51) and MDA-MB-231 (Her2/neu negative, ER negative, PR negative, pu 14) cells were seeded at a density of 2,000

TABLE 6

ADC descriptions and abbreviations

| Name of ADC | ADC Abbreviation (H L) | Phor18 location | Number of Phor18 lytic sequences/Antibody |
|---|---|---|---|
| IgG1 | H1 L1 | None ('Naked') | 0 |
| Phor18-$V_L$-IgG1 | H1 L2 | N-termini light chains ($V_L$) | 2 |
| $C_L$-Phor18-IgG1 | H1 L3 | C-termini light chains ($C_L$) | 2 |
| Phor18-$V_L$-IgG1-$C_L$-Phor18 | H1L 4 | N-termini and C-termini light chains ($V_L$, $C_L$) | 4 |
| Phor18-$V_L$-Phor18-$V_H$-IgG1 | H2 L2 | N-termini heavy and light chains ($V_H$, $V_L$) | 4 |
| Phor18-$V_H$-IgG1 | H2 L1 | N-termini heavy chains ($V_H$) | 2 |
| Phor18-$V_H$-$C_L$-Phor18-IgG1 | H2 L3 | N-termini heavy chains and C-termini light chains ($V_H$, $C_L$) | 4 |
| $C_H$3-Phor18-IgG1 | H3 L1 | C-termini heavy chain ($C_H$3) | 2 |
| Phor18-$V_L$-$C_H$3-Phor18-IgG1 | H3 L2 | N-termini light chains, C-termini heavy chains ($V_L$, $C_H$3) | 4 |
| $C_L$-Phor18-$C_H$3-Phor18-IgG1 | H3 L3 | C-termini light and heavy chains ($C_L$, $C_H$3) | 4 |
| Phor18-$V_L$-$C_L$-Phor18-$C_H$3-Phor18-IgG1 | H3 L4 | N-termini light chains and C-termini both light and heavy chains ($V_L$, $C_L$, $C_H$3) | 6 |
| Phor18-$V_H$-$C_L$-Phor18-$C_H$3-Phor18-IgG1 | H4 L3 | N-termini heavy chains; C-termini both heavy and light chains ($V_H$, $C_L$, $C_H$3) | 6 |
| Phor18-$V_H$-$C_H$3-Phor18-IgG1 | H4 L1 | N- and C-termini heavy chains ($V_H$, $C_H$3) | 4 |
| Phor18-$V_H$-Phor18$V_L$-$C_H$3-Phor18-IgG1 | H4L2 | N-termini heavy and light chains, C-termini heavy chains ($V_H$, $V_L$, $C_H$3) | 6 |

Figure 6:
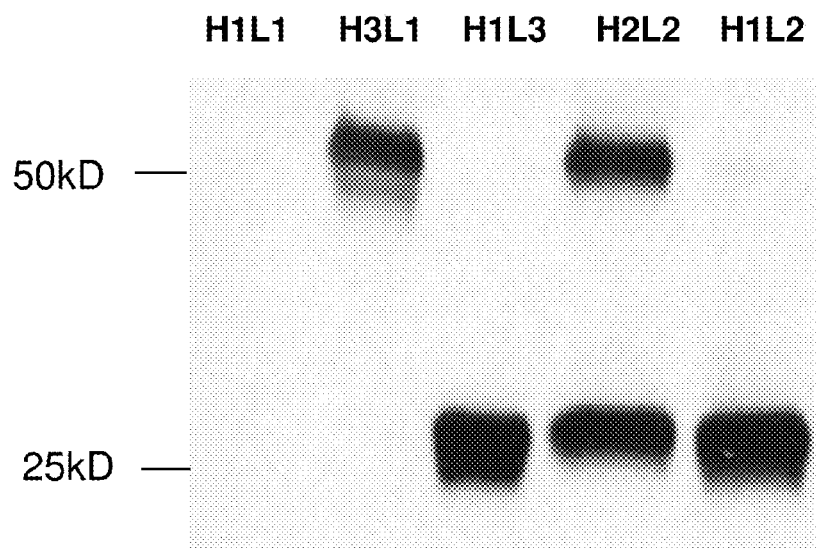
FIG. 6 shows an anti-Phor18 immunoblot of ADCs produced: H1L1 (IgG1), H3L1 ($C_H$3-Phor18-IgG1), H1L3 ($C_L$-Phor18-IgG1), H2L2 (Phor18-$V_L$-Phor18-$V_H$-IgG1) and H1L2 (Phor18-$V_L$-Phor18-IgG).

The quality of ADCs was analyzed on immunoblots of reduced antibodies, allowing heavy and light chains to be visualized. The presence of Phor18 was confirmed on the light (L) chain of H1L2 Phor18-$V_L$-IgG1 (H1L2), on the light (L) chain of H1L3 ($C_L$-Phor18-IgG1) and on the heavy (H) chain of H3L1 ($C_H$3-Phor18-IgG1), which has Phor18 only on the C-terminus of the light chain (FIG. 6).

Figure 7A:
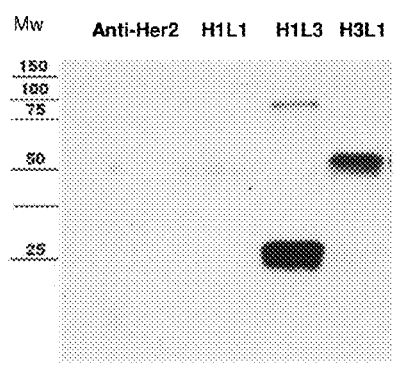
FIGS. 7A and 7B show a quality analysis of ADCs produced: anti Her2-antibody, H1L1 (naked), H1L3 ($C_L$-Phor18-IgG1) and H3L1 ($C_H$3-Phor18-IgG1) using A) anti-Phor18 probe; and B) anti-kappa light (L) chain probe, of reduced proteins.
Figure 7B:
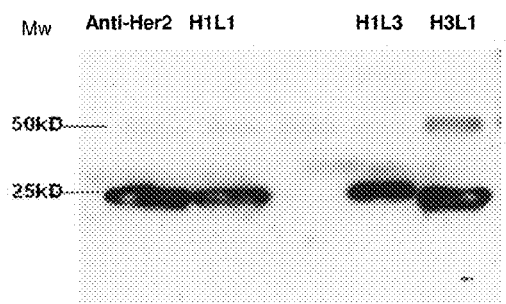

Presence of Phor18 on heavy and light chain was confirmed in westernblot analysis (FIG. 7A) for the heavy chains with Phor18 conjugation. H1L1 and anti-Her2/neu antibody, the naked antibody, served as negative control and did not show a band probing for Phor18. Presence of light chains in recombinantly produced antibodies and antibody conjugates were confirmed in western blot analysis (kappa light chains) for H1L1 (IgG1), H3L1 ($C_H$3-Phor18-IgG1), H1L3 (IgG1-$C_L$-Phor18) and H2L2 (Phor18-$V_L$-Phor18-$V_H$-IgG1) had both heavy and light chains based on IgG western blot analysis, kappa-light chain western blot analysis (FIG. 7B) and anti-Phor18 immuno blots (FIGS. 6 and 7A).

The data indicate that whole antibody-lytic domain (Phor18) conjugates can be produced recombinantly in a mammalian expression system having pre-determined stoicells per well in opaque plates in heat inactivated full medium using cell dissociation buffer. After 2 days, cells were replenished with fresh media (75 µl) and incubated with 25 µl of a 4× serial dilution of each ADC and naked antibody prepared in cell culture media were added.

Cells incubated for 4 hours were assayed for membrane integrity using a luminometric assay kit (Promega, Cytotox Glo G9292 lot #317872). Cell viability was determined was determined after 24, 48 and 72 hours using a luminescent assay kit (Promega, W, Cell Titer Glo, G 7572, lot 31511202). Controls for 100% cell viability (culture media) and 100% cell death (0.1% Triton ×100) were incubated under the same conditions.

Data were processed and analyzed to obtain $IC_{50}$ values using Graph Pad Prizm version 5.00 for Windows, GraphPad Software, San Diego Calif. USA, wwwdotgraphpaddotcom (Graph Pad Prizm, Inc). Statistical analysis for significance was determined by a two-tailed Student's T-test. Each test was conducted using double plates of 2-3 wells each to achieve an N of 4-6 data points per time point.

The concentration of each ADC was determined spectrophotometrically ($OD_{280}$) and in some cases by IgG determination using ELISA assays. Each ADC and naked antibody were prepared from frozen stocks to produce as highest concentration 800 nM or lower depending on the initial concentration.

Serial dilutions were prepared in cell culture media to achieve a final concentration per well of 0, 0.001, 0.01, 0.1, 1, 10, 100 and 200 nM, corresponding to 0.00015, 0.0015, 0.015, 0.15, 1.5, 15, 30 and 60 µg/ml for concentrations determined spectrophotometrically. For studies that had IgG contents the highest possible concentration was tested followed by a 1:1 and 1:10 dilutions for each ADC.

Various time points were included to determine the activity of the recombinantly expressed ADCs. The earliest indication of activity was measured as effect on membrane integration after 4 hours of ADC exposure in Her2/neu positive SKOV-3 cells.

N-terminal conjugated ADC with Phor18 on the variable light chain (Phor18-$V_L$-IgG1) disintegrated the target cell membrane ($IC_{50}$=187.9±12.8 nM). C-terminal conjugated ADC ($C_H$3-Phor18-IgG1) with one Phor18 molecule had no detectable membrane activity. Naked anti-Her2-IgG1 also did not detectably affect membrane integrity.

Table 7 summarizes the results of this activity study. ADCs showed high specificity for the target cell line SKOV-3 compared to the negative control (Her2/neu negative) MDA-MB-231.

Maximal toxicity levels were determined after 48 hours. The $IC_{50}$ values [nM] were in the low nanomolar range for N-terminus conjugated ADC Phor18-$V_H$-IgG1 (13.02±2.3 nM, 2 Phor18/AB, N-terminus) and H2L1 Phor18-$V_L$-IgG1 (6.9±3.4 nM, 2 Phor18/AB, N-terminus), compared to C-terminus conjugated ADC: $C_H$3-Phor18-IgG1 (27.4±5.1 nM, 2 Phor18/AB, H3L1, C-terminus) having 2 Phor18 molecules per antibody.

N-terminal conjugated ADCs with 4 molecules Phor18 on the N-terminus had $IC_{50}$ values of 0.54±0.2 nM (Phor18-$V_L$-Phor18-$V_H$-IgG1, 4 Phor18/AB, N-terminus, H2L2) compared to the C-terminus counterpart $C_L$-Phor18-$C_H$3-Phor18-IgG1 (36.3±10.6 nM, 4 Phor18/AB, H3L3, C-terminus, p<0.001). Lytic domain conjugation at the N-terminus was 70 fold more potent than conjugation at the C-terminus.

These data indicate that ADCs having N-terminal Phor18 conjugation were superior to C-terminal Phor18 conjugation for stoichiometric ratios of 2 and 4 molecules per antibody.

Increase of Phor18 conjugation from 2 to 4 molecules per antibody resulted in a 12 fold more potent ADC with conjugation at the N-terminus, but not at the C-terminus. ADCs conjugated with 6 Phor18 molecules per antibody showed about the same potency with IC50 values of 1.1±0.2 nM for Phor18-$V_L$-$C_L$-Phor18-$C_H$3-Phor18-IgG1 (6 Phor18, N and C terminus, H3L4), and 1.1±0.4 nM for Phor18-$V_H$-$C_L$-Phor18-$C_H$3-Phor18-IgG1 (6 Phor18, H4L3).

Naked anti-Her2-IgG1 showed substantially less cell killing activity in SKOV-3 target cells after 48 hours ($IC_{50}$ values of 234.6±49 nM). None of the ADCs killed target negative MDA-MB-231 cells under the same conditions.

These data show that lytic domain (Phor18)-conjugated anti-Her-2 receptor antibodies (ADCs) are highly specific to Her2/neu expressing cells. Absence of the target receptor leaves cells unharmed.

The potency of lytic domain (Phor18) conjugated antibodies (ADCs) were dependent on the location of conjugation and the number of lytic domain (Phor18) molecules: the highest potency against target cells were observed for the N-terminal lytic domain (Phor18)-antibody conjugates with 2 and 4 lytic domain (Phor18) molecules per antibody. The N-terminal conjugation exhibited a 70 fold activity increase compared to the C-terminal lytic domain (Phor18)-antibody conjugation. N-terminal Phor18 conjugated ADCs were more potent compared to C-terminal Phor18 conjugates having both 2 and 4 Phor18 molecules per antibody. In addition, N-terminal conjugation showed measurable effects on reducing membrane integrity of the target cells SKOV-3.

Increasing the number of conjugated lytic domain (Phor18) molecules to 6 per antibody had maximal activities in the low nanomolar range. Phor18 conjugated ADCs were up to 433 fold more potent compared to the naked antibody.

TABLE 7

In vitro activity of ADCs and naked antibody produced in CHO cells

| ADC and Naked antibody | ADC-ID | Terminus of Conjugation of Phor18 to AB | In vitro activity after 48 hours | |
|---|---|---|---|---|
| | | | $IC_{50}$ [nM] SKOV-3 Her2/neu (+) | $IC_{50}$ [nM] MDA-MB-231 Her2/neu (−) |
| IgG1 | H1L1 | None | 234.6 ± 49 | Not toxic |
| Phor18-$V_L$-IgG1 | H1L2 | N-termini, L chains | 6.9 ± 3.4 | Not toxic |
| Phor18-$V_H$-IgG1 | H2L1 | N-termini, H chains | 13.02 ± 2.3 | Not toxic |
| Phor18-$V_L$-Phor18-$V_H$-IgG1 | H2L2 | N-termini, H and L chains | 0.54 ± 0.2 | Not toxic |
| $C_H$3-Phor18-IgG1 | H3L1 | C termini H chains | 27.4 ± 5.1 | Not toxic |
| $C_L$-Phor18-$C_H$3-Phor18-IgG1 | H3L3 | C-termini H and L chains | 36.3 ± 10.6 | Not toxic |
| Phor18-$V_L$-$C_L$-Phor18-$C_H$3-Phor18-IgG1 | H3L4 | N-termini L chains and C chains H chains | 1.1 ± 0.2 | Not toxic |
| Phor18-$V_H$-$C_L$-Phor18-$C_H$3-Phor18-IgG1 | H4L3 | N-termini H chains and C-termini L chains | 1.1 ± 0.4 | Not toxic |

Example 9

This example includes a description of optimization of ADC expression using IgG kappa signal sequences. An alternate secretion signal peptide was evaluated for improvement of quality and expression levels of ADCs. To produce human IgG kappa signal sequence for expression of heavy and light chains with N-terminal Phor18, new gene synthesis for the L2 (Phor18-V$_L$), L4 (Phor18-V$_L$-C$_L$-Phor18), and H2 (Phor18-V$_H$) antibody heavy (H) and light (L) chain transcripts with the new signal peptide at the 5' end was conducted by Genewiz, Inc. The amino acid sequence of the human IgG kappa signal peptide is MQTDTLLLWVLLL-WVPGSTGA (SEQ. ID. NO. 154) (Felgenhauer M, et al., *Nucleic Acids Res.*, 18:4927 (1990)).

The Phor18-V$_L$-IgG1 and Phor18-V$_L$-Phor18-V$_H$-IgG1 ADCs produced with the igk secretion signal had a strong signal for light chains on immunoblots of reduced proteins probed with anti-C$_L$ kappa and anti-Phor18. Because the IgG kappa signal peptide induced higher expression and quality, the igk transcripts were selected for ADC production. Production levels of ADCs expressed in CHO cells with the IgG kappa signal sequence, based on Elisa quantitation, were: H1L1=0.8 mg/L, C$_L$-Phor18-IgG1=0.8 mg/L, Phor18-V$_L$-IgG1=0.3 mg/L, and Phor18-V$_L$-Phor18-V$_H$-IgG1=0.15 mg/L. Several additional batches of N-terminal Phor18 ADCs with IgG kappa signal sequence were produced and analyzed for expression level, quality and efficacy in vitro with comparable expression levels.

Figure 8:
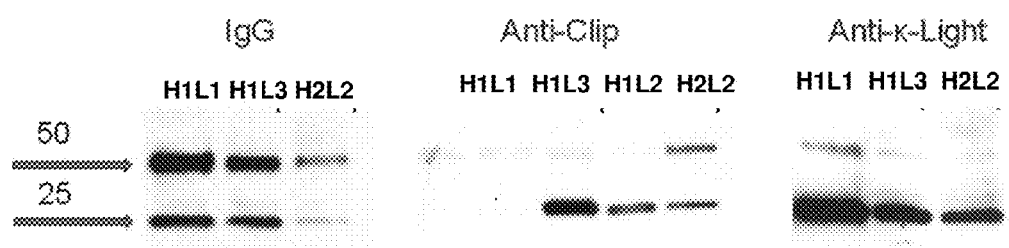
FIG. 8 shows anti IgG and anti-Phor18 Immunoblot of ADCs produced: H1L3 ($C_L$-Phor18-IgG1), H1L2 (Phor18-$V_L$-Phor18-IgG1 and H2L2 (Phor18-$V_L$-Phor18-$V_H$-IgG1).

Phor18-V$_L$-IgG1 (H1L2), IgG1-C$_L$-Phor18-IgG1 (H1L3) and Phor18-V$_L$-Phor18-V$_H$-IgG1 (H2L2). These N-terminal and C-terminal conjugated Phor18 ADCs were analyzed for quality and purity by anti-Phor18 immunoblots, IgG and kappa light chain western blot analysis (FIG. 8). Phor18 presence was confirmed on the heavy and light chains through their molecular weights (FIG. 8).

Immunoblot analysis of ADCs showed that the Phor18-V$_L$-IgG1, C$_L$-Phor18-IgG1 and Phor18-V$_L$-Phor18-V$_H$-IgG1 ADCs produced with the igk secretion signal had heavy and light chains present with Phor18. Expression levels were lower than 0.5 mg/L for both Phor18-V$_L$-IgG1 and Phor18-V$_L$-Phor18-V$_H$-IgG1.

Example 10

This example describes studies to characterize the binding kintetics of Her2/neu protein to Phor18-V$_L$-IgG1 and Phor18-V$_L$-Phor18-V$_H$-IgG1 as compared to the binding of Her2/neu protein to Anti-Her2/neu antibody.

Surface plasmon resonance studies were conducted on a BioRad ProteOn system using a GLM sensor chip coated with goat anti-human IgG. ADCs (Phor18-V$_L$-IgG1 and Phor18-V$_L$-Phor18-V$_H$-IgG1) and Anti-Her2/neu antibody were diluted to concentrations of 5 µg/ml and injected over the anti-human IgG surface for capture. Anti-Her2/neu antibody was captured from 150 RU to 1000 RU. Phor18-V$_L$-IgG1 and Phor18-V$_L$-Phor18-V$_H$-IgG1 capture levels were between 200 to 900 RU.

ErbB2/Her2/neu (Silo Biological #1004-H08H) was analyzed at 50 nM as the highest concentration in a three-fold dilution series (N=4). Data were collected at 25 degrees C. Responses from the target surfaces were subtracted by the reference surface and then globally fit to a 1:1 interaction model. Binding constants were determined as shown in Table 8.

TABLE 8

Binding constants determined at 25 degrees C.

| | $K_a$ (M$^{-1}$s$^{-1}$) | $K_d$ (s$^{-1}$) | $K_D$ (pM) |
|---|---|---|---|
| Phor18-V$_L$-IgG1 | 2.20 × 10$^5$ | 4.43 × 10$^{-5}$ | 201 ± 24 |
| Phor18-V$_L$-Phor18-V$_H$-IgG1 | 2.05 × 10$^5$ | 3.55 × 10$^{-5}$ | 175 ± 13 |
| Anti-Her2/neu antibody | 3.90 × 10$^5$ | 3.28 10$^{-5}$ | 84 ± 13 |

The results indicate that ErbB2 bound to Anti-Her2/neu antibody with an affinity of 84±13 µM and to Phor18-V$_L$-IgG1 and Phor18-V$_L$-Phor18-V$_H$-IgG1 with affinities that were approximately 2.5 and 2-fold weaker at 200±24 and 175±13 µM, respectively. The most significant difference seen was in the association rate for Anti-Her2/neu antibody being about two-fold faster than for Phor18-V$_L$-IgG1 and Phor18-V$_L$-Phor18-V$_H$-IgG1. Thus, the binding kinetics of Phor18-conjugated to a whole antibody are similar to Anti-Her2/neu antibody, indicating that binding properties are barely affected by the conjugation on the variable light and heavy chains.

Example 11

This example describes studies to characterize and evaluate ADCs for cytotoxicity.

Different expression batches were prepared. ADC concentrations were determined from spectrophotometric measurements (OC$_{280}$) and in IgG quantification assays. Serial dilutions of selected ADCs with N-terminal Phor18 conjugation for 2 and 4 Phor18 molecules per antibody (Phor18-V$_L$-IgG1 and Phor18-V$_L$-Phor18-V$_H$-IgG1) were prepared as described in Example 10. The in vitro activity was based on IgG content of each preparation of Phor18-V$_L$-IgG1 and Phor18-V$_L$-Phor18-V$_H$-IgG1.

A 4 h time point was analyzed to determine effects of the ADCs on cell membrane integrity (Table 8). The ADCs with stoichiometric ratios of 2 Phor18/AB and 4 Phor18/AB disintegrated cell membranes of SKOV-3 target positive cells after 4 h exposure (IC50 values of 21.5±1 for Phor18-VL-IgG1 and 2.51±0.2 nM for Phor18-V$_L$-Phor18-V$_H$-IgG1), indicating membrane disruption. The membrane activity was 10 fold higher for N-terminal 4 Phor18 conjugated antibody.

Cell death was measured after 24 hours with IC$_{50}$ values in the low nanomolar range for Phor18-V$_L$-IgG1 (3.7±0.9 nM) and Phor18-V$_L$-Phor18-V$_H$-IgG1 (0.2±0.04 nM). The maximal potency of Phor18-V$_L$-I$_G$G1 and Phor18-V$_L$-Phor18-V$_H$-IgG1 was measured after 48 hours for Phor18-V$_L$-IgG1 (0.54±0.2 nM) and Phor18-V$_L$-Phor18-V$_H$-IgG1 (0.07±0.02 nM; p<0.0001). In both cases the in vitro potency for 4 Phor18 antibody conjugates (Phor18-V$_L$-Phor18-V$_H$-IgG1) was 10-20 fold higher than the 2 Phor18 antibody conjugate (Phor18-V$_L$-IgG1) (p<0.0001). Naked antibody killed Her2/neu positive target cells (SKOV-3) at 225.8±43 and 295.3±80.6 nM after 24 and 48 hours.

Consistent with previous results, Phor18-V$_L$-Phor18-V$_H$-IgG1 was the most active ADC showing a 10 fold higher activity than Phor18-V$_L$-IgG1. The Her2/neu negative control cell line MDA-MB-231 was not killed with either naked antibody or ADCs (Phor18-V$_L$-IgG1 or Phor18-V$_L$-Phor18-V$_H$-IgG1) (Table 9). The data demonstrate that higher numbers of Phor18 (four vs two) conjugated to the N-terminal domain of the antibody are most potent, compared to antibodies with a C-terminal Phor18 conjugation.

TABLE 9

In vitro activities of recombinantly produced ADCs with N-terminal Phor18 conjugations of 2 and 4 peptides against Her2/neu positive ovarian cancer cell line.

| ADC and mAB | In vitro activities Target Cells (SKOV-3) [IC$_{50}$-nM] | | |
|---|---|---|---|
| | 4 hr (Membrane integrity) | 24 hr | 48 hr |
| Anti-Her2-IgG1 | intact | 225.8 ± 43 | 295.3 ± 80.6 |
| Phor18-V$_L$-IgG1 | 21.5 ± 1.0 | 3.7 ± 0.9 | 0.54 ± 0.2 |
| Phor18-V$_L$-Phor18-V$_H$-IgG1 | 2.51 ± 0.2 | 0.2 ± 0.04 | 0.07 ± 0.02 |

Example 12

This example describes production of ADCs that bind to CD20.

CD 20 is expressed on the surface of B-cell malignancies and represents a surface target that is not internalized. Antibody fragment conjugates were produced in *E. coli* (single chain fragments and Phor18-conjugates) and *Pichia pastoris* (single chain dimers and Phor18-conjugates) and whole antibody conjugates with 2, 4, and 6 Phor18 molecules were expressed in CHO cells. Chemical conjugations with anti-CD20 IgG1 antibodies AT80 and MS4A1 were conducted.

Chemical Conjugation—AT80 (Mouse IgG1, Tenovus) and MS4A1 (Rituximab Like, R&D)

Purified antibodies IgG1 AT80 and IgG1 MS4A1 were obtained and used for the chemical conjugation with Phor18. The antibodies were in phosphate buffered saline (PBS) concentrated to a approximately 2 mg/mL. A 20 mM solution of SPDP was freshly prepared in DMSO, and added to the antibody solution in 20-fold excess. The mixture was incubated at room temperature for about 30 minutes to produce the antibody-linker intermediate. Excess unreacted SPDP is removed by size exclusion chromatography. The cytotoxin molecule containing cysteine was thoroughly reduced by reaction with a 10-fold excess of reductacryl reagent before mixing in 10-fold excess with the antibody-linker construct. The reaction is allowed to incubate at room temperature for 18 hours, then desalted to remove unreacted cytotoxin molecule. The solution is filter-sterilized before storage. Concentrations of final ADCs were for the AT80-Phor18 conjugate 0.76 mg/ml and for the MS4A1-Phor18 conjugate 0.34 mg/ml as determined by Bradford protein measurements. Typical number of Phor18 molecules per antibody using the SPDP method for conjugation is 3-5 molecules of Phor18 per antibody.

Two antibodies against CD20 chemically conjugated to Phor18 were analyzed because these bind to different domains of the extracellular CD20 loops. To compare, in in vitro studies, the cytotoxicity of two chemically conjugated CD20 targeting whole antibody IgG1-Phor18 conjugates with "naked" antibody (IgG1) in CD20 positive cells (Daudi and Raji, Burkitt's lymphoma). CD20 negative leukemia cells (U937) served as controls.

Naked antibody anti-CD20-IgG1-Phor18 were chemically conjugated (MS4A and AT80), Mw app. 158,000 g/mol at a concentrations of 0.34 mg/ml (MS4A-Phor18) and 0.76 mg/ml (AT-80-Phor18). Cell lines were obtained at the American Type Cell Collection (Mannassas, Va.). Human Non-Hodgkin's lymphoma cells Daudi (CD20 positive, passage number p2), Raji (CD20 positive p 2) and human leukemia cell line U937 (CD20 negative, p 10) were seeded at a density of 3,000 cells per well in opaque plates in heat inactivated full medium. After 24 hours cells were replenished with fresh media (75 µl) and incubated with 25 µl of a 4× serial dilution of MS4A1-Phor18 and AT80-Phor18 of 0.001, 0.01, 0.1, 1, 10, 100 and 500 nM (N=6). Cells incubated for 2-5 hours were assayed for membrane integrity using a luminometric assay kit (Promega, Madison, Wis., Cytotox Glo G9292 lot #301329). Cell viability was determined was determined after 24, and 48 hours using a luminescent assay kit (Promega, Madison, Wis., Cell Titer Glo, G 7572, lot 30068102).

Chemically conjugated MS4A1-Phor18 and AT80-Phor18 were tested for their membrane activity. MS4A1-Phor18 was not active after 2 or 5 hours in CD20 positive cell lines Raji and Daudi, whereas AT-80-Phor18 destroyed membrane integrity in CD20 positive Daudi cells with a IC$_{50}$ value of 106.1±2.9 nM. Daudi cells were killed by the AT-80-Phor18 conjugate within 48 h with IC$_{50}$ values of 11.9±0.9 nM and Raji cells with IC$_{50}$ values of 6.3±1.02 nM. The CD20 negative control cell line U937 was not killed by either naked AT-80 antibody or AT-80-Phor18 conjugates.

The MS4A1-Phor18 conjugate showed low activity in Raji cells with IC$_{50}$ values of 267±13 and 227±11 nM after 24 and 46 hours. Daudi cells were much more sensitive to the MS4A1-Phor18 conjugate with IC$_{50}$ values of 10.6±2.1 and 3.0±1.2 nM. The naked MS4A1 antibody was not toxic to either Raji or Daudi cell lines. The CD20 negative human leukemia cells (U937) were not killed by either of the ADCs (Table 10).

These data show that chemically conjugated Phor18 ADCs kill CD20 positive cells on contact, and do not appear to require internalization Cytotoxicity is specific for CD20 target and depends on the binding domain of the ADC.

TABLE 10

In vitro activities of chemically conjugated anti-CD20 IgG1-Phor18 conjugates in CD20 positive Non-Hodgkin's lymphoma cell lines Raji and Daudi and the CD20 negative cell line U937

| | Anti-CD20-Phor18 (AT80) [IC$_{50}$ nM] | Anti-CD20 AT80 [IC$_{50}$nM] | Anti-CD20-Phor18 (MS4A1) [IC$_{50}$ nM] | Anti-CD20 MS4A1 [IC$_{50}$nM] |
|---|---|---|---|---|
| Raji | | | | |
| 2 h | 120.8 ± 0.45 | Not toxic | ND | ND |
| 5 h (N = 6) | 138.2 ± 28.8 | Not toxic | ND | ND |
| 24 h | ND | ND | 267.1 ± 13 | Not toxic |
| 46 h | 6.3 ± 1.02 | ND | 227 ± 11 | Not toxic |
| Daudi | | | | |
| 2 h | 126.5 ± 12.1 | Not toxic | Not toxic | Not toxic |
| 5 h (N = 6) | 106.1 ± 2.9 | Not toxic | Not toxic | Not toxic |
| 24 h | ND | ND | 10.6 ± 2.1 | Not toxic |
| 46 h | 11.9 ± 0.9 | 115.5 ± 53 | 3.0 ± 1.2 | Not toxic |
| U937 (CD20 negative) | | | | |
| 2-46 h | Not toxic | Not toxic | Not toxic | Not toxic |

ND = not determined

Example 13

This example describes a comparison of caspase activation of CD20 targeting ADCs.

CD20 targeting ADCs are not internalized. Initiation of cell death can be measured by determining apoptosis related pathways. Early apoptosis processes shows activation of caspases 3 and 7. Caspases are members of the cysteine aspartic acid-specific protease family and play key effector role in apoptosis in mammalian cells. The assay provides a luminogenic caspase-3/7 substrate, which contains the tetrapeptide sequence DEVD, in a reagent optimized for caspase activity, luciferase activity and cell lysis.

To compare, in in vitro studies, the caspase activation of chemically conjugated CD20 targeting whole antibody IgG1-Phor18 conjugate with "naked" antibody (IgG1-AT80) in CD20 positive cells (Daudi Burkitt's lymphoma).

Human Non-Hodgkin's lymphoma cells Daudi (CD20 positive, passage number p2), were seeded at a density of 3,000 cells per well in opaque plates in heat inactivated full medium. After 24 hours cells were fed with fresh media (75 μl) and incubated with AT80-Phor18 (0.76 mg/ml) or naked antibody AT-80 of 15 and 75 μg/ml (100 and 500 nM) (N=6). Staurosporine at 10 μM served as positive control for caspase 3/7 activation. After 5 hours of incubatin cultures were assayed for caspase 3/7 levels using a luminometric assay kit (Promega, Madison, Wis., Caspase Glo 3/7 G811C lot #28731802).

Figure 9:
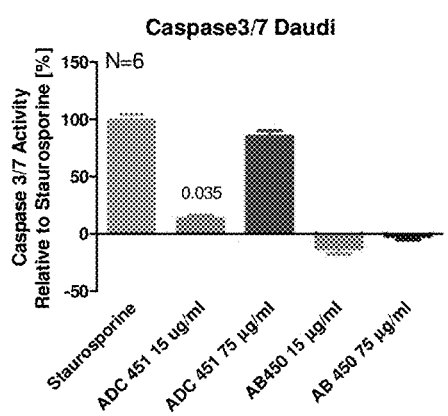
FIG. 9 shows effect of whole antibody CD20 and antibody CD20-Phor18 conjugates—chemically linked—on Caspase 3/7 activities in Daudi cells.

Caspase 3/7 activation was calculated from relative light units from luminometric signals Staurosporine was set at 100% caspase 3/7 activation, cell suspension alone without additions of reagents served as 0% caspase levels. AT80-Phor18 elevated caspase 3/7 levels to 13±2.6% at 15 μg/ml and reached 85.7±5 at 75 μg/ml. Unconjugated AT-80 at 15 or 75 μg/ml concentrations lacked caspase activation (−12.3 and −2.3%). The highest dose of AT80-Phor18 resulted in a caspase activation that was comparable to Staurosporine (p=0.06) (FIG. 9).

Phor18-conjugated ADCs activate caspase 3/7 when bound to the target cells thus promoting apoptotic cell death within 5 hours.

Example 14

This example describes expression constructs and characterization of single chain anti-CD20 Phor18 (scFv-Phor18) conjugates in *E. coli*.

A single chain Fv anti-CD20 fragment was designed by inserting Rituxan CDRs into the humanized variable regions of p185. A poly-histidine tag was added to the N-terminus of the protein for purification. The amino acid sequence is shown below with the inserted CDRs bolded. A poly-glycine flexible linker was inserted between the $V_L$ and $V_H$ domains and Phor18 was placed at the C-terminus after a GS linker

```
Amino acid sequence of the scFv fragment (naked AB); CDRs in bold
                                                      (SEQ ID NO.: 92)
          10         20         30         40         50         60
HHHHHHDIQL TQSPAILSAS PGEKVTMTCR ASSSVSYIHW FQQKPGSSPK PWIYATSNLA 70         80         90        100        110        120
SGVPVRFSGS GSGTSYSLTI SRVEAEDAAT YYCQQWTSNP PTFGGGTKLE IGSTSGGGSG 130        140        150        160        170        180
GGSGGGGSSV QLQQPGAELV KPGASVKMSC KASGYTFTSY NMHWVKQTPG RGLEWIGAIY 190        200        210        220        230        240
PGNGDTSYNQ KFKGKATLTA DKSSSTAYMQ LSSLTSEDSA VYYCARSTYY GGDWYFDVWG

QGTTVTVSS

Amino acid sequence of the scFv-Phor1 8 conjugate (C-terminus);
CDRs in bold
                                                      (SEQ ID NO.: 93)
          10         20         30         40         50         60
HHHHHHDIQL TQSPAILSAS PGEKVTMTCR ASSSVSYIHW FQQKPGSSPK PWIYATSNLA 70         80         90        100        110        120
SGVPVRFSGS GSGTSYSLTI SRVEAEDAAT YYCQQWTSNP PTFGGGTKLE IGSTSGGGSG 130        140        150        160        170        180
GGSGGGGSSV QLQQPGAELV KPGASVKMSC KASGYTFTSY NMHWVKQTPG RGLEWIGAIY 190        200        210        220        230        240
PGNGDTSYNQ KFKGKATLTA DKSSSTAYMQ LSSLTSEDSA VYYCARSTYY GGDWYFDVWG 250        260
QGTTVTVSSG SKFAKFAKKF AKFAKKFAK
```

This antibody fragment was ordered from Genscript USA (Piscataway, N.J.) for production in *E. coli*. Genscript used their pGS21a expression plasmid for production in *E. coli* Arctic Express cells. Genscript isolated the protein from *E. coli* inclusion bodies.

The naked scFv fragment had was purified through affinity chromatography and resulted in a yield of 15 mg/L at a concentration of 0.31 mg/ml. the purity was determined as 85%. The molecular weight was determined using Coomassie stained SDS PAGE analysis with 27,088 g/mol. The Phor18 conjugate had a similar yield of 15 mg/L and a purity of 85% based on Coomassie stained SDS-Page. The molecular weight was measured at 29,349 g/mol. Both naked AB and ADC were provided in 50 mM Tris buffer, pH 8.0.

Anti-CD20 ScFv-Phor18 has a calculated molecular weight if 29.3 kD. The antibody fragment was expressed with a poly-histidine tag for purification. An immunoblot of the protein probed with anti-histidine and SDS-PAGE stained with coomassie blue indicated the molecular weight was in the correct range.

Example 15

This example describes expression and characterization of recombinantly produced CD20 targeting Fv-$C_H$3-$C_H$3-Fv-Phor18 conjugates in *E. coli*:

A bivalent anti-CD20 minibody was designed by adding a flexible glycine-serine linker between the variable domains and between the $C_H$3 domains to result in a Fv-$C_H$3-$C_H$3-Fv minibody. A poly-histidine tag was added to the N-terminus of the protein for purification from inclusion bodies and Phor18 was placed at the C-terminus after a GS linker. The amino acid sequences are shown below with the inserted CDRs bolded in variable domains and the $C_H$3 domain are in lower case letters.

```
Amino acid sequence of the anti-CD20 minibody Fv-C_H3-C_H3-Fv;
CDRs in bold
                                                      (SEQ ID NO.: 94)
         10         20         30         40         50         60
DIQLTQSPAI LSASPGEKVT MTCRASSSVS YIHWFQQKPG SSPKPWIYAT SNLASGVPVR 70         80         90        100        110        120
FSGSGSGTSY SLTISRVEAE DAATYYCQQW TSNPPTFGGG TKLEIGSTSG GGSGGGSGGG 130        140        150        160        170        180
GSSVQLQQPG AELVKPGASV KMSCKASGYT FTSYNMHWVK QTPGRGLEWI GAIYPGNGDT 190        200        210        220        230        240
SYNQKFKGKA TLTADKSSST AYMQLSSLTS EDSAVYYCAR STYYGGDWYF DVWGQGTTVT 250        260        270        280        290        300
VSSGQPREPQ VYTLPPSRDE LTKNQVSLTC LVKGFYPSDI AVEWESNGQP ENNYKTTPPV 310        320        330        340        350        360
LDSDGSFFLY SKLTVDKSRW QQGNVFSCSV MHEALHNHYT QKSLSLSPGK GSTSGGGSGG 370        380        390        400        410        420
GSGGGGSSGQ PREPQVYTLP PSRDELTKNQ VSLTCLVKGF YPSDIAVEWE SNGQPENNYK 430        440        450        460        470        480
TTPPVLDSDG SFFLYSKLTV DKSRWQQGNV FSCSVMHEAL HNHYTQKSLS LSPGKVQLQQ 490        500        510        520        530        540
PGAELVKPGA SVKMSCKASG YTFTSYNMHW VKQTPGRGLE WIGAIYPGNG DTSYNQKFKG 550        560        570        580        590        600
KATLTADKSS STAYMQLSSL TSEDSAVYYC ARSTYYGGDW YFDVWGQGTT VTVSSGSTSG 610        620        630        640        650        660
GGSGGGSGGG GSSDIQLTQS PAILSASPGE KVTMTCRASS SVSYIHWFQQ KPGSSPKPWI 670        680        690        700        710
YATSNLASGV PVFSGSGSGT SYSLTISRVE AEDAATYYCQ QWTSNPPTFG GGTKLEI Amino acid sequence of the anti-CD20-Phor18 minibody conjugate
Fv-C_H3-C_H3-Fv-Phor18; CDRs in bold
                                                      (SEQ ID NO.: 95)
         10         20         30         40         50         60
DIQLTQSPAI LSASPGEKVT MTCRASSSVS YIHWFQQKPG SSPKPWIYAT SNLASGVPVR 70         80         90        100        110        120
FSGSGSGTSY SLTISRVEAE DAATYYCQQW TSNPPTFGGG TKLEIGSTSG GGSGGGSGGG 130        140        150        160        170        180
GSSVQLQQPG AELVKPGASV KMSCKASGYT FTSYNMHWVK QTPGRGLEWI GAIYPGNGDT 190        200        210        220        230        240
SYNQKFKGKA TLTADKSSST AYMQLSSLTS EDSAVYYCAR STYYGGDWYF DVWGQGTTVT 250        260        270        280        290        300
VSSGQPREPQ VYTLPPSRDE LTKNQVSLTC LVKGFYPSDI AVEWESNGQP ENNYKTTPPV 310        320        330        340        350        360
LDSDGSFFLY SKLTVDKSRW QQGNVFSCSV MHEALHNHYT QKSLSLSPGK GSTSGGGSGG 370        380        390        400        410        420
GSGGGGSSGQ PREPQVYTLP PSRDELTKNQ VSLTCLVKGF YPSDIAVEWE SNGQPENNYK 430        440        450        460        470        480
TTPPVLDSDG SFFLYSKLTV DKSRWQQGNV FSCSVMHEAL HNHYTQKSLS LSPGKVQLQQ 490        500        510        520        530        540
PGAELVKPGA SVKMSCKASG YTFTSYNMHW VKQTPGRGLE WIGAIYPGNG DTSYNQKFKG 550        560        570        580        590        600
KATLTADKSS STAYMQLSSL TSEDSAVYYC ARSTYYGGDW YFDVWGQGTT VTVSSGSTSG
```

-continued

```
       610        620        630        640        650        660
GGSGGGSGGG GSSDIQLTQS PAILSASPGE KVTMTCRASS SVSYIHWFQQ KPGSSPKPWI 670        680        690        700        710        720
YATSNLASGV PVFSGSGSGT SYSLTISRVE AEDAATYYCQ QWTSNPPTFG GGTKLEIGSK

730
FAKFAKKFAK FAKKFAK
```

The antibody fragment was obtained from Genscript USA (Piscataway, N.J.) for production in E. coli. Genscript used their pGS21a expression plasmid for production in E. coli Arctic Express cells. Genscript isolated the protein from E. coli inclusion bodies.

The naked anti-CD20 minibody had was purified through affinity chromatography and resulted in a yield of 3 mg/L at a concentration of 0.23 mg/ml. the purity was determined as 80%. The molecular weight was determined using Coomassie stained SDS PAGE analysis with 78,988 g/mol. The Phor18 conjugate had a similar yield of 3 mg/L and a purity of 70% based on Coomassie stained SDS-Page. The molecular weight was measured at 93,515 g/mol. Both naked AB and ADC were provided in 50 mM Tris buffer, 150 mM NaCl, 15-20% glycerol, pH 8-9.5.

The naked single chain Fv and anti-CD20 minibody and scFv-Phor18 and anti CD20-Phor18 conjugates were expressed in E. coli. Distinct molecular weights that corresponded to each antibody fragment backbone were demonstrated on SDS-PAGE gels and Western blots.

Example 16

This example describes the in vitro analysis of the scFv and anti-CD20 naked minibody and Phor18 conjugates in CD20 positive and CD20 negative cell lines.

To compare, in in vitro studies, the cytotoxicity of a recombinantly produced CD20 targeting scFv-Phor18 and anti-CD20-Phor18 minibody in a bacterial expression system with "naked" antibody (scFv and anti-CD20 minibody) in CD20 positive cells (Daudi, Burkitt's lymphoma). CD20 negative leukemia cells (U937) served as controls.

The concentration of each naked antibody fragment and ADC was determined according to Bradford. Naked antibody scFv Mw 27,088 g/mol at a concentration of 0.3 mg/ml, minibody Mw 78,988 g/mol, 0.231 mg/ml; Phor 18 conjugated antibodies were scFv-Phor18 (Mw 29,349 g/mol, 0.9 mg/ml) and minibody-Phor18 (Mw 93,515, 0.48 mg/ml). Cell lines were obtained at the American Type Cell Collection (Mannassas, Va.). Human Non-Hodgkin's lymphoma cells Daudi (CD20 positive, passage number p8) and human leukemia cell line U937 (CD20 negative, p 16) were seeded at a density of 2,000 cells per well in opaque plates in heat inactivated full medium. After 24 hours cells were replenished with fresh media (75 µl) and incubated with 25 µl of a 4× serial dilution of scFv-Phor18 and minibody-Phor18 ADC and naked antibody fragment (scFv and minibody) prepared in cell culture media were added at concentrations of 0.0001, 0.001, 0.01, 0.1, 1, 10, 100, 200, and 500 nM (N=6). Cells incubated for 4 hours were assayed for membrane integrity using a luminometric assay kit (Promega, Madison, Wis., Cytotox Glo G9292 lot #301329). Cell viability was determined after 24, 48 and 72 hours using a luminescent assay kit (Promega, Madison, Wis., Cell Titer Glo, G 7572, lot 30062102).

Controls for 100% cell viability (culture media) and 100% cell death (0.1% Triton X 100) incubated under the same conditions.

Data were processed and analyzed to obtain $IC_{50}$ values using Graph Pad Prizm version 5.00 for Windows, Graph-Pad Software, San Diego Calif. USA, wwwdotgraphpaddotcom (Graph Pad Prizm, Inc). Statistical analysis for significance was determined by a two-tailed Student's T-test. Each test was conducted using 2 plates with 2-3 wells each to achieve an N of 4-6 data points per time point.

Recombinant scFv-Phor18 conjugates were expressed in E. coli. As shown in FIG. 10, Table 11, the anti-CD20-scFv-Phor18 conjugate destroyed membrane integrity in CD20 positive Daudi cells. Human Burkitts lymphoma cells (Daudi) were killed within 48 h, whereas the CD20 negative human leukemia cells (U937) were not killed. Naked scFv antibody did not kill any of the cell lines. Hill plot analysis of the cell viability data resulted in $IC_{50}$ values for the minibody conjugate of 10.02±0.5 nM after 24 h and 1.5±0.3 nM after 48 h in Daudi cells. Naked scFv was not toxic. The CD20 negative cell line U937 was not killed by either naked scFv or scFv-Phor18 or minibody-Phor18 conjugates. In vitro activities of the minibody-Phor18 conjugates were 10.5±0.5 and 3.9±1.6 nM in CD20 positive Daudi cells after 24 and 46 hours. Naked minibody was not toxic.

TABLE 11

In vitro toxicities of scFv-Phor18 and Fv-$C_H$3-$C_H$3-Fv-Phor18, and scFv and Fv-$C_H$3-$C_H$3-Fv targeting CD 20. Daudi cells (NHL) are positive for CD 20, U937 cells (leukemia) are negative for CD20.

|  | scFv [IC$_{50}$ nM] | scFv-Phor18 [IC$_{50}$ nM] | Fv-$C_H$3-$C_H$3-Fv [IC$_{50}$ nM] | Fv-$C_H$3-$C_H$3-Fv-Phor18 [IC$_{50}$ nM] |
|---|---|---|---|---|
| Daudi |  |  |  |  |
| 2 h | Not toxic | 109.8 ± 0.9 | ND | ND |
| 5 h (N = 8) | Not toxic | 111.6 ± 15.1 | ND | ND |
| 24 h (N = 6) | Not toxic | 10.02 ± 0.5 | Not toxic | 10.5 ± 0.5 |
| 46 h (N = 6) | Not toxic | 1.5 ± 0.3 | Not toxic | 3.6 ± 1.6 |
| U937 |  |  |  |  |
| 2-48 h | Not toxic | Not toxic | Not toxic | Not toxic |

ND = Not Determined

Potent scFv-Phor18 and Fv-$C_H$3-$C_H$3-Fv-Phor18 conjugates were expressed in E. coli and were more potent than naked scFv or Fv-$C_H$3-$C_H$3-Fv. CD20 targeted ADCs killed specifically target cells—cell death was independent on internalization. scFv-Phor18 or Fv-$C_H$3-$C_H$3-Fv-Phor18 targeted conjugates but not the naked scFv antibody fragment activated apoptotic pathways. C-terminus conjugated scFv and Fv-$C_H$3-$C_H$3-Fv conjugates showed similar activities in the nanomolar range after 24 hours.

Example 17

This example describes a possible mechanism of action of the CD20 targeted ADC.

In in vitro studies, caspase activation of recombinantly expressed CD20 targeting scFv-Phor18 conjugate with "naked" antibody (scFv) in CD20 positive cells (Daudi Burkitt's lymphoma) was compared. Human Non-Hodgkin's lymphoma cells Daudi (CD20 positive, p 5) and Raji (CD20 positive, passage number p 3), were seeded at a density of 3,000 cells per well in opaque plates in heat inactivated full medium. After 24 hours cells were fed with fresh media (75 µl) and incubated with scFv-Phor18 (0.365 mg/ml) or naked antibody scFv of 5 and 15 µg/ml (100 and 500 nM) (N=6). Staurosporine at 10 µM served as positive control for caspase 3/7 activation. After 5 hours were assayed for caspase 3/7 activation using a luminometric assay kit (Promega, Madison, Wis., Caspase Glo 3/7 G811C lot #28731802).

Figure 11:
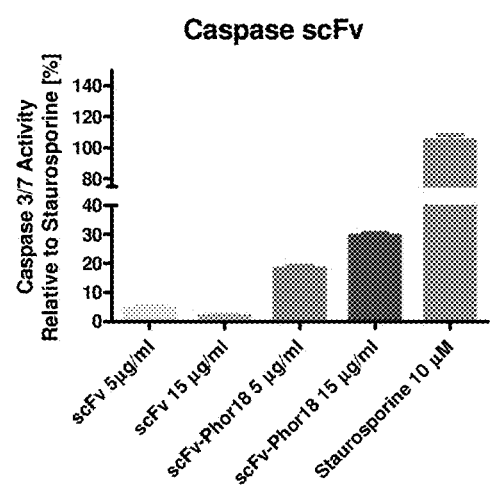
FIG. 11 shows in vitro caspase 3/7 activation measured for naked scFv and scFv-Phor18 conjugates. scFv-Phor 18 increased caspase 3/7 activities in a concentration dependent manner. Staurosporine served as control for caspase activation. Naked scFv did not detectably activate caspases.

Relative caspase 3/7 activation was calculated from relative light units from luminometric signals. Staurosporine was set at 100% caspase 3/7 activation and no reagents for 0% activation controls. scFv-Phor18 at 5 µg/ml had elevated caspase 3/7 levels of 18.3±0.8 and 29.3±0.9% compared to Staurosporine (FIG. 11).

Phor18-conjugated ADCs activate caspase 3/7 in target cells thus promoting apoptotic cell death. Accordingly, antibody Phor18 conjugates as single chain or minibody fragments can be produced recombinantly and are active without internalization on target cells. Caspase activation through ADCs may be a possible mechanism of action.

Example 18

This example describes the expression of CD20 targeted scFvFc Phor18 conjugates having Phor18 conjugated at the N or C terminus and having a stoichiometry of 1 and 2 Phor18 molecules per antibody fragment.

The recombinant series was produced by Genscript, USA (Piscataway, N.J.) in *E. coli* using periplasmatic secretion. Transcripts were synthesized and codon usage was optimized for *E. Coli* The Genscript pGS-21a expression vector was used. The expressed proteins were directed to the periplasm of *E. Coli* cells by addition of a cleavable PelB bacterial signal sequence, composed of the amino acids MKYLLPTAAAGLLLLAAQPAMA (SEQ ID NO.:101), to the N-terminus. The Rituxan CDRs were inserted into the humanized variable regions of p185 Herceptin and are shown in bold. Four glycines and a serine linked the variable regions for added flexibility. Phor18 was positioned at the N-terminus, the C-terminus, or both. The amino acid sequence of the antibody fragment are as follows:

```
Cleaved PelB N-terminal signal sequence MKYLLPTAAAGLLLLAAQPAMA
(SEQ ID NO.: 96)
Amino acid sequences of scFv-Fc (naked antibody); CDRs in bold
                                                        (SEQ ID NO.: 97)
          10         20         30         40         50         60
DIQMTQSPSS LSASVGDRVT ITCRASSSVS YIHWYQQKPG KAPKLLIYAT SNLASGVPSR 70         80         90        100        110        120
FSGSRSGTDF TLTISSLQPE DFATYYCQQW TSNPPTFGQG TKVEIKGGGG SEVQLVESGG 130        140        150        160        170        180
GLVQPGGSLR LSCAASGYTF TSYNMHWVRQ APGKGLEWVA AIYPGNGDTS YNQKFKGRFT 190        200        210        220        230        240
ISADTSKNTA YLQMNSLRAE DTAVYYCSRS TYYGGDWYFD VWGQGTLVTV SSVQPCPAPE 250        260        270        280        290        300
LLGGPSVFLF PPKPKDTLMI SRTPEVTCVV VDVSHEDPEV KFNWYVDGVE VHNAKTKPRE 310        320        330        340        350        360
EQYNSTYRVV SVLTVLHQDW LNGKEYKCKV SNKALPAPIE KTISKAKGQP REPQVYTLPP 370        380        390        400        410        420
SRDELTKNQV SLTCLVKGFY PSDIAVEWES NGQPENNYKT TPPVLDSDGS FFLYSKLTVD 430        440        450
KSRWQQGNVF SCSVMHEALH NHYTQKSLSL SPGK Amino acid sequences of lytic-peptide Phor18-antibody conjugate;
CDRs in bold Phor18-scFv-Fc-Phor18: N- and C-terminal conjugation
                                                        (SEQ ID NO.: 98)
          10         20         30         40         50         60
KFAKFAKKFA KFAKKFAKGS DIQMTQSPSS LSASVGDRVT ITCRASSSVS YIHWYQQKPG 70         80         90        100        110        120
KAPKLLIYAT SNLASGVPSR FSGSRSGTDF TLTISSLQPE DFATYYCQQW TSNPPTFGQG 130        140        150        160        170        180
TKVEIKGGGG SEVQLVESGG GLVQPGGSLR LSCAASGYTF TSYNMHWVRQ APGKGLEWVA 190        200        210        220        230        240
AIYPGNGDTS YNQKFKGRFT ISADTSKNTA YLQMNSLRAE DTAVYYCSRS TYYGGDWYFD 250        260        270        280        290        300
VWGQGTLVTV SSVQPCPAPE LLGGPSVFLF PPKPKDTLMI SRTPEVTCVV VDVSHEDPEV
```

```
              310        320        330        340        350        360
       KFNWYVDGVE VHNAKTKPRE EQYNSTYRVV SVLTVLHQDW LNGKEYKCKV SNKALPAPIE 370        380        390        400        410        420
       KTISKAKGQP REPQVYTLPP SRDELTKNQV SLTCLVKGFY PSDIAVEWES NGQPENNYKT 430        440        450        460        470        480
       TPPVLDSDGS FFLYSKLTVD KSRWQQGNVF SCSVMHEALH NHYTQKSLSL SPGKGSKFAK

490
       FAKKFAKFAK KFAK
```

Amino acid sequences of lytic-peptide Phor18-antibody conjugate;
CDRs in bold Phor18-scFv-Fc: N-terminal conjugation (SEQ ID NO.: 99)

```
               10         20         30         40         50         60
       KFAKFAKKFA KFAKKFAKGS DIQMTQSPSS LSASVGDRVT ITCRASSSVS YIHWYQQKPG 70         80         90        100        110        120
       KAPKLLIYAT SNLASGVPSR FSGSRSGTDF TLTISSLQPE DFATYYCQQW TSNPPTFGQG 130        140        150        160        170        180
       TKVEIKGGGG SEVQLVESGG GLVQPGGSLR LSCAASGYTF TSYNMHWVRQ APGKGLEWVA 190        200        210        220        230        240
       AIYPGNGDTS YNQKFKGRFT ISADTSKNTA YLQMNSLRAE DTAVYYCSRS TYYGGDWYFD

250        260        270        280        290        300
       VWGQGTLVTV SSVQPCPAPE LLGGPSVFLF PPKPKDTLMI SRTPEVTCVV VDVSHEDPEV 310        320        330        340        350        360
       KFNWYVDGVE VHNAKTKPRE EQYNSTYRVV SVLTVLHQDW LNGKEYKCKV SNKALPAPIE 370        380        390        400        410        420
       KTISKAKGQP REPQVYTLPP SRDELTKNQV SLTCLVKGFY PSDIAVEWES NGQPENNYKT 430        440        450        460        470
       TPPVLDSDGS FFLYSKLTVD KSRWQQGNVF SCSVMHEALH NHYTQKSLSL SPGK
```

Amino acid sequences of lytic-peptide Phor18-antibody conjugate;
CDRs in bold Phor18-scFv-Fc: C-terminal conjugation (SEQ ID NO.: 100)

```
               10         20         30         40         50         60
       DIQMTQSPSS LSASVGDRVT ITCRASSSVS YIHWYQQKPG KAPKLLIYAT SNLASGVPSR 70         80         90        100        110        120
       FSGSRSGTDF TLTISSLQPE DFATYYCQQW TSNPPTFGQG TKVEIKGGGG SEVQLVESGG 130        140        150        160        170        180
       GLVQPGGSLR LSCAASGYTF TSYNMHWVRQ APGKGLEWVA AIYPGNGDTS YNQKFKGRFT 190        200        210        220        230        240
       ISADTSKNTA YLQMNSLRAE DTAVYYCSRS TYYGGDWYFD VWGQGTLVTV SSVQPCPAPE 250        260        270        280        290        300
       LLGGPSVFLF PPKPKDTLMI SRTPEVTCVV VDVSHEDPEV KFNWYVDGVE VHNAKTKPRE 310        320        330        340        350        360
       EQYNSTYRVV SVLTVLHQDW LNGKEYKCKV SNKALPAPIE KTISKAKGQP REPQVYTLPP 370        380        390        400        410        420
       SRDELTKNQV SLTCLVKGFY PSDIAVEWES NGQPENNYKT TPPVLDSDGS FFLYSKLTVD 430        440        450        460        470
       KSRWQQGNVF SCSVMHEALH NHYTQKSLSL SPGKGSKFAK FAKKFAKFAK KFAK
```

The ADCs were purified over protein A affinity chromatography columns and stored frozen (−20 degrees C.). The concentration of each naked antibody fragment and ADC was determined spectrophotometrically ($OD_{280}$). Naked antibody scFv-Fc Mw 52,562 g/mol at a concentration of 1.1 mg/ml, Phor 18 conjugated antibodies were Phor18-$V_L$-scFvFc (Mw 54,685 g/mol, 1.0 mg/ml), Phor18-$C_H$3-scFvFc (Mw 54,685 g/mol, 0.8 mg/ml) formed single chains.

Example 19

This example describes activity of scFv-Fc-Phor18 conjugates in in vitro studies.

The cytotoxicity of recombinantly produced CD20 targeting scFv-Fc-Phor18 conjugates in a *E. coli* expression system with Phor18 conjugations at N- or C-terminus and at N- and C-terminus was compared to "naked" antibody (scFv-Fc) in CD20 positive cells (Daudi, Burkitts lymphoma). CD20 negative leukemia cells (U937) served as controls. *E. coli* expressed ADCs represented single chains and were conjugated to 1 Phor18 molecule at the N-terminus of the $V_L$ chain (Phor18-$V_L$-scFv-Fc), at the C-terminus of the $C_H$3 chain (scFv-Fc-$C_H$3-Phor18).

The concentration of each naked antibody fragment and ADC was determined spectrophotometrically ($OD_{280}$). Naked antibody scFv-Fc Mw 52,562 g/mol at a concentration of 1.1 mg/ml, Phor 18 conjugated antibodies were Phor18-$V_L$-scFvFc (Mw 54,685 g/mol, 1.0 mg/ml), scFv-Fc-$C_H$3-Phor18 (Mw 54,685 g/mol, 0.8 mg/ml). Human Non-Hodgkin's lymphoma cells Daudi (CD20 positive, passage number p7) and human leukemia cell line U937 (CD20 negative, p 6) were seeded at a density of 2,000 cells per well in opaque plates in heat inactivated full medium using cell dissociation buffer. After 24 hours cells were replenished with fresh media (75 μl) and incubated and incubated with 25 μl of a 4× serial dilution of each ADC and naked antibody prepared in cell culture media were added at concentrations of 0.01, 0.1, 1, 10, 100, 200 and 500 nM for scFvFc, Phor18-$V_L$-scFvFc and scFv-Fc-$C_H$3-Phor18.

Cells incubated for 4 hours were assayed for membrane integrity using a luminometric assay kit (Promega, Madison, Wis., Cytotox Glo G9292 lot #26229601). Cell viability was determined was determined after 24 hours using a luminescent assay kit (Promega, Madison, Wis., Cell Titer Glo, G7572, lot 30731602). Controls for 100% cell viability (culture media) and 100% cell death (0.1% Triton X 100) incubated under the same conditions.

Data were processed and analyzed to obtain $IC_{50}$ values using Graph Pad Prizm version 5.00 for Windows, GraphPad Software, San Diego Calif. USA, wwwdotgraphpaddotcom (Graph Pad Prizm, Inc). Statistical analysis for significance was determined by a two-tailed Student's T-test. Each test was conducted using 2 plates with 2-3 wells each to achieve an N of 4-6 data points per time point.

Recombinant ScFv-Fc-Phor18 conjugates with 1 Phor18 on the N-terminus or the C-terminus were expressed in *E. coli*. As shown in Table 12, the anti-CD20-Phor18 conjugate Phor18-$V_L$-scFvFc destroyed membrane integrity in CD20 positive Daudi cells after 4 h with $IC_{50}$ values of 277±37.5 nM. A tenfold higher value was obtained for the C-terminal conjugate for scFv-Fc-$C_H$3-Phor18 with 2558±259 nM. Naked scFvFc was not toxic.

Human Burkitts lymphoma cells (Daudi) were killed within 24 h with $IC_{50}$ values of 21.8±0.8 nM for Phor18-$V_L$-scFv-Fc, and 422.6±47.5 nM for scFv-Fc-$C_H$3-Phor18.

Naked scFv caused cell killing at 677.2±45.3 nM in the CD20 positive Daudi cell line. The CD20 negative human leukemia cells (U937) was not killed after 4 hours and showed compared to the target cell line lower sensitivity with $IC_{50}$ values of 495.4±35.2 nM for the naked scFvFc, 105.3±15.6 nM Phor18-$V_L$-scFv-Fc and 722.3±33.2 nM for the scFv-Fc-$C_H$3-Phor18 conjugates.

TABLE 12

In vitro toxicities of Phor18-$V_L$-scFv-Fc and scFv-Fc-$C_H$3-Phor18, and scFv-Fc targeting CD 20. Daudi cells (NHL) are positive for CD 20, U937 cells (leukemia) are negative for CD20.

| | scFvFc naked AB | Phor18-$V_L$-scFv-Fc $IC_{50}$ values [nM] | scFv-Fc-$C_H$3-Phor18 $IC_{50}$ values [nM] |
|---|---|---|---|
| Daudi | | | |
| 4 h (N = 8) | Not toxic | 277 ± 37.5 | 2558 ± 259 |
| 24 h (N = 8) | 677.2 ± 45.3 | 21.8 ± 0.8 | 422.6 ± 47.5 |
| U937 | | | |
| 4 h (N = 8) | Not toxic | Not toxic | Not toxic |
| 24 h (N = 8) | 495.4 ± 35.2 | 105.3 ± 15.6 | 722.3 ± 33.2 |

N-terminus conjugated Phor18 antibody fragments were more toxic compared to C-terminus conjugated Phor18 antibody fragments.

Example 20

This example describes expression and activity of CD20 targeting scFv-Fc-Phor18 conjugates produced in *Pichia Pastoris* (yeast).

Four anti-CD20 single chain Fv-Fc antibody fragments were designed by inserting the Rituxan CDRs into the humanized variable regions of p185. The inserted CDRs are bolded in the amino acid sequences shown below. A poly-G linker was used between the variable regions and human constant domains hinge, $C_H$2 and $C_H$3. The order of the antibody fragment sequences shown below are as follows: naked antibody, C-terminal and N-terminal Phor18, N-terminal Phor18 only, C-terminal Phor18 only. The amino acid sequences for each construct are shown below:

```
Amimo acid sequences of naked antibody; CDRs in bold
                                              (SEQ ID NO.: 101)
          10         20         30         40         50         60
   DIQMTQSPSS LSASVGDRVT ITCRASSSVS YIHWYQQKPG KAPKLLIYAT SNLASGVPSR 70         80         90        100        110        120
   FSGSRSGTDF TLTISSLQPE DFATYYCQQW TSNPPTFGQG TKVEIKGGGG SGGGGSGGGG 130        140        150        160        170        180
   SEVQLVESGG GLVQPGGSLR LSCAASGYTF TSYNMHWVRQ APGKGLEWVA AIYPGNGDTS 190        200        210        220        230        240
   YNQKFKGRFT ISADTSKNTA YLQMNSLRAE DTAVYYCSRS TYYGGDWYFD VWGQGTLVTV
```

```
              250        260        270        280        290        300
       SSTHTCPPCP APELLGGPSV FLFPPKPKDT LMISRTPEVT CVVVDVSHED PEVKFNWYVD 310        320        330        340        350        360
       GVEVHNAKTK PREEQYNSTY RVVSVLTVLH QDWLNGKEYK CKVSNKALPA PIEKTISKAK 370        380        390        400        410        420
       GQPREPQVYT LPPSRDELTK NQVSLTCLVK GFYPSDIAVE WESNGQPENN YKTTPPVLDS 430        440        450        460
       DGSFFLYSKL TVDKSRWQQG NVFSCSVMHE ALHNHYTQKS LSLSPGK

Amino acid sequences of conjugated antibody;
Phor18-V_L-scFv-Fc-C_H3-Phor18 CDRs in bold
                                                          (SEQ ID NO.: 102)
              10         20         30         40         50         60
       KFAKFAKKFA KFAKKFAKGS DIQMTQSPSS LSASVGDRVT ITCRASSSVS YIHWYQQKPG 70         80         90        100        110        120
       KAPKLLIYAT SNLASGVPSR FSGSRSGTDF TLTISSLQPE DFATYYCQQW TSNPPTFGQG 130        140        150        160        170        180
       TKVEIKGGGG SGGGGSGGGG SEVQLVESGG GLVQPGGSLR LSCAASGYTF TSYNMHWVRQ 190        200        210        220        230        240
       APGKGLEWVA AIYPGNGDTS YNQKFKGRFT ISADTSKNTA YLQMNSLRAE DTAVYYCSRS

250        260        270        280        290        300
       TYYGGDWYFD VWGQGTLVTV SSTHTCPPCP APELLGGPSV FLFPPKPKDT LMISRTPEVT 310        320        330        340        350        360
       CVVVDVSHED PEVKFNWYVD GVEVHNAKTK PREEQYNSTY RVVSVLTVLH QDWLNGKEYK 370        380        390        400        410        420
       CKVSNKALPA PIEKTISKAK GQPREPQVYT LPPSRDELTK NQVSLTCLVK GFYPSDIAVE 430        440        450        460        470        480
       WESNGQPENN YKTTPPVLDS DGSFFLYSKL TVDKSRWQQG NVFSCSVMHE ALHNHYTQKS 490        500
       LSLSPGKGSK AFKKAFKAFK KAFKAFK

Amino acid sequences of conjugated antibody Phor18-V_L-scFv-Fc;
CDRs in bold
                                                          (SEQ ID NO.: 103)
              10         20         30         40         50         60
       KFAKFAKKFA KFAKKFAKGS DIQMTQSPSS LSASVGDRVT ITCRASSSVS YIHWYQQKPG 70         80         90        100        110        120
       KAPKLLIYAT SNLASGVPSR FSGSRSGTDF TLTISSLQPE DFATYYCQQW TSNPPTFGQG 130        140        150        160        170        180
       TKVEIKGGGG SGGGGSGGGG SEVQLVESGG GLVQPGGSLR LSCAASGYTF TSYNMHWVRQ 190        200        210        220        230        240
       APGKGLEWVA AIYPGNGDTS YNQKFKGRFT ISADTSKNTA YLQMNSLRAE DTAVYYCSRS

250        260        270        280        290        300
       TYYGGDWYFD VWGQGTLVTV SSTHTCPPCP APELLGGPSV FLFPPKPKDT LMISRTPEVT 310        320        330        340        350        360
       CVVVDVSHED PEVKFNWYVD GVEVHNAKTK PREEQYNSTY RVVSVLTVLH QDWLNGKEYK 370        380        390        400        410        420
       CKVSNKALPA PIEKTISKAK GQPREPQVYT LPPSRDELTK NQVSLTCLVK GFYPSDIAVE 430        440        450        460        470        480
       WESNGQPENN YKTTPPVLDS DGSFFLYSKL TVDKSRWQQG NVFSCSVMHE ALHNHYTQKS

LSLSPGK

Amino acid sequences of conjugated antibody scFv-Fc-C_H3-Phor18;
CDRs in bold
                                                          (SEQ ID NO.: 104)
              10         20         30         40         50         60
       DIQMTQSPSS LSASVGDRVT ITCRASSSVS YIHWYQQKPG KAPKLLIYAT SNLASGVPSR 70         80         90        100        110        120
       FSGSRSGTDF TLTISSLQPE DFATYYCQQW TSNPPTFGQG TKVEIKGGGG SGGGGSGGGG
```

```
                 130        140        150        160        170        180
         SEVQLVESGG GLVQPGGSLR LSCAASGYTF TSYNMHWVRQ APGKGLEWVA AIYPGNGDTS 190        200        210        220        230        240
         YNQKFKGRFT ISADTSKNTA YLQMNSLRAE DTAVYYCSRS TYYGGDWYFD VWGQGTLVTV 250        260        270        280        290        300
         SSTHTCPPCP APELLGGPSV FLFPPKPKDT LMISRTPEVT CVVVDVSHED PEVKFNWYVD 310        320        330        340        350        360
         GVEVHNAKTK PREEQYNSTY RVVSVLTVLH QDWLNGKEYK CKVSNKALPA PIEKTISKAK 370        380        390        400        410        420
         GQPREPQVYT LPPSRDELTK NQVSLTCLVK GFYPSDIAVE WESNGQPENN YKTTPPVLDS 430        440        450        460        470        480
         DGSFFLYSKL TVDKSRWQQG NVFSCSVMHE ALHNHYTQKS LSLSPGKGSK AFKKAFKAFK

KAFKAFK
```

Figure 12:
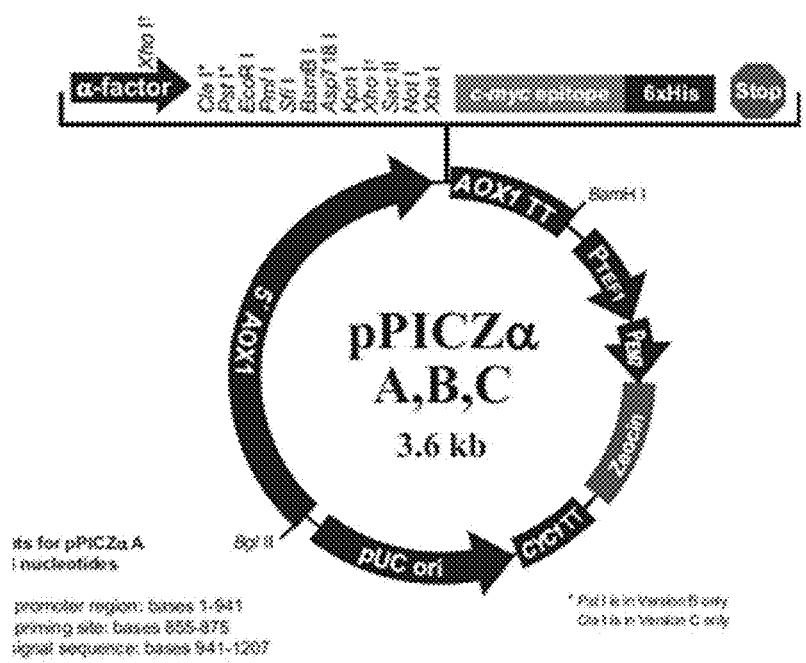
FIG. 12 illustrates expression vector for anti-CD20 ADC and naked antibody expression used for transfection in a yeast system.

The gene synthesis for the four scFv-Fc fragments was ordered from Genescript USA and codons were optimized for production in *Pichia Pastoris* yeast strain GS 115 at Genscript. Genescript subcloned each expression plasmid into the InVitrogen yeast expression plasmid pPICZαA (cat #V195-20 lot #900479, FIG. 12). This expression plasmid has a yeast α-factor secretory signal so that the antibody protein could be isolated from medium.

Characterization of CD20 targeting scFv-Fc-Phor18 conjugates on silver stained SDS PAGE showed that *Pichia pastoris* expressed ADCs represented single chain dimers and were conjugated to 2 or 4 Phor18 molecules at the N-terminus of the $V_L$ chain (Phor18-$V_L$-scFvFc), at the C-terminus of the $C_H3$ chain (scFvFc-$C_H3$-Phor18) and at the N-terminus of the $V_L$ chains and the C-terminus of the $C_H3$ chain (Phor18-$V_L$-scFv-Fc-$C_H3$-Phor18).

The concentration of each naked antibody fragment and ADC was determined spectrophotometrically ($OD_{280}$). Naked antibody scFv-Fc (Mw 102,078 g/mol) at a concentration of 0.26 mg/ml, Phor 18 conjugated antibodies were Phor18-$V_L$-scFvFc (Mw 106,616 g/mol, 0.5 mg/ml), scFvFc-$C_H3$-Phor18 (Mw 106,616 g/mol, 0.17 mg/ml) and Phor18-$V_L$-scFv-Fc-$C_H3$-Phor18 (Mw 111,154 g/mol, 0.7 mg/ml).

To compare, in in vitro studies, the cytotoxicity of recombinantly produced CD20 targeting scFv-Fc-Phor18 conjugates in a yeast expression system with "naked" antibody (scFv-Fc) in CD20 positive cells (Daudi, Burkitts lymphoma). CD20 negative leukemia cells (U937) served as controls. *Pichia* expressed ADCs represented single chain dimers and were conjugated to 2 or 4 Phor18 molecules at the N-terminus of the $V_L$ chain (Phor18-$V_L$-scFvFc), at the C-terminus of the $C_H3$ chain (scFvFc-$C_H3$-Phor18) and at the N-terminus of the $V_L$ chains and the C-terminus of the $C_H3$ chain (Phor18-$V_L$-scFv-Fc-$C_H3$-Phor18).

Human Non-Hodgkin's lymphoma cells Daudi (CD20 positive, passage number p3) and human leukemia cell line U937 (CD20 negative, p 12) were seeded at a density of 2,000 cells per well in opaque plates in heat inactivated full medium using cell dissociation buffer. After 24 hours cells were replenished with fresh media (75 μl) and incubated with 25 μl of a 4× serial dilution of each ADC and naked antibody prepared in cell culture media were added at concentrations of 0.013, 0.133, 1.33, 13.3, 133, 266, and 633 nM for Phor18-$V_L$-scFv-Fc-$C_H3$-Phor18 and Phor18-$V_L$-scFvFc and 0.013-266 nM for the naked antibody scFv-Fc and scFvFc-$C_H3$-Phor18.

Cells incubated for 4 hours were assayed for membrane integrity using a luminometric assay kit (Promega, Madison, Wis., Cytotox Glo G9292 lot #26229601). Cell viability was determined was determined after 24, and 48 hours using a luminescent assay kit (Promega, Madison, Wis., Cell Titer Glo, G 7572, lot 31386501). Controls for 100% cell viability (culture media) and 100% cell death (0.1% Triton X 100) incubated under the same conditions.

Data were processed and analyzed to obtain $IC_{50}$ values using Graph Pad Prizm version 5.00 for Windows, GraphPad Software, San Diego Calif. USA, wwwdotgraphpaddotcom (Graph Pad Prizm, Inc). Statistical analysis for significance was determined by a two-tailed Student's T-test. Each test was conducted using 2 plates with 2-3 wells each to achieve an N of 4-6 data points per time point.

Figure 13:
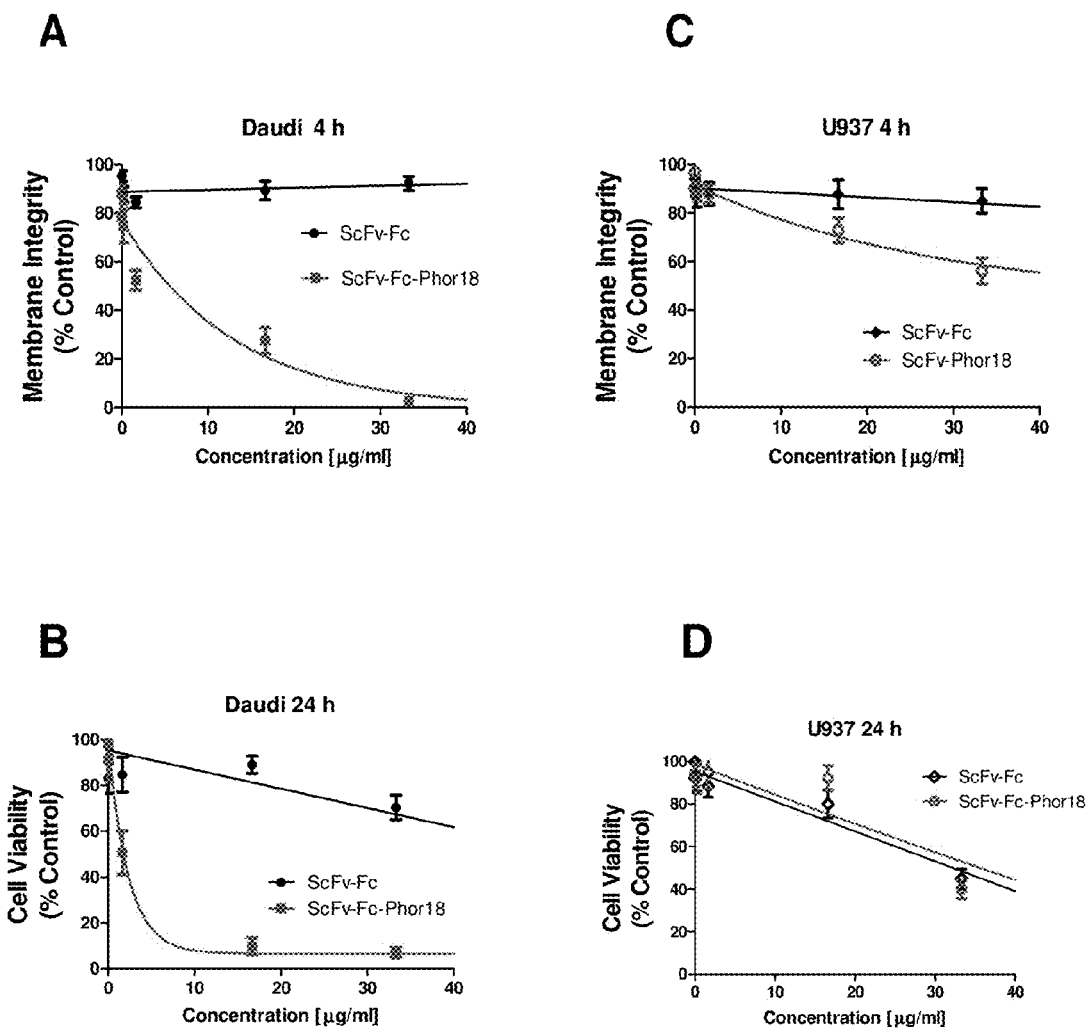
FIGS. 13A-13D show in vitro activities of scFvFc and Phor18-$V_L$-scFvFc-$C_H$3-Phor18 in CD20 positive Daudi cell lines after A) 4 and B) 24 hours, and in CD20 negative U937 cells after C) 4 and D) 24 hours.
Figure 14:
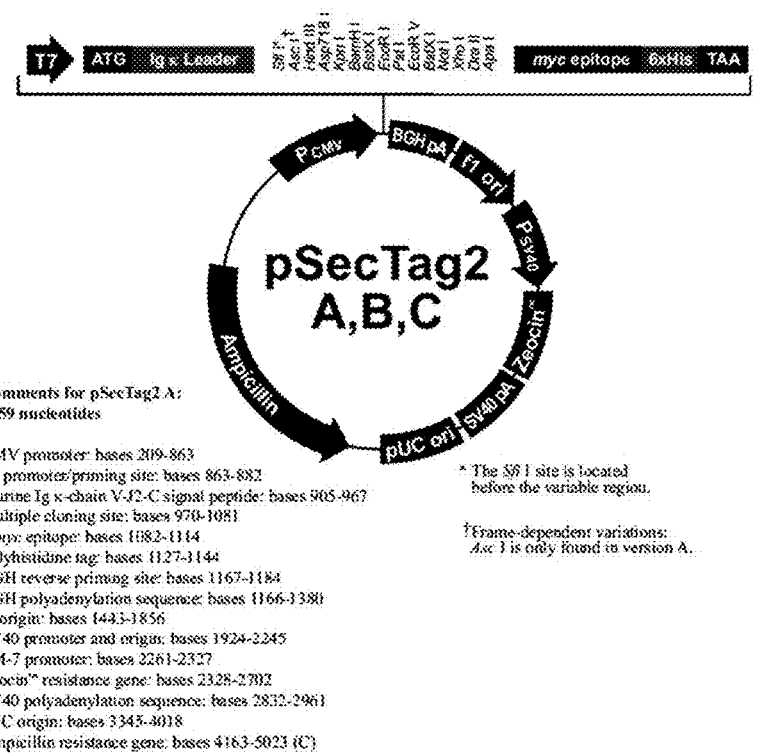
FIG. 14 illustrates expression vector for anti-CD20 ADC and naked antibody expression.

Recombinant ScFv-Fc-Phor18 conjugates were expressed in *Pichia Pastoris*. As shown in FIG. 13 and Table 13, the anti-CD20-Phor18 conjugates destroyed membrane integrity in CD20 positive Daudi cells after 4 h with $IC_{50}$ values of 6.2±2 nM for Phor18-$V_L$-scFv-Fc-$C_H3$-Phor18, and 23.5±2.5 nM for Phor18-$V_L$-scFvFc and 282.4±15 nM for scFv-Fc-$C_H3$-Phor18; unconjugated, naked scFvFc was not toxic. Human Burkitts lymphoma cells (Daudi) were killed within 24 h with $IC_{50}$ values of 9.9±2 nM for Phor18-$V_L$-scFv-Fc-$C_H3$-Phor18, and 18.8±4 nM for Phor18-$V_L$-scFvFc and 141.1±6 nM for scFv-Fc-$C_H3$-Phor18; naked scFvFc had a $IC_{50}$ value of 287±28 nM. The lowest $IC_{50}$ values were measured after 48 hours with 1.6±0.3 nM for Phor18-$V_L$-scFv-Fc-$C_H3$-Phor18, and 3.4±0.05 nM for Phor18-$V_L$-scFvFc and 106±10 nM for scFv-Fc-$C_H3$-Phor18; naked scFvFc had a $IC_{50}$ value of 339±26 nM. The CD20 negative human leukemia cells (U937) showed the same response to either conjugated and unconjugated ADC: after 4 hours no effects on membrane integrity, $IC_{50}$ values after 24 hours were comparable to naked scFv-Fc with 298±13.4, 246.1±14.8 for Phor18-$V_L$-scFv-Fc-$C_H3$-Phor18, 875±81 for Phor18-$V_L$-scFvFc and 274±154 nM for scFv-Fc-$C_H3$-Phor18.

These data demonstrate that N-terminal conjugated ADCs are more potent than C-terminal conjugated ADCs. ADCs with 4 Phor18 molecules were more active than conjugates with 2 Phor18 molecules.

TABLE 13

In vitro toxicities of Phor18-V$_L$-scFv-Fc and scFv-Fc-C$_H$3-Phor18,
Phor18-V$_L$-scFv-Fc-C$_H$3-Phor18 and scFv-Fc targeting CD 20.
Daudi cells (NHL) are positive for CD 20, U937 cells (leukemia) are negative for CD20.

|  | scFvFc (naked) | Phor18-V$_L$-scFv-Fc-C$_H$3-Phor18 | Phor18-V$_L$-scFv-Fc | scFv-Fc-C$_H$3-Phor18 |
|---|---|---|---|---|
| Number of Phor18 | 0 | 4 (N- and C-terminus) | 2 (N-terminus) | 2 (C-terminus) |
|  | IC$_{50}$ values [nM] | IC$_{50}$ values [nM] | IC$_{50}$ values [nM] | IC$_{50}$ values [nM] |
| Daudi |  |  |  |  |
| 4 h (Membrane integrity) | Not toxic | 6.2 ± 2 | 23.5 ± 2.5 | 282.4 ± 15 |
| 24 h | 287 ± 28 | 9.9 ± 2 | 18.8 ± 4 | 141.1 ± 6 |
| 48 h | 339 ± 26 | 1.6 ± 0.3 | 3.4 ± 0.05 | 106 ± 10 |
| U937 |  |  |  |  |
| 4 h (Membrane integrity) | Not toxic | Not toxic | Not toxic | Not toxic |
| 24 h | 298 ± 13.4 | 246.1 ± 14.8 | 875 ± 81 | 274 ± 154 |
| 48 h | 112.7 ± 4 | 117 ± 7 | Not toxic | 116 ± 4.5 |

Potent scFv-Fc-Phor18 conjugates with 2 and 4 Phor18 molecules at the N- or C-terminus and N- and C-terminus were expressed in *Pichia Pastoris*. The ADCs were more potent than naked scFv-Fc. ScFv-Fc-Phor18 conjugates destroyed membrane integrity of the target cells when N and C-terminus was conjugated or N-terminus was conjugated. C-terminus conjugation was 50-100 fold less active compared to N-terminus and C- and N-terminus conjugated ADCs. CD20 targeted ADCs killed specifically target cells—the cell death was independent on internalization. Increasing numbers of Phor18 on ADC resulted in increased potency.

Example 21

This example describes IgG2-Phor18 conjugates produced in mammalian system:

CHO cell expressed CD20 targeting ADCs represented whole antibodies and were conjugated to 2, 4 and 6 Phor18 at different locations. The produced ADCs were characterized to confirm Phor18 presence on heavy and light chains, their molecular weights.

Cytotoxicity was determined in vitro using the recombinantly produced CD20 targeting IgG2-Phor18 conjugates from a CHO cell expression system and compared with "naked" antibody (Rituxan) in CD20 positive cells (Daudi, Burkitts lymphoma). CD20 negative leukemia cells (U937) served as controls.

The V$_L$ and V$_H$ domains of the anti-CD20 ADC are humanized sequences from anti-p185 Herceptin with the CDRs replaced by Rituxan anti-CD20 CDRs. Whole human IgG2 was used for the full antibody backbone with the λ isoform of the constant light (C$_L$) domain.

The IgG2 isoform was chosen to minimize FcR interactions and limit binding and killing of immune cells by Rituxan ADCs. Gene synthesis was conducted by Genscript USA Inc., Piscataway, N.J., with codon usage optimized for CHO cells. The amino acid sequences of the "unconjugated" anti-CD20 antibody Anti-CD20 antibody heavy (H) and light (L) chains are shown below. Rituxan CDRs in variable domains are shown in bold type.

Anti-CD20 Antibody Amino Acid Sequence of Light Chain and Heavy Chain With Rituxan CDRs

```
Light chain: V_L
                                                          (SEQ ID NO.: 105)
         10         20         30         40         50         60
MDIQMTQSPS SLSASVGDRV TITCRASSSV SYIHWYQQKP GKAPKLLIYA TSNLASGVPS 70         80         90        100
RFSGSRSGTD FTLTISSLQP EDFATYYCQQ WTSNPPTFGQ GTKVEIKR C_L (λ)
                                                          (SEQ ID NO.: 106)
         10         20         30         40         50         60
GQPKANPTVT LFPPSSEELQ ANKATLVCLI SDFYPGAVTV AWKADGSPVK AGVETTKPSK 70         80         90        100
QSNNKYAASS YLSLTPEQWK SHRSYSCQVT HEGSTVEKTV APTECS
```

-continued

Heavy chain: V_H (SEQ ID NO.: 107)

```
        10         20         30         40         50         60
MEVQLVESGG GLVQPGGSLR LSCAASGYTF TSYNMHWVRQ APGKGLEWVA AIYPGNGDTS 70         80         90        100        110        120
YNQKFKGRFT ISADTSKNTA YLQMNSLRAE DTAVYYCSRS TYYGGDWYFD VWGQGTLVTV

SS
```

IGg2 C_H1 and hinge (SEQ ID NO.: 108)

```
        10         20         30         40         50         60
ASTKGPSVFP LAPCSRSTSE STAALGCLVK DYFPEPVTVS WNSGALTSGV HTFPAVLQSS 70         80         90        100        110
GLYSLSSVVT VPSSNFGTQT YTCNVDHKPS NTKVDKTVER KCCVECPPCP
```

IGg2 C_H2 and C_H3

(SEQ ID NO.: 109)

```
        10         20         30         40         50         60
APPVAGPSVF LFPPKPKDTL MISRTPEVTC VVVDVSHEDP EVQFNWYVDG VEVHNAKTKP 70         80         90        100        110        120
REEQFNSTFR VVSVLTVVHQ DWLNGKEYKC KVSNKGLPAP IEKTISKTKG QPREPQVYTL 130        140        150        160        170        180
PPSREEMTKN QVSLTCLVKG FYPSDIAVEW ESNGQPENNY KTTPPMLDSD GSFFLYSKLT 190        200        210
VDKSRWQQGN VFSCSVMHEA LHNHYTQKSL SLSPGK
```

Recombinant expression of whole IgG2 antibody-Phor18 (KFAKFAKKFAKFAK KFAK (SEQ ID NO.:4)) conjugates in a mammalian system (CHO cells). Heavy and light chain transcripts were synthesized out of the Genscript DNA transcripts using PCR primers with Asc1 and EcoR1 restriction sites for directional cloning into the pSECTag2 mammalian expression plasmid (Invitrogen cat #V900-20, lot 842626). The pSecTag2 plasmid was chosen because it has a mammalian CMV promoter and an Igk signal sequence for secretion of the antibody. Because of the location of the multiple cloning site in the expression plasmid relative to the signal sequence, cleavage of the signal peptide in the expressed ADC protein leaves the following 6 amino acids on the N-terminus of each peptide because of the plasmid design: DAAQPA (SEQ ID NO.:152).

Genscript ADC transcript DNA sequences are shown below for the full light chain and full heavy chain of the ADC with Phor18 (italics):

Sequence of the Gene for Expression of CD20 Targeting Antibody-Phor18 Conjugates in CHO Cells The full ADC light chain target sequence is:

(SEQ ID NO.:110)

ATGAAGTTCGCAAAGTTCGCCAAAAAGTTCGCAAAGTTCGCAAAAAAGTTCGCCAAAG

*GGTCA*GATATTCAGATGACTCAGAGCCCCAGCTCCCTGTCCGCATCTGTGGGCGACCG

AGTCACTATCACCTGCCGAGCCTCTAGTTCAGTGAGCTACATTCACTGGTATCAGCAGAA

GCCTGGGAAAGCCCCAAAGCTGCTCATCTACGCCACAAGCAACCTGGCTTCCGGTGTG

CCTTCTAGGTTCAGTGGGTCAAGAAGCGGTACAGACTTTACACTGACTATTAGCTCCCTC

CAGCCAGAGGATTTCGCCACTTACTATTGCCAGCAGTGGACTTCCAATCCCCCTACCTTT

GGCCAGGGAACAAAAGTGGAAATCAAGGGGCAGCCCAAAGCTAACCCTACCGTCACAC

TGTTCCCACCCTCTAGTGAGGAACTCCAGGCAAATAAGGCCACTCTGGTGTGTCTCATTT

CCGACTTTTACCCCGGAGCTGTGACCGTCGCTTGGAAGGCAGATGGCTCTCCAGTGAAA

GCAGGAGTCGAGACCACAAAACCCAGTAAGCAGTCAAACAATAAGTACGCCGCTTCAAG

CTATCTGAGTCTCACCCCTGAACAGTGGAAAAGCCATAGGTCCTATTCTTGCCAGGTCAC

TCACGAAGGTAGCACTGTGGAAAAGACTGTCGCACCAACCGAATGTAG*CGGCTCCAAG*

*GCTTTCAAGAAGGCCTTCAAGGCCTTCAAGAAAGCATTCAAGGCCTTTAAA*TGATAA

-continued

The full ADC heavy chain target sequence is:
(SEQ ID NO.:111)

ATGAAGTTCGCCAAATTTGCTAAGAAATTGCAAAGTTTGCCAAGAAATTCGCTAAAG

*GCTCC*GAAGTGCAGCTCGTCGAAAGCGGGGGGGACTCGTGCAGCCAGGGGAAGCC

TCAGACTCTCATGCGCCGCCTCAGGTTATACTTTCACAAGCTACAACATGCACTGGGTCA

GACAGGCACCTGGGAAGGGTCTGGAGTGGGTGGCCGCTATCTACCCAGGCAACGGAG

ACACATCTTATAATCAGAAGTTCAAAGGCCGGTTTACTATTAGCGCAGATACATCCAAGA

ACACTGCCTACCTGCAGATGAATAGCCTCCGGGCTGAAGACACTGCAGTGTACTATTGC

AGTCGCTCAACCTACTATGGCGGAGACTGGTATTTCGATGTGTGGGGGCAGGGTACTCT

GGTCACCGTGAGCTCCGCCTCTACCAAGGGGCCCAGTGTGTTTCCACTGGCTCCCTGC

AGCCGGTCCACCTCTGAGAGTACAGCAGCCCTGGGTTGTCTCGTGAAAGATTACTTCCC

TGAACCAGTCACCGTGTCCTGGAACTCTGGCGCTCTGACCAGCGGAGTCCACACATTTC

CTGCAGTGCTCCAGTCTAGTGGGCTGTACTCCCTCTCAAGCGTGGTCACAGTCCCATCC

TCTAATTTCGGTACTCAGACCTATACATGCAACGTGGACCATAAGCCCTCCAATACTAAG

GTCGATAAAACCGTGGAGCGCAAATGCTGTGTGGAATGCCCACCTTGTCCAGCACCACC

AGTCGCTGGGCCTAGCGTGTTCCTGTTTCCTCCAAAGCCAAAAGACACTCTCATGATCTC

TCGAACTCCCGAGGTCACCTGTGTGGTCGTGGACGTCAGTCACGAGGATCCTGAAGTC

CAGTTTAACTGGTACGTGGATGGAGTCGAAGTGCATAATGCAAAGACCAAACCAAGGGA

GGAACAGTTCAACTCAACCTTTAGAGTCGTGAGCGTGCTGACAGTCGTGCATCAGGACT

GGCTCAACGGGAAGGAGTATAAGTGCAAAGTGTCTAATAAGGGTCTGCCCGCTCCTATC

GAGAAAACAATTAGCAAGACTAAAGGACAGCCTCGAGAACCACAGGTGTACACACTGCC

CCCTAGCAGGGAGGAAATGACAAAGAACCAGGTCTCCCTGACTTGTCTCGTGAAAGGCT

TCTATCCCAGTGACATTGCCGTGGAGTGGGAATCAAATGGACAGCCTGAGAACAATTAC

AAGACCACACCACCCATGCTGGACAGTGATGGCTCATTCTTTCTGTATTCCAAGCTCACC

GTGGATAAATCTAGGTGGCAGCAGGGAAATGTCTTTTCATGTAGCGTGATGCACGAGGC

TCTCCATAACCATTACACCCAGAAGTCCCTGTCACTCTCCCCCGGCAAA*GGCTCCAAGG*

*CTTTCAAGAAGGCCTTCAAGGCCTTCAAGAAAGCATTCAAGGCCTTTAAA*TGATAA

PCR primers used to subclone the light chains and heavy chains are shown below.

ADC PCR Primers:
Forward primers have the ASCI restriction site (GGCGCGCC) at the 5' end.
Reverse primers have the EcoR1 restriction site (GAATTC) at the 5' end.

```
Light chain primers
                                    (SEQ ID NOs.: 112-115)
480L for: GGGGGCGCGCC GATATTCAGATGACTCAGAGCC (Tm = 55.6)

485Lfor: GGGGGCGCGCC AAGTTCGCAAAGTTCGCCAA (Tm = 63)

480Lrev: GGG GAATTC TTATCAGCTACATTCGGTTGGT(Tm = 58.65)

487Lrev: GGG GAATTC TTATCATTTAAAGGCCTTGAATGCT (Tm =
61.37) Mar18
```

-continued

Heavy chain primers
(SEQ ID NOs.: 116-118)
480Hfor: GGG GGCGCGCC GAAGTGCAGCTCGTCGAAAG (Tm = 61)

485Hfor: GGG GGCGCGCC AAGTTCGCCAAATTTGCTAAGA (Tm = 60.25)

480Hrev: GGG GAATTC TTATCATTTGCCGGGGGA (Tm = 62)

The amino acid sequences for each of the naked IgG2 antibody and the Phor18-IgG2 conjugates with 2 Phor18 molecules (Phor18-$V_L$ IgG2, Phor18-$V_H$IgG2), 4 Phor18 molecules (Phor18-$V_L$-Phor18$V_H$-IgG2), 6 Phor18 molecules (Phor18-$V_L$-$C_L$-Phor18-Phor18-$V_H$-IgG2) and 8 Phor18 molecules Phor18-$V_L$-$C_L$-Phor18-$V_H$-Phor18-$C_H$3-Phor18-IgG2 and Phor18-$V_L$-$C_L$-Phor18-$V_H$-Phor18-$C_H$3-IgG2) are shown below.

Amino Acid Sequences of Naked Antibody, Lytic-Peptide Phor18-Antibody Heavy and Light Chain Conjugates

```
IgG2 (480) (naked)
Light chain
                                                    (SEQ ID NO.: 119)
          10         20         30         40         50         60
DIQMTQSPSS LSASVGDRVT ITCRASSSVS YIHWYQQKPG KAPKLLIYAT SNLASGVPSR 70         80         90        100        110        120
FSGSRSGTDF TLTISSLQPE DFATYYCQQW TSNPPTFGQG TKVEIKGQPK ANPTVTLFPP 130        140        150        160        170        180
SSEELQANKA TLVCLISDFY PGAVTVAWKA DGSPVKAGVE TTKPSKQSNN KYAASSYLSL 190        200        210
TPEQWKSHRS YSCQVTHEGS TVEKTVAPTE CS Heavy chain
                                                    (SEQ ID NO.: 120)
          10         20         30         40         50         60
EVQLVESGGG LVQPGGSLRL SCAASGYTFT SYNMHWVRQA PGKGLEWVAA IYPGNGDTSY 70         80         90        100        110        120
NQKFKGRFTI SADTSKNTAY LQMNSLRAED TAVYYCSRST YYGGDWYFDV WGQGTLVTVS 130        140        150        160        170        180
SASTKGPSVF PLAPCSRSTS ESTAALGCLV KDYFPEPVTV SWNSGALTSG VHTFPAVLQS 190        200        210        220        230        240
SGLYSLSSVV TVPSSNFGTQ TYTCNVDHKP SNTKVDKTVE RKCCVECPPC PAPPVAGPSV 250        260        270        280        290        300
FLFPPKPKDT LMISRTPEVT CVVVDVSHED PEVQFNWYVD GVEVHNAKTK PREEQFNSTF 310        320        330        340        350        360
RVVSVLTVVH QDWLNGKEYK CKVSNKGLPA PIEKTISKTK GQPREPQVYT LPPSREEMTK 370        380        390        400        410        420
NQVSLTCLVK GFYPSDIAVE WESNGQPENN YKTTPPMLDS DGSFFLYSKL TVDKSRWQQG 430        440
NVFSCSVMHE ALHNHYTQKS LSLSPGK Phor18-V_L IgG2 (481) (2 Phor18, N-terminus)
Light chain
                                                    (SEQ ID NO.: 121)
          10         20         30         40         50         60
MKFAKFAKKF AKFAKKFAKG SDIQMTQSPS SLSASVGDRV TITCRASSSV SYIHWYQQKP 70         80         90        100        110        120
GKAPKLLIYA TSNLASGVPS RFSGSRSGTD FTLTISSLQP EDFATYYCQQ WTSNPPTFGQ 130        140        150        160        170        180
GTKVEIKGQP KANPTVTLFP PSSEELQANK ATLVCLISDF YPGAVTVAWK ADGSPVKAGV 190        200        210        220        230
ETTKPSKQSN NKYAASSYLS LTPEQWKSHR SYSCQVTHEG STVEKTVAPT ECS Heavy chain
                                                    (SEQ ID NO.: 122)
          10         20         30         40         50         60
EVQLVESGGG LVQPGGSLRL SCAASGYTFT SYNMHWVRQA PGKGLEWVAA IYPGNGDTSY 70         80         90        100        110        120
NQKFKGRFTI SADTSKNTAY LQMNSLRAED TAVYYCSRST YYGGDWYFDV WGQGTLVTVS
```

-continued

```
             130        140        150        160        170        180
        SASTKGPSVF PLAPCSRSTS ESTAALGCLV KDYFPEPVTV SWNSGALTSG VHTFPAVLQS 190        200        210        220        230        240
        SGLYSLSSVV TVPSSNFGTQ TYTCNVDHKP SNTKVDKTVE RKCCVECPPC PAPPVAGPSV 250        260        270        280        290        300
        FLFPPKPKDT LMISRTPEVT CVVVDVSHED PEVQFNWYVD GVEVHNAKTK PREEQFNSTF 310        320        330        340        350        360
        RVVSVLTVVH QDWLNGKEYK CKVSNKGLPA PIEKTISKTK GQPREPQVYT LPPSREEMTK 370        380        390        400        410        420
        NQVSLTCLVK GFYPSDIAVE WESNGQPENN YKTTPPMLDS DGSFFLYSKL TVDKSRWQQG 430        440
        NVFSCSVMHE ALHNHYTQKS LSLSPGK
```

Phor18-V$_H$ IgG2 (483) (2 Phor18, N-terminus)
Light chain

```
                                                          (SEQ ID NO.: 123)
             10         20         30         40         50         60
        DIQMTQSPSS LSASVGDRVT ITCRASSSVS YIHWYQQKPG KAPKLLIYAT SNLASGVPSR 70         80         90        100        110        120
        FSGSRSGTDF TLTISSLQPE DFATYYCQQW TSNPPTFGQG TKVEIKGQPK ANPTVTLFPP 130        140        150        160        170        180
        SSEELQANKA TLVCLISDFY PGAVTVAWKA DGSPVKAGVE TTKPSKQSNN KYAASSYLSL 190        200        210
        TPEQWKSHRS YSCQVTHEGS TVEKTVAPTE CS
```

Heavy chain

```
                                                          (SEQ ID NO.: 124)
             10         20         30         40         50         60
        MKFAKFAKKF AKFAKKFAKG SEVQLVESGG GLVQPGGSLR LSCAASGYTF TSYNMHWVRQ 70         80         90        100        110        120
        APGKGLEWVA AIYPGNGDTS YNQKFKGRFT ISADTSKNTA YLQMNSLRAE DTAVYYCSRS 130        140        150        160        170        180
        TYYGGDWYFD VWGQGTLVTV SSASTKGPSV FPLAPCSRST SESTAALGCL VKDYFPEPVT 190        200        210        220        230        240
        VSWNSGALTS GVHTFPAVLQ SSGLYSLSSV VTVPSSNFGT QTYTCNVDHK PSNTKVDKTV 250        260        270        280        290        300
        ERKCCVECPP CPAPPVAGPS VFLFPPKPKD TLMISRTPEV TCVVVDVSHE DPEVQFNWYV 310        320        330        340        350        360
        DGVEVHNAKT KPREEQFNST FRVVSVLTVV HQDWLNGKEY KCKVSNKGLP APIEKTISKT 370        380        390        400        410        420
        KGQPREPQVY TLPPSREEMT KNQVSLTCLV KGFYPSDIAV EWESNGQPEN NYKTTPPMLD 430        440        450        460
        SDGSFFLYSK LTVDKSRWQQ GNVFSCSVMH EALHNHYTQK SLSLSPGK
```

Phor18-V$_L$-Phor18V$_H$-IgG2 (485) (4 Phor18, 2 N-terminus)
Light chain

```
                                                          (SEQ ID NO.: 125)
             10         20         30         40         50         60
        MKFAKFAKKF AKFAKKFAKG SDIQMTQSPS SLSASVGDRV TITCRASSSV SYIHWYQQKP 70         80         90        100        110        120
        GKAPKLLIYA TSNLASGVPS RFSGSRSGTD FTLTISSLQP EDFATYYCQQ WTSNPPTFGQ 130        140        150        160        170        180
        GTKVEIKGQP KANPTVTLFP PSSEELQANK ATLVCLISDF YPGAVTVAWK ADGSPVKAGV 190        200        210        220        230
        ETTKPSKQSN NKYAASSYLS LTPEQWKSHR SYSCQVTHEG STVEKTVAPT ECS
```

Heavy chain

```
                                                          (SEQ ID NO.: 126)
             10         20         30         40         50         60
        MKFAKFAKKF AKFAKKFAKG SEVQLVESGG GLVQPGGSLR LSCAASGYTF TSYNMHWVRQ 70         80         90        100        110        120
        APGKGLEWVA AIYPGNGDTS YNQKFKGRFT ISADTSKNTA YLQMNSLRAE DTAVYYCSRS
```

-continued

```
              130        140        150        160        170        180
       TYYGGDWYFD VWGQGTLVTV SSASTKGPSV FPLAPCSRST SESTAALGCL VKDYFPEPVT 190        200        210        220        230        240
       VSWNSGALTS GVHTFPAVLQ SSGLYSLSSV VTVPSSNFGT QTYTCNVDHK PSNTKVDKTV 250        260        270        280        290        300
       ERKCCVECPP CPAPPVAGPS VFLFPPKPKD TLMISRTPEV TCVVVDVSHE DPEVQFNWYV 310        320        330        340        350        360
       DGVEVHNAKT KPREEQFNST FRVVSVLTVV HQDWLNGKEY KCKVSNKGLP APIEKTISKT 370        380        390        400        410        420
       KGQPREPQVY TLPPSREEMT KNQVSLTCLV KGFYPSDIAV EWESNGQPEN NYKTTPPMLD 430        440        450        460
       SDGSFFLYSK LTVDKSRWQQ GNVFSCSVMH EALHNHYTQK SLSLSPGK
```

Phor18-$V_L$-$C_L$-Phor18-Phor18-$V_H$-IgG2 (487) (6 Phor18, 2 N and 1 C-terminus)
Light chain

```
                                                            (SEQ ID NO.: 127)
              10         20         30         40         50         60
       MKFAKFAKKF AKFAKKFAKG SDIQMTQSPS SLSASVGDRV TITCRASSSV SYIHWYQQKP 70         80         90         100        110        120
       GKAPKLLIYA TSNLASGVPS RFSGSRSGTD FTLTISSLQP EDFATYYCQQ WTSNPPTFGQ 130        140        150        160        170        180
       GTKVEIKGQP KANPTVTLFP PSSEELQANK ATLVCLISDF YPGAVTVAWK ADGSPVKAGV 190        200        210        220        230        240
       ETTKPSKQSN NKYAASSYLS LTPEQWKSHR SYSCQVTHEG STVEKTVAPT ECSGSKAFKK

250
       AFKAFKKAFK AFK
```

Heavy chain

```
                                                            (SEQ ID NO.: 128)
              10         20         30         40         50         60
       MKFAKFAKKF AKFAKKFAKG SEVQLVESGG GLVQPGGSLR LSCAASGYTF TSYNMHWVRQ 70         80         90         100        110        120
       APGKGLEWVA AIYPGNGDTS YNQKFKGRFT ISADTSKNTA YLQMNSLRAE DTAVYYCSRS 130        140        150        160        170        180
       TYYGGDWYFD VWGQGTLVTV SSASTKGPSV FPLAPCSRST SESTAALGCL VKDYFPEPVT 190        200        210        220        230        240
       VSWNSGALTS GVHTFPAVLQ SSGLYSLSSV VTVPSSNFGT QTYTCNVDHK PSNTKVDKTV 250        260        270        280        290        300
       ERKCCVECPP CPAPPVAGPS VFLFPPKPKD TLMISRTPEV TCVVVDVSHE DPEVQFNWYV 310        320        330        340        350        360
       DGVEVHNAKT KPREEQFNST FRVVSVLTVV HQDWLNGKEY KCKVSNKGLP APIEKTISKT 370        380        390        400        410        420
       KGQPREPQVY TLPPSREEMT KNQVSLTCLV KGFYPSDIAV EWESNGQPEN NYKTTPPMLD 430        440        450        460
       SDGSFFLYSK LTVDKSRWQQ GNVFSCSVMH EALHNHYTQK SLSLSPGK
```

Phor18-$V_L$-$C_L$-Phor18-$V_H$-Phor18-$C_H$3-Phor18-IgG2 (489) (8 Phor18, 2 N and 2 C-terminus)
Light chain

```
                                                            (SEQ ID NO.: 129)
              10         20         30         40         50         60
       MKFAKFAKKF AKFAKKFAKG SDIQMTQSPS SLSASVGDRV TITCRASSSV SYIHWYQQKP 70         80         90         100        110        120
       GKAPKLLIYA TSNLASGVPS RFSGSRSGTD FTLTISSLQP EDFATYYCQQ WTSNPPTFGQ 130        140        150        160        170        180
       GTKVEIKGQP KANPTVTLFP PSSEELQANK ATLVCLISDF YPGAVTVAWK ADGSPVKAGV 190        200        210        220        230        240
       ETTKPSKQSN NKYAASSYLS LTPEQWKSHR SYSCQVTHEG STVEKTVAPT ECSGSKAFKK
```

-continued

```
                250
AFKAFKKAFK AFK

Heavy chain
                                                            (SEQ ID NO.: 130)
         10         20         30         40         50         60
MKFAKFAKKF AKFAKKFAKG SEVQLVESGG GLVQPGGSLR LSCAASGYTF TSYNMHWVRQ 70         80         90        100        110        120
APGKGLEWVA AIYPGNGDTS YNQKFKGRFT ISADTSKNTA YLQMNSLRAE DTAVYYCSRS 130        140        150        160        170        180
TYYGGDWYFD VWGQGTLVTV SSASTKGPSV FPLAPCSRST SESTAALGCL VKDYFPEPVT 190        200        210        220        230        240
VSWNSGALTS GVHTFPAVLQ SSGLYSLSSV VTVPSSNFGT QTYTCNVDHK PSNTKVDKTV 250        260        270        280        290        300
ERKCCVECPP CPAPPVAGPS VFLFPPKPKD TLMISRTPEV TCVVVDVSHE DPEVQFNWYV 310        320        330        340        350        360
DGVEVHNAKT KPREEQFNST FRVVSVLTVV HQDWLNGKEY KCKVSNKGLP APIEKTISKT 370        380        390        400        410        420
KGQPREPQVY TLPPSREEMT KNQVSLTCLV KGFYPSDIAV EWESNGQPEN NYKTTPPMLD 430        440        450        460        470        480
SDGSFFLYSK LTVDKSRWQQ GNVFSCSVMH EALHNHYTQK SLSLSPGKGS KAFKKAFKAF

KKAFKAFK
```

Invitrogen free-style suspension grown CHO cells (Free-style MAX CHO expression system cat #K9000-20) were transfected using Invitrogen protocols. Briefly, FS CHO cells were expanded for 6 to 7 days after thawing to rapid growth phase, doubling every 24 h. The day before transfection, clumps were removed, cells were pelleted and resuspended in P/S-free medium at $5\times10^5$/ml. On the day of transfection, 30 ml cultures of cells were adjusted to $9\times10^5$/ml if necessary and viability should be close to 99%.

Each 125 ml spinner flask (VWR cat #PBV125) of 30 ml cells was transfected with 35 μg of total plasmid DNA mixed with 35 μl of FSMax transfection reagent (Invitrogen cat #16447-100). DNA should be at 1 mg/ml or higher in concentration. Cells were swirled rapidly while adding DNA mixture slowly. Ratios of H:L chains tested were 3:2, 1:1, and 2:3.

Protein was harvested on day 3 and day 6 after transfection. Approximately 0.25 ml of protein A resin (Genscript L00210, capacity >20 mg IgG per ml resin) was used to isolate secreted ADCs from the FS CHO medium using the Genscript protocol provided. The expressed anti-CD20 IgG2 antibody (humanized variable light and heavy domains regions to CD20 receptor) and the various antibody-Phor18 conjugates with stoichiometric ratios of Phor18: AB of 2:1, 4:1 and 6:1 were characterized using SDS PAGE, and Western blot analyses (Table 14).

ADCs were probed on Western blots probed with anti-Phor18. All ADCs have a single Phor18 on the heavy and light chains. Yield, purity and cytotoxicity of recombinantly produced antibodies (as a full IgG2 antibody) with Heavy (H) or Light (L) chain C-terminal- or N-terminal-Phor18 conjugation was analyzed. Two, 4 and 6 molecules of lytic domains (Phor18) conjugated to whole antibody molecule were expressed.

The concentration of recombinantly produced antibody and antibody-Phor18 conjugates was determined using spectrophotometric measurements ($OD_{280}$) and were as follows: IgG2 (Mw 150,000; 1.096 mg/ml), Phor18-$V_L$-IgG2 (Mw 154,340 g/mol, 0.561 mg/ml), Phor18-$V_H$-IgG2 (Mw 154,340 g/mol, 0.1 mg/ml) and Phor18-$V_L$-Phor18$V_H$-IgG2 (Mw 158,400 g/mol, 0.561 mg/ml) and Phor18-$V_L$-Phor18$V_H$-$C_L$-Phor18-IgG2 (Mw 162,600, 0.07 mg/ml).

Example 22

This example describes in vitro activity of recombinantly produced IgG2-Phor18 conjugates.

The cytotoxicity of recombinantly produced CD20 targeting IgG2-Phor18 conjugates in a mammalian expression system was compared with "naked" antibody (IgG2) in CD20 positive cells (Daudi, Burkitts lymphoma). CD20 negative leukemia cells (U937) served as controls. CHO cell

TABLE 14

ADC descriptions for CD20 targeting ADC

| Name of ADC | ID | Phor18 location | Number of Phor18/Antibody |
|---|---|---|---|
| IgG2 | 480 | None ('Naked') | 0 |
| Phor18-$V_L$-IgG2 | 481 | N-termini light chains ($V_L$) | 2 |
| Phor18-$V_H$-IgG2 | 483 | N-termini heavy chains ($V_H$) | 2 |
| Phor18-$V_L$-Phor18-$V_H$-IgG2 | 485 | N-termini heavy and light chains ($V_H$, $V_L$) | 4 |
| Phor18-$V_L$-Phor18-$V_H$-$C_L$-Phor18-IgG2 | 487 | N-termini and C-termini light chains ($V_L$, $V_H$, $C_L$) | 6 |
| Phor18-$V_L$-$C_L$-Phor18-$V_H$-Phor18-$C_H$3-Phor18-IgG2 | 489 | N-termini and C-termini light chains ($V_L$, $C_L$, $V_H$, $C_H$3) | 8 | expressed ADCs represented intact antibodies and were conjugated to 2, 4 and 6 Phor18 molecules at the N-terminus of the $V_L$ chain at the N-terminus of the $V_H$ chain, at the N-terminus of the $V_H$ and $V_L$ chain and at the N-terminus at the $V_L$, $V_H$ and C-terminus of the $C_L$ chain. The sequence descriptions are summarized in Table 14.

Human Non-Hodgkin's lymphoma cells Daudi (CD20 positive, passage number p6) and human leukemia cell line U937 (CD20 negative, p 10) were seeded at a density of 2,000 cells per well in opaque plates in heat inactivated full medium using cell dissociation buffer. After 24 hours cells were replenished with fresh media (75 µl) and incubated with 25 µl of a 4× serial dilution of each ADC and naked antibody prepared in cell culture media were added at concentrations between 0.001-200 nM for IgG2, Phor18-$V_L$-IgG2, Phor18-$V_H$-IgG2 and Phor18-$V_L$-Phor18$V_H$-IgG2, and 0.001-100 nM for Phor18-$V_L$-Phor18$V_H$-CL-Phor18-IgG2.

Cells incubated for 4 hours were assayed for membrane integrity using a luminometric assay kit (Promega, Madison, Wis., Cytotox Glo G9292 lot #317872). Cell viability was determined was determined after 24, and 48 hours using a luminescent assay kit (Promega, Madison, Wis., Cell Titer Glo, G 7572, lot 336262).

Controls for 100% cell viability (culture media) and 100% cell death (0.1% Triton X 100) incubated under the same conditions.

Data were processed and analyzed to obtain $IC_{50}$ values using Graph Pad Prizm version 5.00 for Windows, GraphPad Software, San Diego Calif. USA, wwwdotgraphpaddotcom (Graph Pad Prizm, Inc). Statistical analysis for significance was determined by a two-tailed Student's T-test. Each test was conducted using double plates of 2-3 wells each to achieve an N of 4-6 data points per time point.

Destruction of membrane integrity was measured after 4 hours at nanomolar concentrations of 1,108±198 for Phor18-$V_H$-IgG2 (2 Phor18), 109.6±20.1 for Phor18-$V_L$-Phor18$V_H$-IgG2 (4 Phor18) and 71.6±29 for Phor18-$V_L$-Phor18$V_H$-$C_L$-Phor18-IgG2 (6 Phor18). Naked antibody was not toxic after 24 or 48 hours to the CD20 positive Daudi cells.

Killing of the target cells after 24 h expressed as $IC_{50}$ values [nM] were 824±63, 75.24±37.5, (2 Phor18), 40.1±15.1 (4 Phor18) and 18.8±5.9 (6 Phor18) nM. Maximal effects measured after 48 h (IC50 [nM]>436 (Phor18-$V_L$-IgG2), 4.8±2 Phor18-$V_H$-IgG2 (2 Clips) and 20.4±8.2 nM Phor18-$V_L$-Phor18$V_H$-IgG2 (4 Clips), and 1.9±0.2 nM Phor18-$V_L$-Phor18$V_H$-$C_L$-Phor18-IgG2 (6 Phor18) respectively). The CD20 negative cell line (U937) was not killed by either naked antibodies or both 2 4, and 6 Phor18 conjugated ADCs after 4 and 24 hours. Toxicity levels after 48 hours were similar with $IC_{50}$ values of 249 and 258 nM. These data demonstrate that position of Phor18 determines the potency of a CD20 ADC with increased potency for Phor18-$V_H$-IgG2. Increase of Phor18 molecules per antibody increased the potency.

Whole antibody Phor18 conjugates with Phor18:antibody stoichiometries of 2, 4 and 6 were recombinantly expressed in CHO cells. These antibody drug conjugates had confirmed Phor18 molecules at heavy and light chains They were active in CD20 positive cells in vitro with activities of membrane disintegration after 4 hours. After 48 hours single digit nanomolar activities were measured that were highest in ADC with 6 and 4 Phor18.

Non-internalizing CD20 antibody conjugates destroyed membrane integrity of target cells (Daudi) within 4 h. Cell death was observed after 24 h with $IC_{50}$ values in the low nanomolar range. CD20 negative cells (U937) were not killed. Full IgG2 ADCs having 4 and 6 clips had increased potency to target positive cells compared to 2 Phor18

TABLE 15

In vitro toxicities of anti-CD20 IgG2, Phor18-$V_L$-IgG2, Phor18-$V_H$-IgG2, Phor18-$V_L$-Phor18$V_H$-IgG2 and Phor18-$V_L$-Phor18$V_H$-$C_L$-Phor18-IgG2, targeting CD 20. Daudi cells (NHL) were positive for CD 20, U937 cells (leukemia) are negative for CD20.

| | IgG2 | Phor18-$V_L$-IgG2 $IC_{50}$ [nM] | Phor18-$V_H$-IgG2 $IC_{50}$ [nM] | Phor18-$V_L$-Phor18$V_H$-IgG2 $IC_{50}$ [nM] | Phor18-$V_L$-Phor18$V_H$-$C_L$-Phor18-IgG2 $IC_{50}$ [nM] |
|---|---|---|---|---|---|
| | naked 0 | $V_L$N-terminus 2 Phor18 | $V_H$N-terminus 2 Phor18 | $V_L$ and $V_H$N-terminus 4 Phor18 | $V_L$ and $V_H$N-terminus, $C_L$ C-terminus 6 Phor18 |
| | $IC_{50}$ [nM] | $IC_{50}$ [nM] | $IC_{50}$ [nM] | $IC_{50}$ [nM] | $IC_{50}$ [nM] |
| Daudi | | | | | |
| 4 h (Membrane integrity) | Not toxic | ND | 1108 ± 198 | 109.6 ± 20.1 | 71.6 ± 29 |
| 24 h | Not toxic | 824 ± 63 | 75.24 ± 37.5 | 40.1 ± 15.1 | 18.8 ± 5.9 |
| 48 h | Not toxic | >436 | 4.8 ± 2 | 20.4 ± 8.2 | 1.9 ± 0.2 |
| U937 | | | | | |
| 4 h (Membrane integrity) | Not toxic | Not toxic | Not toxic | Not toxic | Not toxic |
| 24 h | Not toxic | Not toxic | Not toxic | Not toxic | Not toxic |
| 48 h | Not toxic | >1000 | Not toxic | 249.6 ± 29 | 258 ± 41 |

ND = not determined conjugates. The positioning of Phor18 on the N-terminus generated ADCs with higher potencies. Increase of Phor18 numbers per antibody showed increased potencies.

Higher numbers of Phor18 (six vs four vs two) on the antibody conjugated to the N-terminal domain are more potent compared to naked antibodies.

Example 23

This example includes target sequence information for representative target proteins to which antibody and polypeptide conjugates of the invention can be produced and naked antibodies and their Phor18 conjugates ERBB2 (HER2/NEU) Isoform 1 [UniParc]:
(SEQ ID NO.: 131)

```
         10         20         30         40         50         60
MELAALCRWG LLLALLPPGA ASTQVCTGTD MKLRLPASPE THLDMLRHLY QGCQVVQGNL 70         80         90        100        110        120
ELTYLPTNAS LSFLQDIQEV QGYVLIAHNQ VRQVPLQRLR IVRGTQLFED NYALAVLDNG 130        140        150        160        170        180
DPLNNTTPVT GASPGGLREL QLRSLTEILK GGVLIQRNPQ LCYQDTILWK DIFHKNNQLA 190        200        210        220        230        240
LTLIDTNRSR ACHPCSPMCK GSRCWGESSE DCQSLTRTVC AGGCARCKGP LPTDCCHEQC 250        260        270        280        290        300
AAGCTGPKHS DCLACLHFNH SGICELHCPA LVTYNTDTFE SMPNPEGRYT FGASCVTACP 310        320        330        340        350        360
YNYLSTDVGS CTLVCPLHNQ EVTAEDGTQR CEKCSKPCAR VCYGGMEHLR REVRAVTSAN 370        380        390        400        410        420
IQEFAGCKKI FGSLAFLPES FDGDPASNTA PLQPEQLQVF ETLEEITGYL YISAWPDSLP 430        440        450        460        470        480
DLSVFQNLQV IRGRILHNGA YSLTLQGLGI SWLGLRSLRE LGSGLALIHH NTHLCFVHTV 490        500        510        520        530        540
PWDQLFRNPH QALLHTANRP EDECVGEGLA CHQLCARGHC WGPGPTQCVN CSQFLRGQEC 550        560        570        580        590        600
VEECRVLQGL PREYVNARHC LPCHPECQPQ NGSVTCFGPE ADQCVACAHY KDPPFCVARC 610        620        630        640        650        660
PSGVKPDLSY MPIWKFPDEE GACQPCPINC THSCVDLDDK GCPAEQRASP LTSIISAVVG 670        680        690        700        710        720
ILLVVVLGVV FGILIKRRQQ KIRKYTMRRL LQETELVEPL TPSGAMPNQA QMRILKETEL 730        740        750        760        770        780
RKVKVLGSGA FGTVYKGIWI PDGENVKIPV AIKVLRENTS PKANKEILDE AYVMAGVGSP 790        800        810        820        830        840
YVSRLLGICL TSTVQLVTQL MPYGCLLDHV RENRGRLGSQ DLLNWCMQIA KGMSYLEDVR 850        860        870        880        890        900
LVHRDLAARN VLVKSPNHVK ITDFGLARLL DIDETEYHAD GGKVPIKWMA LESILRRRFT 910        920        930        940        950        960
HQSDVWSYGV TVWELMTFGA KPYDGIPARE IPDLLEKGER LPQPPICTID VYMIMVKCWM 970        980        990       1000       1010       1020
IDSECRPRFR ELVSEFSRMA RDPQRFVVIQ NEDLGPASPL DSTFYRSLLE DDDMGDLVDA 1030       1040       1050       1060       1070       1080
EEYLVPQQGF FCPDPAPGAG GMVHHRHRSS STRSGGGDLT LGLEPSEEEA PRSPLAPSEG 1090       1100       1110       1120       1130       1140
AGSDVFDGDL GMGAAKGLQS LPTHDPSPLQ RYSEDPTVPL PSETDGYVAP LTCSPQPEYV 1150       1160       1170       1180       1190       1200
NQPDVRPQPP SPREGPLPAA RPAGATLERP KTLSPGKNGV VKDVFAFGGA VENPEYLTPQ 1210       1220       1230       1240       1250
GGAAPQPHPP PAFSPAFDNL YYWDQDPPER GAPPSTFKGT PTAENPEYLG LDVPV
```

CD19: B-lymphocyte surface antigen B4, component of the B-cell co-receptor, NCBI Reference Sequence: NP_001171569.1:

```
ORIGIN
                                                        (SEQ ID NO.: 132)
  1 mppprllffl lfltpmevrp eeplvvkvee gdnavlqclk gtsdgptqql twsresplkp
 61 flklslglpg lgihmrplai wlfifnvsqq mggfylcqpg ppsekawqpg wtvnvegsge
121 lfrwnvsdlg glgcglknrs segpsspsgk lmspklyvwa kdrpeiwege ppclpprdsl
181 nqslsqdltm apgstlwlsc gvppdsysrg plswthvhpk gpksllslel kddrpardmw
241 vmetglllpr ataqdagkyy chrgnltmsf hleitarpvl whwllrtggw kvsavtlayl
301 ifclcslvgi lhlqralvlr rkrkrmtdpt rrffkvtppp gsgpqnqygn vlslptptsg
361 lgraqrwaag lggtapsygn pssdvqadga lgsrsppgvg peeeegegye epdseedsef
421 yendsnlgqd qlsqdgsgye npedeplgpe dedsfsnaes yenedeeltq pvartmdfls
481 phgsawdpsr eatslagsqs yedmrgilya apqlrsirgq pgpnheedad syenmdnpdg
541 pdpawggggr mgtwstr
```

CD20: a type III transmembrane protein found on B cells that forms a calcium channel in the cell membrane allowing for the influx of calcium required for cell activation; expressed in B-cell lymphomas, hairy cell leukemia, and B-cell chronic lymphocytic leukemia. Important for therapy of those diseases, as an antibody against CD20 exists: Rituximab. NCBI Reference Sequence NP_068769.2, MS4A1-P11836: (SEQ ID NO.:133)

```
  1 mttprnsvng tfpaepmkgp iamqsgpkpl frrmsslvgp tqsffmresk tlgavqimng
 61 lfhialggll mipagiyapi cvtvwyplwg gimyiisgsl laateknsrk clvkgkmimn
121 slslfaaisg milsimdiln ikishflkme slnfirahtp yiniyncepa npseknspst
181 qycysiqslf lgilsvmlif affqelviag ivenewkrtc srpksnivll saeekkeqti
241 eikeevvglt etssqpknee dieiipiqee eeeetetnfp eppqdqessp iendssp
```

CD22: a sugar binding transmembrane protein that specifically binds sialic acid with an immunoglobulin (Ig) domain located at its N-terminus. It is a member of the immunoglobulin superfamily and the SIGLEC family. CD22 functions as an inhibitory receptor for B cell receptor (BCR) signaling. NCBI Reference Sequence NP_001172028.1:

```
ORIGIN
                                                        (SEQ ID NO.: 134)
  1 mhllgpwlll lvleylafsd sskwvfehpe tlyawegacv wipctyrald gdlesfilfh
 61 npeynkntsk fdgtrlyest kdgkvpseqk rvqflgdknk nctlsihpvh lndsgqlglr
121 mesktekwme rihlnvserp fpphiqlppe igesgevtlt cllnfscygy piqlqwlleg
181 vpmrqaavts tsltiksvft rselkfspqw shhgkivtcq lqdadgkfls ndtvglnvkh
241 tpkleikvtp sdaivregds vtmtcevsss npeyttvswl kdgtslkkqn tftlnlrevt
301 kdqsgkyccq vsndvgpgrs eevflqvqyp pkkvttviqn pmpiregdtv tlscnynssn
361 psvtryewkp hgaweepslg vlkignvgwd nttiacaacn swcswaspva lnvqyaprdv
421 rvrkikplse ihsgnsyslq cdfsssshpke vqffwekngr llgkesqlnf dsispedags
481 yscwvnnsig qtaskawtle vlyaprrlrv smspgdqvme gksatltces danppvshyt
541 wfdwnnqslp yhsqklrlep vkvqhsgayw cqgtnsvgkg rsplstltvy yspetigrrv
601 avglgsclai lilaicglkl grrwkrtqsq gglgenssgq sffvrnkkvr raplsegphs
```

```
661 lgcynpmmed gisyttlrfp emniprtgda essemqrppp dcddtvtysa lhkrqvgdye 721 nvipdfpede gihyseliqf gvgerpgage nvdyvilkh
```

CD23: a type II transmembrane protein found on mature B cells, monocytes, activated macrophages, eosinophils, platelets, and dendritic cells that enhances capture and processing of antigen complexed with IgE. NCBI Reference Sequence NP_001193948.2:

```
ORIGIN
                                                          (SEQ ID NO.: 135)
  1 mnppsqeiee lprrrccrrg tgivllglvt aalwaglltl lllwhwdttq slkqleeraa 61 rnvsqvsknl eshhgdgmaq ksgstgisge leelraeqqr lksqdlelsw nlnglqadls 121 sfksgelner neasdllerl reevtklrme lqvssgfvcn tcpekwinfq rkcyyfgkgt 181 kqwvharyac ddmegqlvsi hspeeqdflt khashtgswi glrnldlkge fiwvdgshvd 241 ysnwapgept srsqgedcvm mrgsgrwnda fcdrklgawv cdrlatctpp asegsaesmg 301 pdsrpdpdgr lptpsaplhs
//
```

CD27: TNF-receptor. Present on the surface of resting memory B cells. NCBI Reference Sequence NP_001233.1:

```
ORIGIN
                                                           (SEQ ID NO.:136)
  1 marphpwwlc vlgtlvglsa tpapkscper hywaqgklcc qmcepgtflv kdcdqhrkaa 61 qcdpcipgvs fspdhhtrph cescrhcnsg llvrnctita naecacrngw qcrdkectec 121 dplpnpslta rssgalsphp qpthlpyvse mleartaghm qtladfrqlp artlsthwpp 181 qrslcssdfi rilvifsgmf lvftlagalf lhqrrkyrsn kgespvepae pcryscpree 241 egstipiqed yrkpepacsp
```

CD28: present on all T-cells, and when matched with the appropriate ligand, labeled B7 which can be either CD80 or CD86, it has costimulatory effect on the T-cell. It is also expressed on Eosinophil granulocytes, especially after tissue infiltration. There its ligation leads to release of potent neurotoxins, IL-2 and IL-13 as well as IFN-γ. Checksum 1D9B6552A5878D0F: (SEQ ID NO.:137)

```
         10         20         30         40         50         60
MLRLLLALNL FPSIQVTGNK ILVKQSPMLV AYDNAVNLSC KYSYNLFSRE FRASLHKGLD 70         80         90        100        110        120
SAVEVCVVYG NYSQQLQVYS KTGFNCDGKL GNESVTFYLQ NLYVNQTDIY FCKIEVMYPP 130        140        150        160        170        180
PYLDNEKSNG TIIHVKGKHL CPSPLFPGPS KPFWVLVVVG GVLACYSLLV TVAFIIFWVR 190        200        210        220
SKRSRLLHSD YMNMTPRRPG PTRKHYQPYA PPRDFAAYRS
```

CD30: a type I transmembrane protein present on activated T and B cells that may play a role in cell activation and/or differentiation; expressed in Hodgkin disease, some T-cell lymphomas, and anaplastic large cell lymphomas. (SEQ ID NO.:138)

```
         10         20         30         40         50         60
MRVLLAALGL LFLGALRAFP QDRPFEDTCH GNPSHYYDKA VRRCCYRCPM GLFPTQQCPQ
```

-continued

```
              70         80         90        100        110        120
        RPTDCRKQCE PDYYLDEADR CTACVTCSRD DLVEKTPCAW NSSRVCECRP GMFCSTSAVN 130        140        150        160        170        180
        SCARCFFHSV CPAGMIVKFP GTAQKNTVCE PASPGVSPAC ASPENCKEPS SGTIPQAKPT 190        200        210        220        230        240
        PVSPATSSAS TMPVRGGTRL AQEAASKLTR APDSPSSVGR PSSDPGLSPT QPCPEGSGDC 250        260        270        280        290        300
        RKQCEPDYYL DEAGRCTACV SCSRDDLVEK TPCAWNSSRT CECRPGMICA TSATNSCARC 310        320        330        340        350        360
        VPYPICAAET VTKPQDMAEK DTTFEAPPLG TQPDCNPTPE NGEAPASTSP TQSLLVDSQA 370        380        390        400        410        420
        SKTLPIPTSA PVALSSTGKP VLDAGPVLFW VILVLVVVVG SSAFLLCHRR ACRKRIRQKL 430        440        450        460        470        480
        HLCYPVQTSQ PKLELVDSRP RRSSTQLRSG ASVTEPVAEE RGLMSQPLME TCHSVGAAYL 490        500        510        520        530        540
        ESLPLQDASP AGGPSSPRDL PEPRVSTEHT NNKIEKIYIM KADTVIVGTV KAELPEGRGL 550        560        570        580        590
        AGPAEPELEE ELEADHTPHY PEQETEPPLG SCSDVMLSVE EEGKEDPLPT AASGK
```

P28908-2, Tumor necrosis factor receptor superfamily member 8, Homo sapiens (SEQ ID NO.:139):

```
              10         20         30         40         50         60
        MSQPLMETCH SVGAAYLESL PLQDASPAGG PSSPRDLPEP RVSTEHTNNK IEKIYIMKAD 70         80         90        100        110        120
        TVIVGTVKAE LPEGRGLAGP AEPELEEELE ADHTPHYPEQ ETEPPLGSCS DVMLSVEEEG

130
        KEDPLPTAAS GK
```

CD31: PECAM-1, a cell adhesion molecule on platelets and endothelial cells (SEQ ID NO.:140).

```
              10         20         30         40         50         60
        MQPRWAQGAT MWLGVLLTLL LCSSLEGQEN SFTINSVDMK SLPDWTVQNG KNLTLQCFAD 70         80         90        100        110        120
        VSTTSHVKPQ HQMLFYKDDV LFYNISSMKS TESYFIPEVR IYDSGTYKCT VIVNNKEKTT 130        140        150        160        170        180
        AEYQLLVEGV PSPRVTLDKK EAIQGGIVRV NCSVPEEKAP IHFTIEKLEL NEKMVKLKRE 190        200        210        220        230        240
        KNSRDQNFVI LEFPVEEQDR VLSFRCQARI ISGIHMQTSE STKSELVTVT ESFSTPKFHI 250        260        270        280        290        300
        SPTGMIMEGA QLHIKCTIQV THLAQEFPEI IQKDKAIVA HNRHGNKAVY SVMAMVEHSG 310        320        330        340        350        360
        NYTCKVESSR ISKVSSIVVN ITELFSKPEL ESSFTHLDQG ERLNLSCSIP GAPPANFTIQ 370        380        390        400        410        420
        KEDTIVSQTQ DFTKIASKSD SGTYICTAGI DKVVKKSNTV QIVVCEMLSQ PRISYDAQFE 430        440        450        460        470        480
        VIKGQTIEVR CESISGTLPI SYQLLKTSKV LENSTKNSND PAVFKDNPTE DVEYQCVADN 490        500        510        520        530        540
        CHSHAKMLSE VLRVKVIAPV DEVQISILSS KVVESGEDIV LQCAVNEGSG PITYKFYREK 550        560        570        580        590        600
        EGKPFYQMTS NATQAFWTKQ KASKEQEGEY YCTAFNRANH ASSVPRSKIL TVRVILAPWK 610        620        630        640        650        660
        KGLIAVVIIG VIIALLIIAA KCYFLRKAKA KQMPVEMSRP AVPLLNSNNE KMSDPNMEAN
```

```
              670        680        690        700        710        720
SHYGHNDDVR NHAMKPINDN KEPLNSDVQY TEVQVSSAES HKDLGKKDTE TVYSEVRKAV

730
PDAVESRYSR TEGSLDGT
```

CD33: a marker of unknown function found on immature myeloid cells, including acute myeloid leukemia blasts and mature monocytes. P20138: (SEQ ID NO.:141)

```
              10         20         30         40         50         60
MPLLLLLPLL WAGALAMDPN FWLQVQESVT VQEGLCVLVP CTFFHPIPYY DKNSPVHGYW 70         80         90        100        110        120
FREGAIISRD SPVATNKLDQ EVQEETQGRF RLLGDPSRNN CSLSIVDARR RDNGSYFFRM 130        140        150        160        170        180
ERGSTKYSYK SPQLSVHVTD LTHRPKILIP GTLEPGHSKN LTCSVSWACE QGTPPIFSWL 190        200        210        220        230        240
SAAPTSLGPR TTHSSVLIIT PRPQDHGTNL TCQVKFAGAG VTTERTIQLN VTYVPQNPTT 250        260        270        280        290        300
GIFPGDGSGK QETRAGVVHG AIGGAGVTAL LALCLCLIFF IVKTHRRKAA RTAVGRNDTH 310        320        330        340        350        360
PTTGSASPKH QKKSKLHGPT ETSSCSGAAP TVEMDEELHY ASLNFHGMNP SKDTSTEYSE

VRTQ
```

CD34: stem cell marker, adhesion, found on hematopoietic precursors (found in high concentrations in umbilical cord blood), capillary endothelium, and embryonic fibroblasts. Isoform CD34-F: (SEQ ID NO.:142)

```
              10         20         30         40         50         60
MLVRRGARAG PRMPRGWTAL CLLSLLPSGF MSLDNNGTAT PELPTQGTFS NVSTNVSYQE 70         80         90        100        110        120
TTTPSTLGST SLHPVSQHGN EATTNITETT VKFTSTSVIT SVYGNTNSSV QSQTSVISTV 130        140        150        160        170        180
FTTPANVSTP ETTLKPSLSP GNVSDLSTTS TSLATSPTKP YTSSSPILSD IKAEIKCSGI 190        200        210        220        230        240
REVKLTQGIC LEQNKTSSCA EFKKDRGEGL ARVLCGEEQA DADAGAQVCS LLLAQSEVRP 250        260        270        280        290        300
QCLLLVLANR TEISSKLQLM KKHQSDLKKL GILDFTEQDV ASHQSYSQKT LIALVTSGAL 310        320        330        340        350        360
LAVLGITGYF LMNRRSWSPT GERLGEDPYY TENGGGQGYS SGPGTSPEAQ GKASVNRGAQ 370        380
ENGTGQATSR NGHSARQHVV ADTEL
```

CD40: a costimulatory protein found on antigen presenting cells. CD40 combines with CD154 (CD40L) on T cells to induce antibody isotype switching in B cells. Isoform I: (SEQ ID NO.:143)

```
              10         20         30         40         50         60
MVRLPLQCVL WGCLLTAVHP EPPTACREKQ YLINSQCCSL CQPGQKLVSD CTEFTETECL 70         80         90        100        110        120
PCGESEFLDT WNRETHCHQH KYCDPNLGLR VQQKGTSETD TICTCEEGWH CTSEACESCV 130        140        150        160        170        180
LHRSCSPGFG VKQIATGVSD TICEPCPVGF FSNVSSAFEK CHPWTSCETK DLVVQQAGTN
```

```
              190        200        210        220        230        240
       KTDVVCGPQD RLRALVVIPI IFGILFAILL VLVFIKKVAK KPTNKAPHPK QEPQEINFPD 250        260        270
       DLPGSNTAAP VQETLHGCQP VTQEDGKESR ISVQERQ
```

CD52: P31358m (SEQ ID NO.:144)

```
               10         20         30         40         50         60
       MKRFLFLLLT ISLLVMVQIQ TGLSGQNDTS QTSSPSASSN ISGGIFLFFV ANAIIHLFCF

S
```

Q9UJ81 (SEQ ID NO.:145)

```
                       10
               MKRFLFLLLT ISLLVMVQ
```

CD 56: Neural cell adhesion molecule 1. Short name=N-CAM-1, Alternative name(s). CD_antigen=CD56. Isoform 1: (SEQ ID NO.:146)

```
               10         20         30         40         50         60
       MLQTKDLIWT LFFLGTAVSL QVDIVPSQGE ISVGESKFFL CQVAGDAKDK DISWFSPNGE 70         80         90        100        110        120
       KLTPNQQRIS VVWNDDSSST LTIYNANIDD AGIYKCVVTG EDGSESEATV NVKIFQKLMF 130        140        150        160        170        180
       KNAPTPQEFR EGEDAVIVCD VVSSLPPTII WKHKGRDVIL KKDVRFIVLS NNYLQIRGIK 190        200        210        220        230        240
       KTDEGTYRCE GRILARGEIN FKDIQVIVNV PPTIQARQNI VNATANLGQS VTLVCDAEGF 250        260        270        280        290        300
       PEPTMSWTKD GEQIEQEEDD EKYIFSDDSS QLTIKKVDKN DEAEYICIAE NKAGEQDATI 310        320        330        340        350        360
       HLKVFAKPKI TYVENQTAME LEEQVTLTCE ASGDPIPSIT WRTSTRNISS EEKASWTRPE 370        380        390        400        410        420
       KQETLDGHMV VRSHARVSSL TLKSIQYTDA GEYICTASNT IGQDSQSMYL EVQYAPKLQG 430        440        450        460        470        480
       PVAVYTWEGN QVNITCEVFA YPSATISWFR DGQLLPSSNY SNIKIYNTPS ASYLEVTPDS 490        500        510        520        530        540
       ENDFGNYNCT AVNRIGQESL EFILVQADTP SSPSIDQVEP YSSTAQVQFD EPEATGGVPI 550        560        570        580        590        600
       LKYKAEWRAV GEEVWHSKWY DAKEASMEGI VTIVGLKPET TYAVRLAALN GKGLGEISAA 610        620        630        640        650        660
       SEFKTQPVQG EPSAPKLEGQ MGEDGNSIKV NLIKQDDGGS PIRHYLVRYR ALSSEWKPEI 670        680        690        700        710        720
       RLPSGSDHVM LKSLDWNAEY EVYVVAENQQ GKSKAAHFVF RTSAQPTAIP ANGSPTSGLS 730        740        750        760        770        780
       TGAIVGILIV IFVLLLVVVD ITCYFLNKCG LFMCIAVNLC GKAGPGAKGK DMEEGKAAFS 790        800        810        820        830        840
       KDESKEPIVE VRTEEERTPN HDGGKHTEPN ETTPLTEPEK GPVEAKPECQ ETETKPAPAE

850
       VKTVPNDATQ TKENESKA
```

CD70: Tumor necrosis factor ligand superfamily member 7. P32970 (CD70_HUMAN): (SEQ ID NO.:147)

```
        10         20         30         40         50         60
MPEEGSGCSV RRRPYGCVLR AALVPLVAGL VICLVVCIQR FAQAQQQLPL ESLGWDVAEL 70         80         90        100        110        120
QLNHTGPQQD PRLYWQGGPA LGRSFLHGPE LDKGQLRIHR DGIYMVHIQV TLAICSSTTA 130        140        150        160        170        180
SRHHPTTLAV GICSPASRSI SLLRLSFHQG CTIASQRLTP LARGDTLCTN LTGTLLPSRN

190
TDETFFGVQW VRP
```

CD123: IL3RA. Isoform 1: (SEQ ID NO.:148)

```
        10         20         30         40         50         60
MVLLWLTLLL IALPCLLQTK EDPNPPITNL RMKAKAQQLT WDLNRNVTDI ECVKDADYSM 70         80         90        100        110        120
PAVNNSYCQF GAISLCEVTN YTVRVANPPF STWILFPENS GKPWAGAENL TCWIHDVDFL 130        140        150        160        170        180
SCSWAVGPGA PADVQYDLYL NVANRRQQYE CLHYKTDAQG TRIGCRFDDI SRLSSGSQSS 190        200        210        220        230        240
HILVRGRSAA FGIPCTDKFV VFSQIEILTP PNMTAKCNKT HSFMHWKMRS HFNRKFRYEL 250        260        270        280        290        300
QIQKRMQPVI TEQVRDRTSF QLLNPGTYTV QIRARERVYE FLSAWSTPQR FECDQEEGAN 310        320        330        340        350        360
TRAWRTSLLI ALGTLLALVC VFVICRRYLV MQRLFPRIPH MKDPIGDSFQ NDKLVVWEAG

370
KAGLEECLVT EVQVVQKT
```

CD154: The ligand for CD40. This is a costimulatory molecule that plays many roles, best known for activating B cells but also known to induce the activation of an APC in association with T cell receptor stimulation by MHC molecules on the APC. Q3L8U2: (SEQ ID NO.:149)

```
        10         20         30         40         50         60
MIETYNQTSP RSAATGLPIS MKIFMYLLTV FLITQMIGSA LFAVYLHRRL DKIEDERNLH 70         80         90        100        110        120
EDFVFMKTIQ RCNTGERSLS LLNCEEIKSQ FEGFVKDIML NKEETKKENS FEMQKVLQWA 130        140        150        160        170        180
EKGYYTMSNN LVTLENGKQL TVKRQGLYYI YAQVTFCSNR EASSQAPFIA SLCLKSPGRF 190        200        210        220        230        240
ERILLRAANT HSSAKPCGQQ SIHLGGVFEL QPGASVFVNV TDPSQVSHGT GFTSFGLLKL
```

CD138: syndecan, a plasma cell-surface glycoprotein, known as syndecan-1. Syndecan functions as the alpha receptor for collagen, fibronectin and thrombospondin. P18827: (SEQ ID NO.:150)

```
        10         20         30         40         50         60
MRRAALWLWL CALALSLQPA LPQIVATNLP PEDQDGSGDD SDNFSGSGAG ALQDITLSQQ 70         80         90        100        110        120
TPSTWKDTQL LTAIPTSPEP TGLEATAAST STLPAGEGPK EGEAVVLPEV EPGLTAREQE 130        140        150        160        170        180
ATPRPRETTQ LPTTHLASTT TATTAQEPAT SHPHRDMQPG HHETSTPAGP SQADLHTPHT 190        200        210        220        230        240
EDGGPSATER AAEDGASSQL PAAEGSGEQD FTFETSGENT AVVAVEPDRR NQSPVDQGAT
```

-continued

```
             250        260        270        280        290        300
         GASQGLLDRK EVLGGVIAGG LVGLIFAVCL VGFMLYRMKK KDEGSYSLEE PKQANGGAYQ

310
         KPTKQEEFYA KPTKQEEFYA
```

Oncofetoprotein—5T4 Trophoblast glycoprotein. NCBI Reference Sequence NP_001159864.1:

```
ORIGIN
                                                              (SEQ ID NO.: 151)
   1 mpggcsrgpa agdgrlrlar lalvllgwvs sssptssass fsssapflas avsaqpplpd
  61 qcpalcecse aartvkcvnr nltevptdlp ayvrnlfltg nqlavlpaga farrpplael
 121 aalnlsgsrl devragafeh lpslrqldls hnpladlspf afsgsnasvs apsplvelil
 181 nhivppeder qnrsfegmvv aallagralq glrrlelasn hflylprdvl aqlpslrhld
 241 lsnnslvslt yvsfrnlthl eslhlednal kvlhngtlae lqglphirvf ldnnpwvcdc
 301 hmadmvtwlk etevvqgkdr ltcaypekmr nrvllelnsa dldcdpilpp slqtsyvflg
 361 ivlaligaif llvlylnrkg ikkwmhnird acrdhmegyh yryeinadpr ltnlssnsdv
```

---

What is claimed:

1. An antibody conjugate, comprising an antibody that binds to CD20 or CD19, wherein the antibody is linked to two or more lytic domains, wherein said lytic domains comprises or consists of a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF and KFAKFAKKFAKFAKKFAKFA (SEQ. ID. NOs. 1-6, respectively), or a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF and KFAKFAKKFAKFAKKFAKFA (SEQ. ID. NOs. 1-6, respectively) having one or more of the F, A, or K residues of the lytic domain substituted with a corresponding D-amino acid; and wherein one of said lytic domains is linked to the amino(NH$_2$)-terminus of a Light (L) chain of the antibody, and the other of said lytic domains is linked to the amino(NH$_2$)-terminus of a Heavy (H) chain of the antibody.

2. A polypeptide conjugate, comprising a Heavy (H) chain and a Light (L) chain of an antibody that binds to CD20 or CD19, wherein the Heavy (H) and Light (L) chain variable regions each comprise 3 CDRs, wherein the amino(NH$_2$)-terminus of the Light (L) chain is linked to a lytic domain, wherein the amino(NH$_2$)-terminus of the Heavy (H) chain is linked to a lytic domain, and wherein said lytic domains comprise or consist of a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF and KFAKFAKKFAKFAKKFAKFA (SEQ. ID. NOs. 1-6, respectively), or a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF and KFAKFAKKFAKFAKKFAKFA (SEQ. ID. NOs. 1-6, respectively) having one or more of F, A, or K residues of the lytic domain substituted with a corresponding D-amino acid.

3. The conjugate of claim 1 or 2, further comprising a lytic domain linked to the carboxy(C)-terminus of the Heavy (H) chain.

4. The conjugate of claim 1 or 2, further comprising a lytic domain linked to the carboxy(C)-terminus of the Light (L) chain.

5. The conjugate of claim 1 or 2, wherein the conjugate comprises a plurality of lytic domains linked to the Heavy (H) chain and Light (L) chain, wherein at least one of the lytic domains is linked to the amino(NH$_2$)-terminus of the Heavy (H) chain, and at least one of the lytic domains is linked to the carboxy(C)-terminus of the Heavy (H) chain or is linked to the carboxy(C)-terminus of the Light (L) chain.

6. The conjugate of claim 1 or 2, comprising three, four, five, six, seven or eight lytic domains linked to the Heavy (H) chain or Light (L) chain.

7. The conjugate of claim 6, wherein the lytic domains are linked to the amino(NH₂)-terminus of the Light (L) chains, and have the identical amino acid sequence.

8. The conjugate of claim 1 or 2, wherein said lytic domain linked to the amino(NH₂)-terminus of the Light (L) chain is joined to said Light (L) chain immediately after the last amino acid at the amino(NH₂)-terminus of the Light (L) chain, thereby forming a continuous amino acid sequence between the lytic domain and the Light (L) chain.

9. The conjugate of claim 1 or 2, wherein said Light (L) chain and said lytic domain linked to the amino(NH₂)-terminus of the Light (L) chain are joined by a covalent bond, peptide sequence or a non-peptide linker or spacer.

10. The conjugate of claim 9, wherein said linker or spacer comprises a linear carbon chain.

11. The conjugate of claim 1 or 2, wherein said lytic domain consists of a sequence from about 10 to about 15 L- or D-amino acids, about 15 to about 20 L- or D-amino acids, about 10 to about 28 L- or D-amino acids, about 10 to about 50 L- or D-amino acids.

12. The conjugate of claim 1 or 2, wherein the lytic domain linked to the amino(NH₂)-terminus of the Light (L) chain is cationic.

13. The conjugate of claim 1 or 2, wherein the lytic domain linked to the amino(NH₂)-terminus of the Light (L) chain forms an amphipathic alpha helical structure.

14. The conjugate of claim 1 or 2, wherein the conjugate binds to CD20.

15. The conjugate of claim 1, wherein the antibody comprises an antibody fragment or subsequence that comprises Heavy (H) and Light (L) chain variable regions each comprising 3 CDRs of an antibody that binds to CD20 or CD19.

16. The conjugate of claim 15, wherein said antibody fragment or subsequence comprises an Fab, Fab', F(ab')₂, Fv, Fd, single-chain Fv (scFv), disulfide-linked Fvs (sdFv), $V_L$, $V_H$, Camel Ig, V-NAR, VHH, trispecific (Fab₃), bispecific (Fab₂), diabody (($V_L$-$V_H$)₂ or ($V_H$—$V_L$)₂), triabody (trivalent), tetrabody (tetravalent), minibody ((scF$_v$-$C_H$3)₂), bispecific single-chain Fv (Bis-scFv), IgGdelta$C_H$2, scFv-Fc, (scFv)₂-Fc, affibody, aptamer, avimer or nanobody.

17. The conjugate of claim 1 or 2, wherein said antibody is a monoclonal antibody.

18. The conjugate of claim 1 or 2, wherein said Heavy (H) chain or Light (L) chain is selected from a Heavy (H) or Light (L) chain of an antibody that binds to CD20 or has all 3 CDR sequences of an antibody that binds to CD20 set forth in any of Table C or Examples 14, 15, 18, 20 or 21.

19. The conjugate of claim 1 or 2, wherein said conjugate comprises any Heavy (H) chain conjugate, any Light (L) chain conjugate, any whole antibody conjugate sequence of an antibody that binds to CD20 set forth in any of Table C or Examples 14, 15, 18, 20 or 21.

20. The conjugate of claim 1 or 2, wherein said CD19 comprises all or a portion of SEQ ID NO:132 or wherein said CD20 comprises all or a portion of SEWQ ID NO:133.

21. The conjugate of claim 1 or 2 wherein said CD19 or CD20 is expressed by or on a cell.

22. The conjugate of claim 1 or 2, wherein said antibody or polypeptide conjugate is isolated or purified.

23. A composition comprising the conjugate of claim 1 or 2, and an anti-cell proliferative or immune stimulating agent.

24. A polypeptide comprising a: lytic domain linked to the amino(NH₂)-terminus of the Light (L) chain of an antibody that binds to CD20 or CD19 and a lytic domain linked to the amino(NH₂)-terminus of the Heavy (H) chain of an antibody that binds to CD20 or CD19, wherein one of said lytic domains comprise or consist of a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF and KFAKFAKKFAKFAK-KFAKFA (SEQ. ID. NOs.1-6, respectively), or a peptide selected from KFAKFAKKFAKFAKK, KFAKFAKKFAK-FAKKF, KFAKFAKKFAKFAKKFA, KFAKFAKKFAK-FAKKFAK, KFAKFAKKFAKFAKKFAKF and KFAK-FAKKFAKFAKKFAKFA (SEQ. ID. NOs.1-6, respectively) and optionally having one or more of the F, A, or K residues substituted with a corresponding D-amino acid.

25. A polypeptide comprising two or more lytic domains, wherein the two lytic domains are each linked to the amino(NH₂)-terminus of the Light (L) chains of an antibody that binds to CD20; and a Heavy (H) chain of an antibody that binds to CD20, wherein said Heavy (H) chain and said Light (L) chains have all 3 CDR sequences of an antibody that binds to CD20 set forth in any of Table C or Examples 14, 15, 18, 20 or 21.

26. A method of reducing or inhibiting proliferation of a neoplastic, tumor, cancer or malignant cell, comprising contacting the cell with the conjugate of claim 1 or 2 or polypeptide of claim 24 or 25 in an amount sufficient to reduce or inhibit proliferation of the neoplastic, tumor, cancer or malignant cell.

27. A method of treating a subject having a hyperproliferative disorder, comprising administering to the subject an amount of the conjugate of claim 1 or 2 or polypeptide of claim 24 or 25 sufficient to treat the hyperproliferative disorder.

28. A method of treating a subject having a neoplasia, tumor, cancer or malignancy, comprising administering to the subject an amount of the conjugate of claim 1 or 2 or polypeptide of claim 24 or 25 sufficient to reduce or inhibit proliferation of the neoplasia, tumor, cancer or malignancy.

29. The conjugate of claim 6, wherein the lytic domains linked to the amino(NH₂)-terminus of the Light (L) chains have a different amino acid sequence.

30. The conjugate of claim 1 or 2, wherein the antibody binds to CD20.

31. The conjugate of claim 1 or 2, wherein the antibody binds to CD19.

* * * * *